US008227432B2

(12) United States Patent
Hackett et al.

(10) Patent No.: US 8,227,432 B2
(45) Date of Patent: Jul. 24, 2012

(54) TRANSPOSON SYSTEM AND METHODS OF USE

(75) Inventors: Perry B. Hackett, Shoreview, MN (US); Karl J. Clark, Ramsey, MN (US); Zongbin Cui, Ann Arbor, MI (US); Adam J. Dupuy, Walkersville, MD (US); Aron M. Geurts, Minneapolis, MN (US); Geyi Liu, New York, NY (US)

(73) Assignee: Regents of the University of Minnesota, St. Paul, MN (US)

( * ) Notice: Subject to any disclaimer, the term of this patent is extended or adjusted under 35 U.S.C. 154(b) by 1687 days.

(21) Appl. No.: 10/420,529

(22) Filed: Apr. 22, 2003

(65) Prior Publication Data

US 2004/0077572 A1 Apr. 22, 2004

Related U.S. Application Data

(63) Continuation-in-part of application No. 10/128,998, filed on Apr. 22, 2002, now abandoned.

(60) Provisional application No. 60/379,572, filed on May 10, 2002.

(51) Int. Cl.
*A61K 48/00* (2006.01)
*C07H 21/02* (2006.01)
*C07H 21/04* (2006.01)
*C12N 11/04* (2006.01)

(52) U.S. Cl. .............. 514/44 R; 536/23.1; 536/24.1; 536/24.2; 435/183

(58) Field of Classification Search ............... 536/23.1, 536/23.5, 23.2
See application file for complete search history.

(56) References Cited

U.S. PATENT DOCUMENTS

| | | |
|---|---|---|
| 4,631,259 A | 12/1986 | Clewell et al. |
| 5,464,758 A | 11/1995 | Gossen et al. |
| 5,595,889 A | 1/1997 | Richaud et al. |
| 5,677,170 A | 10/1997 | Devine et al. |
| 5,719,055 A | 2/1998 | Cooper |
| 5,814,618 A | 9/1998 | Bujard et al. |
| 5,879,933 A | 3/1999 | Hodgson |
| 5,928,888 A | 7/1999 | Whitney |
| 5,948,681 A | 9/1999 | Scanlin et al. |
| 6,013,240 A | 1/2000 | Behr |
| 6,051,430 A | 4/2000 | Plasterk et al. |
| 6,225,121 B1 | 5/2001 | Savakis et al. |
| 6,489,458 B2 | 12/2002 | Hackett et al. |
| 6,613,752 B2 | 9/2003 | Kay et al. |
| 7,148,203 B2 | 12/2006 | Hackett et al. |
| 7,160,682 B2 | 1/2007 | Hackett et al. |
| 2002/0103152 A1 | 8/2002 | Kay et al. |
| 2002/0115216 A1 | 8/2002 | Steer et al. |
| 2003/0124668 A1 | 7/2003 | Hackett et al. |
| 2003/0154500 A1 | 8/2003 | Hackett et al. |
| 2004/0077572 A1 | 4/2004 | Hackett et al. |
| 2005/0003542 A1 | 1/2005 | Kay et al. |
| 2006/0026699 A1 | 2/2006 | Largaespada et al. |

FOREIGN PATENT DOCUMENTS

| | | |
|---|---|---|
| EP | 0 485 701 A1 | 5/1992 |
| EP | 0 756 007 A2 | 1/1997 |
| WO | WO 88/01646 | 3/1988 |
| WO | WO 93/04701 | 3/1993 |
| WO | WO 93/25239 | 12/1993 |
| WO | WO 95/01095 | 1/1995 |
| WO | WO 96/01313 | 1/1996 |
| WO | WO 96/40892 | 12/1996 |
| WO | WO 97/15679 | 5/1997 |
| WO | WO 97/29202 | 8/1997 |
| WO | WO 98/24479 | 6/1998 |
| WO | WO 98/40510 | 9/1998 |
| WO | WO 98/56903 | 12/1998 |
| WO | WO 99/25817 | 5/1999 |
| WO | WO 99/59546 | 11/1999 |
| WO | WO 00/30687 | 6/2000 |
| WO | WO 00/68399 | 11/2000 |
| WO | WO 01/30965 A2 | 5/2001 |
| WO | WO 02/13602 A1 | 6/2001 |
| WO | WO 01/81565 A2 | 11/2001 |
| WO | WO 01/89579 A2 | 11/2001 |
| WO | WO 01/91802 A1 | 12/2001 |
| WO | WO 01/89579 A3 | 8/2002 |

OTHER PUBLICATIONS

Richardson, et al. (2002) Stem Cells Concise Review, 20: 105-18.*
Brent, et al. (1989) Molecular Endocrinology, 3(12): 1996-2004, Abstract Only.*
Izsvak, et al. (2002) "Involvement of a Bifunctional, Paired-Like DNA-Binding Domain and a Transpositional Enhancer in Sleeping Beauty Transposition", The Journal of Biological Chemistry, 277(37): 34581-88.*
Adey et al., "Molecular resurrection of an extinct ancestral promoter for mouse L1," *Proc. Natl. Acad. Sci. USA*, 1994;91:1569-1573.
Aldaz et al., "The Interwoven Architecture of the Mu Transposase Couples DNA Synapsis to Catalysis," *Cell*, 1996;85:257-269.
Allende et al., "Insertional mutagenesis in zebrafish identifies two novel genes, pescadillo and dead eye, essential for embryonic development," *Genes Dev.*, 1996;10:3141-3155.
Allingham et al., "Determinants for hairpin formation in Tn10 transposition," *EMBO J.*, 2001;20(11):2931-2942.
Amsterdam et al., "The *Aequorea victoria* green fluorescent protein can be used as a reporter in live zebrafish embryos," *Dev Biol.*, 1995;171(1):123-9.
Anderson et al., "Gene expression in rainbow trout (Oncorhynchus mykiss) following intramuscular injection of DNA," *Mol. Mar. Biol. Biotech.*, 1996;5:105-113.
Aronovich et al., "Sleeping Beauty-mediated Delivery and Expression of the Human Beta-glucuronidase Gene in a Murine Model of Mucopolysaccharidosis Type VIIi," Amer. Soc. Gene Therapy, Boston, MA, Abstract, Jun. 5-9, 2002, 1 pg.

(Continued)

*Primary Examiner* — Robert M Kelly
(74) *Attorney, Agent, or Firm* — Mueting Raasch & Gebhardt, P.A.

(57) ABSTRACT

The present invention is directed to improved transposons and transposases. The present invention also includes gene transfer systems, methods of using the transposons and transposases, and compositions including the transposons and transposases.

37 Claims, 46 Drawing Sheets

OTHER PUBLICATIONS

Aronovich et al., "Hydrodynamic Intravenous Administration of Naked DNA (Sleeping Beauty Transposon) for Expression of Human B-glucuronidase in a Murine Model of Mucopolysaccharidosis Type VII," Amer. Soc. Gene Therapy, Washington D.C., Abstract, Jun. 6-10, 2003, 2 pgs.

Ausubel, *Current Protocols in Molecular Biology*, Contents: vols. 1, 2, and 3, Tables of Contents, 1994.

BD Biosciences Clontech Company, "Bidirectional Tet Expression Vectors, Simultaneously control expression of two genes with one tet-responsive element," [online] Palo Alto, CA [retrieved on Apr. 25, 2000]. Retrieved from the Internet: <http://www.clontech.com/archive/OCT96UPD/pBIVectors.html>; 3 pgs.

BD Biosciences Clontech Company, "Tet Expression Systems & Cell Lines, Mammalian cell cultures systems for tightly regulated, high-level gene expression," [online] Palo Alto, CA [retrieved on May 30, 2000]. Retrieved from the Internet: <http://www.clontech.com/archive/JUL96UPD/Tet.html>, 6 pgs.

BD Biosciences Clontech Company, "Tet System Vectors & Primers, Complete your Tet Systems tool kit with individual regulator and selection plasmids," [online] Palo Alto, CA [retrieved on Apr. 23, 2000]. Retrieved from the Internet: <http://www.clontech.com/archive/OCT96UPD/TetVectors.html>, 3 pgs.

Baker et al., "Division of Labor among Monomers within the Mu Transposase Tetramer," *Cell*, 1993;74:723-733.

Ballinger et al., "Targeted gene mutations in Drosophila," *Proc. Natl. Acad. Sci. USA*, 1989;86:9402-9406.

Bandyopadhyay et al., "Enhanced gene transfer into HuH-7 cells and primary rat hepatocytes using targeted liposomes and polyethylenimine," *Biotechniques*. Aug. 1998;25(2):282-92.

Bandyopadhyay et al., "Nucleotide exchange in genomic DNA of rat hepatocytes using RNA/DNA oligonucleotides. Targeted delivery of liposomes and polyethyleneimine to the asialoglycoprotein receptor," *J Biol Chem.*, 1999;274(15):10163-72.

Bayer et al., "A transgene containing lacZ is expressed in primary sensor neurons in zebrafish," *The Company of Biologists Limited*, 1992;115:421-426.

Becker et al., "Chapter 8: Use of Recombinant Adenovirus for Metabolic Engineering of Mammalian Cells," *Methods in Cell Biology, vol. 43: Protein Expression in Animal Cells*, Roth, ed., Academic Press, New York, 1994; Title page, publication page, table of contents, and pp. 161-189.

Beckwith, "lac: The Genetic System," *The Operon*, second edition, Miller et al., eds., Cold Spring Harbor Laboratory Press, New York, 1980; Title page, publication page, table of contents, and pp. 11-30.

Bell et al., "Insulators and Boundaries: Versatile Regulatory Elements in the Eukaryotic Genome," *Science*, 2001;291:447-450.

Bellen et al., "P-element-mediated enhancer detection: a versatile method to study development in Drosophila," *Genes Dev.*, 1989;3:1288-1300.

Bellon et al., "Aerosol Administration of a Recombinant Adenovirus Expressing CFTR to Cystic Fibrosis Patients: A Phase I Clinical Trial," *Human Gene Ther.*, 1997;8(1):15-25.

Belur et al., "Long-term Expression in Mouse Lung After Non-viral Sleeping Beauty-mediated Gene Transfer," *Mol. Therapy*;3:S60, Amer. Soc. Gene Therapy, Seattle, WA, Abstract, May 30-Jun. 3, 2001, 1 pg.

Belur et al., "Sleeping Beauty: A Non-viral Vector System Mediating Long Term Gene Expression in Mouse Lung and Liver," *Mol. Therapy*;5:S323, Amer. Soc. Gene Therapy, Abstract, 2002, 1 pg.

Belur et al., "Hyperoxia-induced Lung Injury: Treatment with a Heme Oxygenase-1 Transgene Mediated by the Sleeping Beauty Transposon System," Amer. Soc. Gene Therapy, Washington D.C., Abstract, Jun. 6-10, 2003, 1 pg.

Bhasin et al., "Characterization of a Tn5 Pre-cleavage Synaptic Complex," *J. Mol. Biol.*, 2000;302:49-63.

Bingham et al., "Cloning of DNA Sequences from the white Locus of D. melanogaster by a Novel and General Method," *Cell*, 1981;25:693-704.

Birkenmeier et al., "Murine Mucopolysaccharidosis Type VII. Characterization of a Mouse with β-Glucuronidase Deficiency," *J. Clin. Invest.*, 1989;83(3):1258-1266.

Blazar et al., "*In utero* transfer of adult bone marrow cells into recipients with severe combined immunodeficiency disorder yields lymphoid progeny with T- and B-cell functional capabilities," *Blood*, 1995;86(11):4353-66.

Bonaldo et al., "Efficient Gene Trap Screening for Novel Developmental Genes Using IRESβgeo Vector and in Vitro Preselection," *Experimental Cell Research*, 1998;244:125-136.

Borman et al., "Comparison of picornaviral IRES-driven internal initiation of translation in cultured cells of different origins," *Nucleic Acids Res.*, 1997;25:925-932.

Borman et al., "Picornavirus internal ribosome entry segments: comparison of translation efficiency and the requirements for optimal internal initiation of translation in vitro," *Nucleic Acids Res.*, 1995;23:3656-3663.

Bosma et al., "Bilirubin UDP-glucuronosyltransferase 1 is the Only Relevant Bilirubin Glucuronidating Isoform in Man," *J. Biol. Chem.*, 1994;269:17960-17964.

Boussif et al., "A versatile vector for gene and oligonucleotide transfer into cells in culture and in vivo: polyethylenimine," *Proc. Natl. Acad. Sci. USA*, 1995;92(16):7297-301.

Bradley et al., "Formation of germ-line chimaeras from embryo-derived teratocarcinoma cell lines," *Nature*, 1984;309:255-256.

Bragonzi et al., "Comparison between cationic polymers and lipids in mediating systemic gene delivery to the lungs," *Gene Ther.*, 1999;6:1995-2004.

Burcin et al., "Adenovirus-mediated regulable target gene expression in vivo," *Proc. Nat'l. Acad. Sci. USA*, Jan. 19, 1999;96:355-360.

Caldovic et al., "Development of position-independent expression vectors and their transfer into transgenic fish," *Molecular Marine Biology and Biotechnology*, 1995;4:51-61.

Carey, "On the Trail of the Jumping Genes," *Business Week*, Jun. 29, 1998; p. 89.

Carlson et al., "Germline Transposon Mutagenesis of Mouse Using the Sleeping Beauty Transposon System," Mouse Molecular Genetics Meeting, New York, NY, Abstract, Aug. 2002, 1 pg.

Choi et al., "Lactose-Poly(ethylene Glycol)-Grafted Poly-L-Lysine as Hepatoma Cell-Targeted Gene Carrier," *Bioconjugate Chem.*, 1998;9:708-718.

Chowdhury et al., "Isolation of Multiple Normal and Functionally Defective Forms of Uridine Diphosphate-Glucuronosyltransferase from Inbred Gunn Rats," *J. Clin. Invest.*, 1987;79:327-334.

Chowdhury et al., "Gunn rat: a model for inherited deficiency of bilirubin glucuronidation," *Adv. Vet. Sci. Comp. Med.*, 1993;37:149-73.

Clark et al., "Development of Dicistronic Vectors for Analysis of Transgene Expression in Zebrafish," Abstract presented at the 1998 meeting on "Zebrafish Development and Genetics," Cold Spring Harbor Laboratory, Cold Spring Harbor, NY, Apr. 29-May 3, 1998.

Clark et al., "Sleeping Beauty Goes Fishing: Insertional Mutagenesis Screens Using Transposons," Cold Spring Harbor Meeting on Zebrafish Genetics and Development, CSH Laboratory, NY, Abstract, Apr. 26-30, 2000, 1 pg.

Clark et al., "Sleeping Beauty Transposons for Gene Discovery and Analysis," International Zebrafish Meeting, Madison, WI, Abstract, Jun. 12-16, 2002, 1 pg.

Clarke et al., "pPV: a novel IRES-containing vector to facilitate plasmid immunization and antibody response characterization," *Immunotech.*, 1997;3(2):145-153.

Collas et al., "The nuclear localization sequence of the SV40 Tantigen promotes transgene uptake and expression in zebrafish embryo nuclei," *Transgenic Res.*, 1996;5:451-458.

Colloms et al., "DNA binding activities of the Caenorhabditis elegans Tc3 transposase," *Nucl. Acids Res.*, 1994;22:5548-5554.

Converse et al., "Sleeping Beauty-mediated Transposition I Cultured Human Lung and Liver Cells and Murine Hematopoietic Cells," *Mol. Therapy*;3:S64, Amer. Soc. Gene Therapy, Seattle, WA, Abstract, May 30-Jun. 3, 2001, 1 pg.

Cooley et al., "Insertional Mutagenesis of the Drosophila Genome with Single P Elements," *Science*, 1988;239:1121-1128.

Cormack et al., "FACS-optimized mutants of the green fluorescent protein (GFP)," *Gene*, 1996;173:33-38.

Coros et at., "Effect of Mutations in the Mu-host Junction Region on Transpososome Assembly," *J. Mol. Biol.*, 2001;310(2):299-309.

Craig, "Target Site Selection in Transposition," *Annu. Rev. Biochem.*, 1997;66:437-474.

Crameri et al., "Improved green fluorescent protein by molecular evolution using DNA shuffling," *Nat. Biotechnology*, 1996;14(3):315-319.

Critchlow et al., "DNA end-joining: from yeast to man," *Trends Biochem. Sci.*, 1998;23:394-398.

Cui et al., "Structure-Function Analysis of the Inverted Terminal Repeats of the Sleeping Beauty Transposon," *J. Mol. Biol.*, 2002; 318:1221-1235.

Curcio et al., "Regulation of retrotransposition in *Saccharomyces cerevisiae*," *Mol. Microbiol.*, 1991;5(8):1823-1829.

Cusick, "Jumpy Gene Brought Back to Life," *ScienceNOW*, Nov. 19, 1997, 1 page.

Dalton et al., "Separation of Recombinant Human Protein C from Transgenic Animal Milk Using Immobilized Metal Affinity Chromatography," *Adv. Exp. Med. Biol.*, 1997;411:419-428.

Davidson et al., "Sleeping Beauty: An Efficient Method for Gene Delivery in Zebrafish," International Zebrafish Meeting, Madison, WI, Abstract, Jun. 12-16, 2002, 1 pg.

Davis, "Polyethylenimine," *Water Soluble Resins*, Technical Service and Development, the Dow Chemical Company, Midland, MI, 216-226.

Dawson et al., "Sleeping beauty awakes," *Nature Biotechnology*, 1998;16:20-21.

Devon et al., "Splinkerettes—improved vectorettes for greater efficiency in PCR walking," *Nucl. Acids. Res.*, 1995;23:1644-1645.

Diebold et al., "Mannose Polyethylenimine Conjugates for Targeted DNA Delivery into Dendritic Cells," *The Journal of Biological Chemistry*, 1999;274(27):19087-19094.

Doak et al., "A proposed superfamily of transposase genes: Transposon-like elements in ciliated protozoa and a common 'D35E' motif," *Proc. Natl. Acad. Sci. USA*, 1994;91:942-946.

Dubois et al., "Colorimetric Method for Determination of Sugars and related substances," *Anal. Chem.*, 1956:28(3):350-6.

Dupuy et al., "Adapting the *Sleeping Beauty* Transposon for Insertional Mutagenesis in the Mouse," Abstract presented at the 1998 meeting on "Mouse Molecular Genetics," Cold Spring Harbor Laboratory, Cold Spring Harbor, NY, Sep. 2-6, 1998.

Dupuy et al., "Transposition and Gene Disruption in the Male Germline of the Mouse," *Genesis*, 2001;30:82-88.

Dupuy et al., "Mammalian germ-line transgenesis by transposition," *Proc. Natl. Acad. Sci. USA*, 2002;99(7):4495-4499.

Ebert et al., "A Moloney MLV-Rate Somatotropin Fusion Gene Produces Biologically Active Somatotropin in a Transgenic Pig," *Mol. Endo.*, 1988;2(3):277-283.

Eck et al., "Gene-Based Therapy," *Goodman & Gilman's The Pharmacological Basis of Therapeutics*, 1996;Chapter 5:77-101.

Economy Polymers and Chemicals, "Economy Products—Polyethyleneimine," product literature [online]; Houston, TX; [retrieved on May 10, 2001]; Retrieved from the Internet: URL:<http://www.economypolymers.com/polethyl.htm>; 2 pgs.

Ekker et al., "The Sleeping Beauty Transposon System in Zebrafish—its Activity in the 21st Century," Cold Spring Harbor Meeting on Zebrafish Genetics and Development, CSH Laboratory, NY, Abstract, Apr. 26-30, 2000, 1 pg.

Erbacher et al., "Transfection and physical properties of various saccharide, poly(ethylene glycol), and antibody-derivatized polyethylenimines (PEI)," *J. Gene Med.*, 1999;1(3):210-22.

Essner et al., "Expression of Zebrafish *connexin43.4* in the Notochord and Tail Bud of Wild-Type and Mutant *no tail* Embryos," *Developmental Biology*, 1996;177:449-462.

Essner et al., "The zebrafish thyroid hormone recptor α1 is expressed during early embryogenesis and can function in transcriptional repression," *Differentiation*, 1997;62:107-117.

Evans et al., "Gene trapping and functional genomics," *TIG*, 1997;13:370-374.

Factor, "Gene Therapy for Acute Diseases," *Mol. Therapy*, 2001;4(6):515-524.

Fadool et al., "Transposition of the *mariner* element from *Drosophila mauritiana* in zebrafish," *Proc. Nat'l. Acad. Sci. USA*, Apr. 1998;95(9):5182-5186.

Fahrenkrug et al., "Dicistronic Gene Expression in Developing Zebrafish," *Mar. Biotechnol.*, 1999;1:552-561.

Fermentas, "ExGen™ 500 in vivo Transfection Reagent," [online]; retrieved on Apr. 4, 2002, retrieved from the Internet<URL:http://www.fermentas.com/profiles/reagents/pexgen500(20x).htm>;4 pgs.

Ferry et al., "Liver-Directed Gene Transfer Vectors," *Human Gene Ther.*, 1998;9(14):1975-1981.

Fieck et al., "Modifications of the *E. coli* Lac repressor for expression in eukaryotic cells: effects of nuclear signal sequences on protein activity and nuclear accumulation," *Nuc. Acids Res.*, 1992;20(7):1785-1791.

Finkelstein et al., "The use of bi-cistronic transfer vectors for the baculovirus expression system," *J. Biotechnol.*, 1999;75(1):33-44.

Fire et al., "A modular set of *lacZ* fusion vectors for studying gene expression in *Caenorhabditis elegans*," *Gene*, 1990;93(2):189-198.

Fischer et al., "Cis requirements for transposition of Tc1-like transposons in *C. elegans*," *Mol. Gen. Genet.*, 1999;262:268-274.

Fischer et al., "Regulated transposition of a fish transposon in the mouse germ line," *Proc. Natl. Acad. Sci. USA*, 2001;98(12):6759-6764.

Fletcher et al., "Mariner Transposon Mediated Stable Integration of Adenoviral Sequences for Use as Gene Therapy Vector System," Abstract 608, Fortieth Annual Meeting, American Society of Hematology, Miami Beach, Dec. 4-8, *Blood*, Nov. 15, 1998;92(10 Suppl. 1, Part 1 of 2):151a.

Garrick et al., "Repeat-induced gene silencing in mammals," *Nature Genetics*, 1998;18:56-59.

Ghattas et al., "The Encephalomyocarditis Virus Internal Ribosome Entry Site Allows Efficient Coexpression of Two Genes from a Recombinant Provirus in Cultured Cells and in Embryos," *Mol. Cell. Biol.*, 1991;11:5848-5859.

Gibbs et al., "Inheritance of P element and reporter gene sequences in zebrafish," *Mol. Mar. Biol. Biotech.*, 1994;3:317-326.

Gierl et al., "TnpA product encoded by the transposable element En-1 of Zea mays is a DNA binding protein," *EMBO J.*, 1988;7:4045-4053.

Gluzman et al., "Helper-free Adenovirus Type-5 Vectors," *Eukaryotic Viral Vectors*, Gluzman, ed., Cold Spring Harbor Laboratory Press, New York, 1982; title page, publication page, and pp. 187-192.

Gonzales et al., "Transposon mutagenesis of Haemophilus paragallinarum with Tn916," *Vet. Microbiol.*, 1996;48:283-291.

Goodier et al., "Tc1 Transposon-like Sequences are Widely Distributed in Salmonids," *J. Mol. Biol.*, 1994;241:26-34.

Gossen et al., "Tight control of gene expression in mammalian cells by *tetracycline-responsive promoters*," *Proc. Nat'l. Acad. Sci. USA*, 1992;89(12):5547-5551.

Gossen et al., "Transcriptional Activation by Tetracyclines in Mammalian Cells," *Science*, 1995;268:1766-1769.

Gray, "The direct coupling of oligosaccharides to proteins and derivatized gels," *Arch. Biochem. Biophys.*, 1974;163(1):426-8.

Gueiros-Filho et al., "Trans-kingdom Transposition of the *Drosophila* Element *mariner* Within the Protozoan *Leishmania*," *Science*, 1997;276:1716-1719.

Guo et al., "Receptor-targeted gene delivery via folate-conjugated polytheylenimine," *AAPS pharmsci electronic resource*, 1999;1(4):E19.

Gurtu et al., "IRES bicistronic expression vectors for efficient creation of stable mammalian cell lines," *Biochem. and Biophys. Res. Comm.*, 1996;229(1):295-298.

Hackett, Perry B., "Sleeping Beauty Transposon for Gene Therapy," Grant Abstract, Grant No. 5P01HD032652-070006 [online]. National Institute of Child Health and Human Development, [retrieved on Oct. 29, 2003]. Retrieved from the Internet:<URL:http//crisp.cit.nih.gov/crisp/CRISP_LIB.getdoc?textkey=6442591&p_grant_num=5P01...>; 2 pgs.

Hackett, Perry B., "Zebrafish as a Model System for Biomedical Research," Grant Abstract, Grant No. 5R01RR006625-07 [online]. National Center for Research Sources, [retrieved on Jan. 20, 2004]. Retrieved from the Internet<URL:http//crisp.cit.nih.gov/crisp/CRISP_LIB.getdoc?textkey=6056703&p_grant_num=5R01RR006625-07&p_...>; 2 pgs.

Hackett, "The molecular biology of transgenic fish," in *Biochemistry and Molecular Biology of Fishes*, vol. 2, Hochachka et al., eds., Elsevier Science Publisher B.V., Amsterdam, 1993;Chapter 9:pp. 207-240.

Hackett, "Development of Genetic Tools for Genomic Analyses and Transgenesis in Fish," Biotechnology-Aquaculture Interface, USDA meeting, http://nps.ars.usda.gov/static/ arsoibiotecws2001/contributions/Hackettrev.htm, Shepardstown, WV, Abstract, Mar. 5-7; 2001, 5 pgs.

Hackett, "From Tissue Culture to Whole Animals: Development of Genetic Tools for Genomic Analyses and Transgenesis in Fish," Generation of new marine cell lines and transgenic fish meeting, Mount Desert Island Biological Laboratory, Bar Harbor, ME, Abstract, May 4-6, 2001, 2 pgs.

Hackett, "The R's of the Life Sciences: from Repair Replication in Bacteria to Ribosomal RNA and Retroviruses in Animals to Recombination in Zebrafish," Workshop on DNA repair and related DNA transactions, Fallen Leaf Lake, CA, Abstract, Oct. 4-7, 2001, 1 pg.

Hackett, "The Sleeping Beauty Transposon System for Non-viral Gene Delivery into Animal Cells for Long-term Expression," Biophex 2002, Santa Clara, CA, Abstract, Sep. 22-23, 2002, 1 pg.

Hackett, "The Sleeping Beauty Transposon System for Non-viral Gene Delivery into Animal Cells for Long-term Expression," Biophex 2002, San Diego, CA, Abstract, Dec. 9-10, 2002, 8 pgs.

Hackett et al., "Construction of a Transposon System Active in Human Cells," *Keystone Symposia on Molecular & Cellular Biology*, Abstract and Poster, Jan. 20, 1998.

Hackett et al., "Development of Genetic Tools for Transgenic Animals," in: Murray et al., *Transgenic Animals in Agriculture*, CABI Publishing, New York, 1999, Chap. 2, pp. 19-35 (Presentation from a conference held in California in Aug. 1997).

Hackett et al., "Development of Genetic Tools for Transgenic Fish," Abstract, Seminars in Singapore, Jul. 29-30, 1997 & UC Davis Biotechnology Program, Granlibakken Conference Center, Aug. 24-27, 1997.

Hackett et al., "Sleeping Beauty Transposon for Gene Therapy," Grant Abstract, Grant No. 2P01HD032652-060006 [online]. National Institute of Child Health and Human Development, National Institutes of Health, project dates Jan. 10, 1995-Dec. 31, 2002 [retrieved on Jun. 19, 2001]. Retrieved from the Internet: URL: http://commons.cit.nih.gov/crisp3/crisp_lib. getdoc?textkey=6325542& p_grant_num=2P01HD032652-060006&p_query=&ticket=166464&p_audit_session_id=381420&p_keywords=, 2 pages.

Hackett et al., "Zebrafish as a model system for biomedical research," Grant Abstract, Grant No. 2R01RR06625-05A1 [online]. National Center for Research Resources, National Institutes of Health, project dates Aug. 1, 1991-Aug. 31, 2000 [retrieved on Apr. 11, 2001]. Retrieved from the Internet: URL: http://commons.cit.nih.gov/ crisp_historical/crisp_lib.getdoc?textkey=2397786&p_grant_num=2R01RR06625-05A1&p_query=&ticket=73379&p_audit_session_id=425461&p_keywords=, 2 pages.

Hackett et al., "Zebrafish as a Model System for Biomedical Research," Grant Abstract, Grant No. 5R01RR006625-06 [online]. National Center for Research Resources, National Institutes of Health, project dates Aug. 1, 1991-Aug. 31, 2000 [retrieved on Jun. 19, 2001]. Retrieved from the Internet: URL: http://commons.cit.nih. gov/crisp3/crisp_lib.getdoc?textkey=2772010&p_grant_num=5R01RR006625-06&p_query=&ticket=16646&p_audit_session_id=381420&p_keywords=, 2 pages.

Hackett et al., "Activity of the Sleeping Beauty System in Mammalian Cells," Keystone Meeting on Molecular and Cellular Biology of Gene Therapy, UT, Abstract, Jan. 14-20, 1999, 1 pg.

Hackett et al., "Activity of the Sleeping Beauty Transposon System in Zebrafish and Other Vertebrate Cells," NIH Workshop on Genomic and Genetic Tools for the Zebrafish, NIH, Abstract, May 10-11, 1999, 1 pg.

Hackett et al., "Activity of the Sleeping Beauty Transposon System in Zebrafish and Mammalian Cells," Cold Spring Harbor Varmus Meeting, CSH Laboratory, NY, Abstract, Dec. 17-20, 1999, 1 pg.

Hackett et al., "New Genetic Engineering Methods and Goals for Improvement of Fish and Their Interactions with the Environment," World Aquaculture Symposium, Nice, France, Abstract, May 2-7, 2000, 1 pg.

Hackett et al., "Sleeping Beauty: A DNA-Based Transposon System for Gene Delivery and Gene Discovery in Vertebrates," Amer. Soc. Gene Therapy, Denver, CO, Abstract, May 31-Jun. 4, 2000, 1 pg.

Hackett et al., "Sleeping Beauty: A Transposon System for Gene Delivery in Vertebrates," Frontiers in Nephrology Symposium—Gene Therapy, Boulder Creek, CO, Abstract, Jun. 5-6, 2000, 1 pg.

Hackett et al., "New Genetic Engineering Methods for Improvement of Fish," International Marine Biotechnology Conference, Townsville, Australia, Abstract, Sep. 29-Oct. 5, 2000, 1 pg.

Hackett et al., "Applications of the Sleeping Beauty Transposon System in Fish," 3rd IUBS Symposium on Molecular Aspects of Fish Genomes and Development, Singapore, Abstract, Feb. 19-21, 2001, 1 pg.

Hackett et al., "Development of a Transposon System for Gene Delivery and Gene-tagging in Vertebrates," International Symposium for Innovative Technologies, Minneapolis, MN, Abstract, May 2000, 1 pg.

Hackett et al., "Applications of the Sleeping Beauty Transposon System in Animals,", *Dev. Grow. Diff.*;43:S27, 14th Intl. Congress of Developmental Biology, Kyoto, Japan, Abstract, Jul. 8-12, 2001, 1 pg.

Hackett et al., "Structural and Functional Studies with the Sleeping Beauty Transposon System in Vertebrate," UC Davis Transgenic Animal Research Conference III, Tahoe City, CA, Abstract, Sep. 9-12, 2001, 2 pgs.

Hackett et al., "Structure/Function Studies with the Sleeping Beauty Transposon System," 24th Annual Meeting of the Molecular Biology Society of Japan, Yokohama, Japan, Abstract, Dec. 10, 2001, 1 pg.

Hackett et al., "Development of the Sleeping Beauty Transposon System for Non-viral Gene Therapy. Angiogenesis in Cancer and Other Diseases from Genes to Function to Therapy," Keystone Symposium, Banff, Canada, Abstract, Feb. 8-13, 2002, 1 pg.

Hackett et al., "Structural and functional studies with the *Sleeping Beauty* transposon system in vertebrate," *Transgenic Research*, Abstracts of the 3$^{rd}$ UC Davis Transgenic Animal Research Conference, 2002;11:73-94.

Hackett et al., "Application of New Genetic Tools for Understanding Gene Function in Fish," Workshop on Fish Genetics and Development, Wuhan, China, Abstract, Jun. 1-5, 2003, 1 pg.

Hallet et al., "Transposition and site-specific recombination: adapting DNA cut- and-paste mechanisms to a variety of genetic rearrangements," *FEMS Microbiology Reviews*, 1997;21:157-178.

Hammer et al., "Genetic Engineering of Mammalian Embryos," *J. Anim. Sci.*, 1986;63:269-278.

Handler et al., "A Functional Analysis of the P-Element Gene-Transfer Vector in Insects," *Arch. Insect Biochem. Physiol.*, 1993;22:373-384.

Hardy et al., "Construction of Adenovirus Vectors through Cre-*lox* Recombination," *J. Virol.*, 1997;71(3):1842-1849.

Harlow et al., eds., *Antibodies: A Laboratory Manual*, Cold Spring Harbor Laboratory Press, Cold Spring Harbor, New York, NY, 1988; copyright page and table of contents:9 pgs. (corrected entry for "Antibodies . .").

Harris et al., "Construction of a *Tc1*-like transposon *Sleeping Beauty*-based gene transfer plasmid vector for generation of stable transgenic mammalian cell clones," *Analytical Biochemistry*, 2002;310:15-26.

Hartl, Daniel, L., "*Mariner* Sails into *Leishmania*," *Science*, 1997;276:1659-1660.

Hartl et al., "What restricts the activity of mariner-like transposable elements," *Trends Genet.*, 1997;13:197-201.

Hellen et al., "Translation of Encephalomyocarditis Virus RNA by Internal Ribosomal Entry," *Curr. Top. Microbiol. Immunol.*, 1995;203:31-63.

Henikoff, "Conspiracy of silence among repeated transgenes," *BioEssays*, 1998;20(7):532-535.

Hirt, "Selective Extraction of Polyoma DNA from Infected Mouse Cell Cultures," *J. Mol. Biol.*, 1967;26(2):365-369.

Hone et al., "Efficient Chromosomal Transposition of Tc1/Mariner-like Transposon Sleeping Beauty in Mice," *PNAS*, 2001;98(16):9191-9196.

Hu et al., "The Inducible lac Operon-Repressor System Is Functional in Mammalian Cells," *Cell*, 1987;48(4):555-566.

Isner, "Myocardial gene therapy," *Nature*, 2002;415:234-239.

Ivics et al., "Development of Tc1-like transposable elements as genetic tools for Zebrafish (*Danio rerio*)," Abstract presented at "Second Biennial Meeting on Zebrafish Development and Genetics," Cold Spring Harbor Laboratory, Cold Spring Harbor, NY, Apr. 24-28, 1996.

Ivics et al., "Genetic Applications of Transposons and Other Repetitive Elements in Zebrafish," *Meth. Cell Biol.*, 1999;60:99-131.

Ivics et al., "Identification of functional domains and evolution of Tc1-like transposable elements," *Proc. Natl. Acad. Sci. USA*, 1996;93:5008-5013.

Ivics et al., "Molecular Reconstruction of Sleeping Beauty, a Tc1-like Transposon from Fish, and Its Transposition in Human Cells," *Cell*, 1997;91:501-510.

Ivics et al., "Repeated Sequence Elements in Zebrafish and Their Use in Molecular Genetic Studies," *The Zebrafish Science Monitor*, 1995;3:1-4.

Ivics et al., "Molecular Reconstitution of an Active Tc1-like Transposable Element in Salmonid Fish," Keystone Symp. on Transposition and Site-Specific Recombination, Santa Fe, NM, Abstract, Mar. 1-8, 1997, 1 pg.

Ivics et al., "Molecular Reconstitution of an Active Tc1-like Transposable Element in Salmonid Fish," 4th Intl. Biotechnology Conf., Sorrento, Italy, Abstract, Sep. 22-29, 1997, 1 pg.

Ivics et al., "Molecular Archeology and the Development of Sleeping Beauty: a Novel Transposon for Gene Delivery in Vertebrates," Cold Spring Harbor Meeting on Zebrafish Genetics and Development, CSH Laboratory, NY, Abstract, Apr. 29-May 3, 1998, 1 pg.

Izsvak et al., Characterization of a Tc1-like transposable element in zebrafish. (Danio rerio), *Mol. Gen. Genet.*, 1995;247:312-322.

Izsvak et al., "Involvement of a bifunctional, paired-like DNA-binding domain and a transpositional enhancer in Sleeping Beauty transposition," *J. Biol. Chem.*, 2002;277(37):34581-34588.

Izsvak et al., "Nucleic acid sequence alignment and a predicted consensus sequence of the salmonid subfamily of Tc1-like transposable elements isolated from eight fish species," [online]. [retrieved Jun. 5, 2001]. Retrieved from the Internet: <URL:ftp://ftp.ebi.ac.uk/pub/databases/embl/align/ds30090.dat.>; 10 pages.

Izsvak et al., "Repetitive elements and their genetic applications in zebrafish," *Biochem. Cell Biol.*, 1997;75:507-523.

Izsvak et al., "Sleeping Beauty, a wide host-range transposon vector for genetic transformation in vertebrates," *J. Mol. Biol.*, 2000;302:93-102.

Izsvak et al., "Two-Stage Ligation-Mediated PCR Enhances the Detection of Integrated Transgenic DNA," *BioTechniques*, 1993;15:814,816, and 817.

Izsvák et al., "Short Inverted-Repeat Transposable Elements in Teleost Fish and Implications for a Mechanism of Their Amplification" *J. Mol. Evol.*, 1999;48:13-21.

Izsvak et al., "Characterization of a Tc1-like Repetitive Element in Zebrafish," Cold Spring Harbor Meeting on Zebrafish, Abstract, Apr. 27-May 1, 1994:2 pgs.

Izsvak et al., "Composite Retroposons and Inverted Repeat Elements for Phylogenetic Analyses and Genetic Mapping in Zebrafish (*Danio rerio*)," Keystone Symp. On Transposition and Site-Specific Recombination, Santa Fe, NM, Abstract, Mar. 1-8, 1997, 1 pg.

Izsvak et al., "Composite Retroposons and Inverted Repeat Elements for Phylogenetic Analyses and Genetic Mapping in Fish," 4th Intl. Biotechnology Conf., Sorrento, Italy, Abstract, Sep. 22-29, 1997, 1 pg.

Izsvak et al., "Evolution and Genetic Applications of Retroposons and Inverted Repeat Transposable Elements in Zebrafish," Cold Spring Harbor Meeting on Zebrafish Genetics and Development, CSH Laboratory, NY, Abstract, Apr. 29-May 3, 1998, 1 pg.

Jang et al., "Cap independent translation of encephalomyocarditis virus RNA: structural elements of the internal ribosomal entry site and involvement of a cellular 57-kD RNA-binding protein," *Genes Dev.*, 1990;4:1560-1572.

Jermann et al., "Reconstructing the evolutionary history of the artiodactyl ribonuclease superfamily," *Nature*, 1995;374:57-59.

Kaiser et al., "Eukaryotic transposable elements as tools to study gene structure and function," in *Mobile Genetic Elements*, Sherratt, ed., IRL Press at Oxford University Press, Oxford/New York/Tokyo, 1995;pp. 69-100.

Kaminski et al., "Translation of encephalomyocarditis virus RNA: parameters influencing the selection of the internal initiation site," *EMBO J*, 1994;13:1673-1681.

Karsi et al., "Effects of Insert Size on Transposition Efficiency of the Sleeping Beauty Transposon in Mouse Cells," *Mar. Biotechnol.*, 2001;3:241-245.

Kaufman et al., "Improved vectors for stable expression of foreign genes in mammalian cells by use of the untranslated leader sequence from EMC virus," *Nucleic Acids Res.*, 1991;19(16):4485-4490.

Kaufman et al., "Remobilization of Sleeping Beauty Transposons in Zebrafish," Cold Spring Harbor Meeting on Zebrafish Genetics and Development, CSH Laboratory, NY, Abstract, Apr. 26-30, 2000, 1 pg.

Kawakami et al., "Excision of the *Tol2* transposable element of the medaka fish, *Oryzias latipes*, in zebrafish, *Danio rerio*," *Gene*, 1998;225:17-22.

Kawakami et al., "Identification of the *Tol2* transposase of the medaka fish *Oryzias latipes* that catalyzes excision of a nonautonomous *Tol2* element in zebrafish *Danio rerio*," *Gene*, 1999;240:239-244.

Ketting et al., "Target choice determinants of the Tc1 transposon of *Caenorhabditis elegans*," *Nucl. Acids Res.*, 1997;25(20):4041-4047.

Kidwell, "Horizontal transfer," *Curr. Opin. Genet. Dev.*, 1992;2:868-873.

Kircheis et al., "Coupling of cell-binding ligands to polyethylenimine for targeted gene delivery," *Gene Ther.*, 1997;4(5):409-18.

Klotz et al., "Macromolecule-small molecule interactions. Strong binding and cooperativity in a model synthetic polymer," *Biochemistry*, 1969;8(12):4752-6.

Koga et al., "Transposable element in fish," *Nature*, 1996;383:30.

Korswagen et al., "Transposon Tc1-derived, sequence-tagged sites in *Caenorhabditis elegans* as markers for gene mapping," *Proc. Natl. Acad. Sci. USA*, 1996;93:14680-14685.

Koster et al., "Comparison of Monocistronic and Bicistronic Constructs for Neutrophin Transgene and Reporter Gene Expression in Fish Cells," *Mol. Mar. Biol. Biotech.*, 1996;5(1):1-8.

Kren et al., "Alterations in mRNA stability during rat liver regeneration," *Am. J. Physiol.*, 1996;270(5 Pt 1):G763-77.

Kren et al., "Correction of the UDP-glucuronosyltransferase gene defect in the Gunn rat model of Crigler-Najjar Syndrome type I with a chimeric oligonucleotide," *Proc. Natl. Acad. Sci. USA*, 1999;96(18):10349-54.

Kren et al., "In Utero Delivery and Long-term Expression of GFP in Liver Mediated by the Sleeping Beauty Transposon System," *Mol. Therapy*;3:S138, Amer. Soc. Gene Therapy, Seattle, WA, Abstract, May 30-Jun. 3, 2001, 1 pg.

Kutty et al., "Purification and Characterization of Biliverdin Reductase from Rat Liver," *J. Biol. Chem.*, 1981;256:3956-3962.

Lam et al., "Active transposition in zebrafish," *Proc. Natl. Acad. Sci. USA*, 1996;93:10870-10875.

Lam et al., "Discovery of Amphibian Tc1-like Transposon Families," *J. Mol. Biol.*, 1996;257:359-366.

Lampe et al., "A purified mariner transposase is sufficient to mediate transposition in vitro," *EMBO J.*, 1996;15:5470-5479.

Lampe et al., "Factors Affecting Transposition of the *Himar1 mariner* Transposon in Vitro," *Genetics*, 1998;149:179-187.

Lampe et al., "Hyperactive transposon mutants of the *Himar1 mariner* transposon," *Proc. Natl. Acad. Sci. USA*, 1999;96:11428-11433.

Lander et al., "Initial sequencing and analysis of the human genome," *Nature*, 2001;409(6822):860-921.

Larregina et al., "FasL induces Fas/Apo1-mediated apoptosis in human embryonic kidney 293 cells routinely used to generate E1-deleted adenoviral vectors," *Gene Ther.*, 1998;5(4):563-568.

Lee et al., "Tn 10 insertional mutagenesis in Pasteurella multocida," *Vet. Microbiol.*, 1996;50:143-148.

Lee et al., "Importance of the Conserved CA Dinucleotide at Mu Termini," *J. Mol. Biol.*, 2001;314:433-444.

Lewin, Genes VI, "Eukaryotic mRNAs have a methylated cap at the 5' end," Oxford University Press, 1997; pp. 171-172.

Lewin, Genes VI, "Nuclear splicing proceeds through a lariat," Oxford University Press, 1997; pp. 891-893.

Li et al., "Inversion and transposition of Tc1 transposon of *C. elegans* in mammalian cells," *Somat. Cell Mol. Genet.*, 1998;24(6):363-369.

Linehan-Stieers et al., "Uniform distribution and long-term expression of GFP in liver mediated by the Sleeping Beauty transposon system," abstract presented at Fourth Annual Meeting of the American Society of Gene Therapy, Seattle, Washington, May 30-Jun. 3, 2001; 1 pg.

Liu et al., "Development of Expression Vectors for Transgenic Fish," *BioTechnol.*, 1990;8:1268-1272.

Liu et al., "Isolation and characterization of β-actin gene of carp (*Cyprinus carpio*)," *DNA Sequence-J. DNA Sequencing and Mapping*, 1990;1:125-136.

Liu et al., "Functional Analysis of Elements Affecting Expression of the β-Actin Gene of Carp," *Mol. Cell Biol.*, 1990;10(7):3432-3440.

Liu et al., "Hydrodynamics-based transfection in animals by systemic administration of plasmid DNA," *Gene Ther.*, 1999;6:1258-1266.

Liu et al., "In Vivo Transposition Assay of Sleeping Beauty Transposon in Zebrafish," Cold Spring Harbor Meeting on Zebrafish Genetics and Development, CSH Laboratory, NY, Abstract, Apr. 26-30, 2000, 1 pg.

Liu et al., "Improved Sleeping Beauty Transposon System for Use in Gene Therapy," *Mol. Therapy*;5:S333, Amer. Soc. Gene Therapy, Boston, MA, Abstract, Jun. 5-9, 2002, 1 pg.

Liu et al., "Improvements in the Sleeping Beauty Transposon System for Use in Gene Transfer," International Zebrafish Meeting, Madison, WI, Abstract, Jun. 12-16, 2002, 1 pg.

Lohe et al., "Horizontal Transmission, Vertical Inactivation, and Stochastic Loss of Mariner-like Transposable Elements," *Mol. Biol. Evol.*,' 1995;12:62-72.

Lohe et al., "Mutations in the mariner transposase: The D, D(35)E consensus sequence is nonfunctional," *Proc. Natl. Acad. Sci. USA*, 1997;94:1293-1297.

Lönngren et al., "Aldonate coupling, a simple procedure for the preparation of carbohydrate-protein conjugates for studies of carbohydrate-binding proteins," *Arch. Biochem. Biophys.*, 1976;175(2):661-9.

Loukeris et al., "Gene Transfer into the Medfly, Ceratitis capitata, with a Drosophila hydei Transposable Element," *Science*, 1995;270:2002-2005.

Lubon et al., "Blood Proteins from Transgenic Animal Bioreactors," *Transfusion Med. Rev.*, 1996;10:131-143.

Luo et al., "Chromosomal transposition of a Tc1/mariner-like element in mouse embryonic stem cells," *Proc. Natl. Acad. Sci. USA*, 1998;95:10769-10773.

Markkula et al., "Transgenic animals and gonadotrophins," *Rev. Reprod.*, 1996;1:97-106.

Marshall, "Gene Therapy on Trial," *Science*, 2000;288:951-957.

McGrory et al., "A Simple Technique for the Rescue of Early Region I Mutations into Infectious Human Adenovirus Type 5," *Virol.*, 1988;163(2):614-617.

Meng et al., "Promoter analysis in living zebrafish embryos identifies a cis-acting motif required for neuronal expression of GATA-2," *Proc. Natl. Acad. Sci. USA*, 1997;94(12):6267-72.

Merwin et al., "CD5-mediated specific delivery of DNA to T lymphocytes: compartmentalization augmented by adenovirus," *Journal of Immunological Methods*, 1995;186:257-266.

Michael, "Mutagenesis by Incorporation of a Phosphorylated Oligo During PCR Amplification," *BioTechniques*, 1994;16;410-412.

Moav et al. "Regulation of expression of transgenes in developing fish," *Transgenic Research*, 1993;2:153-161.

Moerman et al., "Chapter 22: Mobile Elements in *Caenorhabditis elegans* and Other Nemotodes," *Mobile DNA*, Berg et al., eds., American Society for Microbiology, 1989; Title page, publication page, table of contents, and pp. 537-555.

Mohn et al., "Transposon-Mediated Transgenesis allows stable expression following germ-line transmission," Abstract presented at the 1988 meeting on Zebrafish Development & Genetics, Cold Spring Harbor Laboratory, Cold Spring Harbor, NY, Apr. 29-May 3, 1998.

Mohn et al., "Transposon-Mediated Transgenesis Allows Stable Expression Following Germ-Line Transmission" Cold Spring Harbor Meeting on Zebrafish Genetics and Development, CSH Laboratory, NY, Abstract, Apr. 29-May 3, 1998, 1 pg.

Monsigny et al., Colorimetric determination of neutral sugars by a resorcinol sulfuric acid micromethod, *Anal. Biochem.*, 1988;175(2):525-30.

Moore et al., "Carbohydrate Characterization I. The Oxidation of Aldoses by Hypoiodite in Methanol; II. The Identification of Seven Aldo-Monosaccharides as Benzimidazole Derivatives," *J. Biol. Chem.* 1940;133:293-311.

Morgan et al., "Transposon tools for recombinant DNA manipulation: Characterization of transcriptional regulators from yeast, Xenopus, and mouse," *Proc. Natl. Acad. Sci. USA*, 1996;93:2801-2806.

Morral et al., "Administration of helper-dependent adenoviral vectors and sequential delivery of different vector serotype for long-term liver-directed gene transfer in baboons," *Proc. Nat'l. Acad. Sci. USA*, 1999;6(22):12816-12821.

Mountford et al., "Internal ribosome entry sites and dicistronic RNAs in mammalian transgenesis," *Trends Genet.*, 1995;11:179-184.

Mullins et al., "Perspectives Series: Molecular Medicine in Genetically Engineered Animals—Transgenesis in the Rate and Larger Mammals," *J.Clin. Inv.*, 1996;97(7): 1557-1560.

Nasevicius et al., "Identification of Genes Required for Angiogenesis and Cartilage Formation Using Morphant Technology," 3rd European Zebrafish Conference on Zebrafish Genetics and Development, Paris, France, Abstract, Jun. 11-14, 2003, 1 pg.

National Center for Biotechnology Information, National Library of Medicine, National Institutes of Health, GenBank Locus AAD03792, Accession No. U89799.1, "Tc1-like transposase [Anopheles gambiae]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=40..., 2 pages.

National Center for Biotechnology Information, National Library of Medicine, National Institutes of Health, GenBank Locus AAD03793, Accession No. U89800.1, "Tc1-like transposase [Anopheles gambiae]," [Online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=40..., 2 pages.

National Center for Biotechnology Information, National Library of Medicine, National Institutes of Health, GenBank Locus AAD03794, Accession No. U89803.1, "Tc1-like transposase [Anopheles gambiae]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=40..., 2 pages.

National Center for Biotechnology Information, National Library of Medicine, National Institutes of Health, GenBank Locus CAA82359, Accession No. Z29098.1, "transposase (putative) [Drosophila hydei]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=43..., 2 pages.

National Center for Biotechnology Information, National Library of Medicine, National Institutes of Health, GenBank Locus S26856, Accession No. S26856, "transposase—fruit fly (Drosophila hydei) transposon Minos," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=28..., 2 pages.

National Center for Biotechnology Information, National Library of Medicine, National Institutes of Health, GenBank Locus CAB51371, Accession No. AJ249084.1, "transposase [Pleuronectes platessa]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=55..., 2 pages.

National Center for Biotechnology Information, National Library of Medicine, National Institutes of Health, GenBank Locus CAB51372, Accession No. AJ249085.1, "transposase [Pleuronectes platessa]," [online]: Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=55...>, 2 pages.

National Center for Biotechnology Information, National Library of Medicine, National Institutes of Health, GenBank Locus CAC28060, Accession No. AJ303069.1, "putative transposase [Pleuronectes platessa]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=12...>, 2 pages.

National Center for Biotechnology Information, National Library of Medicine, National Institutes of Health, GenBank Locus AAB02109, Accession No. L76231.1, "transposase [Anopheles albimanus]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=11...>, 1 pg.

National Center for Biotechnology Information, National Library of Medicine, National Institutes of Health, GenBank Locus S33560, Accession No. S33560, "hypothetical protein—fruit fly (Drosophila melanogaster) transposon-like element Bari-1," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=63...>, 2 pages.

National Center for Biotechnology Information, National Library of Medicine, National Institutes of Health, GenBank Locus B46189, Accession No. B46189, "orf within vasotocin gene (Tes1 element)—Pacific hagfish," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=42...>, 1 page.

National Center for Biotechnology Information, National Library of Medicine, National Institutes of Health, GenBank Locus CAB63420, Accession No. Z99288.1, "Hypothetical protein ZK262.5 [Caenorhabditis elegans]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=65...>, 2 pages.

National Center for Biotechnology Information, National Library of Medicine, National Institutes of Health, GenBank Locus No. SMOTC1LT, Accession No. L12206, salmo salar (clone TC-TSS1) Tc1-like interspersed repetitive element encoding TcA-like transposase pseudogene) [online]. Bethesda, MD [retrieved on Apr. 14, 2003]. Retrieved from Internet URL:<http://www.ncbi.nlm.nih.gov/entrez/query.fcgi?cmd=Retrieve&db=nucleotide&list_uids=2...>, 2 pages.

National Center for Biotechnology Information, National Library of Medicine, National Institutes of Health, GenBank Locus No. SMOTC1LTA, Accession No. L12207, salmo salar (clone TC-TSS2) Tc1-like interspersed repetitive element and a transposase pseudogene) [online]. Bethesda, MD [retrieved on Apr. 14, 2003]. Retrieved from Internet URL:<http://www.ncbi.nlm.nih.gov/entrez/query.fcgi?cmd=Retrieve&db=nucleotide&list_uids=2...>, 2 pages.

National Center for Biotechnology Information, National Library of Medicine, National Institutes of Health, GenBank Locus No. EMCPOLYP, Accession No. M81861, encephalomyocarditis virus polyprotein, complete cds.) [online]. Bethesda, MD [retrieved on Apr. 14, 2003]. Retrieved from Internet URL:<http://www.ncbi.nlm.nih.gov/entrez/query.fcgi?cmd=Retrieve&db=nucleotide&list_uids=2...>, 5 pages.

National Institutes of Health, "BLAST 2 Sequences," [online] Bethesda, MD [retrieved Sep. 15, 2000]. Retrieved from the Internet: <http://www.ncbi.nlm.nih.gov/gorf/b12.html>; 1 page (correction of "BLAST 2...").

National Institutes of Health, "BLAST 2 Sequences," [online] Bethesda, MD [retrieved Apr. 9, 2002]. Retrieved from the Internet: <http://www.ncbi.nlm.nih.gov/gorf/b12.html>; 1 page.

Okabe et al., "'Green Mice' as a Source of Ubiquitous Green Cells," *FEBS Letters*, 1997;407:313-319.

Oosumi et al., "Mariner transposons in humans," *Nature*, 1995;378:873.

Osborne et al., "Movers and shakers: maize transposons as tools for analyzing other plant genomes," *Curr. Opin. Cell Biol.*, 1995;7:406-413.

Padgett et al., "Splicing of Messenger RNA Precursors," *Ann. Rev. Biochem. J.*, 1988;55:1119-1150.

Pan et al., "The Binding Site of the IcIR Repressor Protein Overlaps the Promoter of aceBAK," *Journal of Bacteriology*, 1996;178(13):3982-3984.

Panoskaltsis-Mortari et al., "In Utero Delivery of Sleeping Beauty Transposon Results in Long-term Multi-organ Expression: Potential for Prenatal Gene Therapy of Genetic Disorders," Amer. Soc. Hepatology Ann. Meeting, Abstract, 2001, 1 pg.

Parks et al., "A helper-dependent adenovirus vector system: Removal of helper virus by Cre-mediated excision of the viral packaging signal," *Proc. Nat'l. Acad. Sci. USA*, 1996;93:13565-13570.

Pelletier et al., "Internal initiation of translation of eukaryotic mRNA derived from poliovirus RNA," Nature, 1988;334:320-325.

Perucho et al., "Genetic and Physical Linkage of Exogenous Sequences in Transformed Cells," *Cell*, 1980;22:309-317.

Petrov et al., "Diverse transposable elements are mobilized in hybrid dysgenesis in *Drosophila virilis*," *Proc. Natl. Acad. Sci. USA*, 1995;92(17):8050-8054.

Plasterk, "Molecular Mechanisms of Transposition and Its Control," *Cell*, 1993;74:781-786.

Plasterk, "Reverse Genetics: From Gene Sequence to Mutant Worm," *Meth. Cell. Biol.*, Academic Press, Inc., Chapter 3, 1995;8:59-80.

Plasterk, "The Tc1/mariner Transposon Family," *Curr. Top. Microbiol. Immunol.*, 1996;204:125-143.

Plasterk et al., "Resident aliens the Tc1/mariner superfamily of transposable elements," *Trends in Genetics*, 1999;15:326-332.

Plasterk, "RNA Silencing: The Genome's Immune System," *Science*, 2002;296:1263-1265.

Radice et al., "Widespread occurrence of the Tc1 transposon family: Tc1-like transposons from teleost fish," *Mol. Gen. Genet.*, 1994;244:606-612.

Raz et al., "Transposition of the nematode *Caenorhabditis elegans* Tc3 element in the zebrafish *Danio rerio*," *Current Biology*, 1997;8:82-83, 85, 87-88.

Richardson et al., "Gene Repair and Transposon-Mediated Gene Therapy," *Stem Cells*, 2002;20:105-118.

Rio et al., "Evidence for Drosophila P Element Transposase Activity in Mammalian Cells and Yeast," *J. Mol. Biol.*, 1988;200:411-415.

Ryter et al., "Herne oxygenase activity. Current Methods and Applications," *Methods Mol. Biol.*, 2000;99:369-91.

Sambrook et al., *Molecular Cloning: A Laboratory Manual*, Cold Spring Harbor Laboratory Press, 1989; table of contents and title page.

Sarkar et at, "The 'Megaprimer' Method of Site-Directed Mutagenesis," *BioTechniques*, 1990;8:404-407.

Savilahti et al., "Mu Transpositional Recombination: Donor DNA Cleavage and Strand Transfer in *trans* by the Mu Transposase," *Cell*, 1996;85:271-280.

Schleif, "DNA Looping," *Science*, 1988;240:127-128.

Schneider, "BIOPHEX Highlights Gene Therapy Progress," *Gen. Eng. News*, Nov. 15, 2002;22(20):4 pgs.

Schouten et al., "Transposon Tc1 of the nematode *Caenorhabditis elegans* jumps in human cells," *Nucleic Acids Research*, 1998;26(12):3013-3017.

Score et al., "Relative Efficiency of Sleeping Beauty-mediated Transposition in Dividing and Non-dividing Cells," *Mol. Therapy*;5:S330, Amer. Soc. Gene Therapy, Boston, MA, Abstract, Jun. 5-9, 2002, 1 pg.

Score et al., "Molecular Evidence for Sleeping Beauty-mediated Transposition and Long-term Expression in vivo," Amer. Soc. Gene Therapy, Washington D.C., Abstract, Jun. 6-10, 2003, 1 pg.

Sequence search results in U.S. Appl. No. 09/142,593; titles: US-09-142-593-4; US-09-142-593-5; US-09-142-593-8; and US-09-142-593-7; printed Feb. 1 & 2, 2000; GenCore version 4.5; 8 pgs.

Shapiro, "Natural genetic engineering in evolution," *Genetica*, 1992;86:99-111.

Sherratt, *Mobile Genetic Elements*, IRL Press, Oxford, 1995;Title Page and Table of Contents.

Smit et al., "Tiggers and other DNA transposon fossils in the human genome," *Proc. Natl. Acad. Sci. USA*, 1996;93:1443-1448.

Snyder et al., "An improved 2,4,6-trinitrobenzenesulfonic acid method for the determination of amines," *Anal. Biochem.*, 1975;064(1):284-8.

Spradling et al., "Gene disruptions using P transposable elements: An integral component of the Drosophila genome project," *Proc. Natl. Acad. Sci. USA*, 1995;92:10824-10830.

Stein et al., Eds., "IUPAC-IUB Commission on biochemical Nomenclature A One-Letter Notation for Amino Acids Tenative Rules," *Journal of Biological Chemistry*, 1968;243(13):3557-3559.

Stewart, "Active ancestral molecules," *Nature*, 1995;374:12-13.

Suh et al., "Ionization of poly(ethylenimine) and poly(allylamine) at various pH's," *Bioorg. Chem.*, 1994;22(3):318-327.

Szekely et al., "P element mediated germ line transformation of *Drosophila melonogaster* with the Tc1 transposable DNA element from *Caenorhabditis elegans*." *Genome*, 1994;37(3):356-366.

Tatusova et al., "BLAST 2 Sequences, a new tool for comparing protein and nucleotide sequences," *FEMS Microbiol. Lett.*, 1999;174(2):247-250.

Tosi et al., "*cis* and *trans* factors affecting *Mos1* mariner evolution and transposition in vitro, and its potential for functional genomics," *Nucl. Acids Res.*, 2000;28(3):784-790.

Trembley et al., "Differential regulation of cyclin B1 RNA and protein expression during hepatocyte growth in vivo," *Cell Growth Differ.*, 1996;7(7):903-16.

Urabe et al., "A novel dicistronic AAV vector using a short IRES segment derived from hepatitis C virus genome," *Gene: An International Journal on Genes and Genomes*, 1997;200(1-2):157-162.

van Luenen et al., "Mobilization of quiet, endogenous Tc3 transposons of *Caenorhabditis elegans* by forced expression of Tc3 transposase," *EMBO J.*, 1993;12:2513-2520.

van Luenen et al., "Target site choice of the related transposable elements Tc1 and Tc3 of *Caenorhabditis elegans*," *Nucleic Acids Research*, 1994;22:262-269.

van Luenen et al., "The Mechanism of Transposition of Tc3 in *C. elegans*," *Cell*, 1994;79:293-301.

Venter et al., "The Sequence of the Human Genome," *Science*, 2001;291:1304-1351.

Verma et al., "Gene Therapy—Promises, Problems, and Prospects," *Nature*, 1997;389: 239-242.

Vigdal et al., "Common Physical Properties of DNA Affecting Target Site Selection of *Sleeping Beauty* and other Tc1/*mariner* Transposable Elements," *J. Mol. Biol.*, 2002;323(3):441-452.

von Melchner et al., "Identification of Cellular Promoters by Using a Retrovirus Promoter Trap," *J. Virol.*, 1989;63:3227-3233.

Vos et al., "Characterization of the *Caenorhabditis elegans* Tc1 transposase in vivo and in vitro," *Genes. Dev.*, 1993;7:1244-1253.

Vos et al., "Tc1 transposase of *Caenorhabditis elegans* is an endonuclease with a bipartite DNA binding domain," *EMBO J.*, 1994;13:6125-6132.

Vos et al., "Transposase is the only nematode protein required for in vitro transposition of Tc1," *Genes. Dev.*, 1996;10:755-761.

Wall et al., "Transgenic Dairy Cattle: Genetic Engineering on a Large Scale," *J. Dairy Sci.*, 1997;80:2213-2224.

Warren et al., "'Physiological genomics': Mutant screens in zebrafish,"*Am J Physiol.*, 1998;275(1 Pt 2):H1-7.

Weber et al., "An SV40 'Enhancer Trap' Incorporates Exogenous Enhancers or Generates Enhancers from Its Own Sequences," *Cell*, 1984;36:983-992.

Weber et al., "Macrolide-based Transgene Control in Mammalian Cells and Mice," *Nature Biotechnology*, 2002;20:901-907.

Webster, "One-Step, Two-Step Regulation of Therapeutic Genes," *The Scientist*, available on line at http://www.the-scientist.com/yr1999/ apr/opin_990426.html; Apr. 26, 1999.

Weinberg, "Zebrafish genetics: Harnessing horizontal gene transfer," *Current Biology*, 1998;8:R244-R247.

Weng et al., "HO-1 expression in type II pneumocytes after transpulmonary gene delivery," *Am. J. Physiol. Lung Cell. Mol. Physiol.*, 2000;278:L1273-L1279.

Westerfield, *The Zebrafish Book*, University of Oregon Press, Eugene, OR (1995), Title Page & Table of Contents only; text is available at zfish.uoregon.edu/zf_info/zfbook/zfbk.html.

Williams et al., "Organization and dynamics of the Mu transpososome: recombination by communication between two active sites," *Genes Dev.*, 1999;13(20):2725-2737.

Yant et al., "The development of new recombinant adenoviral vectors capable of stable integration into mammalian genomes," Abstract 922, p. 232a, 2nd Annual Meeting of the American Society of Gene Therapy, Jun. 9-13, 1999; Washington, DC.

Yant et al., "Somatic integration and long-term transgene expression in normal and haemophilic mice using a DNA transposon system," *Nat. Genet.*, 2000;25(1):35-41.

Yant et al., "Transposition from a gutless adeno-transposon vector stabilizes transgene expression in vivo," *Nature Biotechnology*, 2002;20(10):999-1005.

Ye et al., "Regulated Delivery of Therapeutic Proteins After in Vivo Somatic Cell Gene Transfer," *Science*, 1999;283:88-91.

Yoon et al., "Targeted gene correction of episomal DNA in mammalian cells mediated by a chimeric RNA-DNA oligonucleotide." *Proc. Natl. Acad. Sci. USA.*, 1996;93(5):2071-6.

Young et al., "Production of Biopharmaceutical Proteins in the Milk of Transgenic Dairy Animals," *BIO PHARM*, 1997;10:34-38.

Youngman et al., "Rte-1, a retrotransposon-like element in *Caenorhabditis elegans*," *FEBS Letter*, 1996;380:1-7.

Zambrowicz et al., "Disruption and sequence identification of 2,000 genes in mouse embryonic stem cells," *Nature*, 1998;392:608-611.

Zanta et al., "Gene delivery: A single nuclear localization signal peptide is sufficient to carry DNA to the cell nucleus," *Proc. Natl. Acad. Sci. USA*, 1999;96:91-96.

Zhang et al., "The Himar1 mariner transposase cloned in a recombinant adenovirus vector is functional in mammalian cells," *Nuc. Acids Res.*, 1998;26(16):3687-3693.

Zhang et al., "High Levels of Foreign Gene Expression in Hepatocytes after Tail Vein Injections of Naked Plasmid DNA," *Hum. Gene Ther.*, 1999;10:1735-1737.

Zhang et al., "Antiangiogenic Gene Therapy in Cancer," *Curr. Genomics*, 2000;1:117-133.

Abdallah et al., "A Powerful Nonviral Vector for In Vivo Gene Transfer into the Adult Mammalian Brain: Polyethylenimine," *Hum. Gene Ther.*, Oct. 20, 1996; 7(16):1947-1954.

Akagi et al., "RTCGD: retroviral tagged cancer gene database," *Nucleic Acids Res.*, Jan. 1, 2004;32:D523-527.

Ambion, Inc., "Poly(A)Purist™ mRNA Purification Kits," datasheet [online]. 2006 [retrieved on Apr. 3, 2006]. Retrieved from the Internet<URL:www.ambion.com/catalog/CATNum.php?1916>; 3 pgs.

Balciunas et al., "Trapping fish genes with transposons," 2005. *Zebrafish* 1:335-340.

Balciunas et al., "Harnessing a High Cargo-Capacity Transposon for Genetic Applications in Vertebrates," 2006, *PloS Genet.* vol. 2, Issue 11;e169.

Balciunas et al., "Enhancer trapping in zebrafish using the *Sleeping Beauty* transposon," *BMC Genomics*, Sep. 3, 2004;5:62:1-15.

Barnes et al., "Targeted disruption of the gene encoding DNA ligase IV leads to lethality in embryonic mice," *Curr. Biol.*, Dec. 31, 1998; 8(25):1395-1398.

Baus et al., "Hyperactive Transposase Mutants of the *Sleeping Beauty* Transposon," *Mol. Ther.*, Dec. 2005; 12(6):1148-1156. [Epub Sep. 8, 2005].

Belur et al., "Gene Insertion and Long-Term Expression in Lung Mediated by the *Sleeping Beauty* Transposon System," *Mol. Therapy*, Sep. 2003;8(3):501-507.

Bestor, "Transposons Reanimated in Mice," *Cell*,:322-325. [Epub DOI:10.1016/j.cell. 2005.07.024].

Bettinger et al., "Size Reduction of Galactosylated PEI/DNA Complexes Improves Lectin-Mediated Gene Transfer into Hepatocytes,"*Bioconjugate Chem.*, 1999; 10:558-561.

Beverly et al., "Perturbation of Ikaros isoform selection by MLV integration is a cooperative event in Notch$^{IC}$-induced T cell leukemogenesis," *Cancer Cell*, Jun. 2003;3:551-564.

Blackwood et al., "Going the Distance: A Current View of Enhancer Action," *Science*, Jul. 3, 1998;281(5373):60-63.

Blaydes et al., "Retroviral Integration at the *Epi1* Locus Cooperates with *Nf1* Gene Loss in the Progression to Acute Myeloid Leukemia," *J. Virol.*, Oct. 2001; 75(19):9427-9434.

Bowers et al., "Neuronal precursor-restricted transduction via *in utero* CNS gene delivery of a novel bipartite HSV amplicon/transposase hybrid vector," *Mol. Ther.*, 2006, 13:580-588.

Carlson et al., "Transposon Mutagenesis of the Mouse Germline," *Genetics*, Sep. 2003;165:243-256.

Carlson et al., "Somatic integration of an oncogene-harboring *Sleeping Beauty* transposon models liver tumor development in the mouse," *PNAS*, Nov. 22, 2005; 102(47): 17059-17064. [Epub Nov. 14, 2005].

Carlson et al., "Insertional Mutagenesis in Mice: New Perspectives and Tools," *Nat. Rev. Genet.*, Jul. 2005; 6(7):568-580.

Chai et al., "Fate of the mammalian cranial neural crest during tooth and mandibular morphogenesis," *The Company of Biologists Limited*, 2000; *Development* 127:1671-1679.

Chen et al., "Gene 'Knockdown' Approaches Using Unconventional Antisense Oligonucleotides," *Fish Development and Genetics, The Zebrafish and Medaka Models*, Hackensack, NJ, 2004, vol. 2, Chap. 13:454-475.

Cherry et al., "Retroviral Expression in Embryonic Stem Cells and Hematopoietic Stem Cells," *Mol. Cell Bio.*, Oct. 2000;20(20):7419-7426.

Clark et al., "Transposon Vectors for Gene-Trap Insertional Mutagenesis in Vertebrates," *Genesis*, 2004;39:225-233.

Coffin et al., Eds., "Synthesis and Processing of Viral RNA," *Retroviruses*, Cold Spring Harbor Laboratory Press, 1997:205-261.

Collier et al., "Cancer gene discovery in solid tumours using transposon-based somatic mutagenesis in the mouse," *Nature*, Jul. 14, 2005; 436(7048):272-276.

Collier et al., "Hopping around the Tumor Genome: Transposons for Cancer Gene Discovery," *Cancer Res.*, Nov. 1, 2005; 65(21):9607-9610.

Collier et al., "Transforming science: cancer gene identification," *Curr. Opin. Genet. Dev.*, Feb. 2006; 16(1):23-29. [Epub Dec. 1, 2005].

Converse et al., "Counterselection and Co-Delivery of Transposon and Transposase Functions for *Sleeeping Beauty*-Mediated Transposition in Cultured Mammalian Cells," *Biosci. Rep.*, Dec. 2004; 24(6):577-594.

Cui et al., "RecA-mediated, Targeted Mutagenesis in Zebrafish," *Mar. Biotechnol.*, 2003; 5:174-184.

Davidson et al., "Efficient gene delivery and gene expression in zebrafish using the *Sleeping Beauty* transposon," *Dev. Biol.*, 2003;263:191-202.

Davies et al., "Mutations of the *BRAF* gene in human cancer," *Nature*, Jun. 27, 2002;417(6892):949-954.

Ding et al., "Efficient Transposition of the *piggyBac* (*PB*) Transposon in Mammalian Cells and Mice," *Cell*, Aug. 12, 2005; 122:473-483. [Epub DOI 10.1016/j.cell.2005.07.013].

Dupuy et al., "Mammalian mutagenesis using a highly mobile somatic *Sleeping Beauty* transposon system," *Nature*, Jul. 14, 2005; 436(7048):221-226.

Dupuy et al., "Sleeping Beauty: a novel cancer gene discovery tool," 2006, *Hum. Mol. Genet.* 15(Suppl1):R75-R79.

Ehrhardt et al., "A Direct Comparison of Two Nonviral Gene Therapy Vectors for Somatic Integration: In Vivo Evaluation of the Bacteriophage Integrase фc31 and the *Sleeping Beauty* Transposase," *Mol. Ther.*, May 2005; 11(5):695-706.

Eisenstein, "Wake-up call for *Sleeping Beauty*," *Nat. Methods*, Sep. 2005; 2(9):637.

Ekker, Stephen C., "Insertional Mutagenesis in Zebrafish by SB Transposons," Grant Abstract, Grant No. 5R01DA014546-04 [online]. National Institute on Drug Abuse, project dates May 1, 2001-Mar. 31, 2006 [retrieved on Feb. 13, 2006]. Retrieved from the Internet: URL: http://crisp.cit.nih.gov/CRISP_LIB.getdoc?textkey=6736301&p_grant_num=5R01D...2 pgs.

Ekker, Stephen C., "Insertional Mutagenesis in Zebrafish by SB Transposons," Grant Abstract, Grant No. 5R01DA014546-05 [online]. National Institute on Drug Abuse, project dates May 1, 2001-Mar. 31, 2006 [retrieved on Feb. 13, 2006]. Retrieved from the Internet: URL: http://crisp.cit.nih.gov/CRISP_LIB.getdoc?textkey=6881460&p_grant_num=5R01D...2 pgs.

Ellisen et al., "*TAN-1*, the Human Homolog of the Drosophila *Notch* Gene, Is Broken by Chromosomal Translocations in T Lymphoblastic Neoplasms," *Cell*, Aug. 23, 1991;66:649-661.

Essner, Jeffrey J., "Angiogenesis Targets for Therapeutic Development," Grant Abstract, Grant No. 1R43CA108117-01 [online]. National Cancer Institute, project dates Jun. 4, 2004-Nov. 30, 2004 [retrieved on Feb. 13, 2006]. Retrieved from the Internet: URL: http://crisp.cit.nih.gov/CRISP_LIB.getdoc?textkey=6790744&p_grant_num=1R4 3C...2 pgs.

Essner et al. "Awakening gene therapy with Sleeping Beauty transposons," *Curr. Opin. Pharmacol.*, 2005; 5:513-519.

Fernando, et al., "*Sleeping Beauty* Transposon-Mediated Nonviral Gene Therapy," 2006. *BioDrugs* 20:219-229.

Finnzymes, Products for PCR and Molecular Biology, "RT-PCR Kits, RobusT™ 1 RT-PCR Kit," datasheet [online]. Finnzymes Oy, Espoo, Finland [retrieved on Apr. 3, 2006]. Retrieved from the Internet:<URL:www.finnzymes.fi/products/products_rtper.htm>; 1 pg.

Frommolt et al., "Sleeping Beauty transposon system—future trend in T-cell-based gene therapies?," 2006. *Future Oncol.* 2:345-349.

Gao et al., "A Critical Role for DNA End-Joining Proteins in Both Lymphogenesis and Neurogenesis," *Cell*, Dec. 23, 1998;95:891-902.

Geurts et al., "Gene Transfer into Genomes of Human Cells by the *Sleeping Beauty* Transposon System," *Mol. Therapy*, Jul. 2003; 8(1):108-117.

Geurts et al., "Structure-based prediction of insertion-site preferences of transposons into chromosomes," 2006, *Nucl. Acids Res.*, 34(9):2803-2811.

Geurts et al., "Conditional gene expression in the mouse using a *Sleeping Beauty* gene-trap transposon," 2006. *BMC Biotech.* 6:30, pp. 1-15.

Geurts et al., "Gene mutations and genomic rearrangements in the mouse as a result of transposon mobilization from chromosomal concatemers," *PloS Genet.* Sep. 2006. 2(9):e156, pp. 1413-1423.

Grabher et al., "Transposon-mediated enhancer trapping in medaka," *Gene*, 2003;322:57-66.

Grabher et al., "Efficient activation of gene expression using a heat-shock inducible Gal4/Vp16-UAS system in medaka," *BMC Biotechnol.*, Oct. 26, 2004;4(26):1-6.

Hackett, "Development of Genetic Tools for Genomic Analyses and Transgenesis in Fish," Tokyo University of Fisheries, Jul. 13, 2001, Abstract. 2 pgs.

Hackett. Commentary. "Integrating DNA vectors for gene therapy," 2007, *Mol. Ther.* 15(1):10-12.

Hackett, Perry. B., "Sleeping Beauty-Mediated Gene Therapy for Hemophilia," Grant Abstract, Grant No. 2R44HL072539-02A1 [online]. National Heart, Lung and Blood Institute, project dates Feb. 1, 2003-Dec. 31, 2006 [retrieved on Feb. 13, 2006]. Retrieved from the Internet: URL: http://crisp.cit.nih.gov/CRISP_LIB.getdoc?textkey=6883402&p_grant_num=2R44H...2 pgs.

Hackett, Perry B., "Transposon-Mediated Gene Therapy for Fanconi Anemia," Grant Abstract, Grant No. 1R43HL076908-01 [online]. National Heart, Lung and Blood Institute, project dates Apr. 1, 2004-Mar. 31, 2005 [retrieved on Feb. 13, 2006]. Retrieved from the Internet: URL: http://crisp.cit.nih.gov/CRISP_LIB.getdoc?textkey=6787819&p_grant_num=1R43H...2 pgs.

Hackett et al., "Applications of Transposable Elements in Fish for Transgenesis and Functional Genomics," *Fish Development and Genetics, The Zebrafish and Medaka Models*, Hackensack, NJ, 2004, vol. 2, Chap. 16:532-580.

Hackett et al., "Sleeping Beauty Transposon-Mediated Gene Therapy for Prolonged Expression," *Adv. Genet.*, 2005; 54:189-232.

Hawley et al., "Versatile retroviral vectors for potential use in gene therapy," *Gene Ther.*, 1994;1:136-138.

He et al., "Insulin expression in livers of diabetic mice mediated by hydrodynamics- based administration," *World J. Gastroenterol.*, 2004;10:567-572.

Heggestad et al., "Transposon-based RNAi delivery system for generating knockdown cell lines," *Biochem. Biophys. Res. Comm.*, 2004;316:643-650.

Hermanson et al., "*Sleeping Beauty* Transposon for Efficient *Gene Delivery*," *Methods in Cell Biology*, 2004, San Diego, CA, vol. 77:349-362.

Horie et al., "Characterization of *Sleeping Beauty* Transposition and Its Application to Genetic Screening in Mice," *Mol. Cell. Biol.*, Dec. 2003;23(24):9189-9207.

Huang et al., "Stable gene transfer and expression in human primary T cells by the *Sleeping Beauty* transposon system," *Blood*, Jan. 15, 2006; 107(2):483-491. [Epub Sep. 27, 2005, DOI 10.1182/Blood-2005-05-2133].

Ivics et al., "Transposable Elements for Transgenesis and Insertional Mutagenesis in Vertebrates: a Contemporary Review of Experimental Strategies," *Methods Mol. Biol., Mobile Genetic Elements*, Totowa, NJ; 2004, vol. 260:255-276.

Ivics et al., "The *Sleeping Beauty* Transposable Element: Evolution, Regulation and Genetic Applications," *Curr. Issues Mol. Biol.*, 2004;6:43-55.

Ivics et al., "A whole lotta jumpin goin' on: new transposon tools for vertebrate functional genomics," *Trends Genet.*, Jan. 2005; 21(1):8-11.

Izsvak et al., "Healing the Wounds Inflicted by *Sleeping Beauty* Transposition by Double-Strand Break Repair in Mammalian Somatic Cells," *Mol. Cell*, Jan. 30, 2004;13:279-290.

Izsvak et al., "*Sleeping Beauty* hits them all: transposon-mediated saturation mutagenesis in the mouse germline," *Nat. Methods*, Oct. 2005; 2(10):735-737.

Izsvak et al., "Sleeping Beauty Transposition: Biology and Applications for Molecular Therapy," *Mol. Therap.*, Feb. 2004;9(2): 147-156.

Ivics et al., "Transposons for Gene Therapy!," 2006, *Curr. Gene Therap.* 6:593-607.

Johansson et al., "Identification of candidate cancer-causing genes in mouse brain tumors by retroviral tagging," *Proc. Natl. Acad. Sci. USA*, Aug. 3, 2004; 101(31):11334-11337.

Jonkers et al., "Retroviral insertional mutagenesis as a strategy to identify cancer genes," *Biochem. Biophys. Acta.*, 1996;1287:29-57.

Kamijo et al., "Tumor Spectrum in *ARF*-deficient Mice," *Cancer Res.*, May 1, 1999;59:2217-2222.

Kawakami et al., "A Transposon-Mediated Gene Trap Approach Identifies Developmentally Regulated Genes in Zebrafish," *Dev. Cell*, Jul. 2004;7:133-144.

Kawakami, "Transposon Tools and Methods in Zebrafish," *Dev. Dyn.*, 2005; 234:244-254.

Keravala et al., "Hyperactive *Himar1* transposase mediates transposition in cell culture and enhances gene expression in vivo." 2006. *Hum. Gene. Ther.* 17(10):1006-18.

Keng et al., "Region-specific saturation germline mutagenesis in mice using the *Sleeping Beauty* transposon system," *Nat. Methods*, Oct. 2005; 2(10):763-769.

Koga et al., "The medaka fish *Tol2* transposable element can undergo excision in human and mouse cells," *J. Hum. Genet.*, 2003; 48:231-235. [Epub Mar. 28, 2003].

Kren et al., "Gene Therapy as an Alternative to Liver Transplantation," *Liver Transpl.*, Dec. 2002;8(12):1089-1108.

Kren et al., "Hepatocyte-targeted delivery of *Sleeping Beauty* mediates efficient gene transfer in vivo," *Gene Ther. Mol. Biol.*, Nov. 2003; 7: 229-238.

Largaespada, "Generating and manipulating transgenic animals using transposable elements," *Reprod. Biol. Endocrinol.*, Nov. 7, 2003; 1(80): 1-10.

Largaespada et al., "Retroviral Integration at the *Evi*-2 Locus in BXH-2 Myeloid Leukemia Cell Lines Disrupts *Nf1* Expression without Changes in Steady-State Ras-GTP Levels," *J. Virol.*, Aug. 1995;69(8);5095-5102.

Larson et al., "Expression of *VE-cadherin* in Zebrafish Embryos: A New Tool to Evaluate Vascular Development," *Dev. Dyn.*, 2004; 231:204-213.

Liu et al., "A Highly Efficient Recombineering-Based Method for Generating Conditional Knockout Mutations," *Genome Res.*, 2003;13:476-484.

Liu et al., "Endothelial Targeting of the *Sleeping Beauty* Transposon within Lung," *Mol. Ther.*, Jul. 2004;10(1):97-105.

Liu et al., "Excision of *Sleeping Beauty* transposons: parameters and applications to gene therapy," *J. Gene Med.*, 2004;6:574-583.

Liu et al., "Target-site Preferences of *Sleeping Beauty* Transposons," *J. Mol. Biol.*, 2005; 346:161-173.

Liu et al., "Sustained FVIII expression and phenotypic correction of hemophilia A in neonatal mice using an endothelial-targeted Sleeping Beauty transposon," 2006. Mol. Ther. 13:1006-1015.

Liu et al., "Sleeping Beauty-mediated eNOS gene therapy attenuates monocrotaline-induced pulmonary hypertension in rats," *FASEB J.* 2006, 20(14):2594-2596. Epub 2006. Oct. 25.

Lund et al., "Genome-wide retroviral insertional tagging of genes involved in cancer in Cdkn2a-deficient mice" *Nat. Genet.*, Sep. 2002;32(1):160-165.

Masuda et al., "Transposon-independent increase of transcription by the Sleeping Beauty transposase," *Biochem. Biophys. Res. Comm.*, 2004;317:796-800.

Mikkelsen et al., "Helper-Independent *Sleeping Beauty* Transposon-Transposase Vectors for Efficient Nonviral Gene Delivery and Persistent Gene Expression in Vivo," *Mol. Therapy*, Oct. 2003;8(4):654-665.

Mikkers et al., "High-throughput retroviral tagging to identify components of specific signaling pathways in cancer," *Nat. Genet.*, Sep. 2002;32(1):153-159.

Miskey et al.,"The *Frog Prince*: a reconstructed transposon from *Rana pipiens* with high transpositional activity in vertebrate cells," *Nucl. Acids Res.*, 2003;31(23):6873-6881.

Miskey et al., "DNA transposons in vertebrate functional genomics," *Cell Mol. Life Sci.*, 2005; 62:629-641.

Montini et al., "In Vivo Correction of Murine Tyrosinemia Type I by DNA-Mediated Transposition," *Mol. Therapy*, Dec. 2002;6(6): 759-769.

Moran et al., "High Frequency Retrotransposition in Cultured Mammalian Cells," *Cell*, Nov. 29, 1996;87:917-927.

"Mouse Transposon Insertion Database" [online]. University of Minnesota, Database Access [retrieved on Dec. 20, 2004]. Retrieved from the Internet:<URL:http://mouse. ccgb.umn.edu/ transposon/>; 1 pg.

Neil et al., "Retroviral insertion sites and cancer: Fountain of all knowledge?" *Cancer Cell*, Oct. 2002;2:253-255.

Nolan et al., "A systematic, genome-wide, phenotype-driven mutagenesis programme for gene function studies in the mouse," *Nat. Genet.*, Aug. 2000; 25(4):440-443.

Ohlfest et al., "Integration and Long-Term Expression in Xenografted Human Glioblastoma Cells Using a Plasmid-Based Transposon System," *Mol. Therapy*, Aug. 2004; 10(2):260-268.

Ohlfest et al., "Phenotypic correction and long-term expression of factor VIII in hemophilic mice by immunotolerization and nonviral gene transfer using the *Sleeping Beauty* transposon system," *Blood*, Apr. 1, 2005; 105(7):2691-2698.

Ohlfest et al., "Combinatorial Antiangiogenic Gene Therapy by Nonviral Gene Transfer Using the *Sleeping Beauty* Transposon Causes Tumor Regression and Improves Survival in Mice Bearing Intracranial Human Glioblastoma," *Mol. Ther.*, Nov. 2005; 12(5):778-788. [Epub doi:10.1016/j.ymthe.2005.07.689, Sep. 16, 2005].

Ortiz-Urda et al., "Sustainable correction of junctional epidermolysis bullosa via transposon-mediated nonviral gene transfer," *Gene Therapy*, 2003;10:1099-1104.

Palmer et al., "RNA Interference and ion channel physiology," 2006. *Cell Biochem. Biophys.* 46:175-192.

Palmer et al., "Protease-activated receptor regulation of CI-secretion in Calu-3 cells requires prostaglandin release and CFTR activation," 2006. *Am. J. Physiol. Cell. Physiol.* 290:C1189-1198.

Palmer et al., "Stable knockdown of CFTR establishes a role for the channel in P2Y receptor-stimulated anion secretion," 2006. *J. Cel. I. Physiol.* 206:759-770.

Park et al., "DNA methylation of Sleeping Beauty with Transposition into the mouse genome," *Genes to Cells*, 2005; 10:763-776.

Park et al., "*Sleeping Beauty* transposition in the mouse genome is associated with changes in DNA methylation at the site of insertion," 2006. *Genomics* 88:203-213.

Retrovirus Tagged Cancer Gene Database, "Mouse Retrovirus Tagged Cancer Gene Database," [online]; [retrieved on Jun. 14, 2006]; Retrieved from the Internet: URL:<http://rtcgd.ncifcrf.gov. htm>; 1 pg.

Richardson et al., "Strategies for Hepatic Gene Correction," *J. Drug Target*, 2002;10(2): 133-141.

Roberg-Perez et al., "MTID: a database of *Sleeping Beauty* transposon insertions in mice," *Nucl. Acids Res.*, 2003;31(1):78-81.

Rumpold et al., "RNAi-mediated knockdown of P-glycoprotein using a transposon-based vector system durably restores imatinib sensitivity in imatinib-resistant CML cell lines," *Exp. Hematol.*, 2005; 33:767-775.

Saeki et al., "Stable CNS gene delivery with *Sleeping Beauty* armed with a high capacity HSV virion," 2006. *Mol. Ther.* 13:457-458.

Score et al., "*Sleeping Beauty*-Mediated Transposition and Long-Term Expression in Vivo: Use of the LoxP/Cre Recombinase System to Distinguish Transposition-Specific Expression," *Mol. Ther.* 13:617-624.

Seidel et al., "Alterations of cancer-related genes in soft tissue sarcomas: hypermethylation of *RASSF1A* is frequently detected in leiomyosarcoma and associated with poor prognosis in sarcoma," *Int. J. Cancer*, Apr. 10, 2005; 114(3):442-447.

Sinzelle et al., "Generation of trangenic *Xenopus laevis* using the *Sleeping Beauty* transposon system," 2006, *Transgenic Res.* 2006, 15:751-760.

Sivasubbu et al., "Gene-breaking transposon mutagenesis reveals an essential role for histone H2afza in zebrafish larval development," 2006. *Mech. Dev.* 123:513-529.

Skarnes et al., "A gene trap approach in mouse embyronic stem cells: the *lacZ* reporter is activated by splicing, reflects endogenous gene expression, and is mutagenic in mice," *Genes Dev.*, Jun. 1992;6(6):903-918.

Soriano et al., "Generalized *lacZ* expression with the ROSA26 Cre reporter strain," *Nat. Genet.*, Jan. 1999;21(1):70-71.

Starr et al., "Cancer Gene Discovery Using the Sleeping Beauty Transposon," *Cell Cycle*, 4(12):e1-e5. [Epub Dec. 2005].

Subramanian et al., "Adeno-associated virus-mediated delivery of a mutant endostatin in combination with carboplatin treatment inhibits orthotopic growth of ovarian cancer and improves long-term survival," 2006. *Cancer Res.* 66:4319-4328.

Tada et al., "Long-Term Reduction of Serum Bilirubin Levels in Gunn Rats by Retroviral Gene Transfer In Vivo," *Liver Transpl. Surg.*, Jan. 1998; 4(1):78-88.

Tafalla et al., "Fish transposons and their potential use in aquaculture," 2005.*J. Biotech.* 123:397-412.

Tolar et al., "Sarcoma Derived from Cultured Mesenchymal Stem Cells," *Stem Cells Express*, published online Oct. 12, 2006; doi:10.1634/stemcells.2005-0620. pp. 1-51.

Tolar et al., "Real-Time In Vivo Imaging of Stem Cells Following Transgenesis by Transposition," *Mol. Ther.*, Jul. 2005; 12(1):42-48.

UCSC Genome Bioinformatics, [online]; [retrieved on Jun. 14, 2006]; Retrieved from the Internet: <URL:http://www.genome.ucsc.edu/>; 2 pgs.

Wacnik et al., "Tumor-induced mechanical hyperalgesia involves CGRP receptors and altered innervation and vascularization of DsRed2 fluorescent hindpaw tumors," *Pain*, 2005; 115(1-2):95-106.

Wadman et al., "Fishing for Answers with Transposons," *Mar. Biotechnol.*, May-Jun. 2005; 7:135-141.

Walisko et al., "Sleeping Beauty transposase modulates cell-cycle progression through interaction with Miz-1." *Proc. Natl. Acad. Sci. USA*, 103:4052-4067.

Weiser et al., "Cancer Biology: Sleeping Beauty awakens," *Nature*, Jul. 14, 2005; 436(7048): 184-186.

Weng et al., "Activating Mutations of *NOTCH1* in Human T Cell Acute Lymphoblastic Leukemia," *Science*, Oct. 8, 2004;306(5694):269-271.

Whitley, Chester B., "Gene Therapy for Metabolic Disorders," Grant Abstract, Grant No. 2P01HD032652-09A1 [online]. National Institute of Child Health and Human Development, project dates Jan. 1, 1997-Dec. 31, 2008 [retrieved on Feb. 13, 2006]. Retrieved from the Internet: URL: http://crisp.cit.nih.gov/CRISP_LIB.getdoc?textkey=6708516&p_grant_num=2P01H...2 pgs.

Wilber et al., "Dynamic Gene Expression After Systemic Delivery of Plasmid DNA as Determined by In Vivo Bioluminescence Imaging," *Hum. Gene Ther.*, Nov. 2005; 16:1325-1332. [Epub Sep. 26, 2005].

Wilber et al., "RNA as a Source of Transposase for *Sleeping Beauty*-Mediated Gene Insertion and Expression in Somatic Cells and Tissues," *Mol. Ther.* 2005, 13:625-630.

Wilson et al., "Functional zinc finger/*sleeping beauty* transposase chimeras exhibit attenuated overproduction inhibition," *FEBS Lett.*, Nov. 7, 2005; 579(27):6205-6209. [Epub Oct. 17, 2005].

Wu et al., "*piggyBac* is a flexible and highly active transposon as compared to *sleeping beauty, To12, and Mos1* in mammalian cells," *Proc. Natl. Acad. Sci. USA*, 2006, 103(41):15008-15013.

Wu et al., "Transcription Start Regions in the Human Genome are Favored Targets for MLV Integration," *Science*, Jun. 13, 2003;300(5626):1749-1751.

Wu et al., "Integration target site selection for retroviruses and transposable elements," *Cell Mol. Life Sci.*, 2004; 61:2588-2596.

Wybranietz et al., "Quantification of VP22-GFP Spread by Direct Fluorescence in 15 Commonly Used Cell Lines," *J. Gene Med.*, Jul.-Aug. 1999;1(4):265-274.

Yae et al., "*Sleeping Beauty* transposon-based phenotypic analysis of mice: lack of *Arpc3* results in defective trophoblast outgrowth," *Mol. Cell. Biol.* 2006, 26:6185-6196.

Yant et al., "Nonhomologous-End-Joining Factors Regulate DNA Repair Fidelity during *Sleeping Beauty* Element Transposition in Mammalian Cells," *Mol. Cell. Biol.*, Dec. 2003;23(23):8505-8518.

Yant et al., "Mutational Analysis of the N-Terminal DNA-Binding Domain of Sleeping Beauty Transposase: Critical Residues for DNA Binding and Hyperactivity in Mammalian Cells," *Mol. Cell. Biol.*, Oct. 2004; 24(20):9239-9247.

Yant et al., "High-Resolution Genome-Wide Mapping of Transposon Integration in Mammals," *Mol. Cell. Biol.*, Mar. 2005; 25(6):2085-2094.

York, "Sleeping beauty offers new method to find cancer genes," *Lancet Oncol.*, Aug. 2005; 6(8):545.

Yusa et al., "Enhancement of *Sleeping Beauty* Transposition by CpG Methylation: Possible Role of Heterochromatin Formation," *Mol. Cell Biol.*, May 2004;24(9):4004-4018.

Zanta et al., "In Vitro Gene Delivery to Hepatocytes with Galactosylated Polyethylenimine," *Bioconjugate Chem.*, 1997; 8:839-844.

Zambrowicz et al., "Disruption of overlapping transcripts in the ROSA βgeo 26 gene trap strain leads to widespread expression of β-galactosidase in mouse embryos and hematopoietic cells," *Proc. Natl. Acad. Sci. USA*, Apr. 1997; 94:3789-3794.

Zayed et al., "The DNA-bending protein HMGB1 is a cellular cofactor of *Sleeping Beauty* transposition," *Nucl. Acids Res.*, 2003;31(9):2313-2322.

Zayed et al., "Development of Hyperactive *Sleeping Beauty* Transposon Vectors by Mutational Analysis," *Mol. Ther.*, Feb. 2004; 9(2):292-304.

\* cited by examiner

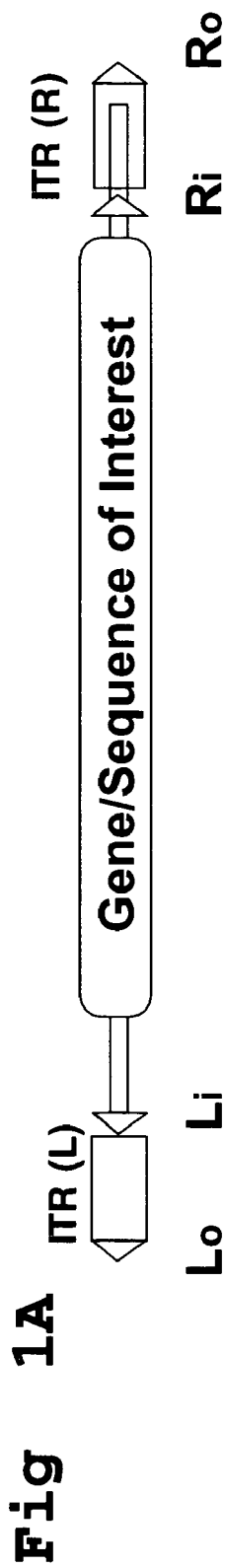

| Construct | DR Sequence | Binding | Transposition | SEQ ID NO: |
|---|---|---|---|---|
| | Outer DR (Lo or Ro) | | | |
| WT-Lo | TACAGTTGAAGTCGGAAGTTTACATACACTTAAG | + | 100% | 19 |
| Lo(S3) | TACAATTGAAGTCGGAAGTTTACATACACTTAAG | + | 39% | 60 |
| Lo(S1,3) | TAAAATTGAAGTCGGAAGTTTACATACACTTAAG | + | bkg | 61 |
| Lo(S4-6) | TACAGCCCAAGTCGGAAGTTTACATACACTTAAG | + | 27% | 62 |
| Lo(S7-9) | TACAGTTGCCCTCGGAAGTTTACATACACTTAAG | + | 47% | 63 |
| Lo(S10-12) | TACAGTTGAAGAACGAAGTTTACATACACTTAAG | − | bkg | 64 |
| Lo(Δ8-11) | TACAGTTGA----GGAAGTTTACATACACTTAAG | − | bkg | 65 |
| Lo(S28-30) | TACAGTTGAAGTCGGAAGTTTACATACACGGGAG | + | 36% | 66 |
| Lo(S27-29) | TACAGTTGAAGTCGGAAGTTTACATACATGGAAG | − | bkg | 67 |
| Lo/Ro(12G→A) | TACAGTTGAAGTCAG====GACTGAAGTTGACAT | + | 67% | 68 |
| | Left Inner DR (Li) | | | |
| WT-Li | TCCAGTGGGTCAGAAGTTTACATACACTAAGT | + | 100% | 23 |
| Li(2C→A) | TACAGTGGGTCAGAAGTTTACATACACTAAGT | + | bkg | 69 |
| Li/Lo(H) | TCCAGTGGGTCAGAAGTTTACATACACTTAAG | + | 110% | 15 |
| | Flanking TA Dinucleotides | | | |
| TALo | TATACAGTTGAAGTCGGAAGTTTACATACACTTAAG | + | 140% | 70 |
| TARo | TATACAGTTGAAGTCGGAAGTTTACATACACCTTAG | + | 195% | 71 |
| TALo/TARo | TATA(Lo)==================(Ro)TATA | + | 160% | |
| TAN₄Lo | TANNNNCAGTTGAAGTCGGAAGTTTACATACACTTAAG | + | 30% | 72 |
| TAN₄Ro | TANNNNCAGTTGAAGTCGGAAGTTTACATACACTTAAG | + | 25% | 73 |
| TAN₄Lo/Ro | TANNNN(Lo)==================(Ro)NNNNTA | + | bkg | |

Fig. 4

| Clones | | Left Junction Sequence | Chromosome | SEQ ID NO: |
|---|---|---|---|---|
| LoLi-RiRo, | ZCJ4 | GTCATCACCTTAGGTACAGTTGAAGTC | 3 | 74 |
| | ZCJ13 | CACTGGAGGTTACATACAGTTGAAGTC | 6 | 75 |
| | ZCJ12 | TGTGTGTGTGTGTGTACAGTTGAAGTC | 19 | 76 |
| TAN₄Ro, | ZCJ45 | AGGTATTTCATATCTACAGTTGAAGTC | 5 | 77 |
| | ZCJ26 | CAGTAAAAAGGACCTACAGTTGAAGTC | 1p33-34.3 | 78 |
| | ZCJ25 | TGAAATGAACACTATACAGTTGAAGTC | UN | 79 |
| TAN₄Lo, | ZCJ69 | TGTTTCTAAGTATA<u>ta</u>CAGTTGAAGTC | 20p12 | 80 |
| | ZCJ67 | ACCCAGCTTCCAGG<u>ta</u>CAGTTGAAGTC | 22 | 81 |
| TALo, | ZCJ44 | AAGACAGAGGAAGTTACAGTTGAAGTC | 5 | 82 |
| | ZCJ42 | AGGGCGCGGACAGATACAGTTGAAGTC | UN | 83 |
| | ZCJ35 | AATGCTGACGTATTTACAGTTGAAGTC | 17, rRNA spacer | 84 |
| | ZCJ23 | AAAGGATTACCTTTTACAGTTGAAGTC | UN | 85 |
| | ZCJ22 | TGAGACAACCCACATACAGTTGAAGTC | UN | 86 |
| Lo(S4-6), | ZCJ39 | TTAATCTAAAATACTACAG<u>CCC</u>AAGTC | 1 | 87 |
| | ZCJ32 | CAAAAGAGTTAACATACAG<u>CCC</u>AAGTC | UN | 88 |
| | ZCJ31 | ATATTCTATTAACATACAG<u>CCC</u>AAGTC | 21q21.1-21.2 | 89 |
| | ZCJ18 | GTCAGGTACAGATATACAG<u>CCC</u>AAGTC | 14 | 90 |
| | ZCJ17 | CTTTTGCCCCTAGATACAG<u>CCC</u>AAGTC | 21q22.2 | 91 |
| Lo(S7-9), | ZCJ34 | GAAGGACGGTACAATACAGTTG<u>CCC</u>TC | 6 | 92 |
| | ZCJ21 | TGCTGGACGGTACTTACAGTTG<u>CCC</u>TC | 6p21.2-21.33 | 93 |
| | ZCJ20 | TAATAATGTTTTTATACAGTTG<u>CCC</u>TC | UN | 94 |
| | ZCJ19 | TCTAGGTCATAAACTACAGTTG<u>CCC</u>TC | Xq12-21.1 | 95 |
| LoLo-RiRo, | ZCJ61 | CAGTAAAAAGGACCTACAGTTGAAGTC | 1p33-34.3 | 96 |
| | ZCJ38 | GTCTTTATTGTCTATACAGTTGAAGTC | UN | 97 |
| LiLoLi-RiRo, | ZCJ6 | GGAGCTGGGTACCA<u>ta</u>CAGTTGAAGTC | UN | 98 |
| | ZCJ5 | CTCCAATGCTTACA<u>ta</u>CAGTTGAAGTC | UN | 99 |
| | ZCJ2 | CCTTCCATTTCTTA<u>ta</u>CAGTTGAAGTC | 11p14.4 | 100 |
| | ZCJ1 | GAAGCACTTAATGA<u>ta</u>CAGTTGAAGTC | UN | 101 |
| | ZBC114 | CCACCAGCCTGGTC<u>ta</u>CAGTTGAAGTC | UN | 102 |
| | ZBC113 | TAATAGGATATATG<u>ta</u>CAGTTGAAGTC | UN | 103 |
| LoLoLi-RiRo, | ZBC104 | AGCTTGGAACTAACTACAGTTGAAGTC | UN | 104 |
| | ZBC102 | GCTACCTGTTTATATACAGTTGAAGTC | UN | 105 |
| | ZBC100 | CAAAGCCTTGACCCTACAGTTGAAGTC | UN | 106 |
| | ZBC98 | AAATATAATATATATACAGTTGAAGTC | 21q22.1 | 107 |
| LoLoLi-RiRo, | ZBC93 | ATTCATACAGCACA<u>ta</u>CAGTTGAAGTC | 14q32.33 | 108 |

Fig. 5

Cis    Trans-Parallel    Trans-Crossed (1)　　(2)　　(3)　　(4)

```
                                  Untitled
LOCUS        pCMV-SB      4732 bp dsDNA    Circular FEATURES                Location/Qualifiers
    CDS                 complement(2454..3314)
                        /note="bla beta-lactamase, ampR ampicillin resistance"
                        /label=AP(R)
    rep_origin          1696
                        /note="origin of replication"
                        /label=PMB1
    promoter            3911..4444
                        /note="immediate early gene promoter/enhancer"
                        /label=CMV\promoter/enhancer
    intron              4550..4709
                        /note="SV40"
                        /label=splice\donor/acceptor
    polyA_site          1045..1243
                        /note="polyadenalation signal"           SEQ ID NO:8
                        /label=SV40\polyA
    CDS                 12..1031
                        /note="Sleeping Beauty Transposase"
                        /label=SB\transposase
ORIGIN
       1 gatccgacat catgggaaaa tcaaaagaaa tcagccaaga cctcagaaaa aaaattgtag
      61 acctccacaa gtctggttca tccttgggag caatttccaa acgcctgaaa gtaccacgtt
     121 catctgtaca aacaatagta cgcaagtata aacaccatgg gaccacgcag ccgtcatacc
     181 gctcaggaag gagacgcgtt ctgtctccta gagatgaacg tactttggtg cgaaaagtgc
     241 aaatcaatcc cagaacaaca gcaaaggacc ttgtgaagat gctggaggaa acaggtacaa
     301 aagtatctat atccacagta aaacgagtcc tatatcgaca taacctgaaa ggccgctcag
     361 caaggaagaa gccactgctc caaaaccgac ataagaaagc cagactacgg tttgcaactg
     421 cacatgggga caaagatcgt acttttttgga gaaatgtcct ctggtctgat gaaacaaaaa
     481 tagaactgtt tggccataat gaccatcgtt atgtttggag gaagaagggg gaggcttgca
     541 agccgaagaa caccatccca accgtgaagc acggggggtgg cagcatcatg ttgtgggggt
     601 gctttgctgc aggagggact ggtgcacttc acaaaataga tggcatcatg aggaaggaaa
     661 attatgtgga tatattgaag caacatctca agacatcagt caggaagtta aagcttggtc
     721 gcaaatgggt cttccaaatg gacaatgacc ccaagcatac ttccaaagtt gtggcaaaat
     781 ggcttaagga caacaaagtc aaggtattgg agtggccatc acaaagccct gacctcaatc
     841 ctatagaaaa tttgtgggca gaactgaaaa agcgtgtgcg agcaaggagg cctacaaacc
     901 tgactcagtt acaccagctc tgtcaggagg aatgggccaa aattcaccca acttattgtg
     961 ggaagcttgt ggaaggctac ccgaaacgtt tgacccaagt taaacaattt aaaggcaatg
    1021 ctaccaaata ctagaattgg ccgcggggat ccagacatga taagatacat tgatgagttt
    1081 ggacaaacca caactagaat gcagtgaaaa aaatgcttta tttgtgaaat ttgtgatgct
    1141 attgctttat ttgtaaccat tataagctgc aataaacaag ttaacaacaa caattgcatt
    1201 cattttatgt ttcaggttca gggggaggtg tgggaggttt tttcggatcc tctagagtcg
    1261 acctgcaggc atgcaagctt ggcgtaatca tggtcatagc tgtttcctgt gtgaaattgt
    1321 tatccgctca caattccaca acatacga gccggaagca taagtgtaa gcctggggt
    1381 gcctaatgag tgagctaact cacattaatt gcgttgcgct cactgcccgc tttccagtcg
    1441 ggaaacctgt cgtgccagct gcattaatga atcggccaac gcgcgggag aggcggtttg
    1501 cgtattgggc gctcttccgc ttcctcgctc actgactcgc tgcgctcggt cgttcggctg
    1561 cggcgagcgg tatcagctca ctcaaaggcg gtaatacggt tatccacaga atcaggggat
    1621 aacgcaggaa agaacatgtg agcaaaaggc cagcaaaagg ccaggaaccg taaaaaggcc
    1681 gcgttgctgg cgttttccca taggctccgc cccctgacg agcatcacaa aaatcgacgc
    1741 tcaagtcaga ggtggcgaaa cccgacagga ctataaagat accaggcgtt ccccctgga
    1801 agctccctcg tgcgctctcc tgttccgacc ctgccgctta ccggatacct gtccgccttt
    1861 ctcccttcgg gaagcgtggc gctttctcat agctcacgct gtaggtatct cagttcggtg
```

Fig. 9(C)

Untitled

```
1921 taggtcgttc gctccaagct gggctgtgtg cacgaacccc ccgttcagcc cgaccgctgc
1981 gccttatccg gtaactatcg tcttgagtcc aacccggtaa gacacgactt atcgccactg
2041 gcagcagcca ctggtaacag gattagcaga gcgaggtatg taggcggtgc tacagagttc
2101 ttgaagtggt ggcctaacta cggctacact agaaggacag tatttggtat ctgcgctctg
2161 ctgaagccag ttaccttcgg aaaaagagtt ggtagctctt gatccggcaa acaaaccacc
2221 gctggtagcg tggttttttt tgtttgcaag cagcagatta cgcgcagaaa aaaaggatct
2281 caagaagatc ctttgatctt ttctacgggg tctgacgctc agtggaacga aaactcacgt
2341 taagggattt tggtcatgag attatcaaaa aggatcttca cctagatcct tttaaattaa
2401 aaatgaagtt ttaaatcaat ctaaagtata tatgagtaaa cttggtctga cagttaccaa
2461 tgcttaatca gtgaggcacc tatctcagcg atctgtctat ttcgttcatc catagttgcc
2521 tgactccccg tcgtgtagat aactacgata cgggagggct taccatctgg ccccagtgct
2581 gcaatgatac cgcgagaccc acgctcaccg gctccagatt tatcagcaat aaaccagcca
2641 gccggaaggg ccgagcgcag aagtggtcct gcaactttat ccgcctccat ccagtctatt
2701 aattgttgcc gggaagctag agtaagtagt tcgccagtta atagtttgcg caacgttgtt
2761 gccattgcta caggcatcgt ggtgtcacgc tcgtcgtttg gtatggcttc attcagctcc
2821 ggttcccaac gatcaaggcg agttacatga tcccccatgt tgtgcaaaaa agcggttagc
2881 tccttcggtc ctccgatcgt tgtcagaagt aagttggccg cagtgttatc actcatggtt
2941 atggcagcac tgcataattc tcttactgtc atgccatccg taagatgctt ttctgtgact
3001 ggtgagtact caaccaagtc attctgagaa tagtgtatgc ggcgaccgag ttgctcttgc
3061 ccggcgtcaa tacgggataa taccgcgcca catagcagaa ctttaaaagt gctcatcatt
3121 ggaaaacgtt cttcggggcg aaaactctca aggatcttac cgctgttgag atccagttcg
3181 atgtaaccca ctcgtgcacc caactgatct tcagcatctt ttactttcac cagcgtttct
3241 gggtgagcaa aaacaggaag gcaaaatgcc gcaaaaaagg gaataagggc gacacggaaa
3301 tgttgaatac tcatactctt cctttttcaa tattattgaa gcatttatca gggttattgt
3361 ctcatgagcg gatacatatt tgaatgtatt tagaaaaata aacaaatagg ggttccgcgc
3421 acatttcccc gaaaagtgcc acctgacgtc taagaaacca ttattatcat gacattaacc
3481 tataaaaata ggcgtatcac gaggcccttt cgtctcgcgc gtttcggtga tgacggtgaa
3541 aacctctgac acatgcagct cccggagacg gtcacagctt gtctgtaagc ggatgccggg
3601 agcagacaag cccgtcaggg cgcgtcagcg ggtgttggcg ggtgtcgggg ctggcttaac
3661 tatgcggcat cagagcagat tgtactgaga gtgcaccata tgcggtgtga ataccgcac
3721 agatgcgtaa ggagaaaata ccgcatcagg cgccattcgc cattcaggct gcgcaactgt
3781 tgggaagggc gatcggtgcg ggcctcttcg ctattacgcc agctggcgaa aggggggatgt
3841 gctgcaaggc gattaagttg ggtaacgcca gggttttccc agtcacgacg ttgtaaaacg
3901 acggccagtg aattcgagct tgcatgcctg caggtcgtta caacttac ggtaaatggc
3961 ccgcctggct gaccgcccaa cgacccccgc ccattacgt caataatgac gtatgttccc
4021 atagtaacgc caatagggac tttccattga cgtcaatggg tggagtattt acggtaaact
4081 gcccacttgg cagtacatca agtgtatcat atgccaagta cgccccctat tgacgtcaat
4141 gacggtaaat ggcccgcctg gcattatgcc cagtacatga ccttatggga cttccctact
4201 tggcagtaca tctacgtatt agtcatcgct attaccatgg tgatgcggtt ttggcagtac
4261 atcaatgggc gtggatagcg gtttgactca cggggatttc caagtctcca ccccattgac
4321 gtcaatggga gtttgttttg gcaccaaaat caacgggact ttccaaaatg tcgtaacaac
4381 tccgccccat tgacgcaaat gggcggtagg cgtgtacggt gggaggtcta taagcaga
4441 gctcgtttag tgaaccgtca gatcgcctgg agacgccatc cacgctgttt tgacctccat
4501 agaagacacc gggaccgatc cagcctccgg actctagagg atccggtact cgaggaactg
4561 aaaaaccaga aagttaactg gtaagtttag tcttttttgtc ttttatttca ggtcccggat
4621 ccggtggtgg tgcaaatcaa agaactgctc ctcagtggat gttgccttta cttctaggcc
4681 tgtacggaag tgttacttct gctctaaaag ctgcggaatt gtacccgcgg cc
```

Fig. 9(E)

```
                                          Untitled
LOCUS          pCMV-SB/ DDE 4410 bp dsDNA    Circular FEATURES               Location/Qualifiers
     CDS               complement(1639..2499)
                       /note="bla beta-lactamase, ampR ampicillin resistance"
                       /label=AP(R)
     rep_origin        881
                       /note="origin of replication"
                       /label=PMB1
     promoter          3096..3629
                       /note="immediate early gene promoter/enhancer"
                       /label=CMV\promoter/enhancer
     intron            3735..3894
                       /note="SV40"
                       /label=splice\donor/acceptor
     polyA_site        230..428                                    SEQ ID NO:9
                       /note="polyadenalation signal"
                       /label=SV40\polyA
ORIGIN
        1 ccatcacaaa gccctgacct caatcctata gaaaatttgt gggcagaact gaaaaagcgt
       61 gtgcgagcaa ggaggcctac aaacctgact cagttacacc agctctgtca ggaggaatgg
      121 gccaaaattc acccaactta ttgtgggaag cttgtggaag gctacccgaa acgtttgacc
      181 caagttaaac aatttaaagg caatgctacc aaatactaga attggccgcg gggatccaga
      241 catgataaga tacattgatg agtttggaca accacaact agaatgcagt gaaaaaatg
      301 ctttatttgt gaaatttgtg atgctattgc tttatttgta accattataa gctgcaataa
      361 acaagttaac aacaacaatt gcattcattt tatgtttcag gttcagggg aggtgtggga
      421 ggttttttcg gatcctctag agtcgacctg caggcatgca agcttggcgt aatcatggtc
      481 atagctgttt cctgtgtgaa attgttatcc gctcacaatt ccacacaaca tacgagccgg
      541 aagcataaag tgtaaagcct ggggtgccta atgagtgagc taactcacat taattgcgtt
      601 gcgctcactg cccgctttcc agtcgggaaa cctgtcgtgc cagctgcatt aatgaatcgg
      661 ccaacgcgcg gggagaggcg gtttgcgtat gggcgctct tccgcttcct cgctcactga
      721 ctcgctgcgc tcggtcgttc ggctgcggcg agcggtatca gctcactcaa aggcggtaat
      781 acggttatcc acagaatcag gggataacgc aggaaagaac atgtgagcaa aaggccagca
      841 aaaggccagg aaccgtaaaa aggccgcgtt gctggcgttt ttccataggc tccgccccc
      901 tgacgagcat cacaaaaatc gacgctcaag tcagaggtgg cgaaacccga caggactata
      961 aagataccag gcgtttcccc ctggaagctc cctcgtgcgc tctcctgttc cgaccctgcc
     1021 gcttaccgga tacctgtccg cctttctccc ttcgggaagc gtggcgcttt ctcatagctc
     1081 acgctgtagg tatctcagtt cggtgtaggt cgttcgctcc aagctgggct gtgtgcacga
     1141 accccccgtt cagcccgacc gctgcgcctt atccggtaac tatcgtcttg agtccaaccc
     1201 ggtaagacac gacttatcgc cactggcagc agccactggt aacaggatta gcagagcgag
     1261 gtatgtaggc ggtgctacag agttcttgaa gtggtggcct aactacggct acactagaag
     1321 gacagtattt ggtatctgcg ctctgctgaa gccagttacc ttcggaaaaa gagttggtag
     1381 ctcttgatcc ggcaaacaaa ccaccgctgg tagcggtggt ttttttgttt gcaagcagca
     1441 gattacgcgc agaaaaaaag gatctcaaga agatcctttg atcttttcta cggggtctga
     1501 cgctcagtgg aacgaaaact cacgttaagg gattttggtc atgagattat caaaaaggat
     1561 cttcacctag atccttttaa attaaaaatg aagttttaaa tcaatctaaa gtatatatga
     1621 gtaaacttgg tctgacagtt accaatgctt aatcagtgag gcacctatct cagcgatctg
     1681 tctatttcgt tcatccatag ttgcctgact ccccgtcgtg tagataacta cgatacggga
     1741 gggcttacca tctggcccca gtgctgcaat gataccgcga gacccacgct caccggctcc
     1801 agatttatca gcaataaacc agccagccgg aagggccgag cgcagaagtg gtcctgcaac
     1861 tttatccgcc tccatccagt ctattaattg ttgccgggaa gctagagtaa gtagttcgcc
     1921 agttaatagt ttgcgcaacg ttgttgccat tgctacaggc atcgtggtgt cacgctcgtc
     1981 gtttggtatg gcttcattca gctccggttc ccaacgatca aggcgagtta catgatcccc
     2041 catgttgtgc aaaaaagcgg ttagctcctt cggtcctccg atcgttgtca gaagtaagtt
```

Fig. 9(F)

Untitled

```
2101 ggccgcagtg ttatcactca tggttatggc agcactgcat aattctctta ctgtcatgcc
2161 atccgtaaga tgcttttctg tgactggtga gtactcaacc aagtcattct gagaatagtg
2221 tatgcggcga ccgagttgct cttgcccggc gtcaatacgg gataataccg cgccacatag
2281 cagaacttta aaagtgctca tcattggaaa acgttcttcg gggcgaaaac tctcaaggat
2341 cttaccgctg ttgagatcca gttcgatgta acccactcgt gcacccaact gatcttcagc
2401 atcttttact ttcaccagcg tttctgggtg agcaaaaaca ggaaggcaaa atgccgcaaa
2461 aaagggaata agggcgacac ggaaatgttg aatactcata ctcttccttt ttcaatatta
2521 ttgaagcatt tatcagggtt attgtctcat gagcggatac atatttgaat gtatttagaa
2581 aaataaacaa ataggggttc cgcgcacatt tccccgaaaa gtgcc acctg acgtctaaga
2641 aaccattatt atcatgacat taacctataa aaataggcgt atcacgaggc ctttcgtct
2701 cgcgcgtttc ggtgatgacg gtgaaaacct ctgacacatg cagctcccgg agacggtcac
2761 agcttgtctg taagcggatg ccgggagcag acaagcccgt cagggcgcgt cagcgggtgt
2821 tggcgggtgt cggggctggc ttaactatgc ggcatcagag cagattgtac tgagagtgca
2881 ccatatgcgg tgtgaaatac cgcacagatg cgtaaggaga aaataccgca tcaggcgcca
2941 ttcgccattc aggctgcgca actgttggga agggcgatcg gtgcgggcct cttcgctatt
3001 acgccagctg gcgaaagggg gatgtgctgc aaggcgatta agttgggtaa cgccagggtt
3061 ttcccagtca cgacgttgta aaacgacggc cagtgaattc gagcttgcat gcctgcaggt
3121 cgttacataa cttacggtaa atggcccgcc tggctgaccg cccaacgacc cccgcccatt
3181 gacgtcaata atgacgtatg ttcccatagt aacgccaata gggactttcc attgacgtca
3241 atgggtggag tatttacggt aaactgccca cttggcagta catcaagtgt atcatatgcc
3301 aagtacgccc cctattgacg tcaatgacgg taaatggccc gcctggcatt atgcccagta
3361 catgacctta tgggactttc ctacttggca gtacatctac gtattagtca tcgctattac
3421 catggtgatg cggttttggc agtacatcaa tgggcgtgga tagcggtttg actcacgggg
3481 atttccaagt ctccacccca ttgacgtcaa tgggagtttg ttttggcacc aaaatcaacg
3541 ggactttcca aaatgtcgta acaactccgc cccattgacg caaatgggcg gtaggcgtgt
3601 acggtgggag gtctatataa gcagagctcg tttagtgaac cgtcagatcg cctggagacg
3661 ccatccacgc tgttttgacc tccatagaag acaccgggac cgatccagcc tccggactct
3721 agaggatccg gtactcgagg aactgaaaaa ccagaaagtt aactggtaag tttagtcttt
3781 ttgtctttta tttcaggtcc cggatccggt ggtggtgcaa atcaaagaac tgctcctcag
3841 tggatgttgc ctttacttct aggcctgtac ggaagtgtta cttctgctct aaaagctgcg
3901 gaattgtacc gcgggccgat ccgacatcat gggaaaatca aagaaatca gccaagacct
3961 cagaaaaaaa attgtagacc tccacaagtc tggttcatcc ttgggagcaa tttccaaacg
4021 cctgaaagta ccacgttcat ctgtacaaac aatagtacgc aagtataaac accatgggac
4081 cacgcagccg tcataccgct caggaaggag acgcgttctg tctcctagag atgaacgtac
4141 tttggtgcga aaagtgcaaa tcaatcccag aacaacagca aaggaccttg tgaagatgct
4201 ggaggaaaca ggtacaaaag tatctatatc cacagtaaaa cgagtcctat atcgacataa
4261 cctgaaaggc cgctcagcaa ggaagaagcc actgctccaa aaccgacata agaaagccag
4321 actacggttt gcaactgcac atggggacaa agatcgtact ttttggagaa atgtcctctg
4381 gtctgatgaa acaaaaatag aactgtttgg
```

Fig. 9(H)

```
                            Untitled
LOCUS       -pTSVNeo     4928 bp dsDNA     Circular FEATURES             Location/Qualifiers
     3'UTR           complement(3141..3350)
                     /note="SV40 3'UTR and polyA"
                     /label=sv40\3'/pA
     CDS             complement(3327..4118)
                     /note="Neo resistance"
                     /label=Neo
     promoter        complement(4154..4479)
                     /note="SV40"
                     /label=SV40
     promoter        complement(2082)
                     /note=" bla gene promoter "
                     /label=P(BLA)
     CDS             complement(1190..2047)
                     /note=" bla gene- Ap(r) determinant "
                     /label=AP(R)
     promoter        complement(68)
                     /note=" lac promoter "
                     /label=P(LAC)
     rep_origin      428
                     /note=" RNaseH cleavage point "
                     /label=ORI
     CDS             4673..4900
                     /note="T.albonubes (R)IR/DR"
                     /label=IR/DR(R)
     CDS             complement(2665..2890)              SEQ ID NO:10
                     /note="T. albonubes TCE"
                     /label=IR/DR(L)
ORIGIN
        1 ggcatgcaag cttggcgtaa tcatggtcat agctgtttcc tgtgtgaaat tgttatccgc
       61 tcacaattcc acacaacata cgagccggaa gcataaagtg taaagcctgg ggtgcctaat
      121 gagtgagcta actcacatta attgcgttgc gctcactgcc cgctttccag tcgggaaacc
      181 tgtcgtgcca gctgcattaa tgaatcggcc aacgcgcggg gagaggcggt ttgcgtattg
      241 ggcgctcttc cgcttcctcg ctcactgact cgctgcgctc ggtcgttcgg ctgcggcgag
      301 cggtatcagc tcactcaaag gcggtaatac ggttatccac agaatcaggg gataacgcag
      361 gaaagaacat gtgagcaaaa ggccagcaaa aggccaggaa ccgtaaaaag gccgcgttgc
      421 tggcgttttt ccataggctc cgcccccctg acgagcatca caaaaatcga cgctcaagtc
      481 agaggtggcg aaacccgaca ggactataaa gataccaggc gtttccccct ggaagctccc
      541 tcgtgcgctc tcctgttccg accctgccgc ttaccggata cctgtccgcc tttctccctt
      601 cgggaagcgt ggcgctttct catagctcac gctgtaggta tctcagttcg gtgtaggtcg
      661 ttcgctccaa gctgggctgt gtgcacgaac cccccgttca gcccgaccgc tgcgccttat
      721 ccggtaacta tcgtcttgag tccaacccgg taagacacga cttatcgcca ctggcagcag
      781 ccactggtaa caggattagc agagcgaggt atgtaggcgg tgctacagag ttcttgaagt
      841 ggtggcctaa ctacggctac actagaagga cagtatttgg tatctgcgct ctgctgaagc
      901 cagttacctt cggaaaaaga gttggtagct cttgatccgg caaacaaacc accgctggta
      961 gcggtggttt ttttgtttgc aagcagcaga ttacgcgcag aaaaaaagga tctcaagaag
     1021 atcctttgat cttttctacg ggtctgacgc tcagtggaac gaaaactca cgttaaggga
     1081 ttttggtcat gagattatca aaaaggatct tcacctagat ccttttaaat taaaaatgaa
     1141 gttttaaatc aatctaaagt atatatgagt aaacttggtc tgacagttac caatgcttaa
     1201 tcagtgaggc acctatctca gcgatctgtc tatttcgttc atccatagtt gcctgactcc
     1261 ccgtcgtgta gataactacg atacgggagg gcttaccatc tggccccagt gctgcaatga
     1321 taccgcgaga cccacgctca ccggctccag atttatcagc aataaaccag ccagccggaa
```

Fig. 9(I)

Untitled

```
1381 gggccgagcg cagaagtggt cctgcaactt tatccgcctc catccagtct attaattgtt
1441 gccgggaagc tagagtaagt agttcgccag ttaatagttt gcgcaacgtt gttgccattg
1501 ctacaggcat cgtggtgtca cgctcgtcgt ttggtatggc ttcattcagc tccggttccc
1561 aacgatcaag gcgagttaca tgatccccca tgttgtgcaa aaaagcggtt agctccttcg
1621 gtcctccgat cgttgtcaga agtaagttgg ccgcagtgtt atcactcatg gttatggcag
1681 cactgcataa ttctcttact gtcatgccat ccgtaagatg cttttctgtg actggtgagt
1741 actcaaccaa gtcattctga gaatagtgta tgcggcgacc gagttgctct tgcccggcgt
1801 caatacggga taataccgcg ccacatagca gaactttaaa agtgctcatc attggaaaac
1861 gttcttcggg gcgaaaactc tcaaggatct taccgctgtt gagatccagt tcgatgtaac
1921 ccactcgtgc acccaactga tcttcagcat cttttacttt caccagcgtt tctgggtgag
1981 caaaaacagg aaggcaaaat gccgcaaaaa agggaataag ggcgacacgg aaatgttgaa
2041 tactcatact cttccttttt caatattatt gaagcattta tcagggttat tgtctcatga
2101 gcggatacat atttgaatgt atttagaaaa ataaacaaat aggggttccg cgcacatttc
2161 cccgaaaagt gccacctgac gtctaagaaa ccattattat catgacatta acctataaaa
2221 ataggcgtat cacgaggccc tttcgtctcg cgcgtttcgg tgatgacggt gaaaacctct
2281 gacacatgca gctcccggag acggtcacag cttgtctgta agcggatgcc gggagcagac
2341 aagcccgtca ggcgcgtca gcggtgttg gcgggtgtcg gggctggctt aactatgcgg
2401 catcagagca gattgtactg agagtgcacc atatgcggtg tgaaataccg cacagatgcg
2461 taaggagaaa ataccgcatc aggcgccatt cgccattcag gctgcgcaac tgttgggaag
2521 ggcgatcggt gcgggcctct tcgctattac gccagctggc gaaaggggga tgtgctgcaa
2581 ggcgattaag ttgggtaacg ccagggtttt cccagtcacg acgttgtaaa acgacggcca
2641 gtgaattcga gctcggtacc ctacagttga agtcggaagt ttacatacac ttaagttgga
2701 gtcattaaaa ctcgtttttc aactacacca caaatttctt gttaacaaac aatagttttg
2761 gcaagtcagt taggacatct actttgtgca tgacacaagt catttttcca acaattgttt
2821 acagacagat tatttcactt ataattcact gtatcacaat tccagtgggt cagaagttta
2881 catacactaa gttgactgtg ccttttaaaca gcttggaaaa ttccagaaaa tgatgtcatg
2941 gctttagaag cttctgatag actaattgac atcatttgag tcaattggag gtgtacctgt
3001 ggatgtattt caagggatcc agacatgata agatacattg atgagtttgg acaaaccaca
3061 actagaatgc agtgaaaaaa atgctttatt tgtgaaattt gtgatgctat tgctttattt
3121 gtaaccatta taagctgcaa taaacaagtt ggggtgggcg aagaactcca gcatgagatc
3181 cccgcgctgg aggatcatcc agccggcgtc ccggaaaacg attccgaagc ccaaccttc
3241 atagaaggcg gcggtggaat cgaaatctcg tgatggcagg ttgggcgtcg cttggtcggt
3301 catttcgaac cccagagtcc cgctcagaag aactcgtcaa gaaggcgata gaaggcgatg
3361 cgctgcgaat cgggagcggc gataccgtaa agcacgagga gcggtcagc ccattcgccg
3421 ccaagctctt cagcaatatc acgggtagcc aacgctatgt cctgatagcg gtccgccaca
3481 cccagccggc cacagtcgat gaatccagaa agcggccat tttccaccat gatattcggc
3541 aagcaggcat cgccatgggt cacgacgaga tcctcgccgt cgggcatgcg cgccttgagc
3601 ctggcgaaca gttcggctgg cgcgagcccc tgatgctctt cgtccagatc atcctgatcg
3661 acaagaccgg cttccatccg agtacgtgct cgctcgatgc gatgtttcgc ttggtggtcg
3721 aatgggcagg tagccggatc aagcgtatgc agccgccgca ttgcatcagc catgatggat
3781 actttctcgg caggagcaag gtgagatgac aggagatcct gccccggcac ttcgcccaat
3841 agcagccagt cccttcccgc ttcagtgaca acgtcgagca cagctgcgca aggaacgccc
3901 gtcgtggcca gccacgatag ccgcgctgcc tcgtcctgca gttcattcag ggcaccggac
3961 aggtcggtct tgacaaaaag aaccgggcgc cctgcgctg acagccggaa cacggcggca
4021 tcagagcagc cgattgtctg ttgtgcccag tcatagccga atagcctctc cacccaagcg
4081 gccggagaac ctgcgtgcaa tccatcttgt tcaatcatgc gaaacgatcc tcatcctgtc
4141 tcttgatcag atccgaaaat ggatatccaa gctcccggga gcttttgca aaagcctagg
4201 cctccaaaaa agcctcctca ctacttctgg aatagctcag aggccgaggc ggcctcggcc
4261 tctgcataaa taaaaaaaat tagtcagcca tggggcggag aatgggcgga actgggcgga
4321 gttagggggcg ggatgggcgg agttagggggc gggactatgg ttgctgacta attgagatgc
4381 atgctttgca tacttctgcc tgctggggag cctggggact ttccacacct ggttgctgac
4441 taattgagat gcatgctttg catacttctg cctgcctggg gagcctgggg acttttccaca
4501 ccctaactga cacacattcc acagaattcc catcacaaag ctctgacctc aatcctatag
4561 aaaggaggaa tgagccaaaa ttcacccaac ttattgtggg aagcttgtgg aaggctactc
```

Fig. 9(J)

```
                               Untitled
4621 gaaatgtttg acccaagtta aacaatttaa aggcaatgct accaaatact aattgagtgt
4681 atgttaactt ctgacccact gggaatgtga tgaaagaaat aaaagctgaa atgaatcatt
4741 ctctctacta ttattctgat atttcacatt cttaaaataa agtggtgatc ctaactgacc
4801 ttaagacagg gaatctttac tcggattaaa tgtcaggaat tgtgaaaaag tgagtttaaa
4861 tgtatttggc taaggtgtat gtaaacttcc gacttcaact gtaggggatc ctctagagtc
4921 gacctgca
//
```

Fig. 9(L)

```
LOCUS       pT/HindIII      3497 bp    DNA     circular 30-DEC-2002
FEATURES             Location/Qualifiers
     rep_origin      1571..2451
                     /vntifkey="33"
                     /label=ColE1\Ori
     CDS             complement(2515..3372)
                     /vntifkey="4"
                     /label=Amp
                     /note="Ampicillin Resistance Gene"
     rep_origin      6..462
                     /vntifkey="33"
                     /label=F1\Ori
                     /note="Phagemid origin"
     promoter        complement(1355..1477)
                     /vntifkey="30"
                     /label=lacZ\promoter
     promoter        625..645
                     /vntifkey="30"
                     /label=T7
     promoter        complement(1311..1330)
                     /vntifkey="30"
                     /label=T3
     CDS             1024..1251
                     /vntifkey="4"
                     /label=IR/DR(R)
                     /note="T.albonubes (R)IR/DR"
     CDS             complement(668..896)
                     /vntifkey="4"
                     /label=IR/DR(L)
                     /note="T. albonubes TCE"
     primer          complement(1570..1594)
                     /vntifkey="27"
                     /label=o-lac-R
     primer          complement(1430..1454)               SEQ ID NO:11
                     /vntifkey="27"
                     /label=i-lac-R
     primer          317..346
                     /vntifkey="27"
                     /label=F1\ex-primer
BASE COUNT       895 a        836 c        821 g        945 t
ORIGIN
    1 cacctgacgc gccctgtagc ggcgcattaa gcgcggcggg tgtggtggtt acgcgcagcg
   61 tgaccgctac acttgccagc gccctagcgc ccgctccttt cgctttcttc ccttcctttc
  121 tcgccacgtt cgccggcttt ccccgtcaag ctctaaatcg gggctccct ttagggttcc
  181 gatttagtgc tttacggcac ctcgacccca aaaacttga ttagggtgat ggttcacgta
  241 gtgggccatc gccctgatag acgttttc gcccttgac gttggagtcc acgttcttta
  301 atagtggact cttgttccaa actggaacaa cactcaaccc tatctcggtc tattcttttg
  361 atttataagg gatttgccg atttcggcct attggttaaa aaatgagctg atttaacaaa
  421 aatttaacgc gaattttaac aaaatattaa cgcttacaat ttccattcgc cattcaggct
  481 gcgcaactgt tgggaagggc gatcggtgcg ggcctcttcg ctattacgcc agctggcgaa
  541 agggggatgt gctgcaaggc gattaagttg ggtaacgcca gggttttccc agtcacgacg
  601 ttgtaaaacg acggccagtg aattgtaata cgactcacta tagggcgaat tggagctcgg
  661 taccctacag ttgaagtcgg aagtttacat acacttaagt tggagtcatt aaaactcgtt
  721 tttcaactac accacaaatt tcttgttaac aaacaatagt tttggcaagt cagttaggac
  781 atctactttg tgcatgacac aagtcatttt tccaacaatt gtttacagac agattatttc
  841 acttataatt cactgtatca caattccagt gggtcagaag tttacataca ctaagttgac
  901 tgtgccttta aacagcttgg aaaattccag aaaatgatgt catggcttta gaagcttgtg
  961 gaaggctact cgaaatgttt gacccaagtt aaacaattta aaggcaatgc taccaaatac
 1021 taattgagtg tatgttaact tctgacccac tgggaatgtg atgaaagaaa taaaagctga
 1081 aatgaatcat tctctctact attattctga tatttcacat tcttaaaata aagtggtgat
```

Fig. 9(M)

```
1141 cctaactgac cttaagacag ggaatcttta ctcggattaa atgtcaggaa ttgtgaaaaa
1201 gtgagtttaa atgtatttgg ctaaggtgta tgtaaacttc cgacttcaac tgtaggggat
1261 cctctagcta gagtcgacct cgaggggggg cccggtaccc agcttttgtt ccctttagtg
1321 agggttaatt tcgagcttgg cgtaatcatg gtcatagctg tttcctgtgt gaaattgtta
1381 tccgctcaca attccacaca acatacgagc cggaagcata agtgtaaag cctggggtgc
1441 ctaatgagtg agctaactca cattaattgc gttgcgctca ctgcccgctt tccagtcggg
1501 aaacctgtcg tgccagctgc attaatgaat cggccaacgc gcggggagag gcggtttgcg
1561 tattgggcgc tcttccgctt cctcgctcac tgactcgctg cgctcggtcg ttcggctgcg
1621 gcgagcggta tcagctcact caaaggcggt aatacggtta ccacagaat caggggataa
1681 cgcaggaaag aacatgtgag caaaaggcca gcaaaaggcc aggaaccgta aaaaggccgc
1741 gttgctggcg ttttccata ggctccgccc cctgacgag catcacaaaa atcgacgctc
1801 aagtcagagg tggcgaaacc cgacaggact ataaagatac caggcgtttc ccctggaag
1861 ctccctcgtg cgctctcctg ttccgaccct gccgcttacc ggatacctgt ccgcctttct
1921 cccttcggga agcgtggcgc tttctcatag ctcacgctgt aggtatctca gttcggtgta
1981 ggtcgttcgc tccaagctgg gctgtgtgca cgaacccccc gttcagcccg accgctgcgc
2041 cttatccggt aactatcgtc ttgagtccaa cccggtaaga cacgacttat cgccactggc
2101 agcagccact ggtaacagga ttagcagagc gaggtatgta ggcggtgcta cagagttctt
2161 gaagtggtgg cctaactacg gctacactag aaggacagta tttggtatct gcgctctgct
2221 gaagccagtt accttcggaa aaagagttgg tagctcttga tccggcaaac aaaccaccgc
2281 tggtagcggt ggtttttttg tttgcaagca gcagattacg cgcagaaaaa aaggatctca
2341 agaagatcct ttgatctttt ctacggggtc tgacgctcag tggaacgaaa actcacgtta
2401 agggattttg gtcatgagat tatcaaaaag gatcttcacc tagatccttt taaattaaaa
2461 atgaagtttt aaatcaatct aagtatata tgagtaaact ggtctgaca gttaccaatg
2521 cttaatcagt gaggcaccta tctcagcgat ctgtctattt cgttcatcca tagttgcctg
2581 actccccgtc gtgtagataa ctacgatacg ggagggctta ccatctggcc ccagtgctgc
2641 aatgataccg cgagacccac gctcaccggc tccagattta tcagcaataa accagccagc
2701 cggaagggcc gagcgcagaa gtggtcctgc aactttatcc gcctccatcc agtctattaa
2761 ttgttgccgg gaagctagag taagtagttc gccagttaat agtttgcgca acgttgttgc
2821 cattgctaca ggcatcgtgg tgtcacgctc gtcgtttggt atggcttcat tcagctccgg
2881 ttcccaacga tcaaggcgag ttacatgatc ccccatgttg tgcaaaaaag cggttagctc
2941 cttcggtcct ccgatcgttg tcaagtaa gttggccgca gtgttatcac tcatggttat
3001 ggcagcactg cataattctc ttactgtcat gccatccgta agatgctttt ctgtgactgg
3061 tgagtactca accaagtcat tctgagaata gtgtatgcgg cgaccgagtt gctcttgccc
3121 ggcgtcaata cgggataata ccgcgccaca tagcagaact ttaaaagtgc tcatcattgg
3181 aaaacgttct cggggcgaa aactctcaag gatcttaccg ctgttgagat ccagttcgat
3241 gtaacccact cgtgcaccca actgatcttc agcatctttt actttcacca gcgtttctgg
3301 gtgagcaaaa acaggaaggc aaaatgccgc aaaaaaggga taagggcga cacggaaatg
3361 ttgaatactc atactcttcc tttttcaata ttattgaagc atttatcagg gttattgtct
3421 catgagcgga tacatatttg aatgtattta gaaaaataaa caaatagggg ttccgcgcac
3481 atttccccga aaagtgc
//
```

Fig. 9(O)

```
LOCUS       pFV3CAT       6782 bp dsDNA    Circular
FEATURES             Location/Qualifiers
    CDS              2876..3422
                     /label=CAT
    promoter         236..1371
                     /note="Carp β-actin proximal enhancer/promoter"
                     /label=β-actin\promoter
    misc_feature     1377..1468
                     /label=β-actin\exon\1
    intron           1469..2732
                     /label=β-actin\intron\1
    polyA_signal     3547..3904
                     /note="Chinook salmon growth hormone poly(A) signal"
                     /label=CSGH(A)
    rep_origin       5903..6782
                     /label=ColE1\Ori
    CDS              4982..5839
                     /label=Amp
    rep_origin       4144..4581                              SEQ ID NO:12
                     /label=M13\Ori
ORIGIN
        1 agcgcccaat acgcaaaccg cctctccccg cgcgttggcc gattcattaa tgcagctggc
       61 acgacaggtt tcccgactgg aaagcgggca gtgagcgcaa cgcaattaat gtgagttagc
      121 tcactcatta ggcaccccag gctttacact ttatgcttcc ggctcgtatg ttgtgtggaa
      181 ttgtgagcgg ataacaattt cacacaggaa acatctagaa ccatgattac gccaagcttt
      241 tagaccttct tactttggg gattatataa gtattttctc aataaatatc tcatatctta
      301 ctgtggttta actgctgaat ctaaaatttt aatacaaaag tagttatatt tgttgtacat
      361 tgtaaactat aacttaactt cagtttcaga gaaactcatg tgctcaaaat gtaaaaaaag
      421 tttcctgtta aatattttgt aaatgtattg aagacaaaat aagaaaaaaa aaaatataag
      481 ccactaaatc acactgtcct tggtatcagc aagagattct gacataatca gctgtttttg
      541 tttattactg ccattgaagg ccatgtgcat tagtcccaag ttacacatta aaaagtcaca
      601 tgtagcttac caacatcagt gctgttcaag cacagcctca tctactattc aaactgtggc
      661 accatctaaa atatgccaga attttttat ttaatgaatt tgaccctgaa atatgtatta
      721 atatcactcc tgtgattttt ttgtaatcag cttacaatta caggaatgca agcctgattc
      781 attacaagtt tcactacact ttctctgaca acatcaccta ctgaactcag accagctagt
      841 tgctccttaa gtatacaatc atgtcactaa tcctcatttc aatgaaaaat accctattg
      901 tacttggtac ttggtagata accacagagc agtattatgc cattattgtg aatacaataa
      961 gaggtaaatg acctacagag ctgctgctgc tgttgtgtta gattgtaaac acagcacagg
     1021 atcaaggagg tgtccatcac tatgaccaat actagcactt tgcacaggct ctttgaaagg
     1081 ctgaaaagag ccttattggc gttatcacaa caaatacgc aaatacggaa acaacgtat
     1141 tgaacttcgc aaacaaaaaa cagcgatttt gatgaaaatc gcttaggcct tgctcttcaa
     1201 acaatccagc ttctccttct ttcactctca agttgcaaga agcaagtgta gcaatgtgca
     1261 cgcgacagcc gggtgtgtga cgctggacca atcagagcgc agagctccga aagtttacct
     1321 tttatggcta gagccggcat ctgccgtcat ataaaagagc gcgcccagcg tctcagcctc
     1381 actttgagct cctccacacg cagctagtgc ggaatatcat ctgcctgtaa cccattctct
     1441 aaagtcgaca aaccccccca aacctaaggt gagttgatct ttaagctttt tacatttca
     1501 gctcgcatat atcaattcga acgtttaatt agaatgttta aataaagcta gattaaatga
     1561 ttaggctcag ttaccggtct ttttttctc atttacgtgc gaactctgct taaactctag
     1621 ttattcttta ttaatatgtg gttattttta tatgtatg ttatcataac tgtactggct
     1681 atgtcaggtg gtaatgactg taacgttacg ttactcgttg taggcacgac attgaatggg
     1741 ccggtgttga aataagtctt caaccccttt taacctcaaa atgtgctctg gttaacaagg
     1801 attttaacag ctatcagtat gactgtgcgg ttttaaagcc gttagtgagg cacgttgcac
     1861 acttgatgga tggccggaat gggaagttct ttatgcaggc agtgctgcag cagggtgtga
```

Fig. 9(P)

pFV3CAT

```
1921 cctactttag ctaacgttag ccggctaacc agcattcatc tgccggtaac ttgagtctaa
1981 tattctctat gtgatatcga agtgatcaaa gacacgtctg ttagctcact ttaaccaact
2041 gtagtgaaaa atagcgcagt gtgcagccct tcaagtcttt catttaggct gattattcaa
2101 tcattttatt aactattaac gcgttactaa acgtaaggta acgtagtcag tttttaataa
2161 ctggtgaaaa gtactggttg ggtttaaatg gtgacttata attgtgttgg agggggaaac
2221 cttttgata aaggctatat aatctcaaat gaatgggctg aggatggtgt tcacaggtgc
2281 tttagtgaag tccgctcgtg aagagtcgct gaagtgactg cagatctgta gcgcatgcgt
2341 tttggcagac ggccgttgaa attcggttga gtaattgata ccaggtgagg ctagaggatg
2401 tagaaattca tttgtgtaga atttagggag tggcctggcg tgatgaatgt cgaaatccgt
2461 tccttttac tgaaccctat gtctctgctg agtgccacac cgccggcaca aagcgtctca
2521 aaccattgcc ttttatggta ataatgagaa tgcagaggga cttcctttgt ctggcacatc
2581 tgaggcgcgc attgtcacac tagcacccac tagcggtcag actgcagaca acaggaagc
2641 tgactccaca tggtcacatg ctcactgaag tgttgacttc cctgacagct gtgcactttc
2701 taaaccggtt ttctcattca tttacagttc agccgggtac cctcgaccga gcttggcgag
2761 attttcagga gctaaggaag ctaaaatgga gaaaaaaatc actggatata ccaccgttga
2821 tatatcccaa tggcatcgta aagaactttt gaggcatttc agtcagttgc tcaatgtacc
2881 tataaccaga ccgttcagct ggatattacg gcctttttta aagaccgtaa agaaaaataa
2941 gcacaagttt tatccggcct ttattcacat tcttgcccgc ctgatgaatg ctcatccgga
3001 attccgtatg gcaatgaaag acggtgagct ggtgatatgg gatagtgttc acccttgtta
3061 caccgttttc catgagcaaa ctgaaacgtt ttcatcgctc tggagtgaat accacgacga
3121 tttccggcag tttctacaca tatattcgca agatgtggcg tgttacggtg aaaacctggc
3181 ctatttccct aaagggttta ttgagaatat gttttcgtc tcagccaatc cctgggtgag
3241 tttcaccagt tttgatttaa acgtggccaa tatggacaac ttcttcgccc cgttttcac
3301 catgggcaaa tattatacgc aaggcgacaa ggtgctgatg ccgctggcga ttctggttca
3361 tcatgccgtc tgtgatggct tccatgtcgg cagaatgctt aatgaattac aacagtactg
3421 cgatgagtgg cagggcgggg cgtaatttt taaggcagt tattggtgcc cttaaacgcc
3481 tggtgctacg cctgaataag tgataataag cggatgaatg cagaaattc gccggatcgg
3541 gtaccctaga gtaattttat tttggatctg gtagtagcct gactccaggg gttttcaggc
3601 atttgcattt ttttctctga aatcaataac aacactttct atattgactc tatcactctg
3661 agctaccatt gattagtaca tttatattaa aggttattaa atgtcttatt tagatatatg
3721 gttcatggcg gtgctactta tgcactacgt taatatttag gggtgaaatg ggaacttgta
3781 gagctccaag cttttggata atatatttta gagtaatttc ctttaagtat tttcattcct
3841 taatcttatt gtttgaaact aatagtgatt catgtttcaa taaagatgtt cattctctgc
3901 aaagaattcc actggccgtc gttttacaac gtctagactg ggaaaaccct ggcgttaccc
3961 aacttaatcg ccttgcagca catccccctt tcgccagctg gcgtaatagc gaagaggccc
4021 gcaccgatcg cccttcccaa cagttgcgca gcctgaatgg cgaatggcgc ctgatgcggt
4081 attttctcct tacgcatctg tgcggtattt cacaccgcat acgtcaaagc aaccatagta
4141 cgcgccctgt agcggcgcat taagcgcggc gggtgtggtg gttacgcgca gcgtgaccgc
4201 tacacttgcc agcgccctag cgcccgctcc tttcgctttc ttcccttcct ttctcgccac
4261 gttcgccggc tttccccgtc aagctctaaa tcggggctc cctttagggt tccgatttag
4321 tgctttacgg cacctcgacc ccaaaaaact gatttgggt gatggttcac gtagtgggcc
4381 atcgccctga tagacggttt ttcgcccttt gacgttggag tccacgttct ttaatagtgg
4441 actcttgttc caaactggaa caacactcaa ccctatctcg ggctattctt ttgatttata
4501 agggatttg ccgatttcgg cctattggtt aaaaaatgag ctgatttaac aaaaatttaa
4561 cgcgaatttt aacaaaatat taacgtttac aatttatgg tgcactctca gtacaatctg
4621 ctctgatgcc gcatagttaa gccagccccg acacccgcca cacccgctg acgcgccctg
4681 acgggcttgt ctgctcccgg catccgctta cagacaagct gtgaccgtct ccgggagctg
4741 catgtgtcag aggttttcac cgtcatcacc gaaacgcgcg agacgaaagg cctcgtgat
4801 acgcctattt ttataggtta atgtcatgat aataatggtt tcttagacgt caggtggcac
4861 ttttcgggga atgtgcgcg gaacccctat tgtttattt tctaaatac attcaaatat
4921 gtatccgctc atgagacaat aaccctgata atgcttcaa taatattgaa aaaggaagag
4981 tatgagtatt caacatttcc gtgtcgccct tattcccttt ttgcggcat tttgccttcc
5041 tgttttgct cacccagaaa cgctggtgaa agtaaaagat gctgaagatc agttgggtgc
5101 acgagtgggt tacatcgaac tggatctcaa cagcggtaag atccttgaga gttttcgccc
```

Fig. 9(Q)

```
5161 cgaagaacgt tttccaatga tgagcacttt taaagttctg ctatgtggcg cggtattatc
5221 ccgtattgac gccgggcaag agcaactcgg tcgccgcata cactattctc agaatgactt
5281 ggttgagtac tcaccagtca cagaaaagca tcttacggat ggcatgacag taagagaatt
5341 atgcagtgct gccataacca tgagtgataa cactgcggcc aacttacttc tgacaacgat
5401 cggaggaccg aaggagctaa ccgctttttt gcacaacatg ggggatcatg taactcgcct
5461 tgatcgttgg gaaccggagc tgaatgaagc cataccaaac gacgagcgtg acaccacgat
5521 gcctgtagca atggcaacaa cgttgcgcaa actattaact ggcgaactac ttactctagc
5581 ttccggcaa caattaatag actggatgga ggcggataaa gttgcaggac cacttctgcg
5641 ctcggccctt ccggctggct ggtttattgc tgataaatct ggagccggtg agcgtgggtc
5701 tcgcggtatc attgcagcac tggggccaga tggtaagccc tcccgtatcg tagttatcta
5761 cacgacgggg agtcaggcaa ctatggatga acgaaataga cagatcgctg agataggtgc
5821 ctcactgatt aagcattggt aactgtcaga ccaagtttac tcatatatac tttagattga
5881 tttaaaactt catttttaat ttaaaaggat ctaggtgaag atccttttg ataatctcat
5941 gaccaaaatc ccttaacgtg agttttcgtt ccactgagcg tcagacccg tagaaaagat
6001 caaaggatct tcttgagatc cttttttct gcgcgtaatc tgctgcttgc aaacaaaaaa
6061 accaccgcta ccagcggtgg tttgtttgcc ggatcaagag ctaccaactc ttttttccgaa
6121 ggtaactggc ttcagcagag cgcagatacc aaatactgtc cttctagtgt agccgtagtt
6181 aggccaccac ttcaagaact ctgtagcacc gcctacatac ctcgctctgc taatcctgtt
6241 accagtggct gctgccagtg gcgataagtc gtgtcttacc gggttggact caagacgata
6301 gttaccggat aaggcgcagc ggtcgggctg aacggggggt tcgtgcacac agcccagctt
6361 ggagcgaacg acctacaccg aactgagata cctacagcgt gagctatgag aaagcgccac
6421 gcttcccgaa gggagaaagg cggacaggta tccggtaagc ggcagggtcg aacaggaga
6481 gcgcacgagg gagcttccag ggggaaacgc ctggtatctt tatagtcctg tcgggtttcg
6541 ccacctctga cttgagcgtc gatttttgtg atgctcgtca gggggggcgga gcctatggaa
6601 aaacgccagc aacgcggcct ttttacggtt cctggccttt tgctggcctt ttgctcacat
6661 gttctttcct gcgttatccc ctgattctgt ggataaccgt attaccgcct ttgagtgagc
6721 tgataccgct cgccgcagcc gaacgaccga gcgcagcgag tcagtgagcg aggaagcgga
6781 ag
//
```

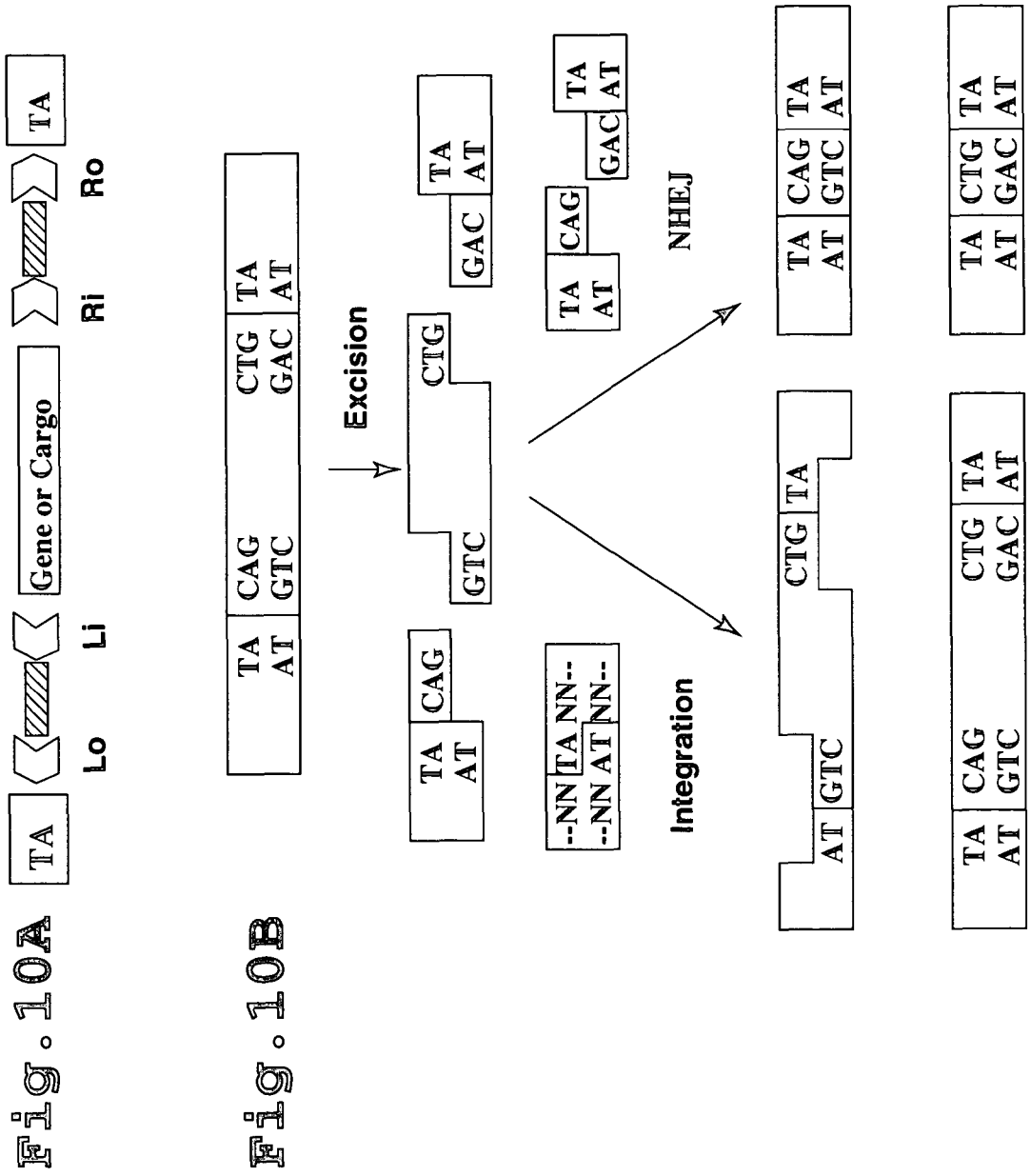

GG LoLi/RiRo TA: CGGTACCC GG CAG TA GGGGATCCT

TA LoLi/RiRo GG: CGGTACCC TA CTG GG GGGGATCCT

Fig. 23A  Fig. 23B
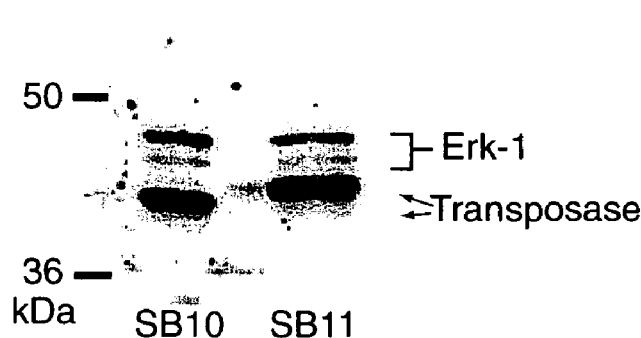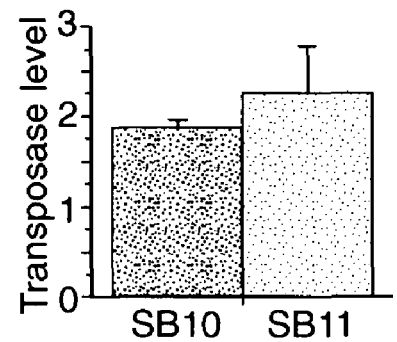
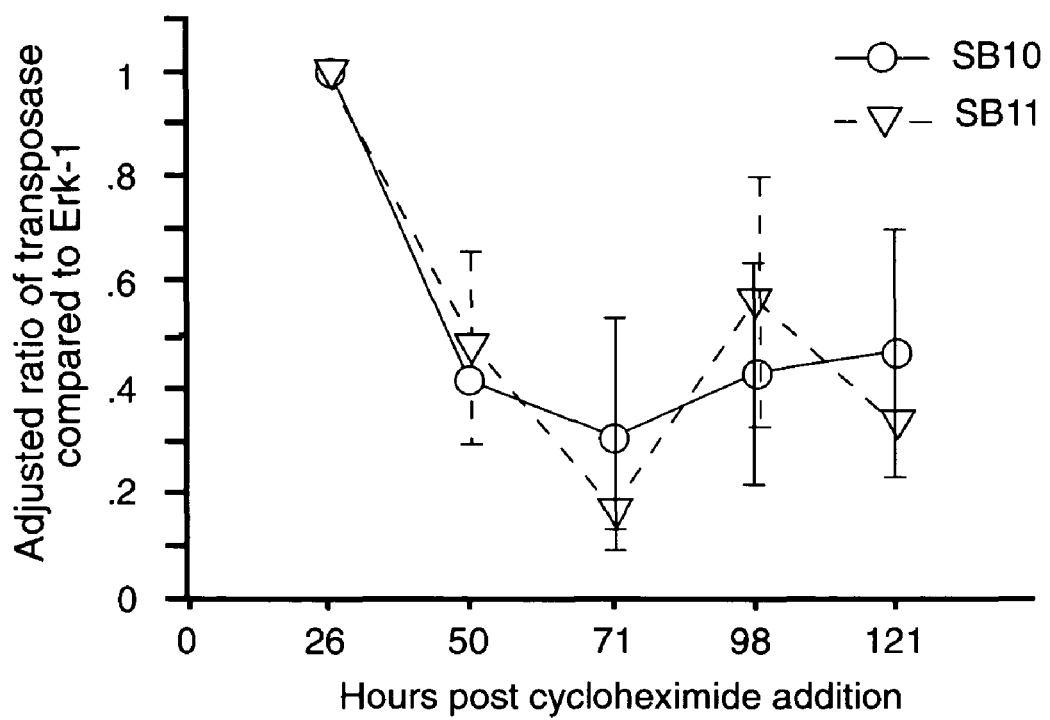
Fig. 23C

```
                                                                    left inner di-
       left outer direct repeat                                  rect repeat
5'-CAGTTGAAGTCGGAAGTTTACATACACTTRAGTTGGAGTCATTAAAACTCGTTTTCAACYACWCCACAAATTTCTTGTTAACAAACWATAGTTTTGGCAAGTRA
   GTCAACTTCAGCCTTCAAATGTATGTGAANTCAACCTCAGTAATTTTGAGCAAAAAGTTGNTGNGGTGTTAAAGAACAATTGTTGNTATCAAAACGTTCANT GTTAGGACATCTACTTGTGCATGACACAAGTMATTTTTCCAACAATTGTTTACAGACAGATTATTTCACTGTATCACAATTCCAGTGGGTCAGAAG
CAATCCTGTAGATGAACACGTACTGTGTTCANTAAAAAGGTTGTTAACAAATGTCTGTCTAATAAAGTGAATATTAAGTGACATAGTGTTAAGGTCACCAGTCTTC rect repeat                                                       TTGAGTGTATGTTAACTTCTGACCCACTGGG
TTTACATACACTAAGT           nucleic acid sequence                  AACTCACATACAATTGAAGACTGGGTGACCC
AAATGTATGTGATTCA                                                      right inner direct repeat AATGTGATGAAAGAAGAAATAAAGCTGAAATGAATCATTCTCTCTACTATTATTCTGYTATTTCACATTCTTAAAATAAAGTGGTGATCCTAACTGACCTTAAGACAGGGA
TTACACTACTTTCTTTATTTCGACTTTACTTAGTAAGAGATGATAATAAGTGTAAGAATTTATTTCACCACTGACGATTGACTGGAATTCTGTCCCT ATCTTTACTCGGATTAAATGTCAGGAATTGTGAAAAASTGAGTTTAAATGTATTTGGCTAAGGTGTATGTAAACTTCCGACTTCAACTG-3'
TAGAAATGAGCCTAATTACAGTCCTTAACACTTTTTNACTCAAATTTACATAAACCGATTCCACATACATTTGAAGGCTGAAGTTGAC-5'
                                                          right outer direct repeat
```

SEQ ID NO:26

```
   1 ATGGGAAAA TCAAAAGAAA TCAGCCAAGA CCACAGAAAA
     TACCCTTTT AGTTTTCTTT AGTCGGTTCT GGAAGCTTTT

51 AAAATTGTAG ACCTCCACAA GTCTGGTTCA TCCTTGGGAG CAATTTCCAA
     TTTTAACATC TGGAGGTGTT CAGACCAAGT AGG!JCCCTC GTTAAJGGTT

101 ACGCCTGAAA GTACCACGTT CATCTGTACA AACAATAGTA CGCAAGTATA
     TGCGGACTTT CATGGTGCAA GTAGACATGT TTGTTATCAT GCGTTCATAT

151 AACACCATGG GACCACGCAG CCGTCATACC GCTCAGGAAG GAGACGCGTT
     TTGTGGTACC CTGGTGCGTC GGAAGTATGG CGAGTCCTTC CTCTGCGCAA

201 CTGTCTCCTA GAGATGAACG TACTTTGGTG CGAAAAGTGC AAATCAATCC
     GACAGAGGAT CTCTACTTGC ATGAAACCAC GCTTTTCACG TTTAGTTAGG

251 CAGAACAACA GCAAAGGACC TTGTGAAGAT GCTGGAGGAA ACAGGTACAA
     GTCTTGTTGT CGTTTCCTGG AACACTTCTA CGACCTCCTT TGTCCATGTT

301 AAGTATCTAT ATCCACAGTA AAACGAGTCC TATATCGACA TAACCTGAAA
     TTCATAGATA TAGGTGTCAT TTTGCTCAGG ATATAGCTGT ATTGGACTTT

351 GGCCGCTCAG CAAGGAAGAA GCCACTGCTC CAAAACCGAC ATAAGAAAGC
     CCGGCGAGTC GTTCCTTCTT CGGTGACGAG GTTTTGGCTG TATTCTTTCG

401 CAGACTACGG TTTGCAACTG CACATGGGGA CAAAGATCGT ACTTTTTGGA
     GTCTGATGCC AAACGTTGAC GTGTACCCCT GTTTCTAGCA TGAAAAACCT

451 GAAATGTCCT CTGGTCTGAT GAAACAAAAA TAGAACTGTT TGGCCATAAT
     CTTTACAGGA GACCAGACTA CTTTGTTTTT ATCTTGACAA ACCGGTATTA

501 GACCATCGTT ATGTTTGGAG GAAGAAGGGG GAGGCTTGCA AGCCGAAGAA
     CTGGTAGCAA TACAAACCTC CTTCTTCCCC CTCCGAACGT TCGGCTTCTT

551 CACCATCCCA ACCGTGAAGC ACGGGGGTGG CAGCATCATG TTGTGGGGGT
     GTGGTAGGGT TGGChCTTCG TGCCCCCACC GTCGTAGTAC AACACCCCCA

601 GCTTTGCTGC AGGAGGGACT GGTGCACTTC ACAAAATAGA TGGCATCATG
     CGAAACGACG TCCTCCCTGA CCACGTGAJG TGTTTTATCT ACCGTAGTAC

651 AGGAAGGAAA ATTATGTGGA TATATTGAAG CAACATCTCA AGACATCAGT
     TCCTTCCTTT TAATACACCT ATATAACTTC GTTGTAGAGT TCTGTAGTCA

701 CAGGAAGTTA AAGCTTGGTC GCAAATGGGT CTTCCAAATG GACAATGACC
     GTCCTTCAAT TTCGAACCAG CGTTTACCCA GAAGGTTTAC CGTTTACTGG

751 CCAAGCATAC TTCCAAAGTT GTGGCAAAAT GGCTTAAGGA CAACAAAGTC
     GGTTCGTATG AAGGTTTCAA CACCGTTTTA CCGAATTCCT GTTGTTTCAG

801 AAGGTATTGG AGTGGCCATC ACAAAGCCCT GACCTCAATC CTATAGAAAA
     TTCCATAACC TCACCGGTAG TGTTTCGGGA CTGGAGTTAG GATATCTTTT

851 TTTGTGGGCA GAACTGAAAA AGCGTGTGCG AGCAAGGAGG CCTACAAACC
     AAACACCCGT CTTGACTTTT TCGCACACGC TCGTTCCTCC GGATGTTTGG

901 TGACTCAGTT ACACCAGCTC TGTCAGGAGG AATGGGCCAA AATTCACCCA
     ACTGAGTCAA TGTGGTCGAG ACAGTCCTCC TTACCCGGTT TTAAGTGGGT

951 ACTTATTGTG GGAAGCTTGT GGAAGGCTAC CCGAAACGTT TGACCCAAGT
     TGAATAACAC CCTTCGAACA CCTTCCGATG GGCTTTGCAA ACTGGGTTCA

1001 TAAACAATTT AAAGGCAATG CTACCAAATA CTAG
     ATTTGTTAAA TTTCCGTTAC GATGGTTTAT GATC
```

```
SEQ ID NO:5              Paired-like domain with Leucine-zipper
  1   MGKSKEISQD  LRKKIVDLHK  SGSSLGAISK  RLKVPRSSVQ  TIVRKYKHHG 51   TTQPSYRSGR  RRVLSPRDER  TLVRKVQINP  RTTAKDLVKM  LEETGTKVSI
                  ─ NLS ─
101   STVKRVLYRH  NLKGRSARKK  PLLQNRHKKA  RLRFATAHGD  KDRTFWRNVL
                                                     Glycine-rich box
151   WSDETKIELF  GHNDHRYVWR  KKGEACKPKN  TIPTVKHGGG  SIMLWGCFAA

201   GGTGALHKID  GIMRKENYVD  ILKQHLKTSV  RKLKLGRKWV  FQMDNDPKHT

251   SKVVAKWLKD  NKVKVLEWPS  QSPDLNPIEN  LWAELKKRVR  ARRPTNLTQL

301   HQLCQEEWAK  IHPTYCGKLV  EGYPKRLTQV  KQFKGNATKY
                                    DD(34)E box
```

Fig. 25B

SEQ ID NO:27
ATGGGAAAATCAAAAGAAATCAGCCAAGACCTCAGAAAAAAATTGTAGACCTCCACAA
GTCTGGTTCATCCTTGGGAGCAATTTCCAAACGCCTGAAAGTACCACGTTCATCTGTAC
AAACAATAGTACGCAAGTATAAACACCATGGGACCACGCAGCCGTCATACCGCTCAGGA
AGGAGACGCGTTCTGTCTCCTAGAGATGAACGTACTTTGGTGCGAAAAGTGCAAATCAA
TCCCAGAACAACAGCAAAGGACCTTGTGAAGATGCTGGAGGAAACAGGTACAAAAGTAT
CTATATCCACAGTAAAACGAGTCCTATATCGACATAACCTGAAAGGCCGCTCAGCAAGG
AAGAAGCCACTGCTCCAAAACCGACATAAGAAAGCCAGACTACGGTTTGCA<u>NNN</u>GCACA
TGGGGACAAAGATCGTACTTTTTGGAGAAATGTCCTCTGGTCTGATGAAACAAAAATAG
AACTGTTTGGCCATAATGACCATCGTTATGTTTGGAGGAAGAAGGGGGAGGCTTGCAAG
CCGAAGAACACCATCCCAACCGTGAAGCACGGGGGTGGCAGCATCATGTTGTGGGGGTG
CTTTGCTGCAGGAGGGACTGGTGCACTTCACAAAATAGATGGCATCATGAGGAAGGAAA
ATTATGTGGATATATTGAAGCAACATCTCAAGACATCAGTCAGGAAGTTAAAGCTTGGT
CGCAAATGGGTCTTCCAA<u>NNN</u>GACAATGACCCCAAGCATACTTCCAAA<u>NNN</u>GTG<u>NNN</u>AA
ATGGCTTAAGGACAACAAAGTCAAGGTATTGGAGTGGCCATCACAAAGCCCTGACCTCA
ATCCTATAGAAAATTTGTGGGCAGAACTGAAAAAGCGTGTGCGAGCAAGGAGGCCTACA
AACCTGACTCAGTTACACCAGCTCTGTCAGGAGGAATGGGCCAAAATTCACCCAACTTA
TTGTGGGAAGCTTGTGGAAGGCTACCCGAAACGTTTGACCCAAGTTAAACAATTTAAAG
GCAATGCTACCAAATACTAG

Fig. 25C

SEQ ID NO:20

```
  1  MGKSKEISQDLRKKIVDLHKSGSSLGAISKRLKVPRSSVQTIVRKYKHHG
 51  TTQPSYRSGRRRVLSPRDERTLVRKVQINPRTTAKDLVKMLEETGTKVSI
101  STVKRVLYRHNLKGRSARKKPLLQNRHKKARLRFAXAHGDKDRTFWRNVL
151  WSDETKIELFGHNDHRYVWRKKGEACKPKNTIPTVKHGGGSIMLWGCFAA
201  GGTGALHKIDGIMRKENYVDILKQHLKTSVRKLKLGRKWVFQXDNDPKHT
251  SKXVXKWLKDNKVKVLEWPSQSPDLNPIENLWAELKKRVRARRPTNLTQL
301  HQLCQEEWAKIHPTYCGKLVEGYPKRLTQVKQFKGNATKY
```

Fig. 25D

SEQ ID NO:28
ATGGGAAAATCAAAAGAAATCAGCCAAGACCTCAGAAAAAAAATTGTAGACCTCCACAA
GTCTGGTTCATCCTTGGGAGCAATTTCCAAACGCCTGAAAGTACCACGTTCATCTGTAC
AAACAATAGTACGCAAGTATAAACACCATGGGACCACGCAGCCGTCATACCGCTCAGGA
AGGAGACGCGTTCTGTCTCCTAGAGATGAACGTACTTTGGTGCGAAAAGTGCAAATCAA
TCCCAGAACAACAGCAAAGGACCTTGTGAAGATGCTGGAGGAAACAGGTACAAAAGTAT
CTATATCCACAGTAAAACGAGTCCTATATCGACATAACCTGAAAGGCCGCTCAGCAAGG
AAGAAGCCACTGCTCCAAAACCGACATAAGAAAGCCAGACTACGGTTTGCAAGAGCACA
TGGGGACAAAGATCGTACTTTTTGGAGAAATGTCCTCTGGTCTGATGAAACAAAAATAG
AACTGTTTGGCCATAATGACCATCGTTATGTTTGGAGGAAGAAGGGGGAGGCTTGCAAG
CCGAAGAACACCATCCCAACCGTGAAGCACGGGGTGGCAGCATCATGTTGTGGGGGTG
CTTTGCTGCAGGAGGGACTGGTGCACTTCACAAAATAGATGGCATCATGAGGAAGGAAA
ATTATGTGGATATATTGAAGCAACATCTCAAGACATCAGTCAGGAAGTTAAAGCTTGGT
CGCAAATGGGTCTTCCAAATGGACAATGACCCCAAGCATACTTCCAAACACGTGAGAAA
ATGGCTTAAGGACAACAAAGTCAAGGTATTGGAGTGGCCATCACAAAGCCCTGACCTCA
ATCCTATAGAAAATTTGTGGGCAGAACTGAAAAAGCGTGTGCGAGCAAGGAGGCCTACA
AACCTGACTCAGTTACACCAGCTCTGTCAGGAGGAATGGGCCAAAATTCACCCAACTTA
TTGTGGGAAGCTTGTGGAAGGCTACCCGAAACGTTTGACCCAAGTTAAACAATTTAAAG
GCAATGCTACCAAATACTAG

Fig. 25E

SEQ ID NO:21

```
1    MGKSKEISQDLRKKIVDLHKSGSSLGAISKRLKVPRSSVQTIVRKYKHHG
51   TTQPSYRSGRRRVLSPRDERTLVRKVQINPRTTAKDLVKMLEETGTKVSI
101  STVKRVLYRHNLKGRSARKKPLLQNRHKKARLRFARAHGDKDRTFWRNVL
151  WSDETKIELFGHNDHRYVWRKKGEACKPKNTIPTVKHGGGSIMLWGCFAA
201  GGTGALHKIDGIMRKENYVDILKQHLKTSVRKLKLGRKWVFQQDNDPKHT
251  SKHVRKWLKDNKVKVLEWPSQSPDLNPIENLWAELKKRVRARRPTNLTQL
301  HQLCQEEWAKIHPTYCGKLVEGYPKRLTQVKQFKGNATKY
```

Fig. 25F

TRANSPOSON SYSTEM AND METHODS OF USE

CONTINUING APPLICATION DATA

This application is a continuation-in-part of U.S. application Ser. No. 10/128,998, filed Apr. 22, 2002, and claims the benefit of U.S. Provisional Application Serial No. 60/379,572, filed May 10, 2002, which is incorporated by reference herein.

GOVERNMENT FUNDING

The present invention was made with government support under Grant No. R01-RR066525-07 and P01-HD32652, awarded by National Institutes of Health. The Government has certain rights in this invention.

BACKGROUND

DNA transposons are mobile elements that can move from one position in a genome to another. Naturally, transposons play roles in evolution as a result of their movements within and between genomes. Geneticists have used transposons as tools for both gene delivery and insertional mutagenesis or gene tagging in lower animals (Shapiro, Genomics, 1992; 86:99-111) but not, until recently, in vertebrates. Transposons are relatively simple genetic systems, consisting of some genetic sequence bounded by inverted terminal repeats and a transposase enzyme that acts to cut the transposon out of one source of DNA and paste it into another DNA sequence (Plasterk, Cell, 1993; 74:781-786). Autonomous transposons carry the transposase gene inside the transposon whereas non-autonomous transposons require another source of transposase for their mobilization. Among the DNA transposable elements, members of Tc1/mariner family have been found in a wide variety of organisms, ranging from fungi to humans (Doak et al., Proc. Natl. Acad. Sci. USA, 1994; 91:942-946; Radice et al., Mol. Gen. Genet., 1994; 244:606-612). Both the Tc1 and mariner transposons can be transposed using purified transposase protein (Lampe et al., EMBO J., 1996; 15:5470-5479; Vos et al., Genes Dev., 1996; 10:755-761; Tosi et al., Nucl. Acids Res., 2000; 28:784-790). This simplicity in mechanism and broad range of invasion suggested that such a transposon would be useful to develop into a vertebrate transformation vector. However, following an intensive search in vertebrates, primarily fish, not a single active Tc1/mariner-type transposon was found (Izsvák et al., Mol. Gen. Genet., 1995; 247:312-322; Ivics et al., Proc. Natl. Acad. Sci. USA, 1996; 93:5008-5013). Of the nearly 10,000 Tc1/mariner-type transposons found in the haploid human genome, none appear to have active transposase genes (Lander et al., Nature, 2001; 409:860-921; Venter et al., Science, 2001; 291:1304-1351).

Accordingly, a functional Tc1-like transposon system was reconstructed from sequences found in salmonid fish. The synthetic transposase was named Sleeping Beauty (SB), owing to its restoration to activity from a transposon that lost its activity more than 10 million years ago (Ivics et al., Cell, 1997; 91:501-510). The SB transposon appears to obey a cardinal rule of Tc1/mariner transposons, it integrates only into a TA-dinucleotide sequence, which is duplicated upon insertion in the host genome (Ivics et al., Cell, 1997; 91:501-510; Luo et al., Proc. Natl. Acad. Sci. USA, 1998; 95:10769-10773). Transposons in the Tc1/mariner superfamily can be sorted into three groups based on the different length of inverted terminal repeats (ITRs) and the different numbers and patterns of transposase-binding sites in the ITRs (Plasterk et al., Trends Genet., 1999; 15:326-332). One group of transposons has a structure that suggests that there are direct repeats (DRs) within the ITRs or inverted repeat (IR) sequences that have accumulated mutations over time. These are referred to as the IR/DR group, whose members have a pair of binding-sites containing short, 15-20 bp DRs at the ends of each IR, which are about 200-250 bp in length. SB transposons were placed in this group (Ivics et al., Proc. Natl. Acad. Sci. USA, 1996; 93:5008-5013; Ivics et al., Cell, 1997; 91:501-510). Both binding sites are essential for transposition-deletion or mutation of either DR or ITR virtually abolishes transposition (Ivics et al., Cell, 1997; 91:501-510; Izsvák et al., J. Mol. Biol., 2000; 302:93-102).

The SB system is functional in a wide range of vertebrate cells, from fish to humans (Plasterk et al., Trends Genet., 1999; 15:326-332; Izsvák et al., J. Mol. Biol., 2000; 302:93-102). It has been used to deliver genes for long-term gene expression in mice (Yant et al., Nature Genet., 2000; 25:35-40; Fischer et al., Proc. Nail Acad. Sci. USA, 2001; 98:6759-6764; Dupuy et al., Genesis, 2001; 30:82-88; Dupuy et al., Proc. Natl. Acad. Sci. USA, 2002; 99:4495-4499; Horie et al., Proc. Natl. Acad. Sci. USA, 2001; 98:9191-9196) and zebrafish. The SB system is nearly 10-fold more efficient than other Tc1/mariner-type transposons in human cells (Fischer et al., Proc. Natl. Acad. Sci. USA, 2001; 98:6759-6764), although the efficiency drops off as the size of the transposon increases (Izsvák et al., J. Mol. Biol., 2000; 302:93-102; Karsi et al., Mar. Biotechnol., 2001; 3:241-245). These findings suggest that the SB system has considerable promise as a tool for transgenesis and insertional mutagenesis in vertebrates as well as gene therapy in humans.

For such applications, highly active transposons are required. Early results suggested that the SB system in mice might be extremely low because mobilization was extremely infrequent in ES cells (Luo et al., Proc. Natl. Acad. Sci. USA, 1998; 95:10769-10773). However more recent results involving remobilization of SB transposons suggest that the system may be a useful tool in mammals (Yant et al., Nature Genet., 2000; 25:35-40; Fischer et al., Proc. Natl. Acad. Sci. USA, 2001; 98:6759-6764; Dupuy et al., Genesis, 2001; 30:82-88; Dupuy et al., Proc. Natl. Acad. Sci. USA, 2002; 99:4495-4499; Horie et al., Proc. Natl. Acad. Sci. USA, 2001; 98:9191-9196).

SUMMARY OF THE INVENTION

The SB transposon system can be improved in either of three ways: 1) increasing the recombinational catalytic activity of the transposase; 2) improving the structure of the SB transposon, and 3) finding optimal conditions for transposition. The present invention includes improved transposases and improved transposons. Accordingly, the present invention provides a polynucleotide, or complement thereof, that includes a nucleic acid sequence flanked by first and second inverted repeats. The first inverted repeat includes a first outer direct repeat and a first inner direct repeat. The first outer direct repeat includes a nucleotide sequence having at least about 80% identity to SEQ ID NO:3, and the first inner direct repeat includes a nucleotide sequence having at least about 80% identity to SEQ ID NO:4. The second inverted repeat includes a second inner direct repeat and a second outer direct repeat, where the second inner direct repeat includes a complement of a nucleotide sequence having at least about 80% identity to SEQ ID NO:4, and the second outer direct repeat includes a complement of a nucleotide sequence having at least about 80% identity to SEQ ID NO:3. Each direct repeat binds SB polypeptide. Preferably, the first inverted repeat includes SEQ ID NO:1, or the complement thereof, and the second inverted repeat includes SEQ ID NO:2, or the complement thereof. The polynucleotide transposes from a donor polynucleotide to a target polynucleotide at a frequency at least about 50% greater than the frequency of transposition of a transposon having nucleotides 2664 to 4901 of SEQ ID NO:10. The polynucleotide may be part of a vector, preferably a plasmid. The nucleic acid sequence flanked by first and second inverted repeats may include a coding sequence.

The present invention is also directed to gene transfer system to introduce a polynucleotide into the DNA of a cell. The system includes an SB polypeptide or a polynucleotide encoding an SB polypeptide, and a polynucleotide, or complement thereof, including a nucleic acid sequence flanked by first and second inverted repeats. Preferably, the SB polypeptide has the amino acid sequence SEQ ID NO:20. The polynucleotide encoding the SB polypeptide may be RNA. In some aspects, the polynucleotide encoding the SB transposase is integrated into the genome of a cell. The SB polypeptide may have the amino acid sequence SEQ ID NO:20

The polynucleotide may be part of a vector, preferably a plasmid. The nucleic acid sequence flanked by first and second inverted repeats may include a coding sequence.

Also provided by the present invention is a method for introducing a polynucleotide into DNA in a cell. The cell may be a vertebrate cell, preferably, an ex vivo vertebrate cell. The method includes introducing to a cell a polynucleotide, or a complement thereof, that includes a nucleic acid sequence flanked by first and second inverted repeats. The method may include introducing an SB polypeptide or a polynucleotide encoding an SB polypeptide into the cell. The SB polypeptide may include an amino acid sequence having at least about 80% identity to SEQ ID NO:21, wherein the SB polypeptide catalyzes transposition of the polypeptide from a donor polynucleotide to a target polynucleotide at a frequency at least about 50% greater than the frequency of transposition of the transposon catalyzed by an SB polypeptide having the amino acid sequence SEQ ID NO:5. The cell may include a polynucleotide encoding an SB polypeptide, and the polynucleotide encoding the SB polypeptide can be integrated into the cell genome. The nucleic acid sequence flanked by first and second inverted repeats may include a coding sequence.

The present invention further provides a composition that includes a cell having a polynucleotide, or complement thereof, including a nucleic acid sequence flanked by first and second inverted repeats. The cell may be a vertebrate cell, preferably, an ex vivo vertebrate cell. Also provided by the invention is a vector that includes a polynucleotide, or complement thereof, having a nucleic acid sequence flanked by first and second inverted repeats. The vector, preferably a plasmid, includes nucleotides TATA juxtaposed to the 5' end of the polynucleotide and nucleotides ATAT juxtaposed to the 3' end of the polynucleotide. An SB polypeptide catalyzes the transposition of the polynucleotide.

The present invention provides an SB polypeptide or a polynucleotide encoding an SB polypeptide, wherein the SB polypeptide includes an amino acid sequence having at least about 80% identity to SEQ ID NO:21, wherein the SB polypeptide catalyzes transposition of a transposon from a donor polynucleotide to a target polynucleotide at a frequency at least about 50% greater than the frequency of transposition of the transposon catalyzed by an SB polypeptide comprising SEQ ID NO:5. In some aspects, the amino acid sequence of the SB polypeptide is SEQ ID NO:20. The present invention also includes compositions including an SB polypeptide and a cell. The cell may be a vertebrate cell, preferably, an ex vivo vertebrate cell.

Unless otherwise specified, "a," "an," "the," and "at least one" are used interchangeably and mean one or more than one.

BRIEF DESCRIPTION OF THE FIGURES

FIG. 1. Structure of Sleeping Beauty transposon and the DR components of its inverted terminal repeat sequences. A) Structure of a SB transposon showing its right and left inverted terminal repeats (ITRs) and the direct repeats (DRs) contained therein. Each DR is labeled according to its position in the left (L) or right (R) ITR and whether the DR is at the outer (o) end or inner (i) end of the ITR. B) Detailed sequence analysis of the DRs. The DRs Ri (SEQ ID NO:24) and Ro (SEQ ID NO:185) are shown as their complementary sequences to facilitate comparisons. The TA sequences at the ends of the outer sequences are derived from the duplicated insertion site of the transposon. The underlined bases in the Lo sequence (SEQ ID NO:19) indicate conserved differences between the outer and inner DRs. The DRLi sequence is SEQ ID NO:23. The dotted lines underneath the DR consensus sequences show the regions footprinted by the N123 peptide (Ivics et al., *Cell*, 1997; 91:501-510). The aligned consensus sequences (SEQ ID NOS:3, 4, and 18) are shown with a two base-pair gap (dashes) in the DRi consensus sequence to maximize identity. Dots in the DR consensus sequence at the bottom indicate differences between the outer and inner DR sequences. The box shows the minimal-core required for binding of SB transposase (SEQ ID NO:34).

FIG. 4. Effects of specific alterations of base-pairs in the DR sequences on binding of N123 peptide and on transposition in HeLa cells. The name of the construct is in the first column, and the sequences (variations are bolded and underlined) from the flanking reference TA dinucleotide base-pairs flanking the Lo sequence (also bolded but not underlined) are in the second column. N123-binding and transposition rates based on the competition assays shown in FIGS. 2 and 3, respectively, are given in the third and fourth columns. The fifth column indicates the sequence identifier (SEQ ID NOS: 15, 19, 23, and 60-73). Gaps are indicated by the dashes. For convenience in comparing the sequences, the sequence of DRo in construct Lo/Ro(12G->A) is shown as the complementary sequences relative to the Lo strand in order to emphasize the alignments of the sequences in the inverted repeats.

FIG. 5. Analysis of transposon-chromosomal junctions following integration and selection of the SV40neo cassette in HeLa cells. The constructs and HeLa clone identifiers are given in the first column. The junction sequence is shown in the second column, with the transposon and TA insertion site in bold. Outer DRs in all constructs, where cleavage occurred, are indicated by the single underlining. TA sites regenerated during the transposition are indicated by the underlined lower case to dinucleotide basepair. The Lo sequence is conserved except where site-specific changes, described in the text and identified by the double underlining, were made. The chromosomal locus of the insertion site is identified in the third column. The sequence identifier is shown in the fourth column (SEQ ID NOS:74-108). UN, unknown.

FIG. 10. The Sleeping Beauty transposon and its transposition. (A) The structure of the terminal repeats of the Sleeping Beauty transposon. The DRs of the ITRs are designated by arrowheads and are labeled according to their positions in the transposons used in this study. The boxed TA's flanking the transposon result from duplication of the original TA insertion site. (B) "Cut-and-paste" mechanism of SB transposition revised from Luo et al., "Chromosomal transposition of a Tc1/mariner-like element in mouse embryonic stem cells," *Proc. Natl. Acad. Sci. USA*, 1998; 95:10769-10773, and Plasterk, "Molecular mechanisms of transposition and its control," *Cell*, 1993; 74:781-786. Illustrated are two major steps involved in transposition, the excision of the transposon from a donor site and the integration of the transposon into a target site. In addition, the two broken ends at the donor sites are joined together by the host repair machinery in a process called non-homologous end joining (NHEJ), which leaves a footprint at the site where the transposon was. At the target sites, the SB transposon only integrates into TA-dinucleotides.

FIG. 23. Expression levels and stabilities of SB10 and SB11 transposases. Plasmids containing CMV-SB10 and CMV-SB11 were transfected independently into HeLa cells. 72 hours post transfection, 100 μg/mL cycloheximide was added and lysates prepared every 24 hours for western blotting with antibodies against SB transposase and Erk-1, which cross-reacts with Erk-2, for a control. A) Western blot showing relative expression levels and mobilities of SB10 and SB11 compared to the control Erk-1 (MAPK1 at 43 kDa) before cycloheximide addition. B) Quantitative comparison of the expression levels of each transposase as compared to Erk-1. C) Plot of the presences of SB10 and SB11 as individual ratios of transposase/Erk-1 overtime.

FIG. 24. Schematic representation of a transposon. A transposon is depicted with nucleic acid sequence flanked by one inverted repeat on each side. The inverted repeat on the left or 5' side of the transposon includes SEQ ID NO:6 (the nucleotide sequence in bold), with the left outer repeat (SEQ ID NO:22) and left inner repeat (SEQ ID NO:23) underlined. The inverted repeat on the right or 3' side of the transposon includes SEQ ID NO:7 (the nucleotide sequence in italics), with the right outer repeat and right inner repeats present in the complementary strand underlined. Thus, the nucleotide sequence of the right inner direct repeat is 5'-CCCAGTGGGTCAGAAGTTAACATACACTCAA (SEQ ID NO:24), and the nucleotide sequence of the right outer repeat is 5'-CAGTTGAAGTCGGAAGTTTACATA-CACCTTAG (SEQ ID NO:25)

FIG. 25. (A) is a double-stranded nucleic acid sequence encoding an SB polypeptide (SEQ ID NO:26). (B) is the amino acid sequence (SEQ NO:5) of an SB transposase. The major functional domains are highlighted; NLS, a bipartite nuclear localization signal; the boxes marked D and E including the DDE domain (Doak, et al., *Proc. Natl. Acad. Sci., USA*, 91, 942-946 (1994)) that catalyzes transposition; DD(34)E box, a catalytic domain containing two invariable aspartic acid residues, D(153) and D(244), and a glutamic acid residue, E(279), the latter two separated by 43 amino acids. (C) is a nucleotide sequence (SEQ ID NO:27) encoding an SB transposase (SEQ ID NO:20). (D) SEQ ID NO:20 is identical to SEQ ID NO:5, but SEQ ID NO:20 has an arginine, a lysine, or a histidine at position 136, a glutamine or a asparagine at position 243, an arginine, a lysine, or a histidine at position 253, and an arginine, a lysine, or a histidine at position 255. (E) is a nucleotide sequence (SEQ ID NO:28) encoding an SB transposase (SEQ ID NO:21). (F) SEQ ID NO:21 is identical to SEQ ID NO:5, but SEQ ID NO:21 has an arginine at position 136, a glutamine at position 243, a histidine at position 253, and an arginine at position 255.

DETAILED DESCRIPTION OF PREFERRED EMBODIMENTS OF THE INVENTION

Transposons

Figure 2A:
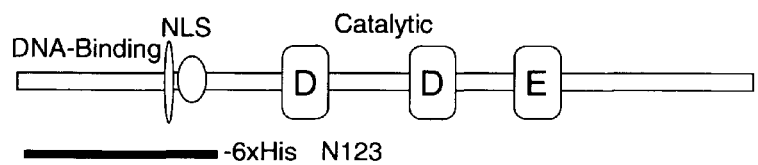
FIG. 2. Electrophoretic mobility shift assays with the N123 peptide from SB transposase. A) Structure of Sleeping Beauty transposase and the source of the amino-terminal N123 peptide that can be purified by the His6 tag at its carboxyl terminus. DNA-binding, the DNA binding domain; NLS, nuclear localizing domain; catalytic, catalytic domain including the amino acids D, D, and E. B) N123 binding to the standard LoLi left hand ITR and two variants with identical DRs in the left ITR. The triangles at the tops of each gel indicate increasing concentration of the N123 peptide. The drawing in the left margin identifies the bands in the gel. The labeled probe is shown below each set of assays. C) Competition of Lo and Li against an ITR-L with two Li DRs. D) Competition of Li and Lo against an ITR-L with two Lo DRs.

The present invention includes transposable elements, also referred to herein as "transposons." Preferably, the transposon is able to excise from a donor polynucleotide, for instance, a vector, and integrate into a target site, for instance, a cell's genomic or extrachromosomal DNA. A transposon includes a polynucleotide that includes a nucleic acid sequence flanked by cis-acting nucleotide sequences on the termini of the transposon.

As used herein, the term "polynucleotide" refers to a polymeric form of nucleotides of any length, either ribonucleotides or deoxynucleotides, and includes both double- and single-stranded DNA and RNA, and combinations thereof. A polynucleotide may include nucleotide sequences having different functions, including for instance coding sequences, and non-coding sequences such as regulatory sequences. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, or a fragment. A "coding sequence" or a "coding region" is a polynucleotide that encodes a polypeptide and, when placed under the control of appropriate regulatory sequences, expresses the encoded polypeptide. The boundaries of a coding region are generally determined by a translational start codon at its 5' end and a translational stop codon at its 3' end. A regulatory sequence is a nucleotide sequence that regulates expression of a coding region to which it is operably linked. Nonlimiting examples of regulatory sequences include promoters, transcriptional initiation sites, translational start sites, translational stop sites, transcriptional terminators (including, for instance, poly-adenylation signals), and intervening sequences (introns). "Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence.

As used herein, "polypeptide" refers to a polymer of amino acids and does not refer to a specific length of a polymer of amino acids. Thus, for example, the terms peptide, oligopeptide, protein, antibody, and enzyme are included within the definition of polypeptide. This term also includes post-expression modifications of the polypeptide, for example, glycosylations (e.g., the addition of a saccharide), acetylations, phosphorylations and the like.

An "isolated" polypeptide or polynucleotide means a polypeptide or polynucleotide that has been either removed from its natural environment, produced using recombinant techniques, or chemically or enzymatically synthesized. Preferably, a polypeptide or polynucleotide of this invention is purified, i.e., essentially free from any other polypeptide or polynucleotide and associated cellular products or other impurities.

A nucleic acid sequence is "flanked by" cis-acting nucleotide sequences if at least one cis-acting nucleotide sequence is positioned 5' to the nucleic acid sequence, and at least one cis-acting nucleotide sequence is positioned 3' to the nucleic acid sequence. Cis-acting nucleotide sequences include at least one inverted repeat (also referred to herein as an inverted terminal repeat, or ITR) at each end of the transposon, to which a transposase, preferably a member of the Sleeping Beauty (SB) family of transposases, binds. The SB family of transposases is described in greater detail below.

Each cis-acting inverted repeat that flanks a nucleic acid sequence preferably includes two or more direct repeats. A direct repeat is typically between about 25 and about 35 base pairs in length, preferably about 29 to about 31 base pairs in length. One direct repeat of an inverted repeat is referred to herein as an "outer repeat," and is present at the end of the inverted repeat that is distal to the nucleic acid flanked by the inverted repeats. When a transposon excises from a donor polynucleotide (e.g., a vector) and integrates into a cell's genomic or extrachromosomal DNA, the outer repeats are juxtaposed to the cell's genomic or extrachromosomal DNA. The other direct repeat of an inverted repeat is referred herein as an "inner repeat," and is present at the end of the inverted repeat that is proximal to the nucleic acid flanked by the inverted repeats. Thus, an inverted repeat on the 5' or "left" side of a transposon of this embodiment typically comprises a direct repeat (i.e., a left outer repeat), an intervening region, and a second direct repeat (i.e., a left inner repeat). An inverted repeat on the 3' or "right" side of a transposon of this embodiment comprises a direct repeat (i.e., a right inner repeat), an intervening region, and a second direct repeat (i.e., a right outer repeat) (see, for instance, FIG. 24). Further, an inverted repeat and the direct repeats within the inverted repeat on one side of a transposon are inverted with respect to the inverted repeat and the direct repeats within the inverted repeat on the other side of a transposon. Unless noted otherwise, the nucleotides of the inverted repeats as disclosed herein are on the same strand of DNA. It is understood that the complement of a left inverted repeat can be used on the right side of a transposon, and the complement of a right inverted repeat can be used on the left side of a transposon. Unless noted otherwise, the direct repeats are represented herein in a different manner: the nucleotide sequence of a direct repeat begins at the end of the inverted repeat that is distal to the nucleic acid flanked by the inverted repeats. Thus, a direct repeat present at the left side of a transposon is not on the same strand of DNA as a direct repeat present on the right side of a transposon (see FIG. 24).

The present invention is not limited to the use of a particular transposon element, and includes those described in, for instance Plasterk et al., Trends Genet., 15,326-332 (1999), U.S. Pat. No. 6,051,430 (Plasterk et al.), WO 01/30965 (Kay et al.), and WO 01/81565 (Ivics and Izsvak). Preferably, the inverted repeats that bind SB transposase contain outer direct repeats that preferably have, in increasing order of preference, at least about 80% identity, at least about 90% identity, at least about 95% identity, most preferably, at least about 98% identity to a consensus direct repeat having the sequence 5'-CAGTTGAAGTCGGAAGTTTACATACACYTAAG (SEQ ID NO:3). Preferably, the inverted repeats that bind SB transposase contain inner direct repeats that preferably have, in increasing order of preference, at least about 80% identity, at least about 90% identity, at least about 95% identity, most preferably, at least about 98% identity to a consensus direct repeat having the sequence 5'-YCCAGTGGGTCA-GAAGTTTACATACACTWART (SEQ ID NO:4). Nucleotide identity is defined in the context of a comparison between a direct repeat and SEQ ID NO:3 or SEQ ID NO:4, and is determined by aligning the residues of the two polynucleotides (i.e., the nucleotide sequence of the candidate direct repeat and the nucleotide sequence of SEQ ID NO:3 or SEQ ID NO:4) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate direct repeat is the direct repeat being compared to SEQ ID NO:3 or SEQ ID NO:4. Preferably, two nucleotide sequences are compared using the Blastn program of the BLAST 2 search algorithm, as described by Tatusova, et al. (FEMS Microbiol Lett, 174, 247250 (1999)), and available at www.ncbi.nlm.nih.gov/gorf/b12.html. Preferably, the default values for all BLAST 2 search parameters are used, including reward for match=1, penalty for mismatch=−2, open gap penalty=5, extension gap penalty=2, gap×dropoff=50, expect=10, wordsize=11, and optionally, filter on. In the comparison of two nucleotide sequences using the BLAST search algorithm, nucleotide identity is referred to as "identities."

Examples of direct repeat sequences that bind to an SB polypeptide include: a left outer repeat 5'-CAGT-TGAAGTCGGAAGTTTACATACACTTRAG (SEQ ID NO:22); a left inner direct repeat 5'-TCCAGTGGGTCAG AAGTTTACAT ACACTAAGT (SEQ ID NO:23); a right inner direct repeat 5'-CCCAGTGGGTCAGAAGTTAA-CATACACTCAA (SEQ ID NO:24) and a right outer repeat is 5'-CAGTTGAAGTCGGAAGTTTACATACACCTTAG (SEQ ID NO:25). Preferred examples of direct repeat sequences that bind to an SB polypeptide include: a left outer repeat 5'-CAGTTGAAGTCGGAAGTTTACATACACT-TAAG-3' (SEQ ID NO:13); left inner repeats 5'-TC-CAGTGGGTCAGAAGTTTACATACACTAAGT-3' (SEQ ID NO: 14) and 5'-TCCAGTGGGTCAGAAGTTTACATA-CACTTAAG-3' (SEQ ID NO:15); right inner repeats 5'-CCCAGTGGGTCAGAAGTTTACATACACTCAAT-3' (SEQ ID NO:16); and a right outer repeat 5'-CAGT-TGAAGTCGGAAGTTTACATACACCTTAG-3' (SEQ ID NO:17).

In one embodiment the direct repeat sequence includes at least 5'-TCRGAAGTTTACATACAC (SEQ ID NO:34), more preferably 5'-GTCRGAAGTTTACATACAC (SEQ ID NO:29).

The intervening region within an inverted repeat is generally at least about 150 base pairs in length, preferably at least about 160 base pairs in length. The intervening region is preferably no greater than about 200 base pairs in length, more preferably no greater than about 180 base pairs in length. In a transposon, the nucleotide sequence of the intervening region of one inverted repeat may or may not be similar to the nucleotide sequence of an intervening region in another inverted repeat.

Preferably, the inverted repeats that bind SB transposase contain intervening regions that preferably have, in increasing order of preference, at least about 80% identity, at least about 90% identity, at least about 95% identity, most preferably, at least about 98% identity to SEQ ID NO:30, or the complement thereof.

Preferred examples of intervening regions include SEQ ID NO:30
5' TTGGAGTCAT TAAAACTCGT TTTTCAACYA CWCCACAAAT TTCTTGTTAA CAAACWATAG TTTTGGCAAG TCRGTTAGGA CATCTACTTT GTGCATGACA CAAGTMATTT TTCCAACAAT TGTTTACAGA CAGATTATTT CACTTATAAT TCACTGTATC ACAAT 3',
and the complement thereof,
SEQ ID NO:31
5' AATGTGATGA AAGAAATAAA AGCTGAAATG AATCATTCTC TCTACTATTA TTCTGAYATT TCA-CATTCTT AAAATAAAGT GGTGATCCTA ACT-GACCTTA AGACAGGGAA TCTTTACTCG GAT-TAAATGT CAGGAATTGT GAAAAASTGA GTTTAAATGT ATTTGG-3',
and the complement thereof,
and SEQ ID NO:32
5' AATGTGATGA AAGAAATAAA AGCTGAAATG AAT-CATTCTC TCTACTATTA TTCTGAYATT TCACATTCTT AAAATAAAGT GGTGATCCTA ACTGACCTAA GACAGGGAAT TTTTACTAGG ATTAAATGTC AGGAATTGTG AAAASGTGAG TTTAAATGTA TTTGG-3',
and the complement thereof.

Preferably, inverted repeats that bind SB transposase have, in increasing order of preference, at least about 80% identity, at least about 90% identity, at least about 95% identity, most preferably, at least about 98% identity to SEQ ID NO:1, or the complement thereof. Nucleotide identity is determined as described hereinabove.

One preferred left inverted repeat sequence of this invention is SEQ ID NO:6

```
5' CAGTTGAAGT CGGAAGTTTA CATACACTTA RGTTGGAGTC

ATTAAAACTC GTTTTTCAAC YACWCCACAA ATTTCTTGTT

AACAAACWAT AGTTTTGGCA AGCRAGTTAG GACATCTACT

TTGTGCATGA CACAAGTMAT TTTTCCAACA ATTGTTTACA

GACAGATTAT TTCACTTATA ATTCACTGTA TCACAATTCC

AGTGGGTCAG AAGTTTACAT ACACTAAGT-3'
``` and the complement thereof, and another preferred inverted repeat sequence of this invention is SEQ ID NO:7

```
5' TTGAGTGTAT GTTAACTTCT GACCCACTGG GAATGTGATG

AAAGAAATAA AAGCTGAAAT GAATCATTCT CTCTACTATT

ATTCTGAYAT TTCACATTCT TAAAATAAAG TGGTGATCCT

AACTGACCTT AAGACAGGGA ATCTTTACTC GGATTAAATG

TCAGGAATTG TGAAAAASTG AGTTTAAATG TATTTGGCTA

AGGTGTATGT AAACTTCCGA CTTCAACTG-3'
``` and the complement thereof.

The inverted repeat (SEQ ID NO:7) contains the poly(A) signals AATAAA at nucleotides 46-51 and 104-109. These poly(A) signals can be used by a coding sequence present in the transposon to result in addition of a poly(A) tail to an mRNA. The addition of a poly(A) tail to an mRNA typically results in increased stability of that mRNA relative to the same mRNA without the poly(A) tail.

A more preferred inverted repeat sequence of this invention SEQ ID NO:1

```
5' CAGTTGAAGT CGGAAGTTTA CATACACTTA AGTTGGAGTC

ATTAkAACTC GTTTTTCAAC TACTCCACAA ATTTCTTGTT

AACAAACAAT AGTTTTGGCA AGTCAGTTAG GACATCTACT

TTGTGCATGA CACAAGTCAT TTTTCCAACA ATTGTTTACA

GACAGATTAT TTCACTTATA ATTCACTGTA TCACAATTCC

AGTGGGTCAG AAGTTTACAT ACACTAAGT-3'
``` and the complement thereof.

Another more preferred inverted repeat sequence of this invention is SEQ ID NO:2

```
5' ATTGAGTGTA TGTAAACTTC TGACCCACTG GGAATGTGAT

GAAAGAAATA AAAGCTGAAA TGAATCATTC TCTCTACTAT

TATTCTGAYA TTTCACATTC TTAAAATAAA GTGGTGATCC

TAACTGACCT AAGACAGGGA ATTTTTACTA GGATTAAATG

TCAGGAATTG TGAAAASGTG AGTTTAAATG TATTTGGCTA

ACGTGTATGT AAACTTCCGA CTTCAACTG-3',
``` and the complement thereof.

Yet another more preferred left inverted repeat sequence of this invention is SEQ ID NO:33

```
5' CAGTTGAAGT CGGAAGTTTA CATACACGGG GTTTGGAGTC

ATTAAAACTC GTTTTTCAAC TACTCCACAA ATTTCTTGTT

AACAAACAAT AGTTTTGGCA AGTCAGTTAG GACATCTACT

TTGTGCATGA CACAAGTCAT TTTTCCAACA ATTGTTTACA

GACAGATTAT TTCACTTATA ATTCACTGTA TCACAATTCC

AGTGGGTCAG AAGTTTACAT ACACTAAGT-3',
``` and the complement thereof.

The nucleotide symbols used herein have the following meaning: R=G or A, Y=T or C, M=A or C, S=G or C, and W=A or T.

In some preferred aspects of the present invention, a transposon includes SEQ ID NO:1 as the left inverted repeat and SEQ ID NO:2 as the right inverted repeat, or the complement of SEQ ID NO:2 as the left inverted repeat and the complement of SEQ ID NO:1 as the right inverted repeat. In another preferred aspect, a transposon includes SEQ ID NO:33 as the left inverted repeat and the complement of SEQ ID NO:33 as the right inverted repeat.

A transposon of the present invention is able to excise from a donor polynucleotide (for instance, a vector) and integrate into a cell's genomic or extrachromosomal DNA. In some aspects, a transposon of the present invention preferably transposes at a frequency that is greater than a "baseline" transposon having SEQ ID NO:6 as a left inverted repeat, SEQ ID NO:7 as a right inverted repeat, and a nucleic acid sequence of between about 1 kilobases and about 10 kilobases flanked by the inverted repeats. Preferably, the nucleic acid sequence flanked by the inverted repeats encodes a detectable marker and/or a selectable marker. Preferably, the coding region encodes resistance to the neomycin analog G418 (for instance, the coding region disclosed at the complement of nucleotides 3327-4118 of SEQ ID NO:10). A preferred example of a baseline transposon having these characteristics is disclosed herein at nucleotides 2664 to 4901 of SEQ ID NO:10. Preferably, the transposition event is catalyzed by an SB polypeptide having the amino acid sequence SEQ ID NO:5. Assays for measuring the excision of a transposon from a vector, the integration of a transposon into the genomic or extrachromosomal DNA of a cell, and the ability of transposase to bind to an inverted repeat are described herein and are known to the art (see, for instance, (Ivics et al. Cell, 91, 501-510 (1997); WO 98/40510 (Hackett et al.); WO 99/25817 (Hackett et al.), WO 00/68399 (McIvor et al.), and U.S. Application serial number 10/128,998 (Steer et al.). For purposes of determining the frequency of transposition of a transposon of the present invention, the activity of the baseline transposon is normalized to 100%, and the relative activity of the transposon of the present invention determined. Preferably, a transposon of the present invention transposes at a frequency that is, in increasing order of preference, at least about 50%, at least about 100%, at least about 200%, most preferably, at least about 300% greater than a baseline transposon. Preferably, both transposons (i.e., the baseline transposon and the transposon being tested) are flanked by the same nucleotide sequence in the vector containing the transposons.

Preferably, the assay for measuring transposition uses a mammalian cell line, preferably HeLa cells. The cells can be cultured using routine methods, preferably by culturing in DMEM supplemented with about 10% fetal bovine serum (for instance, characterized fetal bovine serum, available from Hyclone, Logan, Utah), about 2 mM L-glutamine, and antibiotics (for instance, antimycotic, available from Gibco-BRL, Carlsbad, Calif.). Typically, the cells are seeded at a density of about $3 \times 10^5$ cells per 6-cm plate one day prior to transfection. The cells are transfected with from about 450 nanograms (ng) to about 550 ng, preferably about 500 ng vector containing the transposon, and from about 450 ng to about 550 ng, preferably 500 ng of vector encoding the SB polypeptide. Preferably, the vector pCMV-SB (SEQ ID NO:8) is used as the source of SB polypeptide. Methods for transfecting mammalian cells with DNA are routine. Preferably, the transfection reagent TransIT-LTI (available from Mirus, Madison, Wis.) is used. At about 24 hours post transfection, cells are typically washed with 1×PBS and fresh medium added. At about 2 days post-transfection, the transfected cells are typically trypsinized, resuspended in serum-containing DMEM, and about $3 \times 10^4$ cells may be seeded onto several 10 cm plates in medium, supplemented with the appropriate selective agent if necessary. After about two to about three weeks of growth, the number of colonies expressing the marker are counted. For instance, when the cells encode resistance to the neomycin analog G418, the cells can be fixed with about 10% formaldehyde in PBS for about 15 minutes, stained with methylene blue in PBS for bout 30 minutes, washed extensively with deionized water, air dried and counted.

A transposon of the present invention may be present in a vector. A vector is a replicating polynucleotide, such as a plasmid, to which another polynucleotide may be attached so as to bring about the replication of the attached polynucleotide. The vector may include a coding sequence. A vector can provide for further cloning (amplification of the polynucleotide), i.e., a cloning vector, or for expression of the polypeptide encoded by the coding region, i.e., an expression vector. A vector can be both a cloning vector and an expression vector. The term vector includes, but is not limited to, plasmid vectors, cosmid vectors, artificial chromosome vectors, or, in some aspects of the invention, viral vectors. Examples of viral vectors include adenovirus, herpes simplex virus (I-ISV), alphavirus, simian virus 40, picornavirus, vaccinia virus, retrovirus, lentivirus, and adeno-associated virus. Preferably the vector is a plasmid. In some aspects of the invention, a vector is capable of replication in the cell to which it is introduced; in other aspects the vector is not capable of replication. In some preferred aspects of the present invention, the vector is unable to mediate the integration of the vector sequences into the genomic or extrachromosomal DNA of a cell. An example of a vector that can mediate the integration of the vector sequences into the genomic or extrachromosomal DNA of a cell is a retroviral vector, in which the integrase mediates integration of the retroviral vector sequences.

Preferably, the vector includes specific nucleotide sequences which are juxtaposed to the transposon. For instance, a vector includes a "TAACCC" on one the right side of the transposon and a "GGGGA" on the left side of the transposon, or an "AAATA" on one the right side of the transposon and a "TGTCT" on the left side of the transposon, or a "TTGAT" on the right side of the transposon and a "CTCGG" on the left side of the transposon, or a "TGCCT" on the right side of the transposon and a "ACGTA" on the left side of the transposon. More preferably, the vector includes specific nucleotide sequences which are juxtaposed to the transposon, and increase the frequency of transposition of the transposon compared to the frequency of transposition of the transposon when the vector includes, for instance, a "TAACCC' on one the right side of the transposon and a "GGGGA" on the left side of the transposon. For instance, a vector more preferably includes a "TATA" nucleotide sequence that is present the left side of the transposon, or an "ATAT" on the right side of the transposon. even more preferably, the vector includes a "TATA" nucleotide sequence that is present on the left side, and an "ATAT" on the right side of the transposon. Alternatively, the vector may include a "TGATA" on the right side of the transposon and a "CTGTA" on the left side of the transposon. Preferably, the vector does not include a "TTAAG" on one the right side of the transposon and an "AATAA" on the left side of the transposon, or an "AACTA" on one the right side of the transposon and a "TGGCT" on the left side of the transposon, or an "AGCCA" on one the right side of the transposon and a "TAGTT" on the left side of the transposon.

The nucleic acid sequence flanked by the cis-acting nucleotide sequences can include a non-coding sequence and/or a coding sequence. A coding sequence present in the nucleic acid sequence flanked by the cis-acting nucleotide sequences may encode a biologically active polypeptide. "Biologically active polypeptides" include polypeptides that are able to modify a cell in any way, including modifying the metabolism of the cell, the structure of the cell, the function of the cell, and also include polypeptides that permit the cell containing the polypeptide to be detected. "Biologically active polypeptides" include polypeptides that can be used to correct a genetic deficiency, and polypeptides that are a selectable marker and/or a detectable marker. Selectable markers permit the selection of cells containing the selectable marker. An example of a type of selectable marker is drug resistance, including, for instance, resistance to the neomyicn analog G418. Detectable markers may permit identification of cells containing the detectable marker. Examples of such detectable markers that can be used in this way include fluorescent proteins (e.g., green, yellow, blue, or red fluorescent proteins), luciferase, and chloramphenicol acetyl transferase, p-galactosidase, and other molecules detectable by their fluorescence, enzymatic activity or immunological properties, and are typically useful when detected in a cell, for instance, a cultured cell, or a tissue sample that has been removed from an animal. Detectable markers also include markers that are secreted by cells to allow identification of an animal that contains a cell containing the detectable marker, for instance, secreted alkaline phosphatase, adn alpha-1-antitrypsin.

Biologically active polypeptides encoded by a coding sequence present on a transposon of the present invention may be therapeutic (i.e., able to treat or prevent a disease) or non-therapeutic (i.e., not directed to the treatment or prevention of a disease). Examples of diseases that can be treated or prevented with therapeutic biologically active polypeptides include, for instance, liver specific diseases (such as hemophilia A, hemophilia B, Crigler-Najjar syndrome Type I, and ornithine transcarbamylase deficiency) and pulmonary diseases (such as hyperoxia, cystic fibrosis, emphysema, pulmonary edema, infectious diseases, alpha-1-antitrypsin deficiency, and lung cancer). Non-therapeutic biologically active polypeptides include detection or diagnostic polypeptides, including markers, that can be used in, for instance, detecting the transposons of the present invention function when delivered to cells using the compositions of the present invention.

Transposases

The present invention is not limited to the use of a particular transposase, provided the transposase binds an inverted sequence of the present invention or a direct repeat of the present invention, and preferably catalyzes the excision of a transposon from a donor polynucleotide (e.g., a vector) and subsequent integration of the transposon into the genomic or extrachromosomal DNA of a target cell. The transposase may be present as a polypeptide. Alternatively, the transposase is present as a polynucleotide that includes a coding sequence encoding a transposase. The polynucleotide can be RNA, for instance an mRNA encoding the transposase, or DNA, for instance a coding sequence encoding the transposase. When the transposase is present as a coding sequence encoding the transposase, in some aspects of the invention the coding sequence may be present on the same vector that includes the transposon, i.e., in cis. In other aspects of the invention, the transposase coding sequence may be present on a second vector, i.e., in trans.

A preferred transposase for use in the invention is "Sleeping Beauty" transposase, referred to herein as SB transposase or SB polypeptide (Ivics et al. Cell, 91,501-510 (1997); WO 98/40510 (Hackett et al.); WO 99/25817 (Hackett et al.), WO 00/68399 (McIvor et al.)). SB transposase is able to bind the inverted repeat sequences of SEQ ID NOs:6-7 and direct repeat sequences (SEQ ID NOs:13-17) from a transposon, as well as a consensus direct repeat sequence (SEQ ID NO:3 or SEQ ID NO:4). SB transposase includes, from the amino-terminus moving to the carboxy-terminus, a DNA-binding domain, nuclear localizing domains (NLS) domains and a catalytic domain including a DD(34)E box and a glycine-rich box, as described in WO 98/40510 (Hackett et al.). The SB family of polypeptides includes the polypeptide having the amino acid sequence of SEQ ID NO:5, SEQ ID NO:20, and SEQ ID NO:21, and the polypeptides described in WO 01/81565 (Ivics et al.).

Preferably, a member of the SB family of polypeptides also includes polypeptides with an amino acid sequence that shares at least about 80% amino acid identity to SEQ ID NO:21, more preferably, it shares at least about 90% amino acid identity therewith, most preferably, about 95% amino acid identity. Amino acid identity is defined in the context of a comparison between the member of the SB family of polypeptides and SEQ ID NO:21, and is determined by aligning the residues of the two amino acid sequences (i.e., a candidate amino acid sequence and the amino acid sequence of SEQ ID NO:21) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence is the amino acid sequence being compared to an amino acid sequence present in SEQ ID NO:21. A candidate amino acid sequence can be isolated from a natural source, or can be produced using recombinant techniques, or chemically or enzymatically synthesized. Preferably, two amino acid sequences are compared using the Blastp program of the BLAST 2 search algorithm, as described by Tatusova et al. (FEMS Microbiol Lett., 174, 247-250 (1999)), and available at www.ncbi.nlm.nih.gov/gorf/b12.html. Preferably, the default values for all BLAST 2 search parameters are used, including matrix=BLOSUM62; open gap penalty=11, extension gap penalty=1, gap×dropoff=50, expect=10, word-size=3, and optionally, filter on. In the comparison of two amino acid sequences using the BLAST2 search algorithm, amino acid identity is referred to as "identities." SB polypeptides preferably have a molecular weight range of about 35 kDa to about 40 kDa on about a 10% SDS polyacrylamide gel.

In some aspects, an SB polypeptide of the present invention preferably catalyzes the transposition of a transposon at a frequency that is greater than a "baseline" transposase. Preferably, the baseline transposase has the amino acid sequence of SEQ ID NO:5. Preferably, the transposon used to evaluate the ability of a transposase to mediate transposition has SEQ ID NO:6 as a left inverted repeat, SEQ ID NO:7 as a right inverted repeat, and a nucleic acid sequence of between about 1 kb to about 10 kb flanked by the inverted repeats. Preferably, the nucleic acid sequence flanked by the inverted repeats encodes a detectable marker and/or a selectable marker. Preferably, the coding region encodes resistance to the neomycin analog G418 (for instance, the coding region disclosed at the complement of nucleotides 3327-4118 of SEQ ID NO: 10. A preferred example of a baseline transposon having these characteristics is disclosed herein at nucleotides 2664 to 4901 of SEQ ID NO:10. For purposes of determining the frequency of transposition mediated by a transposase of the present invention, the activity of the baseline transposase is normalized to 100%, and the relative activity of the transposase of the present invention determined. Preferably, a transposase of the present invention causes transposition at a frequency that is, in increasing order of preference, at least about 50%, at least about 100%, at least about 200%, most preferably at least about 300% greater than a "baseline" transposase. Preferably, both transposons (i.e., the baseline transposon and the transposon being tested) are flanked by the same nucleotide sequence in the vector containing the transposons.

Preferably, the assay for measuring transposition uses a mammalian cell line, preferably HeLa cells. The cells can be cultured using routine methods, preferably by culturing in DMEM supplemented with about 10% fetal bovine serum (for instance, characterized fetal bovine serum, available from Hyclone, Logan, Utah), about 2 mM L-glutamine, and antibiotics (for instance, antimycotic, available from Gibco-BRL, Carlsbad, Calif.). Typically, the cells are seeded at a density of about $3 \times 10^5$ cells per 6-cm plate one day prior to transfection. The cells are transfected with from about 450 nanograms (ng) to about 550 ng, preferably about 500 ng vector containing the transposon, and from about 450 ng to about 550 ng, preferably 500 ng of vector encoding the SB polypeptide. Preferably, the vector pCMV-SB (SEQ ID NO:8) is used as the source of SB polypeptide. Methods for transfecting mammalian cells with DNA are routine. Preferably, the transfection reagent TransIT-LTI (available from Mirus, Madison, Wis.) is used. At about 24 hours post transfection, cells are typically washed with 1X PBS and fresh medium added. At about 2 days post-transfection, the transfected cells are typically trypsinized, resuspended in serum-containing DMEM, and about $3 \times 10^4$ cells may be seeded onto several 10 cm plates in medium, supplemented with the appropriate antibiotic if necessary. After growth for an appropriate period of time, the number of cells or colonies expressing the marker are counted. For instance, when the cells encode resistance to the neomycin analog G418, the cells can be fixed with about 10% formaldehyde in PBS for about 15 minutes, stained with methylene blue in PBS for bout 30 minutes, washed extensively with deionized water, air dried and counted.

The SB polypeptides useful in some aspects of the invention include an active analog of SEQ ID NO:5, SEQ ID NO:20, or SEQ ID NO:21. An active analog can bind the inverted repeat sequences of SEQ ID NOs:6-7 and direct repeat sequences (SEQ ID NOs: 13-17) from a transposon, as well as a consensus direct repeat sequence (SEQ ID NO:3 or SEQ ID NO:4). An active analog of an SB polypeptide is one that is able to mediate the excision of a transposon from a donor polypeptide, preferably a vector.

Active analogs, as that term is used herein, include modified polypeptides. Modifications of polypeptides of the invention include chemical and/or enzymatic derivatizations at one or more constituent amino acids, including side chain modifications, backbone modifications, and—and C-terminal modifications including acetylation, hydroxylation, methylation, amidation, and the attachment of carbohydrate or lipid moieties, cofactors, and the like.

The present invention further includes polynucleotides encoding the amino acid sequence of SEQ ID NO:5, SEQ ID NO:20, or SEQ ID NO:21. An example of the class of nucleotide sequences encoding such the polypeptide disclosed in SEQ ID NO:5 is SEQ ID NO:19, and the nucleotide sequences encoding the polypeptides disclosed at SEQ ID NO:20 and SEQ ID NO:21 can be easily determined by taking advantage of the degeneracy of the three letter codons used to specify a particular amino acid. The degeneracy of the genetic code is well known to the art and is therefore considered to be part of this disclosure. The classes of nucleotide sequences that encode the polypeptides SEQ ID NO:5, SEQ ID NO:20, or SEQ ID NO:21 are large but finite, and the nucleotide sequence of each member of the classes can be readily determined by one skilled in the art by reference to the standard genetic code.

The present invention further includes compositions that include a transposon of the present invention, a transposase of the present invention (either a polypeptide or a polynucleotide encoding the transposase), or both a transposon and a transposase. The compositions of the present invention optionally further include a pharmaceutically acceptable carrier. The compositions of the present invention may be formulated in pharmaceutical preparations in a variety of forms adapted to the chosen route of administration. Formulations include those suitable for parenteral administration (for instance intramuscular, intraperitoneal, in utero, or intravenous), oral, transdermal, nasal, or aerosol.

The formulations may be conveniently presented in unit dosage form and may be prepared by methods well known in the art of pharmacy. All methods of preparing a pharmaceutical composition include the step of bringing the active compound (e.g., a transposon, a transposase, or a combination thereof) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

The present invention also provides methods of using the transposons and transposases disclosed herein. Such methods of use are described in, for instance, Ivics et al. (Cell, 91, 501-510 (1997)), WO 98/40510 (Hackett et al.), WO 99/25817 (Hackett et al.), WO 00/68399 (McIvor et al.), and U.S. application Ser. No. 10/128,998 (Steer et al.). For instance, the present invention includes a method for introducing a polynucleotide into DNA in a cell, preferably, a vertebrate cell. The method includes introducing to a cell a polynucleotide, or a complement thereof, that includes a nucleic acid sequence flanked by first and second inverted repeats of the present invention. In some aspects, the transposon transposes at a frequency at least about 50% greater than the frequency of transposition of a transposon comprising nucleotides 2664 to 4901 of SEQ ID NO:10. Assays for measuring transposition are described herein. Optionally, an SB polypeptide of the present invention, or a polynucleotide encoding the SB polypeptide is also introduced to the cell. Alternatively, the cell may include a polynucleotide encoding an SB polypeptide. The polynucleotide encoding an SB polypeptide may be integrated into the cell's genome or extrachromosomal DNA. Methods for introducing molecules, for instance, polynucleotides and polypeptides, into cells are routine in the art and include, for instance, particle bombardment, electroporation, microinjection, combining the molecule to be introduced with lipid-containing vesicles or DNA condensing reagents, and incorporating the polynucleotide into a viral vector and contacting the viral vector with the cell.

The cell, preferably may be ex vivo or in vivo. As used herein, the term "ex vivo" refers to a cell that has been removed, for instance, isolated, from the body of a subject. Ex vivo cells include, for instance, primary cells (e.g., cells that have recently been removed from a subject and are capable of limited growth or maintenance in tissue culture medium), and cultured cells (e.g., cells that are capable of extended growth or maintenance in tissue culture medium). As used herein, the term "in vivo" refers to a cell that is within the body of a subject.

The cell to which a transposon and transpose of the present invention are delivered can vary. Preferably, the cell is a vertebrate cell. The vertebrate cell may be, for instance, mouse, rat, livestock (e.g., pig, horse, cow, goat, sheep), fish (e.g., zebrafish), or primate (e.g., monkey, human). In some aspects, the cell is preferably a somatic cell.

The invention also provides a gene transfer system to introduce a polynucleotide into the DNA of a cell. The system includes a polynucleotide, or complement thereof, including a nucleic acid sequence flanked by first and second inverted repeats of the present invention, and an SB polypeptide of the present invention, or a nucleic acid encoding the SB polypeptide. In some aspects, the transposon transposes at a frequency at least about 50% greater than the frequency of transposition of a baseline transposon comprising nucleotides 2664 to 4901 of SEQ ID NO:10. Assays for measuring transposition are described herein. In other aspects, the transposase catalyzes the integration of a transposon at a frequency at least about 50% greater than the frequency of transposition catalyzed by a baseline transposase.

The present invention is illustrated by the following examples. It is to be understood that the particular examples, materials, amounts, and procedures are to be interpreted broadly in accordance with the scope and spirit of the invention as set forth herein.

EXAMPLES

Example 1

Structure-Function Analysis of the Inverted Terminal Repeats of the Sleeping Beauty Transposon This example demonstrates the analysis of the role of the inverted repeats, direct repeats, and nucleotides flanking the transposon in transposition, and presents the construction of an improved transposon.

Materials and Methods
T transposons with mutated DRs and/or ITRs

The pT/SV40neo construct of Ivics et al., Cell, 1997; 91:501-510, was the basis for all of the transposons used in this example. The constructs are referred to by the DRs in relationship to the neo marker gene. Hence, pT/SV40neo in this example is referred to as RoRi-LiLo because it has an inverted neo expression cassette relative to the constructs used in this example (FIG. 1A). Three polymerase chain reaction (PCR)-based strategies were exploited to make vectors with mutations in the DRs and ITRs. In the first strategy, PCR was performed with Vent DNA polymerase (New England Biolabs) to generate blunt-ended DNA fragments. The blunt-ended PCR products were digested with DpnI to remove the template DNA, and then treated with T4 polynucleotide kinase followed by ligation, transformation and mini-preparation. In the second strategy, PCR primers were designed to contain certain restriction sites at the 5' end. PCR products were treated with the appropriate restriction enzymes to generate DNA fragments with cohesive ends, which could substitute their counterparts in LoLi-RiRo to make constructs with mutated DRs or ITRs. To avoid the nonspecific binding of PCR primers, two constructs, named LoLi and RiRo were first made by deleting either the right ITR or left ITR in the LoLi-RiRo vector and used as the template DNA for mutagenic PCR reactions. Table 1 shows the constructs and primers for making them. There is a single MfeI site between the two left-DR sites. The sequence between the two Lo motifs is the same as that between Lo and Li so that there are two MfeI sites in the left ITR of LoLoLi- RiRo. Two other constructs with three DRs in the left ITR, LiLoLi-RiRo and LoLoLo-RiRo, were made by cloning the middle Lo site from LoLoLi-RiRo into the MfeI restriction site between the DRs in LiLi and LoLo, respectively, in LiLi-RiRo and LoLo-RiRo. Most constructs in Table 1 contain a single SacI site outside the left ITR, a single BamHI site outside right ITR and a single HindIII site between the two ITRs. These restriction sites were used for constructs such as LiLi-RiRi, LoLo-RoRo, LO[ΔL, R, or M]Li-Ri[ΔM]Ro (where the Δ indicates deletion of sequences from the Left, Right and Middle portions of the inter-DR sequence). TALo, TARo, TALo/Li,TAN$_4$Lo, TAN$_4$Ro and TAN$_4$Lo/Ro were made by ligating mutated parts from other constructs together following PCR-mediated mutagenesis. The SV40neo cassette was cloned into the Hind III site of the engineered constructs.

TABLE 1

Primers used for constructing site-specific mutations in pTI

| pTI/constructs | Primer 1 (5'-') | SEQ ID NO: Primer 1 | Primer 2 (5'-3') | SEQ ID NO: Primer 2 | R. enzymes |
|---|---|---|---|---|---|
| LoLi | CCTCTAGCTAGAGTCGACC | 114 | CCACAAGCTTCTAAAGCC | 149 | |
| RiRo | CATGGCTCGAGf1AAGC | 115 | CAGTGGTCGAAATCTTCGAAC | 150 | |
| Lo-RiRo | TAACACTATGTCACTTAATATTC | 116 | ACTGACACCGAAATTGTCG | 151 | |
| Li-RiRo | ATCCCATGGCTCGAGGTr | 117 | AACCTCAGTAATTTTGAGCAA | 152 | |
| LiLi-RiRi | TCAGAAGTTTACATACACTAAGTTTGGAGTCATTAAAACTCGTTTTTCAAC | 118 | CCCCACTGGATAGGGTACCGAGCTCCAATTCGCCC | 153 | |
| LoLi-RiRi | AAGTTAACATACACTCAATCCAAATACATTTAAACTCATTTTTCACAATTCC | 119 | CTGACCCCACTGGGTAGGGGATCCTCTAGCTAGAGTCGACCTCGAG | 154 | |
| LoLo-RiRo | TCGGAAGTACATACACTTAAGTGACTGTGCCTTTAAACAGCTTGG | 120 | CTTCAACTGATTGTGATACAGTGAATTATAAGTGAAATAATCTG | 155 | |
| LoLi-RoRo | CGACTTCAACTGAATGTGATGAAGAATAAAAGCTGAAATGAATC | 121 | GAAGTTTACATACACnAGTAGTATTTG-GTAGCATTGCCTTTAAATTGTTTAAC | 156 | |
| | | | TGTTTAAC | 157 | |
| LoLoLi-RiRo | GAAGTTTACATACACTTAAGTTGGAGTC | 122 | CGACTTCAACTGATTGTGATACAGTGAATTATAAGTG | 158 | |
| Lo[A60L]Li-RiRo | CTTAAGTGTATGTAAACTTCCGAC | 123 | TTTTGGCAGTCAGTTAGGACATC | 159 | |
| Lo[A50M]Li-RiRo | AAACTATTGTTTGTTAAC | 124 | CAACAATTGTTTACAGAC | 160 | |
| Lo[A50R]Li-RiRo | GAAAAATGACTTGTGTCATGC | 125 | ATTCCAGTGGGTCAGAAGTTTAC | 161 | |
| LoLi-Ri[A50M]Ro | ATAATAGTAGAGAGAATGATTC | 126 | GACAGGGAATCTTTACTCGG | 162 | |
| Lo[S48M]Li-RiRo | CAATAGCATCACAAATTTCACAAACAACAATTGTTTACAGAC | 127 | CTTTATTTGTAACCATTATAAGCTCAAAACTATTGTTGTTAAC | 163 | |
| LiLo(H) | GAAGACTGGGTGACCTTAACACTATGTCACTTAATATTC | 128 | AAATGTATGTGAATTCAAATCTTCGAACACCTTCCG | 187 | |
| Lo(S27-29) | CCAACTTCCATGTATGTAAACTTCCGACTTC | 129 | AGTCATTAAAACTCGTTT | 187 | |
| Lo(S28-30) | CCAACTCCCGTATGTAAACTTCCGACTTTC | 130 | AGTCATTAAAACTCGTTT | 164 | |
| Lo(S1,3) | TGGAGCTCGGTACCCTAAAATTTGAAGTCGGAAGTT | 131 | GAGTAGCCTTCCACAAG | 164 | SacI, HindIII |
| Lo(S4-6) | TGGAGCTCGGTACCCTACAGCCCAAGTCGGAAGTT | 132 | GAGTAGCCTTTTCCACAAG | 164 | SacI, HindIII |
| Lo(S7-9) | TGGAGCTCGCTACCCTACAGTTGCCCTCGGAAGTT | 133 | GAGTAGCCFITCCACAAG | 164 | SacI, HindIII |
| Lo(S10-12) | TGGAGCTCGGTACCCTACAGTTGAAGAACGAAGTT | 134 | GAGTAGCCTTCCACAAG | 164 | SacI, HindIII |

TABLE 1-continued

Primers used for constructing site-specific mutations in pTI

| pT/constructs | Primer 1 (5'-) | SEQ ID NO: Primer 1 | Primer 2 (5'-3') | SEQ ID NO: Primer 2 | R. enzymes |
|---|---|---|---|---|---|
| TALo | GGAGCTCGGATCCCTATACAGTTGAAGTCGGAAGT | 135 | GAGTAGCCTTCCACAAG | 165 | Sacl, HindIII |
| TARo | GGAGCTCGGATCCCTATACAGTTGAAGTCGGAAGT | 136 | TGATGTCATGGCTTTAGAAG | 164 | BamHI, HindIII |
| TAM₄Lo | GGAGCTCCCTATAGGGCAGTTGAAGTCGGAAGT | 137 | GAGTAGCCTTCCACAAG | 165 | Sacl, HindIII |
| TAM₄Ro | GAGGATCCCTATAGGGCAGTTGAAGTCGGAAGT | 138 | TGATGTCATGGCTTTAGAAG | 165 | BamHI, HindIII |
| RoRi-RiRo | TGGAGCTCGGTACCCTACAGTTGAAGTCGGAAGT | 139 | TGATGTCATGGCTTTAGAAG | 164 | BamHI, HindIII |
| LoLi-LiLo | GAGGATCCCTACAGTTGAAGTCGGAAGT | 140 | GAGTAGCCTTCCACAAG | 164 | BamHI, HindIII |
| Lo(S3) | TGGAGCTCGGTACCCTACAATTGAAGTCGGAAGTTTA | 141 | GAGTAGCCTTCCACAAG | 164 | Sacl, HindIII |
| Lo(Δ8-11) | TGGAGCTCGQTACCGTACAGTTGAG-GAAGTTTACATACACTTAAGTTG | 142 | GAGTAGCCTTCCACAAG | 164 | Sacl, HindIII |
| Li(2C→A) | TGGAGCTCGGTACCCTACAGTGGGTCGGAAGTTTA | 143 | GAGTAGCCTTCCACAAG | 164 | Sacl, HindIII |
| Lo/Ro(12G→A) | GGAGCTCGGATCCCTACAGTTGAAGTCAGAAGTTT | 144 | | | Sacl, HindIII, BamHI |
| Rmut52 | GTGAAAAACTGAGTTTAAATGTATTTGGC | 145 | CTCAGTTTTTCACAATTCCTGACATTTA | 166 | |
| Rmut[80,87,Δ101] | GGGAATTTTTACTAGGATTAAATGTCAGG | 146 | GTAAAAATTCCCTGTCTTAGGTCAGTTAGG | 167 | |
| Rmut142 | CTGACATTTCACATTCTTAAAATAAGTGG | 147 | GAATGTGAAATGTCAGAATAATAGTAGAGAAG | 168 | |
| Rmut217 | GTATGTAAACTTCTGACCCACTGGGAATGTGAT | 148 | GAAGTTTACATACACTCAATTAGTATTTGGTAGCA | 169 | |

Mutations to ITR-R were made by site-directed mutagenesis of RiRo. In the third PCR-mutagenesis strategy, primers were designed to amplify the plasmid and generate overlapping 12-16 bp homologous ends containing the mutations. The primers used for Rmut52, Rmut[80,87,Δ101], Rmut142, and Rmut217 are given in Table 1. Once amplified, PCR reactions were digested with DpnI to remove template DNA. PCR products were transformed into TOP 10F' competent cells (Invitrogen) and recombination by the bacteria lead to the desired products. The HindIII-XhoI fragment of each mutated ITR-R's was swapped into pT/HindIII to give new transposon cloning vectors containing the mutated ITR-Rs. The SV40Neo cassette was cloned into the HindIII site in the sense orientation.

To construct pT2/SV40Neo, the HindIII-AflIII fragment of Rmut217 replaced the homologous part of the ITR-R of pT/HindIII-TATA (the precursor to TALo/TARo). The mutagenic PCR was performed to add the Rmut[80, 87, Δ101] mutations to give pT2/HindIII. The SV40Neo cassette was cloned into the HindIII site to give pT2/SV40Neo.

Electrophoretic Mobility Shift Assay (EMSA)

DNA fragments with one to three DRs were obtained by digestion of the appropriate transposon with HindIII and SacI. To determine the core sequence for SB binding, DNA fragments with mutations in the outer or inner DR were made by PCR followed by enzyme digestion. DNA fragments were end-labeled with [$\alpha^{32}$P]-dCTP. Nucleoprotein complexes were formed in a buffer as described by Ivics et al., *Cell*, 1997; 91:501-510. Reactions contained 100 picogram (pg) DNA probes, 1 microgram (μg) poly[dI:dC], and 1 microliter (μl) N123 in a total volume of 20 μl. After a 60 minutes incubation at 30° C., 10 ml of loading dye containing 50% glycerol and bromophenol blue were added and the samples were loaded onto 4%-6% polyacrylamide gels, which were run for 2-3 hours at 120 volts. 4% gels were used for EMSA assays with triple-DR probes while 6% gels were used with double-DR probes. Competitor concentrations were as described in Ivics et al., *Cell*, 1997; 91:501-510. Dried gels were exposed to the phosphor for 6-9 hours and imaged on a Storm 840 Imager (Molecular Dynamics).

Transposition Assays

The assays were essentially as described in Ivics et al., *Cell*, 1997; 91:501-510, with modifications. Cells were cultured in DMEM supplemented with 10% fetal bovine serum, seeded at a density of 3×10$^5$ cells per 6-cm plate one day prior to transfection and transfected with 500 nanograms (ng) transposon vector, 500 ng pCMV-SB [or 500 ng pGL-1 (Gibco BRL) for controls] in TransIT-LT1 (Mirus, Madison, Wis.). At 24 hours post transfection, cells were washed with 1X PBS and provided fresh medium. Two days post-transfection, the transfected cells were trypsinized, resuspended in 4 ml of serum-containing DMEM and 3×10$^4$ cells were seeded onto several 10 cm plates in medium containing 800 mg/ml G-418 (Mediatech). After two to three weeks of selection, cell clones were either picked and expanded into individual cultures, or fixed with 10% formaldehyde in PBS for 15 minutes, stained with methylene blue in PBS for 30 minutes, washed extensively with deionized water, air dried and counted.

Analysis of Transposition Junction Sequences G418-resistant clones of HeLa cells were collected from the individual clones described above and genomic DNAs were isolated with phenol/chloroform extraction followed by ethanol precipitation. About 0.5 μg of genomic DNA was digested with Sau3AI and a Splinkerette-mediated PCR was performed following modifications of the protocol described by Dupuy et al., *Genesis*, 2001; 30:82-88; Dupuy, et al., *Proc. Natl. Acad Sci. USA*, 2002; 99:4495-4499. DNA fragments were purified with a QIAquick™ PCR purification kit from Qiagen (Valencia, Calif.) and sequenced directly or cloned into pZero2/TA vector before sequencing.

Excision Analyses

Constructs were co-transfected with pCMV-SB into HeLa cells using the same conditions as in the transposition assay. At 48 hours post-transfection, plasmids were extracted using the Hirt, *J. Mol. Biol.*, 1967; 26:365-369, method of isolation of low molecular weight DNAs from cell lysates. After digestion of the Hirt supernatant with HindIII to eliminate the majority of the unexcused transposon plasmid, primers flanking the transposon were used to amplify the excision products using conditions similar to those of Kawakami et al., *Gene*, 1998; 225:17-22, with appropriate modifications of the primers flanking the transposon.

Results

The Outer and Inner DRs of the ITRs of the SB Transposon are not Identical

Early alignments of inactive transposon sequences in fish suggested that each SB-like transposon in fish had four nearly identical sequences of about 30 bases that were protected from nuclease digestion by SB transposase (FIG. 1A). The most conservative alignment (Ivics et al., *Cell*, 1997; 91:501-510) has a 2-base gap in the two inner DRs (DRi's) opposite the two A/T base pairs at positions 8 and 9 in the outer DRs (DRo's). This alignment results in six differences between DRo's and DRi's (dots in the consensus DR sequence at the bottom of FIG. 1B) compared with eleven differences if the gap is not introduced (underlined bases in Lo in the top line of FIG. 1B). For simplicity and to avoid confusion with previous reports, the transposase-binding sites are referred to as DRs even though they are not true direct repeats. In our coordinate system the numbering begins after the conserved TA dinucleotides in the DRo's that mark the insertion sequence for the transposon. The conserved differences between the DRo's and DRi's raised the question whether they are important for transposition.

Figure 2B:
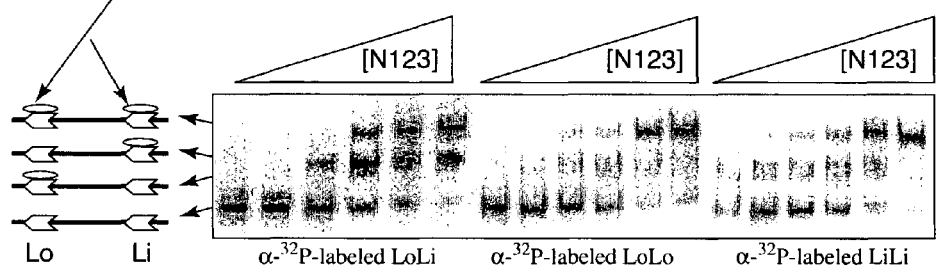

The Outer and Inner DRs have Different Binding Affinities to the DNA-binding Domain of SB Transposase The initial step of SB transposition involves the specific binding of transposase to both ITRs of SB transposon. Two DRs in each ITR are required because deletion of one or the both severely reduces transposition (Izsvák et al., *J. Mol. Biol.*, 2000; 302:93-102). First examined was whether the differences in DR sequences affected the binding of SB transposase. The N123 fragment of SB transposase was used (FIG. 2A), which includes the DR-recognition domain of SB (Ivics et al., *Cell*, 1997; 91:501-510). Three $^{32}$P-labeled ITR probes were made for these experiments. The first was a left-hand ITR designated LoLi, the second had a DR-Li sequence that replaced the DR-Lo sequence (designated LiLi) and the third had a DR-Lo sequence that replaced the DR-Li sequence (designated LoLo). The ITRs have been named by the DR sequences they contain. FIG. 2B shows that N123 bound non-cooperatively to all three ITR probes at two sites according to the availability of binding protein. With the LoLo or LiLi probes, there were four distinct bands on the EMSA films. The top and bottom bands are either the ITRs bound by two N123 molecules or ITRs free of N123, respectively.

Figure 2C:
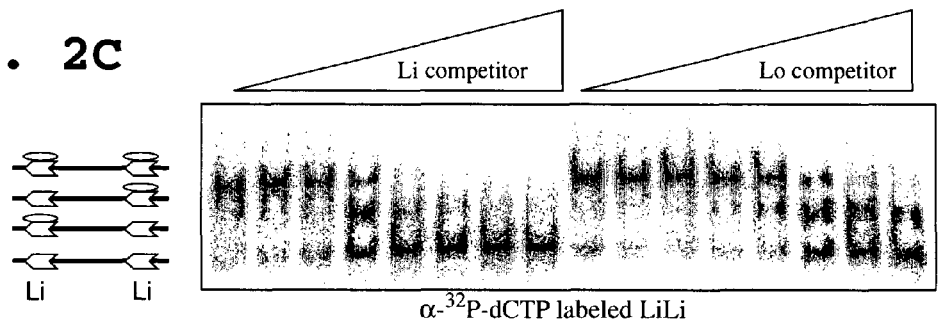
Figure 2D:
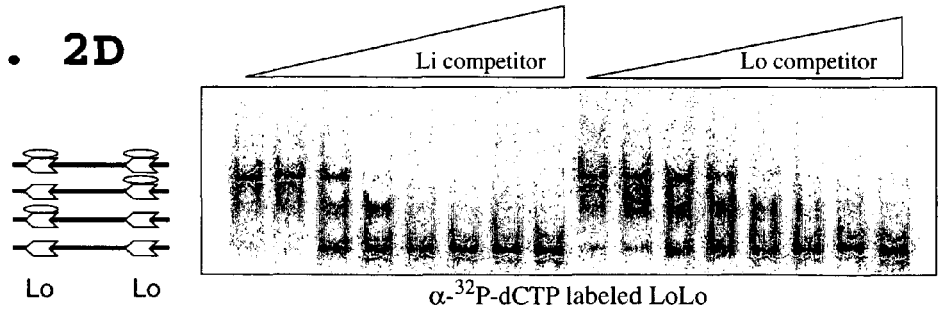

The two thin bands in the middle are the ITRs bound by a single N123 molecule at either Lo or Li. The differences in mobility are due to the differences in conformation because the DRs are not symmetrically placed from each end of the ITRs. The consistent difference in intensity of the middle two bands with the LoLi probes was the first indication that there are differences in affinity for SB transposase between the outer and inner DRs. The abilities of unlabeled Lo and Li to compete the labeled probes for N123 were examined to determine which DRs had the higher binding strengths to N123 (FIGS. 2C and D). FIG. 2C shows that the Lo sequence was not as efficient at competing with LiLi as was Li, suggesting that N123 bound to Li more tightly than to Lo. This conclusion was confirmed by the finding that Li could out-compete Lo sites on a LoLo probe (FIG. 2D). Thus, N123 binds more strongly to Li than to Lo based on these competitive kinetics of Li and Lo. Similar results were obtained using RoRi probes from pT2. Together these experiments indicated that the outer and inner DRs are neither equivalent in sequence nor in binding. Moreover, the inner DRs bind transposase more tightly than the outer DRs, the sites at which cutting and pasting occurs.

The Outer and Inner DRs are Necessary and not Interchangeable in Transposition

Figure 3:
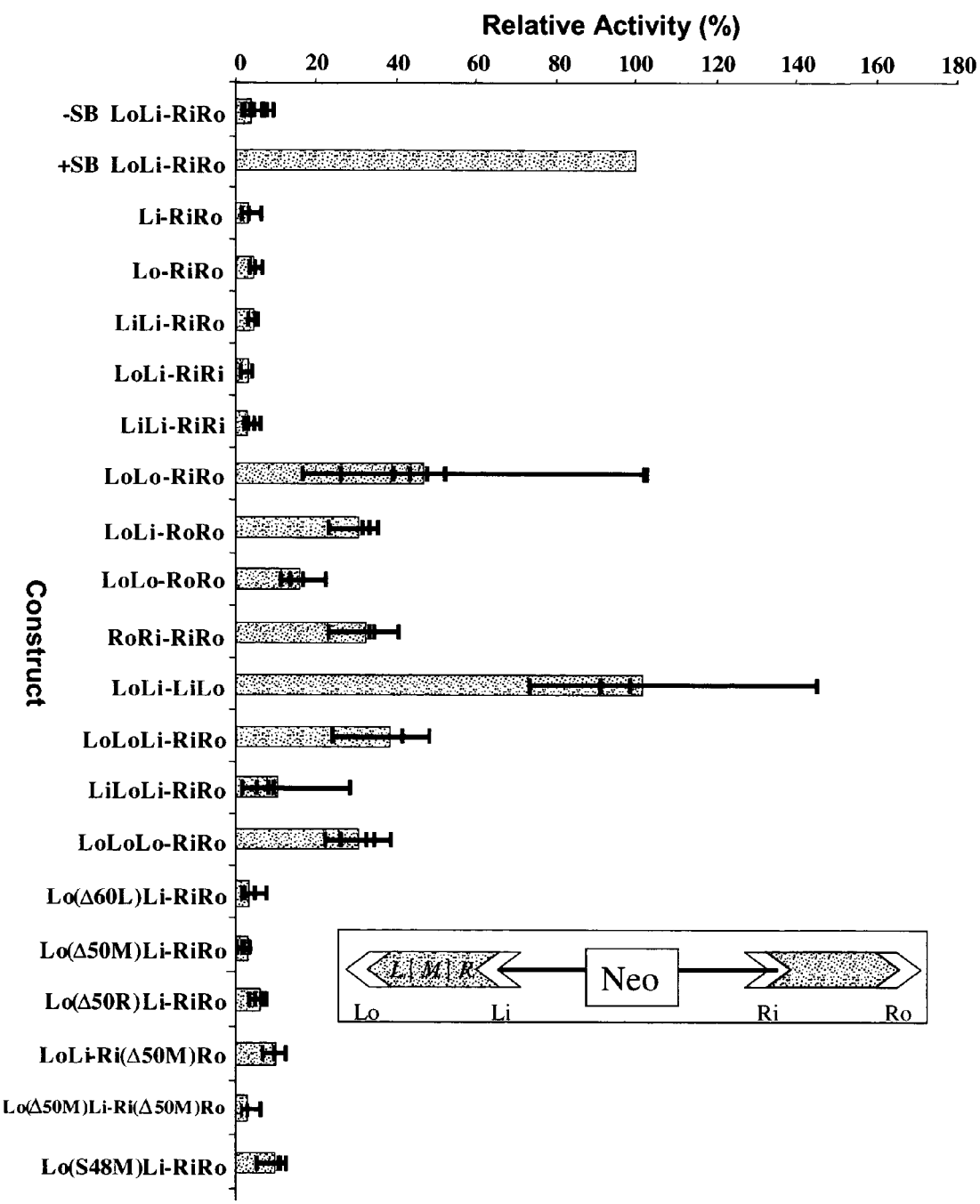
FIG. 3. Effects of alterations in the DR and ITR structures on transposition by SB transposase. The standard pT/SV40neo (LoLi-RoRi construct) was used as a reference in all experiments and normalized to 100%. The result of each individual experiment is shown as a cross-hatch and the line indicates the total variation in the levels of activity for each construct. Integration of SV40neo from the LoLi-RiRo construct in the absence of SB transposase (top bar) was used as a negative control to determine the rate of random recombination of the selectable marker following lipofection. The structure in the box is a map of the DR components. Relative Activity (%), neo-resistant colony formation relative to the number of colonies from the standard pT/SV40neo (LoLi-RoRi) construct.

The above findings raised two questions. First, extrapolating from the binding of N123, does the difference in apparent binding affinities between SB transposase and the inner and outer DRs affect transposition? Second, if the outer DRs are replaced with inner DR sequences, which bind N123 more tightly, will rates of transposition improve? To answer these questions, a series of mutant transposons were made with the SV40-neo cassette flanked by various DRs in their ITRs. The effects of DR replacements were tested using HeLa cells where successful transposition could be quantified by the numbers of colonies resistant to G418 (Ivics et al., *Cell*, 1997; 91:501-510). FIG. 3 shows the results of many such experiments. As noted above, the transposons are named by the DRs that are in their left and right ITRs. In all experiments except the one shown at the top, pCMV-SB encoding SB transposase was co-transfected with plasmids containing experimental transposons. The first two bars at the top show that SB transposase increased integration by about 20-40 fold for our standard transposon, LoLi-RiRo. The increase was similar for the RoRi-LiLo construct, the original pT/SV40neo construct of Ivics et al., *Cell*, 1997; 91:501-510, in which the inserted marker gene is in the reverse orientation of that found in natural transposons. The "background" resistant colonies are due to random recombination of the transposon-containing plasmids into genomic DNA. As further controls for this study, previous work (Izsvák et al., *J. Mol. Biol.*, 2000; 302: 93-102) was confirmed that elimination of a single DR on one side of the transposon abolished transposition (FIG. 3, constructs Lo-RiRo and Li-RiRo). Substitution of one or both of the outer DRs with inner DRs essentially abolished transposition, reducing the gene transfer rate to background (LiLi-RiRo, LoLi-RiRi and LiLi-RiRi). In these experiments, the donor vector sequences, including the TAs, flanking the transposon were identical to those in the standard LoLi-RiRo construct.

In contrast, replacing one inner DR with an outer DR (FIG. 3, constructs LoLo-RiRo and LoLi-RoRo) only reduced transposition about 50%. However, replacement of both DRi's with DRo's (LoLo-RoRo) reduced transposition nearly 85%. These results suggest that 1) the outer and inner DRs play different roles in the SB transposition, 2) the differences in binding strengths suggested by the EMSA results with N123 (FIG. 2) apply to the whole SB transposase enzyme, and 3) the increased binding of SB transposase to the outer termini of the ITRs reduces transposition.

Is the presence of a DRo plus a DRi in an ITR sufficient for transposition? As noted, switching the orientation of the marker gene inside the transposon had little effect. But, do the left and right ITRs serve symmetrically in transposition? We got an answer to this question by constructing two symmetrical transposons, RoRi-RiRo and LoLi-LiLo that respectively have either two ITR-Ls or two ITR-Rs. In all cases the flanking sequences were maintained. As shown in FIG. 3, transposons with just right-hand ITRs were about 50% as efficient as the standard transposon whereas the transposon with two ITR-L's was nearly as active as the standard LoLi-RiRo. Thus, besides the DR sequences, the ITRs contain sequences important for modulating transposition and the differences in the sequences separating the DRs in each ITR appear to be important. The effects of the inter-DR sequences were examined as well as the types of DRs in the ITRs by altering the numbers of DRs in ITR-L or by removing various portions of the inter-DR spacer in ITR-L. As shown by the transposition rates of LoLoLi-RiRo, LiLoLi-RiRo and LoLoLo-RiRo, increasing the number of DRs in ITR-L did not improve transposition efficiency and indeed, the construct having Li at the outer position was the least efficient. EMSA analysis of the binding of N123 protein to the triple-DR constructs showed that binding could occur at all three sites independently, although the preference for binding at Li sites persisted. The transposition efficiencies for LoLoLi-RiRo and LoLoLo-RiRo were significantly decreased to about the same level as with LoLo-RiRo. In these constructs, as with the LiLoLi-RiRo transposon, there was no TA dinucleotide to the left of the middle Lo sequence. Nevertheless, some transposition occurred with LiLoLi-RiRo. A determination of which DR sequences served as termini of their respective transposons is discussed below when it is shown that the chromosomal insertions are indeed the result of transposition rather than random recombination.

Although our EMSA experiments have never indicated the presence of cellular factors binding in a specific way to the ITRs, the spacing between DRs might be important for transposition. The finding that the symmetrical transposon RoRi-RiRo had a reduced transposition frequency raised the question of what sequences between the DRs cause the differences in transposition rates. The question of spacing is important because transposition rates are inversely proportional to the length of the transposon (Izsvák et al., *J. Mol. Biol.*, 2000; 302:93-102; Karsi et al., *Mar. Biotechnol*, 2001; 3:241-245). Hence, if portions of the 230-bases ITRs could be removed, the transposons might be mobilized at higher rates. Accordingly, portions of the inter-DR sequence were removed from ITR-L. These deletions were either from the left (D60L), middle (D50M) or right (D50R) regions of the inter-DR sequence. As shown in FIG. 3, both of the three deletions reduced gene transfer into HeLa chromosomes to about background. The reduction could have been due to an imbalance in the lengths of the two sides of the transposon. Accordingly, the middle 50 bp were deleted in both ITR-L and ITR-R, Lo(D50M)Li-Ri(D50M)Ro—again, the transposition was dramatically reduced. To see if there was sequence specificity in the intervening sequence, the middle 48 bases of the inter-DR spacer was substituted with a different sequence in Lo(S48M)Li-RiRo. This construct also was inactive in transposition. Reductions in spacers of 48 and 65 bases, which would alter the rotational geometry of Lo with respect to Li, eliminated transposition as well. These results suggest that some combination of the inter-DR spacing, sequence, and geometry of the DRs with respect to each other, is very important for transposition. This could be due to agents that bind to the ITRs in the inter-DR spacer or because the sequence has certain properties required for transposase-mediated recombination.

Transposase Binding to a Core DR Sequence is Required but not Sufficient for Transposition The transposase-binding sites were determined originally by sequence conservation as well as DNA footprinting (Ivics et al., Cell, 1997; 91:501-510). The previous experiments indicated that the differences of just a few bases in the outer and inner DRs have major effects on transposition. The differences in the DRo and DRi sequences are mainly at their left ends. Izsvák et al., J. Mol. Biol., 2000; 302:93-102, showed that three mutations at positions 21, 25 and 26 (FIG. 1B) in the right half of Ri severely reduced transposition. We investigated in more detail which sequences in the Lo region were critical to transposition by engineering a series of substitutions and measuring both N123 binding and transposition (FIG. 4). The binding of N123 to Lo was not affected by single, double and even the triple mutations in the first nine base-pairs of Lo [constructs Lo (S3), (S1, 3), (S4-6), and (S7-9); see FIG. 1B for coordinates] nor at the last three base pairs of Lo (S28-30). However, mutations beyond position 9 [Lo(S10-12)] or deletion of bases 8-11 [Lo(D8-11)] abolished binding and transposition as did mutations at positions 27-29 [Lo(S27-29)]. Moreover, the 3' end of Li could be substituted with the 3' end of Lo and still bind N123 and transposase [Li/Lo(H) in FIG. 4]. All these findings suggest that the minimal core-sequence for SB transposase binding is the 18-bp internal sequence TCRGAAGTTTACATACAC (SEQ ID NO:34).

Because differences in sequence between the outer and inner DRs were important for transposition (FIG. 3), the effects of site-specific changes in the left-hand most three base-pairs of Lo and Li on transposition were examined. A single mutation of the third base-pair of Lo [Lo(S3)] reduced transposition by more than 50% although binding of N123 was not affected and changing the first and third base-pairs [Lo(S1, 3)] virtually abolished transposition. One clear difference between the DRo's and DRi's is the G vs. A at position 12 (FIG. 1B) in the core SB-binding region. Substitution in Lo and Ro at bp-12 from G->A reduced transposition about 30% [FIG. 4, Lo/Ro(126->A)], consistent with the previous findings that substitution of Li for Lo reduces transposition. Substitutions of three base-pairs at a time farther into Lo, from between position 6 and position 12 lowered transposition. Mutation beyond position 12, in the previously identified core-binding sequence, eliminated both binding and transposition (FIG. 4). Likewise, mutation of just the second base-pair in the outer Li of LiLi-RiRo [construct Li(2C->A)], to introduce a TA flanking sequence similar to that for Lo, did not raise transposition above background. The reduction in transposition of this construct demonstrates that Li, even with a flanking TA dinucleotide base pair, cannot effectively substitute for Lo in transposition. Taken together, these results suggest that the integrity of the 5'-flanking sequences of the outer DRs is very important for transposition but not to binding of the transposase DNA-binding domain.

Compared with the DNA sequence of the inner DR, the sequences juxtaposed to Lo and Ro have TA dinucleotide basepairs that may influence transposition. The TA entry site required for Tc1/mariner transposons is duplicated upon transposition. This raised the question whether the TA dinucleotide repeats are essential in the donor construct for transposition, presumably at the excision step. If so, must the TAs be immediately juxtaposed to the transposon? That is, if there is a separation of a few base pairs between the conserved ends of the transposon and the TA, will the cleavage be at the TA border or at the transposon border? Several transposons were constructed to answer these questions. Constructs TAN$_4$Lo, TAN$_4$Ro and TAN$_4$Lo/Ro (FIG. 4, bottom) were constructed to test whether the TA dinucleotide base-pairs flanking transposons are necessary for transposition. In these constructs, four base-pairs separated the TAs in Lo and Ro either singly or together from the DRs. The transposition efficiency decreased to about 30% for TAN$_4$Lo, 25% for TAN$_4$Ro and background for the combination. These data suggest that having a TA flanking both sides of the transposon is advantageous, but not essential, whereas that having at least one TA flanking one side is essential. Alternatively, whether there might be an advantage in having double TA sites at each end of the transposon was examined. For this TALo, TARo and TALo/TARo (FIG. 4) were constructed. These constructs had 50% to 100% higher transposition frequencies than the standard transposon.

The Precision of SB Transposition in HeLa Cells

All of the data presented thus far are consistent with the DRs influencing transposition rather than random recombination. However, to prove that transposition actually occurred, the junction sequences for several of the unusual transposons were determined. This was especially important for the constructs that lacked TAs flanking the outer DRs (e.g., TAN$_4$Lo and TAN$_4$Ro) and those with three DRs (e.g., LiLoLi, LoLoLi and LoLoLo) where there was more than one possible cleavage site for transposon. FIG. 5 shows the results of sequencing the junctions. LoLi-RiRo is the standard pT/SV40neo construct. Constructs that had substitutions in their Lo sequences [Lo(S4-6) and Lo(S7-9)] showed precise transposition in every sequenced insertion site. In every clone that was analyzed from cellular transfection with the TAN$_4$Lo and TAN$_4$Ro, the transposons all integrated into a genomic TA site and regenerated the appropriate flanking TAs. However, SB transposition was not detected if both flanking TAs were deleted, as with TAN$_4$Lo/Ro. There were no integration sites compatible with cleavage at the outside TA site for constructs with double TA flanking elements (e.g., TALo). These data suggest that transposase has a strong preference, if not a requirement, for transposing sequences from the immediate ends of the DRo's. Similar results were obtained with several of the ITRs containing triple DRs. Importantly, although there was no TA flanking the middle Lo of LiLoLi-RiRo, several transposition events were recorded, apparently by cleavage of transposon at the end of the internal Lo site. That is, an Lo sequence lacking a bordering TA was preferable to an Li sequence juxtaposed to TA. In the LoLoLi-RiRo transposon, transposition occurred preferentially at the outer Lo site in four of five instances, presumably because the outer Lo was flanked by a TA sequence. Nevertheless, in one of the five cases, precise cleavage and transposition was at the internal Lo, with regeneration of the flanking TA from the integration site. These results and those from the TAN4Lo construct support the earlier finding that a transposon lacking flanking TA on one side can be excised for mobilization to another site and that the TA sequence is regenerated when a SB transposon leaves a TA-less site. This conclusion is further supported by excision PCR, which is described next.

Relationship of Excision and Integration of SB Transposons

Figure 6A:
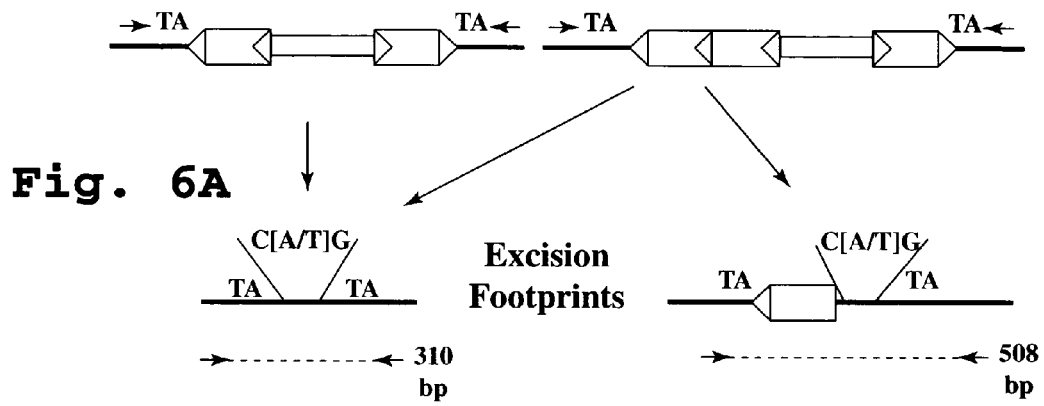
FIG. 6. Transposon excision analysis. A) Schematic of expected products from excision of transpsons with either two DR sequences (left construct) or three DR sequences (right construct) in the left ITR. Left and right primers to sequences flanking the transposon in the plasmid are shown by the black arrows. Excision from a standard transposon, LoLiRiRo is expected to give a consensus footprint of CAGTA or CTGTA plus the original TA sequence on the right, represented as TAC[A or T] TA in PCR product of 310 basepairs. Excision of a transposon with 3 DRs could give either of two footprints, one of 310 basepairs, if the excision occurred at the left-hand-most DR or a footprint of 508 basepairs if excision occurred at end of the middle DR. B) Results of excision analyses of experimental transposons described in FIGS. 3 and 4. Control excision reactions with the standard transposon, LoLiRiRo, without (−) and with (+) SB transposase are shown in the second and third lanes; M is a market lane with size standards. Transposition from experimental constructs, in the presence of SB transposase, are shown in the other lanes. The data show that transposition occurs when the outer DR is Dro rather than Dri, that a flanking TA is not absolutely required for excision at Dro, and that longer ITRs are less effective than the standard length ITR.
Figure 6B:
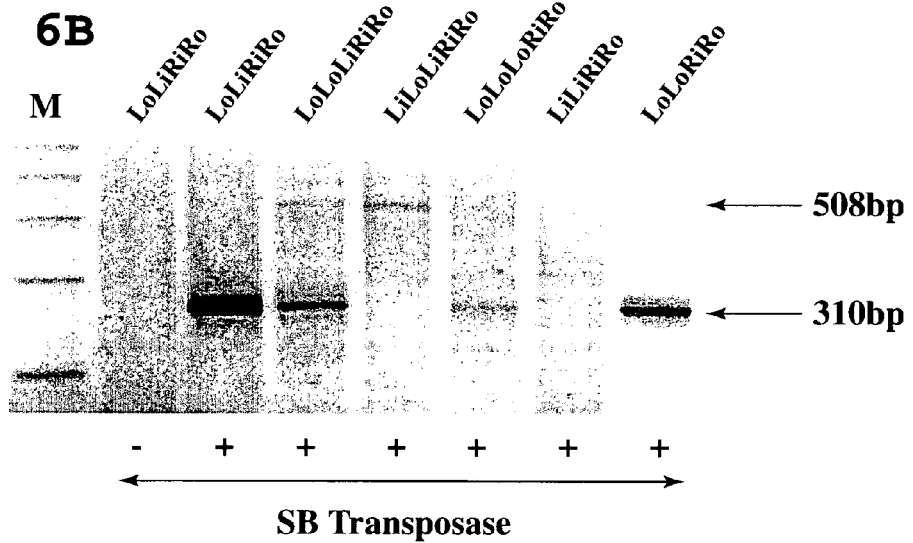

The data in FIG. 4 showed that although binding of N123 to modified DR elements was far less perturbed than the transposition frequency of transposons with the same mutations, full-length SB transposase could still direct specific cleavages at the termini of transposons (FIG. 5). This raised the question whether excision could be used as a reliable indicator of transposition efficiency and a means for estimating the relative frequencies at which various termini might be recognized during the excision step of transposition. These questions were answered by amplifying sequences from which transposons were excised (FIG. 6A). The PCR-amplified fragments show that excision was precise and yielded the expected-size products for those transposons with high transposition rates (FIG. 6B, LoLi-RiRo, LoLo-RiRo, and LoLoLi-RiRo) and at very low yields with poorly transposing constructs such as LiLoLi-RiRo and LoLoLo-RiRo. In conformation of the junction sequence analysis shown in FIG. 5, LoLoLi-RiRo gave two amplification bands, the 310-bp band that is the expected size for excision from the outer Lo site and a 508-bp band from excision at the inner Lo site. In contrast, the LoLoLo construct only showed excision from the outer site whereas the LiLoLi construct only indicated excision from the middle Lo site even though it did not have a flanking TA. This assay only provides products wherein excision is between the primer-binding sites in the vector flanking the transposon. Regardless of this limitation, these data are consistent with the findings that excision can occur from TA-less sites and that Li sites are relatively inactive for excision and transposition. Together, these data suggest that excision is a reliable assay for a complete transposition set of reactions.

Site-specific Mutations in the ITRs Produce an Improved Transposon

Figure 7A:
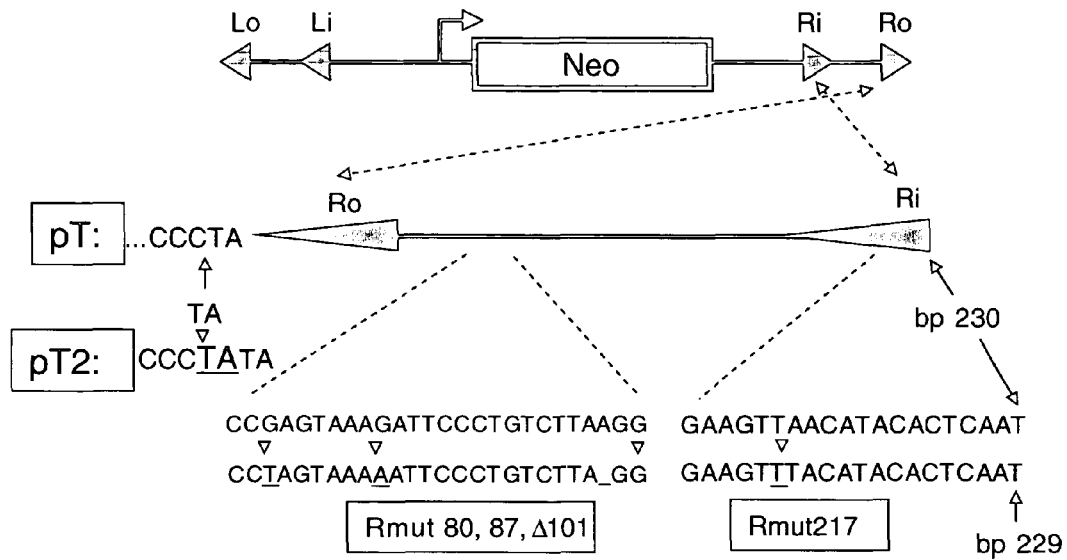
FIG. 7. Site-specific mutagenesis of ITR-R to improve transposition. (A) Schematic of a neo transposon in the sense orientation (Ro is SEQ ID NO:109 and Ri is SEQ ID NO:111) with detailed mutations to convert pT to pT2 (Ro is SEQ ID NO:110 and Ri is SEQ ID NO:186); site-specific mutations are denoted by black arrows and numbered starting with bp-1 at the right-hand flank (Ro) of the transposon. (B) Transposition efficiencies of various transposons. The first construct, RiRo-LiLo (pT/SV40Neo) co-transfected with either a control plasmid, pGL-1 rather than with pCMV-SB10, which accompanied all of the other transposons.
Figure 7B:
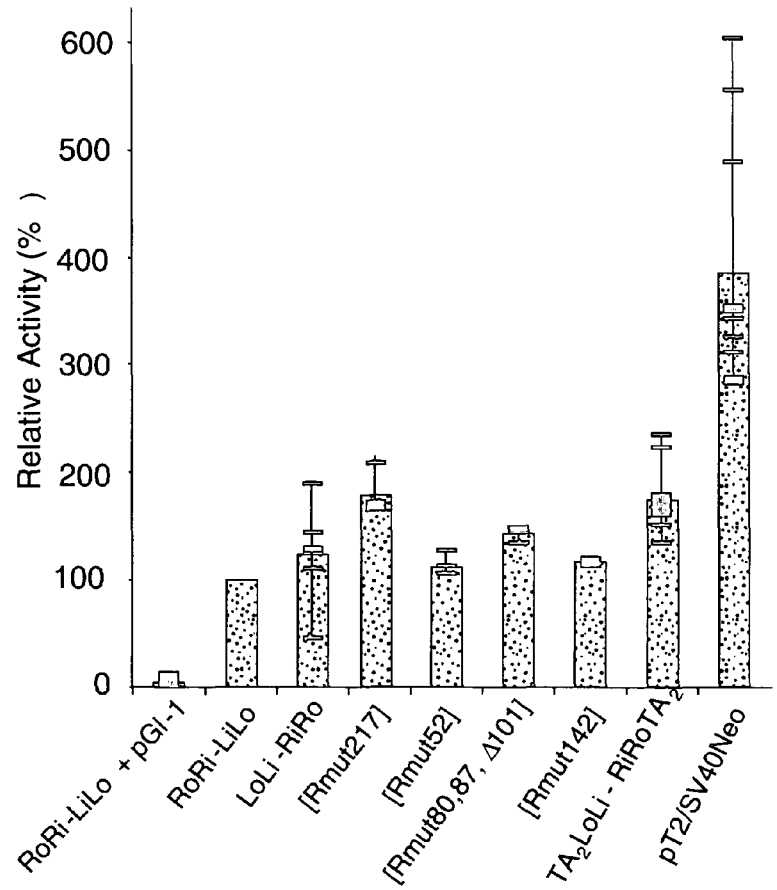

Besides the overall differences in the DRo and DRi consensus sequences, there are several sites in particular DRs that diverge from the consensus. A T->A substitution at bp-19 in DRi (FIG. 1B coordinates) is particularly evident. Reverting this presumptive mutation in DRi (Rmut217, FIG. 7A) boosted transposition about 80% (FIG. 7B). Three other alterations in the ITR-R spacer between DRo and DRi were brought into closer alignment with consensus sequences derived from defective transposons found in fish genomes (Ivics et al., *Proc. Natl. Acad. Sci. USA*, 1996; 93:5008-5013). Using a coordinate system where the outer most basepair of DRo is position 1, to maintain consistency with FIG. 1A, the altered ITR-R constructs were denoted Rmut52(C->G), Rmut[80(G->T), 87(G->A), Δ101 (A)] and Rmut 142(A->G). Only the triple mutant showed a consistent increase over the original RoRi-LiLo of approximately 40% (FIG. 7B). All of the site-specific mutations that increased transposition activity, Rmut217, and Rmut[80, 87, Δ101] were combined with the double-TA flanks to the transposon, TALo/TARo in FIG. 4, to produce a new transposon cloning vector pT2/HindIII. The SV40Neo cassette was cloned into the HindIII site to give pT2/SV40Neo. The pT2/SV40Neo produced just under a four-fold increase in activity over the standard pT/SV40neo vector.

Discussion

The Contributions of the DR Sequences in the ITRs are Distinct in Transposition

A significant finding reported here is that the sequence variations between the left and right ITRs, as well as between the inner and outer DR sequences, are important for high level transposition. The sequences in the middle of both ITRs are quite similar but only the right ITR contains a natural polyadenylation signal, presumably for the transposase mRNA that was originally enclosed in natural transposons. Transposons with two right ITRs are less active than mixed transposons whereas those with two left ITRs are fully active (FIG. 3). It is concluded that transposition is modulated by the sequences and/or spacing between the DR motifs in the ITRs.

By site-specific mutagenesis, it is shown here that the core transposase-binding site for the SB transposase is shorter than the functional limits of the DR in terms of transposition. These results are consistent with those in Tc3 of Colloms et al., *Nucl. Acids. Res.*, 1994; 22:5548-5554, who found that the sequence of the terminal base-pairs in the DRs are not required for binding of the transposase. More interesting is the finding that the inner DRs have a stronger binding affinity for N123, and presumably full-length SB transposase, than the outer DRs where the cleavage and ligation reactions occur. Replacement of the outer DRs with inner DR sequences abolished transposition, while replacing inner DRs with outer DRs substantially reduced transposition, suggesting that the relative strengths of binding of transposase to the DRs are unequal and cannot be varied substantially without interfering with the overall reaction. Increasing the binding affinity of transposase to the outer DRs blocks transposition and thereby eliminates strategies for improving transposition by selection of tighter binding transposases. The binding affinities are balanced for dynamic activity of cutting, mobilization, and pasting the liberated transposon into a new site.

Like the SB transposon system, the Tc3 transposon of *C. elegans* has two DR-like elements in each ITR (Plasterk et al., *Trends Genet.*, 1999; 15:326-332). In both the Tc3 and SB transposons, the terminal base pairs are necessary for efficient transposition (Fischer et al., *Mol. Gen. Genet.*, 1999; 262: 268-274). However, unlike the requirement for both a DRo and DRi in the SB system, Tc3 looses little activity when the internal transposase-binding site is deleted (Plasterk et al., *Trends Genet.*, 1999; 15:326-332). The cause of the differences between the requirement for two DRs is not known. But, it may be related to apparent simplicity of the nematode transposons, which like those from Drosophila, are able to transpose in vitro. There are no reports of transposition by SB transposase in vitro. There may be a linkage between the higher transposition activity of the SB system in vertebrate cells and its greater complexity.

Role of TA-sequences Flanking the Transposon in Transposition.

Because the core site to which SB transposase binds is embedded within highly conserved sequence (FIG. 1B), the role of the flanking TA in the donor source of plasmid was tested. The results show that a flanking TA is not essential on both ends. The deletion of a single TA is less influential than deletion of an entire DR (FIGS. 3 and 5). However, deletion of TAs on both ends is nearly fatal for transposition. This was seen in both transposons with normal ITRs that had one or both flanking TA dinucleotide base-pairs deleted as well as with ITRs with two Lo motifs that could serve as sites for cleavage. In these cases cleavage occurred followed by regeneration of the flanking TA from the insertion site in the acceptor HeLa cell genome. These data are especially interesting because of the correlation between rates of cleavage and liberation of the transposon seen in the excision assay (FIG. 6B) and the corresponding rates of transposition seen in gene transfer (FIGS. 3 and 5) of the SV40neo cassette. In contrast, a related transposon, Tc3, does not require TA flanks (van Luenen et al., *Cell*, 1994; 79:293-301). These examples suggest that their model of excision, which involves staggered cleavages that do not involve the TA sites (Luo et al., *Proc. Natl. Acad. Sci. USA*, 1998; 95:10769-10773; Plasterk et al., *Trends Genet.*, 1999; 15:326-332), may not apply to transposition by SB transposase. The data presented herein does suggest that excision is a good indicator of transposition efficiency and that it will be very worth while to determine optimal flanking sequences for excision.

Model of SB Transposition

In summary the following has been found: 1) The DR sequences within each ITR are different although they have the same core transposase-binding domain. 2) The difference in the DRs affects binding affinity for SB transposase such that SB transposase binds more strongly to the inner DRs than to the outer DRs. 3) Two DRs are necessary for transposition. 4) The inner DR is rarely if ever an effective site for cleavage leading to transposition. 5) The spacing between the DRs appears to be important; deletions from the left, middle or right end of the inter-DR spacer blocked transposition.

These findings led to considering models (FIG. 8) for transposition by the SB transposase. Tc1/mariner transposons are presumed to interact in order to synapse and bring their termini together for recombination into an acceptor site. The models in panel A show three possible geometries for two SB transposase molecules to associate with each other. The Cis model is unlikely because it does not juxtapose the two ends of the transposon for insertion into a new site. Both of the Trans models allow for cooperative interactions between two transposases bound at each ITR. The inner DRs to which SB transposase binds with high affinity would anchor the recombinase-complexes on the transposon. In the studies with N123 peptide, cooperative binding was never seen, but when full length SB transposase was used, high molecular weight associations of protein plus ITRs were formed, indicative of networking of ITRs held together by SB transposase molecules. The Trans-crossed configuration would draw the two ends of the transposon together in the same manner as that thought to occur for Mu transposase-mediated transposition (Aldaz et al., *Cell*, 1996; 85:257-269; Savilahti et al., *Cell*, 1996; 85:271-280). The bacterial transposon Mu also has two transposase binding sites in each ITR and transposase molecules can interact with each other (Baker et al., *Cell*, 1993; 74:723-733). Both Trans models predict that high expression of SB transposase will be inhibitory, which is observed.

Figure 8A:
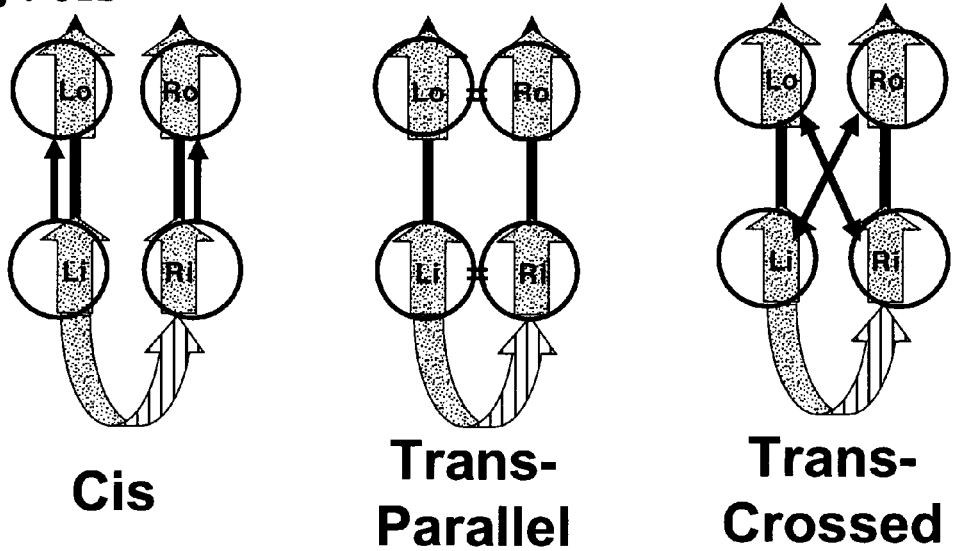
FIG. 8. Proposed models of the transposition complex mediated by Sleeping Beauty transposase. (A) The transposon is shown as an U-shaped DNA with ITRs composed of DRo's (Lo and Ro) and DRi's (Li and Ri). The cargo sequence in the transposon is illustrated by the hatched ribbon arrows. In the Cis model, the narrow black arrows show the association of two SB transposase molecules (circles) bound to the same ITR. In the Trans-Parallel and Trans-Crossed models, an SB transposase associate with another SB molecule only when it is on another ITR. The associations are shown by=signs (Trans-Parallel) and by arrows (Trans-Crossed). The Trans-Crossed model is based on that for Mu transposase (Williams et al., "Organization and dynamics of the Mu transpososome: recombination by communication between two active sites," *Genes Dev.*, 1999; 13: 2725-2737). (B) Possible associations of SB transposase for the LoLoLi-RiRo transposon in either the Trans-Parallel configuration [(1) and (2)] or the Trans-Crossed configuration [(3) and (4)]. In the figures, the heavy black bar in front of the inside Lo sequence represents the absence of a flanking TA dinucleotide basepairs. (C) Possible associations of SB transposase for the LiLoLi-RiRo transposon, as in panel B.
Figure 8B:
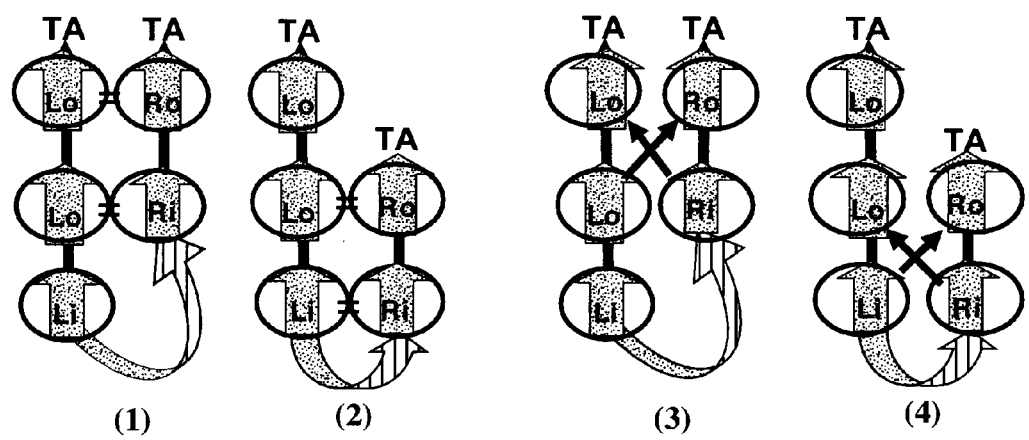

The Trans-crossed model in FIG. 8 has further support from the apparent necessity for a rather large separation between the DRs on each ITR, seen in the deletion experiments with the Lo($\Delta$X)Li-RiRo (where $\Delta$X are the deletions of left, middle or right portions of the inter-DR spacer in the left ITR) as well as with 50-bp deletions in both the left middle and right middle ITRs (FIGS. 3 and 4). Looping of the inter-DR sequence between transposases bound in the Cis model, as occurs with DNA sequences bound by other interacting DNA binding molecules (Schleif, *Science*, 1988; 240:127-128), needs far less than the 165-166 bp that appear to be required for transposition. The same argument holds for the Trans-parallel model. On the other hand, the Trans-crossed association shown in FIG. 8 could require greater spacing than the cis configuration. Whether longer spacers between the DRs also altered transposition rates was not investigated directly. Further experiments are needed to resolve the actual geometry of the SB transposase interactions. The data do however show that the interactions of the four presumed transposase molecules that bind to the four DR sites in the flanks of the transposons are complex.

Figure 8C:
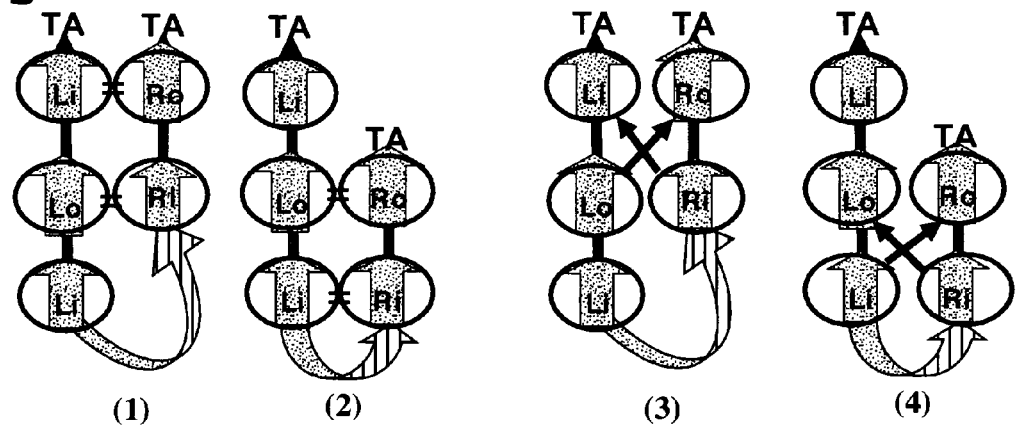

Panels B and C of FIG. 8 demonstrate alternative associations of SB transposase in the Trans models. These models can be used to demonstrate the internal consistency of these findings and account quantitatively for the reductions in transposition of transposons with three DRs in their ITR-Ls if both configurations (1) and (2) (or 3 and 4) occur with equal frequency. In both panels, configurations (1) and (2) apply to the Trans-parallel model and cases (3) and (4) apply to the Trans-crossed model. The data in FIG. 4 (TAN$_4$Lo or TAN$_4$Ro) show that transposition was reduced to about 30% when a flanking TA is missing on one side of a transposon. The data in FIG. 3 show that either Li or Ri cannot measurably act as a cleavage site for transposition, even when a flanking TA is present, and that LoLo-RiRo transposons are about 50% efficient. Accordingly, these data would predict that for the LoLoLi-RiRo transposon, arrangements (1) or (3) would be predicted to have 50% efficiency and configurations (2) or (4) would have 30% efficiency. The sum would be a transposition rate of about 40% [(50%×50%)+(50%×30%)], which is what is observed for LoLoLi-RiRo (FIG. 3). Likewise, for the LiLoLi-RiRo transposon shown in FIG. 8C, arrangements (1) or (3) would be predicted to have 0% efficiency because of Li blocking transposition and configurations (2) or (4) would have 30% efficiency. For LiLoLi-RiRo the sum would be about 15% [(50%×0%)+(50%×30%)], which is what is observed (FIG. 3).

Besides elucidating the mechanics of SB-mediated transposition, more investigations are needed to improve activities of the transposon. The results with the TAN$_4$Lo, TAN$_4$Ro and TAN$_4$Lo/Ro constructs as well as the duplicated TA constructs (FIG. 5) indicate that the flanking sequences play a role in excision and subsequent translocation of the transposon. Hints that flanking sequences might play a role were seen in the remobilization studies in mice and cell culture (Luo et al., *Proc. Natl. Acad. Sci. USA*, 1998; 95:10769-10773; Izsvák et al., *J. Mol. Biol.*, 2000; 302:93-102; Dupuy et al., *Genesis*, 2001; 30:82-88). These results point to a need to determine the effects of flanking sequences on both excision of the transposon as well as selection of new entry sites, which can be influenced by sequence flanking the TA target site in nematodes (Ketting et al., *Nucl. Acids Res.*, 1997; 25:4041-4047). Improvement of the activity of the transposase itself and its requirements for transposition, similar to that obtained for the Himr1 mariner transposase (Lampe et al., *Genetics*, 1998; 149:179-187; Lampe et al., *Proc. Natl. Acad. Sci. USA*, 1999; 96:11428-11433), has been initiated.

Example 2

Excision of Sleeping Beauty Transposons:
Parameters and Applications to Gene Therapy This example discloses the development of a plasmid-based excision assay for the SB transposon system to study the different steps of transposition in more detail. Using this assay, the footprints of SB in tissue cultured cells as well as in zebrafish embryos and mice were analyzed. The results of these studies directed design of a better transposon as well as led to the development of a method for determining transposition from a plasmid in organs of mice.

Materials and Methods

Figure 9A:
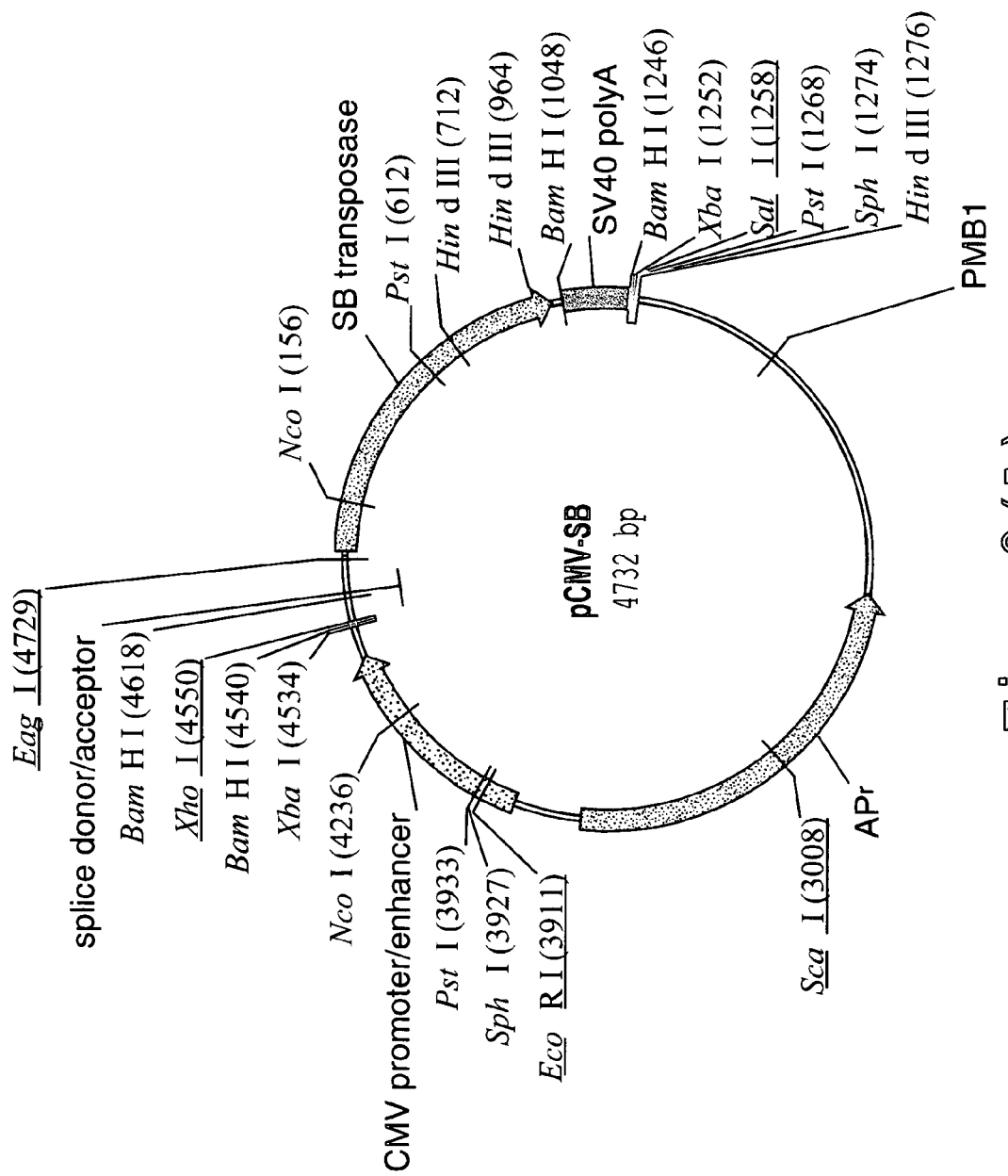
FIG. 9. The maps and nucleotide sequences for plasmids pCMV/SB (SEQ ID NO:8), pCMV/SB-DDE (SEQ ID NO:9), pT/SVneo (SEQ ID NO:10), pT/HindIIIneo (SEQ ID NO:11) and pFV3CAT (SEQ ID NO:12).
Figure 9D:
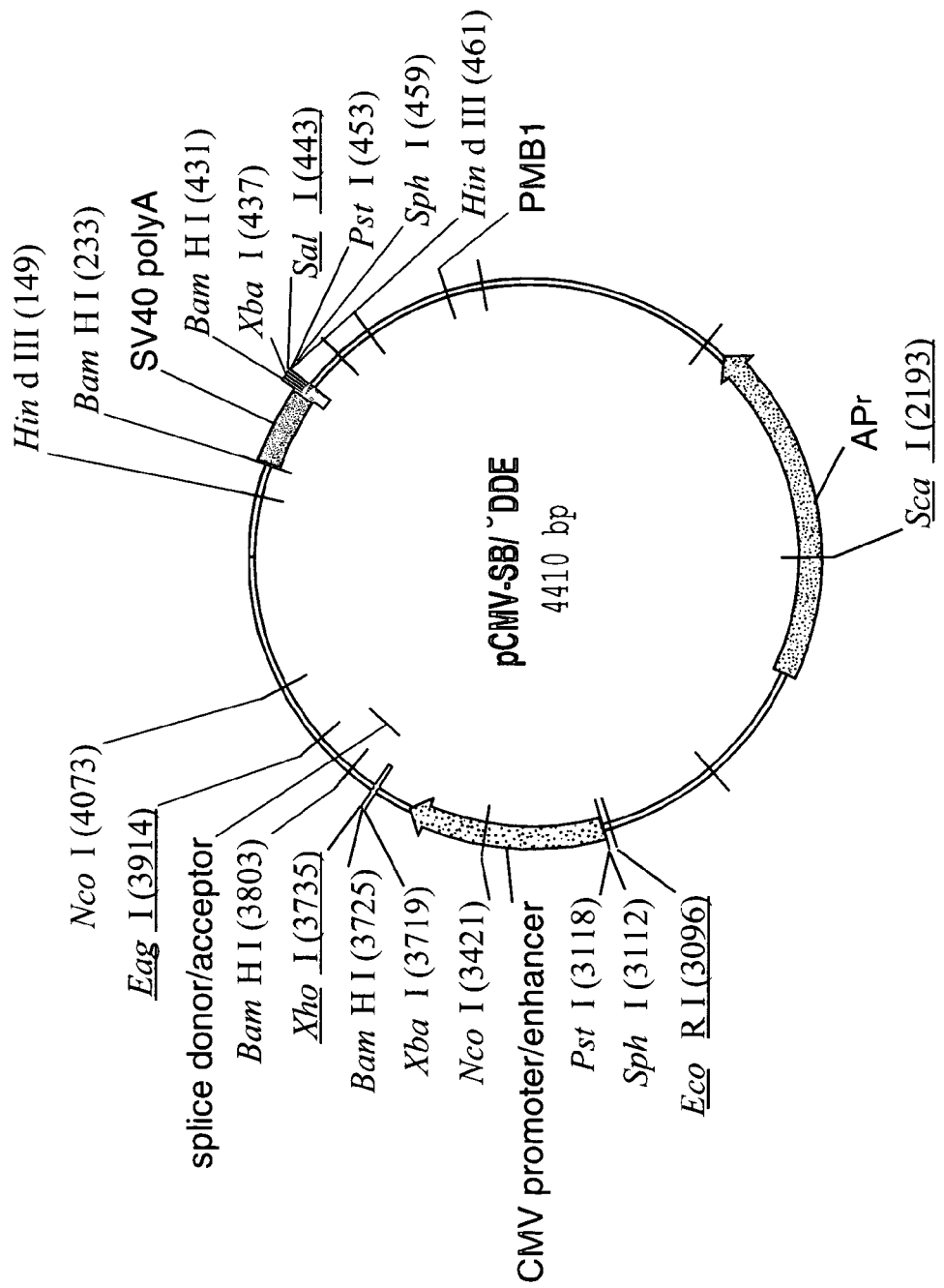
Figure 9G:
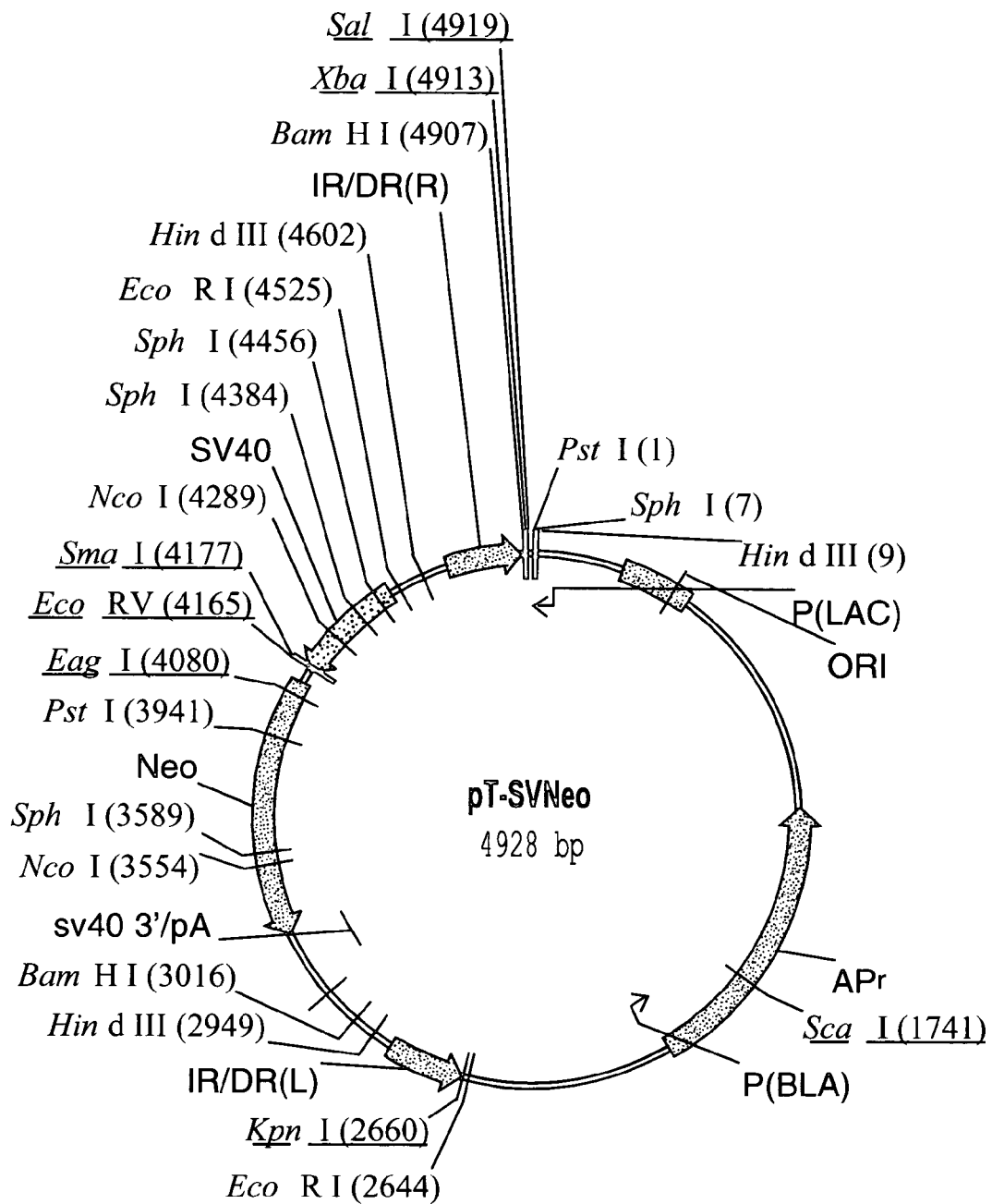
Figure 9:
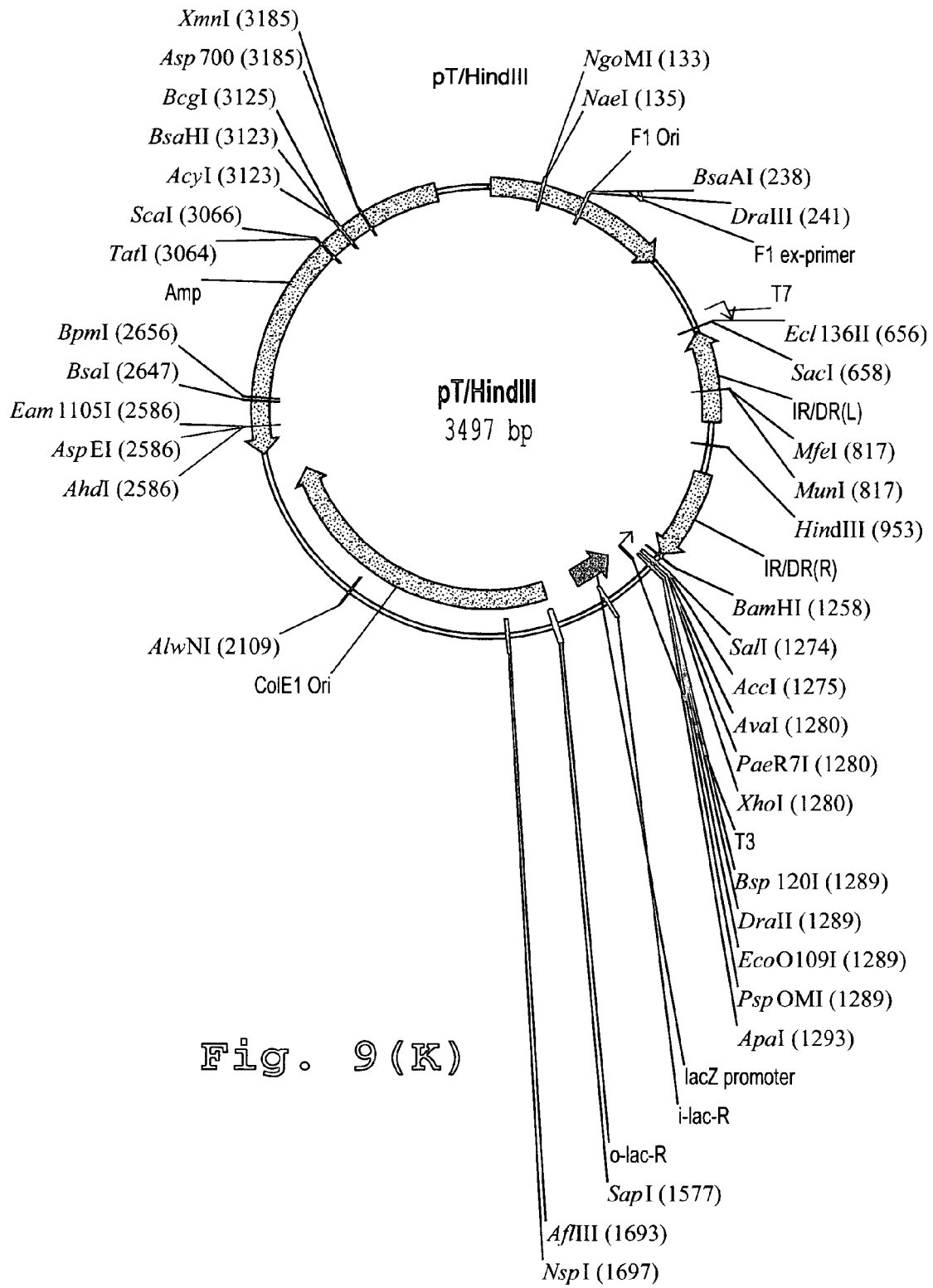
Figure 9N:
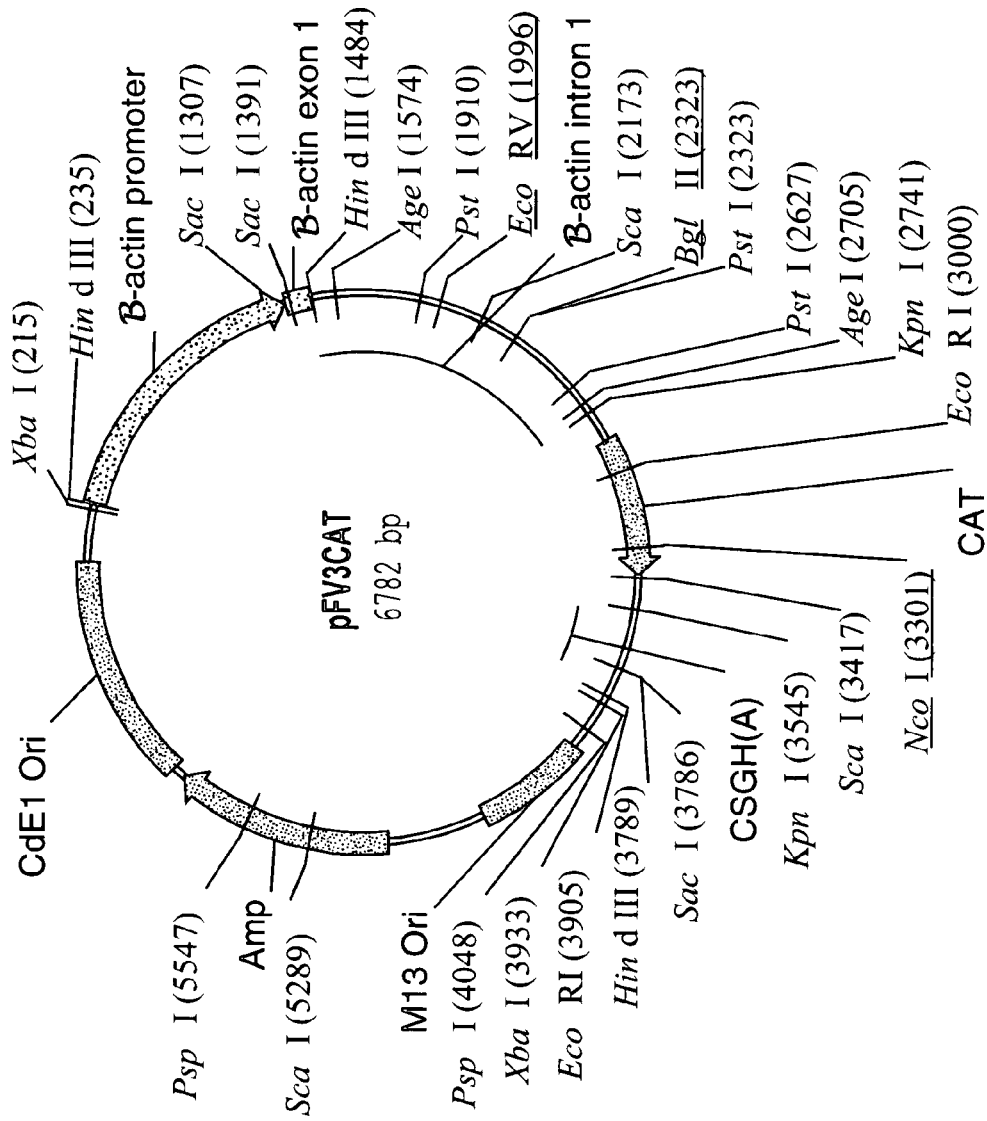

The maps and sequences for plasmids pSB10 (also referred to as pCMV/SB) and pSB10-$\Delta$DDE (also referred to as pCMV/SB-DDE), which contain an active and inactive transposase gene, respectively, and pT/neo (also referred to as pT/SVneo) which contains a transposon (Ivics et al., *Cell*, 1997; 91:501-510) as well as pT/HindIIIneo are disclosed at FIG. 9. pT/HindIIIneo variants are named by the DRs that are in their left and right IRs. All variant pT/HindIIIneo constructs were made by PCR-mediated, site-directed mutagenesis described previously for LoLiLiLo, RoRiRiRo, LiLiRiRo and LoLoRiRo (Cui et al., *J. Mol. Biol.*, 2002; 318:1221-1235). Mutagenic primers SacI+Lo and BamHI+Ro were used to amplify complete variant transposons on pT/HindIIIneo. After digesting with SacI and BamHI, the PCR fragments were ligated into the SacI/BamHI vector fragment of pT/HindIIIneo. All constructs were confirmed by sequencing.

Mutagenic primers we used are listed below with specific mutations underlined:

```
SacI+ Lo(AAA):
TTGGAGCTCGGTACCCTAAAATTGAAGTC      (SEQ ID NO: 35)

SacI+ Lo(CAA):
TTGGAGCTCGGTACCCTACAATTGAAGTC      (SEQ ID NO: 36)

SacI+ Lo(AAG):
TTGGAGCTCGGTACCCTAAAGTTGAAGTC      (SEQ ID NO: 37)
```

```
BamHI+ Ro(AAA):
AGCTAGAGGATCCCCTAAAATTGAAGTCG    (SEQ ID NO: 38)

BamHI+ Ro(CAA):
AGCTAGAGGATCCCCTACAATTGAAGTCG    (SEQ ID NO: 39)

BamHI+ Ro(AAG):
AGCTAGAGGATCCCCTAAAGTTGAAGTCG    (SEQ ID NO: 40)

BamHI+ Ro(CC):
AGCTAGAGGATCCCCCCCAGTTGAAGTCG    (SEQ ID NO: 41)

SacI+ Lo(GG):
TTGGAGCTCGGTACCCGGCAGTTGAAGTC    (SEQ ID NO: 42)
```

Plasmid-based Excision Analysis

Excision in HeLa cells: 500 ng pT/neo or pT/HindIIIneo mutation constructs were co-transfected with 100 ng pSB10 (or pSB10-ΔDDE) into 3×10$^5$ HeLa cells. Four days post-transfection, cells were collected and lysed in 200 ml lysis buffer [50 mM KCl, 10 mM Tris-HCl (pH8.3), 2.5 mM MgCl$_2$, 10 mM EDTA, 0.45% (w:v) NP40, 0.45% (w:v) Tween-20, 100 μg/ml Proteinase K] and incubated at 55° C. for two to three hours followed by 95° C. for 20 minutes to inactivate the Proteinase K. For temporal analyses, 5 μl of lysate was added to the PCR mixture [1×NH$_4$ PCR buffer, 3 mM MgC12, 0.2 mM dNTP, 10 pmol forward and reverse primer each, 0.5 μl Biolase, buffer and enzyme from Bioline USA]. The PCR conditions were as follows: 94° C. for 5 minutes, 60 cycles of (94° C. 30 seconds, 64° C. 30 seconds, 72° C. 20 seconds), followed by 72° C. for 10 minutes. 5 μl of 1/50 dilution of the above PCR product was used for the second round PCR using nested primers and 1.5 mM MgCl$_2$; the composition of the PCR mixture was otherwise the same. Nested PCR was performed in 94° C. for 5 minutes, 35 cycles of (94° C. 30 seconds, 64° C. 30 seconds, 72° C. 5 seconds), followed by 72° C. for 10 minutes. For pT/neo, only one round of PCR was performed and gave products of about 582 bp. Primers were: o-lac-L: 5'-GGCTGGCTTAACTATGCG-GCATCAG (SEQ ID NO:43), o-lac-R: 5'-GTCAGTGAGC-GAGGAAGCGGAAGAG (SEQ ID NO:44). For pT/HindII-Ineo and its mutation constructs, nested PCR gave products of about 316 bp. Primers were: 1st round: F1-ex: 5'-CCAAACTGGAACAACACTCAACCCTATCTC (SEQ ID NO:45), o-lac-R: 5'-GTCAGTGAGCGAGGAAGCG-GAAGAG (SEQ ID NO:46). 2nd round: KJC031: 5'-CGAT-TAAGTTGGGTAACGCCAGGGTTT (SEQ ID NO:47), i-lac-R: 5'-AGCTCACTCATTAGGCACCCCAGGC (SEQ ID NO:48).

Excision in zebrafish embryos: 25 ng/μl pT/neo was co-injected with 25 ng/μl SB mRNA into one-cell stage zebrafish embryos. SB transposase mRNA was synthesized by in vitro transcription using mMessage mMachine Large Scale in vitro Transcription Kit (Ambion). The injection volume for each embryo was 1-3 nl. 24 hours after injection, single embryos were lysed in 50 μl lysis buffer [10 mM EDTA, 10 mM Tris-HCl (PH8.0), 200 μg/ml Proteinase K] as in (Kawakami et al., Gene, 1998; 225:17-22; Kawakami et al., Gene, 1999; 240:239-244) for 3 hours at 50° C., followed by 20 minutes incubation in 95° C. to inactivate the Proteinase K. 2 μl of embryo lysate was used for PCR. The program used for PCR was as follows: 94° C. 5 minutes, 30 cycles of (94° C. 30 seconds, 67° C. 30 seconds), 25 cycles of (94° C. 30 seconds, 67° C. 30 seconds, 72° C. 5 seconds) followed by 72° C. for 10 minutes.

Excision in mouse liver: DNA was isolated from 8 mm$^3$ frozen liver specimens using Puregene DNA purification kit (Gentra Systems, Minneapolis, Minn.). PCR was performed in 2 rounds of amplification. PCR I was carried out in a 50-μl reaction mixture containing 1 DNA, 5% DMSO, 5% glycerol, 10 pmol each forward and reverse primer, a 0.2 mM concentration of each dNTP, 1×PCR buffer A (Invitrogen, Carlsbad, Wis.), and 5U Taq DNA polymerase (Promega, Madison, Wis.). PCR conditions were: 95° C. for 5 minutes followed by 45 cycles of 95° C. for 40 seconds, 58° C. for 30 seconds and 72° C. for 1 minute with the final extension of 5 minutes at 72° C. A 10 μl aliquot of the primary PCR product was used for secondary amplification in a 100-ml reaction with nested primers (10 μm concentration) and the same cycling conditions except that the number of cycles was 35. The amplicons were analyzed by electrophoresis of 8-μl aliquots in a 2% agarose gel containing ethidium bromide (0.5 μg/ml) and visualized in UV light. The expected size of the amplified excision product was approximately 456 bp. The primers used for the excision assay were outside left and right ITRs. The primer sequences were: FP1: 5'-TGACGTTGGAGTC-CACGTTC (SEQ ID NO:188), RP1: 5'-GGCTCGTATGT-TGTGTGG (SEQ ID NO:49), FP2: 5'-CTGGAACAA-CACTCAACCCT (SEQ ID NO:50), and RP2: 5'-CACACAGGAAACAGCTATGA (SEQ ID NO:51).

Detection and Quantification of the PCR Product

The excision PCR products were separated on 3% low-melt gels (GenePure Sieve GQA agarose, ISC Bioexpress) and stained with 50 μg/ml ethidium bromide. For better resolution and quantification, PCR products were separated on 6% polyacrylamide gels and stained with 1:10,000 dilution of SYBR green I (Molecular Probes, Inc.) for 45 minutes. The gels were scanned with Storm Phosphor Imager (Molecular Dynamics) at 850V in the blue fluorescence mode to visualize the bands. To standardize the input total plasmid DNA for each PCR, a 1/5000 dilution of initial lysate was used to amplify a segment of the ampicillin-resistance gene on both pSB10 and pT/neo. These products were separated on 1% agarose gel and stained with 50 μg/ml ethidium bromide.

Relative excision abundance was measured as a ratio of the band intensity of the excision PCR products to that of the ampicillin segment. The excision activity is indicated as a percentage of the excision activity of the control transposon pT/HindIIIneo, for which a standard curve derived from the ratio of the different dilutions of the transposon was constructed.

The intensity of each band was measured using Gel-Pro analyzer imaging software (Media Cybernetics). The background was corrected using the Filtered Profile method, as instructed by the manufacturer.

Footprint Sequencing

To sequence the footprint, the PCR products were gel-extracted (for mutations with low excision activity, reamplified with the nested PCR), cloned into the TOPO TA cloning vector (Invitrogen) and sequenced by the Advanced Genetics Analysis Center at the University of Minnesota.

Transposon Delivery to Mouse Livers:

The transposon-containing plasmid pT/CAGGS-GUSB (transposon) and the transposase-expressing plasmid pSB10 were used to assay transposition in adult mouse tissues. The transposon contains an expression cassette for the GUSB gene to restore activity to mutant mice deficient in b-glucuronidase activity. The mucopolysaccharidosis (MPS) type VII mice (B6.C-H-2bml/ByBir-gus$^{mps}$) were obtained from Jackson Laboratories (Bar Harbor, Me.) and maintained in the AAALAC-accredited Specific Pathogen-Free mouse facility at the University of Minnesota. The plasmids were injected into the tail vein of homozygous 12-16-wk old MPS VII mice using a 3-ml latex-free syringe with a 27½ G needle. The hydrodynamics-based procedure was performed as described (Liu et al., Gene Ther., 1999; 6:1258-1266; Zhang et al., Hum. Gene Ther., 1999; 10:1735-1737). Each mouse received plasmid DNA in lactated Ringer's solution in a total volume equal to 10% of body weight. 25 μg of a single preparation of transposon pT/CAGGS-GUSB was injected either alone (Treatment Group 1), or with pSB10 at 10:1 transposon to transposase molar ratio (Treatment Group 2). 37.5 μg DNA was injected into all mice with pBluescript plasmid as a "filler"; the sham treatment control group of MPS VII mice was injected with pBluescript alone. All injections were performed only once. The mice were euthanized one-week post-injection, livers were harvested and frozen at −80° C. Excision assays were done as described above.

Results

Assay for the Excision Step of Transposition

The SB transposon system consists of two parts—the transposon, consisting of inverted terminal repeats and the SB transposase that catalyzes the mobilization of the transposon. Like other members of the Tc1/mariner transposon family, SB transposons are mobilized via a cut-and-paste mechanism (FIG. 10A). There are two major steps involved in transposition, the excision of the transposon from the donor site and the integration of the transposon into the target site (Plasterk et al., *Trends Genet.*, 1999; 15:326-332). Excision from the donor site involves staggered, double-stranded DNA breaks at each side of the transposon, which result in a small number of nucleotides at the termini of the transposon being left behind (Plasterk et al., *Trends Genet.*, 1999; 15:326-332; Luo et al., "Chromosomal transposition of a Tc1/mariner-like element in mouse embryonic stem cells," *Proc. Natl. Acad. Sci. USA*, 1998; 95:10769-10773). The majority of Tc1/mariner transposons integrate into TA-dinucleotide basepairs in a fairly random manner (Dupuy et al., *Proc. Nail. Acad. Sci. USA*, 2002; 99:4495-4499; Vigdal et al., *J. Mol. Biol.*, 2002; 323:441-452). As a result of the staggered cut at the TA target sites, the transposons are flanked by TA-dinucleotides on both sides after integration (FIG. 10B), a phenomenon called target-site duplication (Plasterk et al., *Trends Genet.*, 1999; 15:326-332; Ivics et al., *Cell*, 1997; 91:501-510).

The inverted terminal repeats of the current SB transposon came from a single Tc1-like element from a salmonid, *Tanichthys albonuibes*—referred to as T. T has two inverted repeats (IRs) at its termini and two "direct repeats" (DRs) within each IR (FIG. 10A). The outer DRs, Lo and Ro, are located at the left and right termini of the transposon, respectively, and the inner DRs, Li and Ri, are located further inside the transposon. Both DRs contain binding sites for SB transposase (Ivics et al., *Cell*, 1997; 91:501-510) and the middle 18-bp within the DRs have been suggested to comprise a minimal core sequence for transposase-binding (Cui et al., *J. Mol. Biol.*, 2002; 318:1221-1235). Both the outer and inner DRs are required for efficient transposition (Ivics et al., *Cell*, 1997; 91:501-510), but they are not interchangeable, indicating that their roles in transposition are different (Cui et al., *J. Mol. Biol*, 2002; 318:1221-1235).

PCR-based excision analysis has been used to detect excision from a chromosomal location by SB transposase (Fischer et al., *Proc. Natl Acad. Sci. USA*, 2001; 98:6759-6764; Horie et al., *Proc. Natl Acad. Sci. USA*, 2001; 98:9191-9196; Dupuy et al., *Proc. Natl. Acad. Sci. USA*, 2002; 99:4495-4499; Luo et al., Proc. Natl. Acad. Sci. USA, 1998; 95:10769-10773). However, this method is not suitable for studying the mechanism of transposition because the excision is limited to a particular transposon and a particular donor site in the chromosomal position. Plasmid-based excision assays, on the other hand, are more versatile and easier to perform (Kawakami et al., *Gene*, 1998; 225: 17-22; Kawakami et al., *Gene*, 1999; 240:239-244). Here, a plasmid-based excision assay was developed for the Sleeping Beauty transposon system in HeLa cells and zebrafish embryos to both study the mechanisms of transposition as well as to evaluate gene transfer in whole animals.

Figure 11:
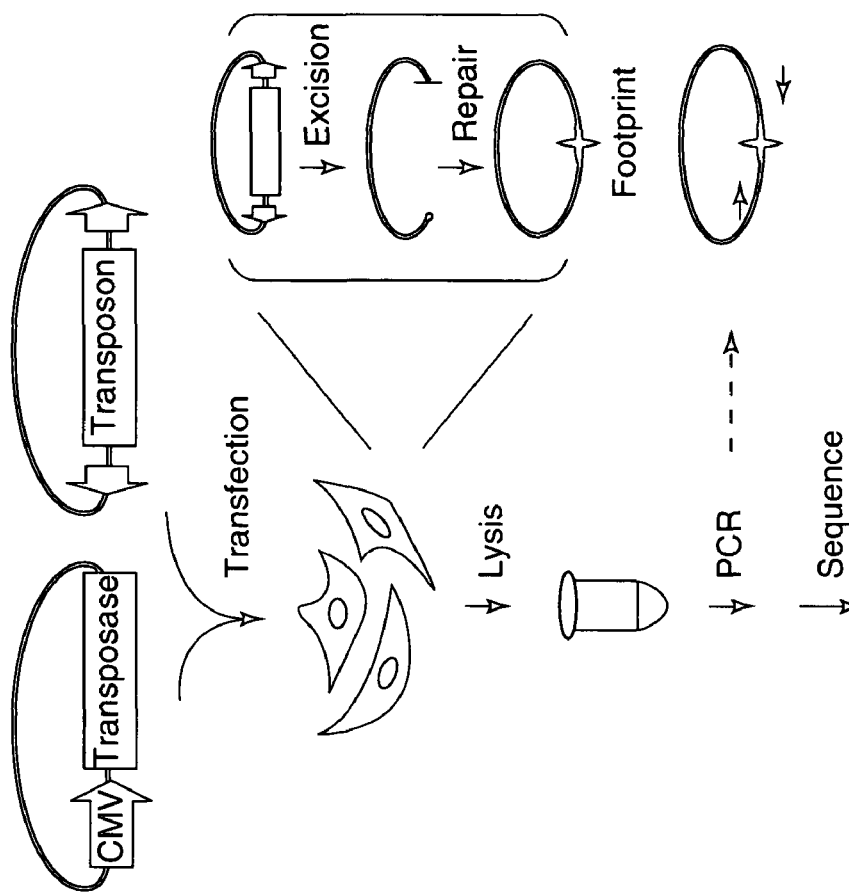
FIG. 11. Schematic of the excision assay. Plasmids containing a transposon and SB10 transposase were co-transfected into HeLa cells. Four days post-transfection, cell lysates were obtained and used for PCR with primers flanking the donor sites. The PCR products were sequenced to determine the footprints of the excision. The procedure is shown on the left and the state of the transposon and its excision product are shown on the right.
Figure 12A:
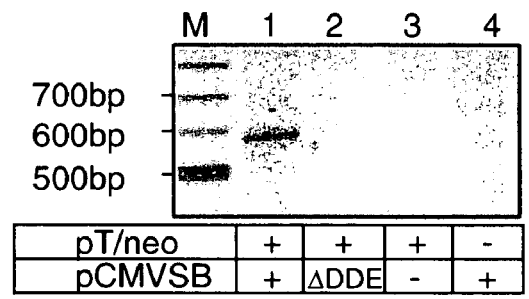
FIG. 12. PCR analysis of transposon excision from plasmids in HeLa cells (A and B) and in zebrafish embryos (C). (A) Plasmids with transposons and SB10 transposase (pT/neo and pSB10) were cotransfected into the HeLa cells. Cell lysate was obtained for nested-PCR using primers outside the transposon. The marker lane (M) on the left of the gels in panels A and C is a 100 bp ladder (New England Biolabs). A band of approximately 582-bp was amplified only when both pT/neo and pSB10 were present. DDDE is a transposase without a catalytic domain. (B) Time course accumulation of excision products from HeLa cells. Hours post-transfection are marked on top of the gel. Each time point is represented by two separate transfections. (C) SB mRNA was co-injected into one-cell stage zebrafish embryos with plasmids containing a transposon (pT/neo). 24 hrs after microinjection, lysates from single embryos were used for PCR analysis. Two different embryos were used in the last three categories. *: pT/neo plasmids mixed with embryo lysate were used as template in this case.
Figure 12B:
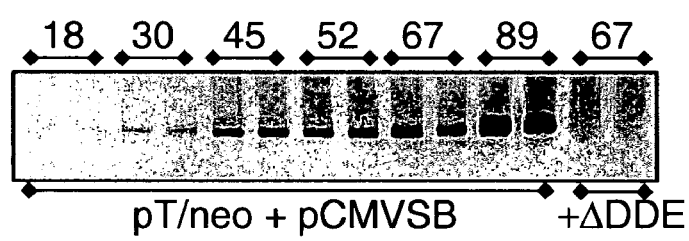
Figure 12C:
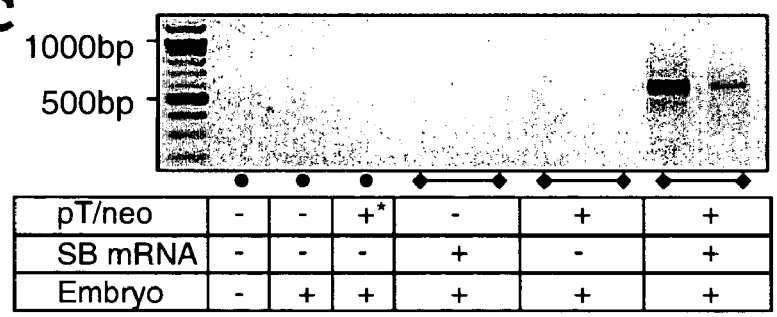

We developed and used the excision assay first in HeLa cells where we co-transfected the transposon plasmid pT/neo and the transposase-expressing plasmid pSB10 (FIG. 11). Three days after transfection, the plasmids in the cell lysate were used as templates for PCR. Using primers flanking the donor sites, we detected excision by amplifying a PCR product that corresponded to the size of a rejoined vector after the excision of the transposon. As shown in FIG. 12A, a PCR product of approximately 582-bp was amplified in cell lysates from a pSB10 and pT/neo co-transfection. The PCR product appeared to be specific to SB excision because neither pSB10-ΔDDE, which has a mutated catalytic domain, the transposon plasmids alone, nor the transposase plasmids alone produced the 582-bp product. FIG. 12B shows the accumulation of the excision products over several days. Excision products were detectable 18 hours after transfection and their levels continued to rise through 89 hours after transfection. In subsequent experiments, we collected samples at 72 hours for quantification of excision events under different conditions. FIG. 12C shows the same excision assay carried out in zebrafish embryos. We co-injected transposon plasmids and SB mRNA as the source of the transposase. Extracts of 24-hr embryos were used for analysis of excision by PCR. As with the cell cultures, excision was evident only in the presence of SB transposase, which supports our previous preliminary findings (Dupuy et al., *Proc. Natl. Acad. Sci. USA*, 2002; 99:4495-4499).

Footprints of SB Excision

We cloned and sequenced the excision PCR products to study the footprints left by the transposons. Table 2 shows the summary of the footprint sequences acquired from HeLa cells and zebrafish embryos. The two flanking sides of the transposon had footprints of varying lengths that we categorized in one of three ways-canonical footprint, non-canonical footprint, gap/insertion. Canonical footprints had 3-bp insertions (CAG or CTG) between the two flanking TAs that conform to the standard model (FIG. 10B). Non-canonical footprints had 0-bp to 3-bp deletions from the canonical footprint. Gaps had large deletions (17-bp to 89-bp) on either or both sides of the flanking sequences. In one case, we observed a 20-bp insertion of unknown origin between the two flanking sites. Most of the footprints in zebrafish embryos were canonical footprints, whereas the footprints in HeLa cells consisted of similar percentages of canonical and non-canonical footprints. This raises the question as to whether the differences in the footprint patterns were due to the different cell types, which we address later.

TABLE 2

Footprint sequences from HeLa cells and zebrafish embryos

| Systems | Category | Left-flanking | Footprint | Right-flanking | Events |
| --- | --- | --- | --- | --- | --- |
| HeLa cells | Complete footprints | TTCGAGCTCGGTACCC | TA CAG TA | GGGGATCCTCTAGAGT | 4 |
| | | TTCGAGCTCGGTACCC | TA CTG TA | GGGGATCCTCTAGAGT | 2 |
| | | TTCGAGCTCGGTACCC | T- --G TA | GGGGATCCTCTAGAGT | 3 |
| | | TTCGAGCTCGGTACCC | TA --- TA | GGGGATCCTCTAGAGT | 2 |

TABLE 2-continued

Footprint sequences from HeLa cells and zebrafish embryos

| Systems | Category | Left-flanking | Footprint | Right-flanking | Events |
|---|---|---|---|---|---|
| | Incomplete footprints | TTCGAGCTCGGTACCC TA | C-- TA | GGGGATCCTCTAGAGT | 1 |
| | | TTCGAGCTCGGTACCC T- | -TG TA | GGGGATCCTCTAGAGT | 1 |
| | | TTCGAGCTCGGTACCC TA | C-- -A | GGGGATCCTCTAGAGT | 1 |
| | Gaps | (82-bp deletion) -- | --G TA | GGGGATCCTCTAGAGT | 1 |
| | | (67-bp deletion) -- | --- -- | (89bp deletion) | 1 |
| | Insertions | TTCGAGCT | TGCATGTGGGAGGTTTTTC | GGATCCTCTANAGT | 1 |
| Zebrafish embryos | Complete footprints | TTCGAGCTCGGTACCC TA | CTG TA | GGGGATCCTCTAGAGT | 5 |
| | | TTCCAACNCGGTACCC TA | CAG TA | GGGAATCCTCTAGAGT | 4 |
| | Gaps/ Insertions | (17bp deletion) -- | --- -- | (19bp deletion) | 1 |

The excision sites were sequenced by using primers outside the transposon. Short lines indicate the lost nucleotides.

Excision Rate Correlates to Transposition Rate

Figure 13:
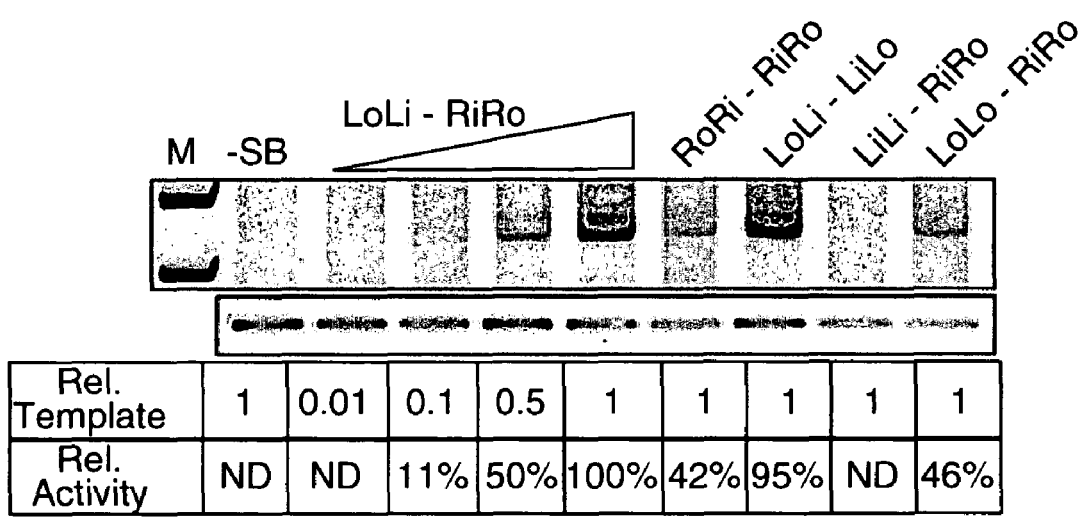
FIG. 13. Comparison of excision and transposition rates. Excision levels of four IR/DR mutations were measured relative to the activity of LoLi-RiRo (the pT/HindIIIneo transposon). The top gel shows excision PCR products run on a 6% polyacrylamide gel stained by SYBR green I. The lower gel shows PCR amplification of a segment of the backbone of pT/neo and pSB10 (or pSB10-ΔDDDE) as an input control for the total plasmid in the lysate. They were run on 1% agarose gel stained with ethidium bromide. The relative excision abundance is measured as a ratio of the band intensity of the excision PCR products to that of the amplification of the segment on the plasmid backbone. "Rel. template" indicates the relative amount of the input lysate. Relative excision activity ("Rel. activity") is indicated as a percentage of control activity using the ratio for each mutation compared to a standard curve derived from the ratio of the different dilutions of the original pT/HindIIIneo activity. ND indicates non-detectable. The triangle immediately above the gel indicates the increasing concentration of the standard LoLiRiRo transposon to establish a standard curve.

A preliminary study suggested that excision rates correlate to transposition rates (Cui et al., *J Mol Biol*., 2002; 318:1221-1235). We examined this hypothesis by measuring the excision rates of IR/DR mutations shown to have different transposition rates to evaluate its validity. To quantify the levels of excision, we generated a set of standards using dilutions of the excision lysate of the original pT/HindIIIneo. In addition, we used the amplification of a segment in the backbone of the plasmid as the control for total input plasmid. The relative excision activity was calculated as a percentage of the pT/HindIIIneo activity. FIG. 13 shows one example of a gel scan and the quantification of the excision footprints. We compared these excision rates with the earlier reported transposition rates measured by a transposition assay (Cui et al., *J. Mol. Biol*., 2002; 318:1221-1235). In this assay, transposon-mediated chromosome integration was indicated by the increase in the number of G418-resistant colonies, and the transposition rate was measured as the percentage of the pT/HindIIIneo activity. The comparisons of the rates of transposition and excision are summarized in Table 3. Mutations with high excision rates correlated with high transposition rates and mutations with low excision rates correlated with low transposition rates. Although transposition rates varied between parallel experiments, the excision rates approximated transposition rates within the range of the standard deviations. We conclude that excision can be used as an indicator of transposition efficiency.

TABLE 3

Comparison of excision and transposition rates

| Constructs | Excision rate | Transposition rate |
|---|---|---|
| LoLiRiRo + ΔDDE | nd | bg |
| LoLiRiRo | 100% | 100% (+/− 25%) |
| RoRiRiRo | 43% | 29% (+/− 7%) |
| LoLiLiLo | 95% | 101% (+/− 31%) |
| LiLiRiRo | nd | bg |
| LoLoRiRo | 46% | 45% (+/− 33%) |

The excision rate is as measured in FIG. 4. nd, non-detectable. The transposition rate is from Cui et al., 2002. Numbers are averages of four to seven independent transfections +/− standard deviation. bg, background due to random integration. LoLiRiRo is our standard transposon, pT/HindIIIneo.

Use of the Excision Assay to Improve the SB Transposon System

Figure 14A:
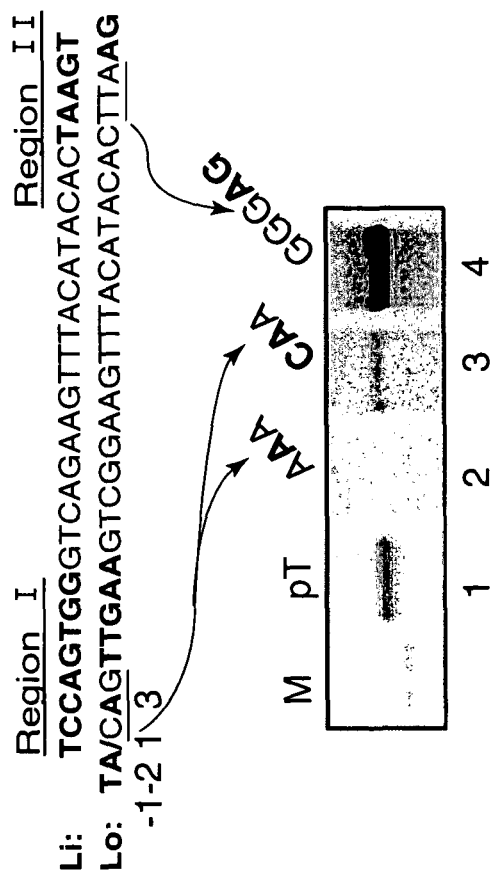
FIG. 14. Terminal nucleotides in the outer DRs are important for excision. (A) Sequence comparison of Lo and Li. Two regions of sequence divergence are marked: Region I and Region II. Mutations made in these two regions are underlined. Different levels of excision are seen as compared to the original pT/HindIIIneo activity. (B) Analysis of the first and third positions at the tip of Lo. Mutations are underlined. Lo(CAG)Li-Ri(CTG)Ro indicates the pT/HindIIIneo transposon. Quantification of the excision activity is as described in FIG. 13. The triangle immediately above the gel indicates the decreasing concentration of the mutated transposon Lo(S1-3)LiRiRo(S1-3).

The outer DRs and inner DRs have different roles in excision and transposon can be excised efficiently only at the outer DRs (Cui et al., *J. Mol. Biol*, 2002; 318:1221-1235). These results suggested that it is not the location but the differences in sequence between Lo and Li that gives them different functional roles. Comparison of the Lo and Li sequences showed that there are two discrete regions in Lo that are different from Li, Region I and Region II (FIG. 14A). To determine which region is critical for excision, we made mutations in each and tested whether excision activity was impaired.

Figure 14B:
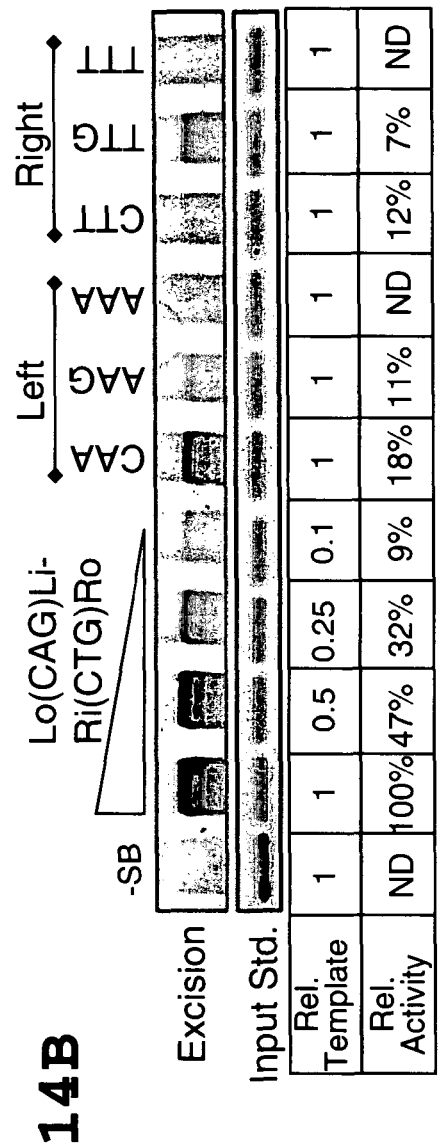

Two positions in Region I were analyzed because the model in FIG. 10 predicts that the C in the first position (C1) and the G in the third position (G3) at the tip of Lo demarcate the staggered cuts. These positions, which are the same on the left and right IRs, should thus be vital to the overall interaction between transposon and transposase in this region. If true, changing the nucleotides at these two positions should affect this interaction and cause reduced excision activity. As shown in FIG. 14A, lanes 2 and 3, single nucleotide mutations at position 3 reduced excision activity, and the double mutation at +1 and +3 reduced excision activity below the limit of detection. These data suggest that the nucleotides in the first and the third positions at the termini of the outer DRs in Region I are critical for excision. FIG. 14B shows a more detailed analysis of these two positions. When we changed either C1 or G3 in Lo, excision activity was reduced to 11% and 18%, respectively, indicating that both C1 and G3 contribute to excision activity. The same mutations were made in Ro and the effects were similar, indicating that these positions have the same functions on both sides.

The requirement for Region II was tested by mutating three out of the five terminal basepairs (TTAAG to GGGAG). If the sequence in this region were important for excision, as suggested by Cui et al., *J. Mol. Biol*, 2002; 318:1221-1235, we expected that this mutation would reduce excision activity. Unexpectedly, this mutation in Region II increased excision activity (FIG. 14A, lane 4). This novel finding suggests that the role of this region on excision is influential, rather than being a direct requirement.

TA Dinucleotides Flanking the Transposon Affect Excision

Figures 15A, 15B:
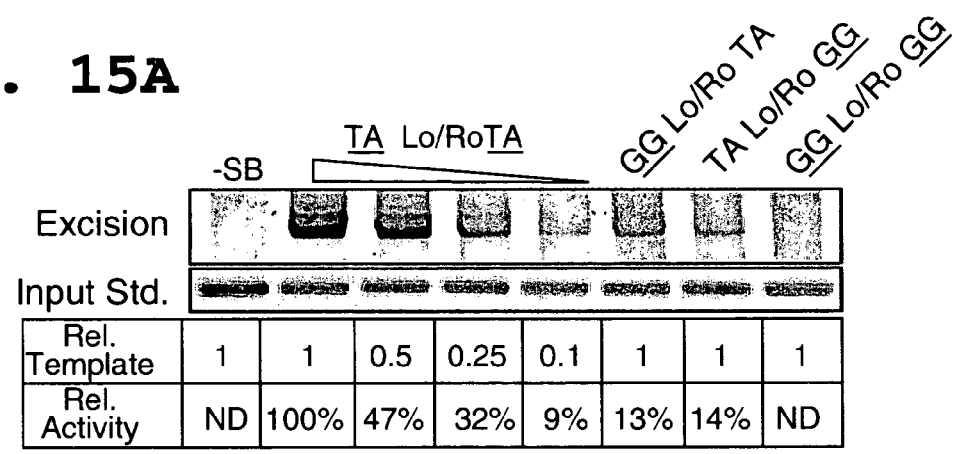
FIG. 15. Effect of TA dinucleotides on excision. (A) Excision analysis of TA mutations on either side and both sides of the transposon. TA Lo/Ro TA indicates the pT/HindIIIneo transposon. Mutations are underlined. The triangle immediately above the gel indicates the decreasing concentration of the standard LoLiRiRo transposon flanked by TA base pairs at each end. (B) Sequences of the excision site of the mutation transposons. The footprints are underlined. The top sequence is SEQ ID NO:112 and the bottom sequence is SEQ ID NO:113.

The TA dinucleotides flanking the transposon are of special interest. SB transposons insert only into TA dinucleotides,

*where a target-site duplication event leads to TA flanks on both sides of the transposon (Plasterk, Curr. Top. Microbiol. Immunol.*, 1996; 204:125-143). This raised the question of whether there is a functional requirement for TA in excision. This question was examined by replacing the TA dinucleotides flanking the transposon. Excision could still occur when only one flanking TA is present, although activity was dramatically reduced. When both TAs were replaced, the excision rate was reduced to below the limit of detection (FIG. 15A). These results show that the TAs flanking the transposon are strongly involved in excision and confirm our earlier finding of their importance in the overall transposition process (Cui et al., *J. Mol. Biol.*, 2002; 318:1221-1235).

We were able to acquire complete footprints from the two mutation constructs lacking TA on one side (FIG. 15B). The footprints showed that when GG replaced the TA outside the outer DR, the substitution remained in the footprints. This supports the current model that the TA nucleotides flanking the transposon are not part of the transposon and are not carried over into a target site.

Figure 16:
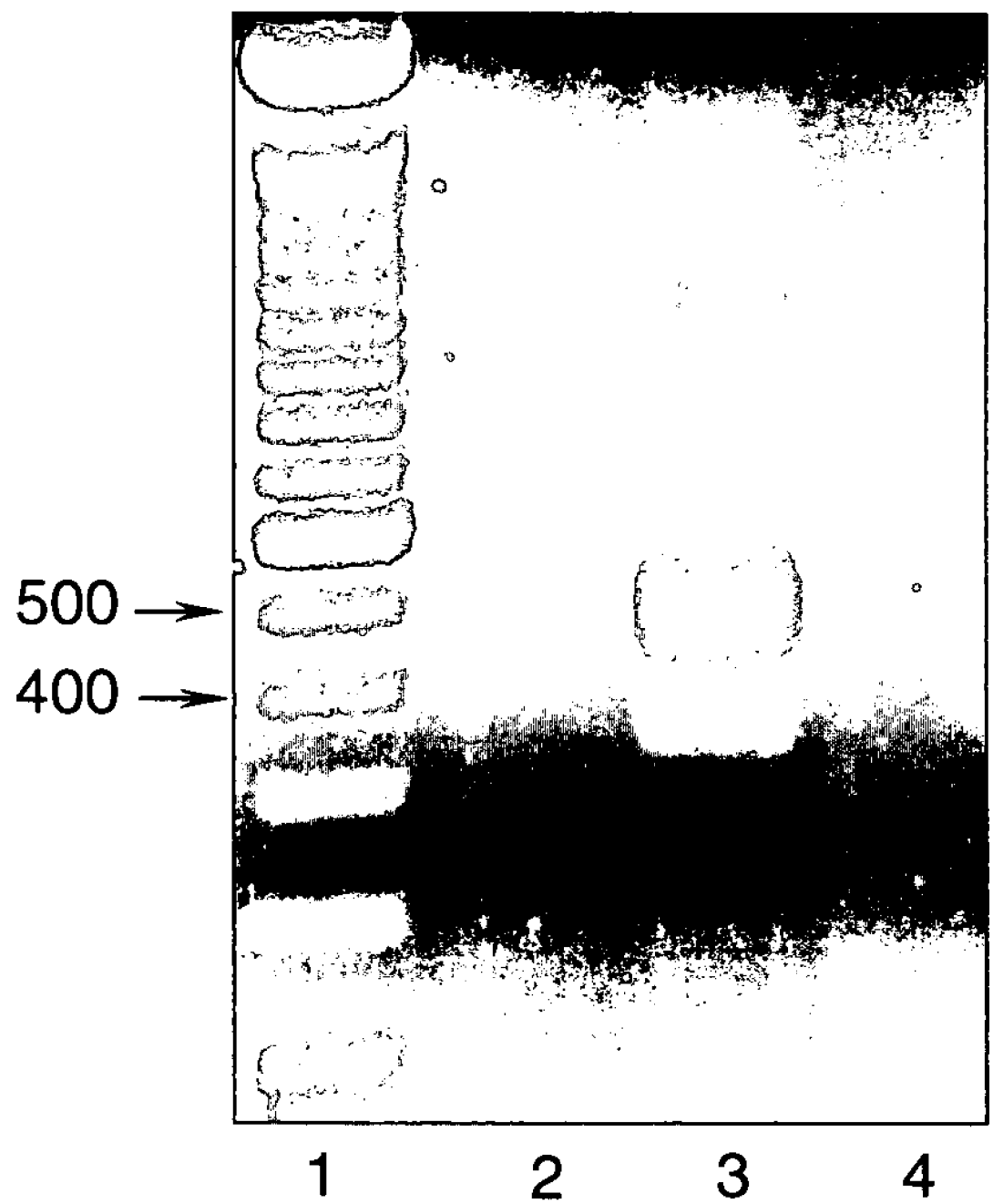
FIG. 16. Excision products in the livers of SB transposon-treated MPS VII mice resolved by electrophoresis in a 2% agarose gel. Lane 1,100 bp-interval markers; lane 2, treatment with pT/CAGGS-GUSB alone; lane 3, treatment with pT/CAGGS-GUSB+pSB10, lane 4, sham-treated with pBluscript.

Invest., 1989; 83:1258-1266). The transposon plasmid constructed by us contained an expression cassette for β-glucuronidase CAGGS-GUSB. Two groups of mice were injected with pT/CAGGS-GUSB: Treatment Group 1 received only the transposon-containing plasmid, Treatment Group 2 was co-injected with pSB10 plasmid at a molar ratio of 10:1 transposon to transposase. As in zebrafish, we detected excision events only when both transposon and transposase was injected (FIG. 16). The PCR bands were excised from the gel for cloning and sequencing as described in the previous section. The predominant band of 456-bp yielded eight readable sequences, seven of which gave canonical footprints of TAC (A/T)G (Table 5), similar to those found in zebrafish embryos and mouse ES cells (Table 4) and one of which appeared to be a transposition event using an alternative TA excision site. Another six events were sequenced from smaller, minor bands that showed deletions of various sizes and nucleotide sequences that indicated illegitimate recombination that did not use SB transposase. Taken together, the data suggest that the excision assay is useful for quickly evaluating transposition of transgenes into multicellular tissues of living animals.

TABLE 4

Comparison of SB footprints in different systems.

| | Canonical footprint | Non-canonical footprint missing 1 bp | Non-canonical footprint missing 2 bp | Non-canonical footprint missing 3 bp | Gaps/ insertions | Total events | Reference |
|---|---|---|---|---|---|---|---|
| HeLa cell culture | 35% | 0 | 18% | 29% | 18% | 17 | This study |
| Zebrafish embryo | 96% | 0 | 0 | 0 | 4% | 25 | Here & Dupuy et al., 2002 |
| Mouse spermatids | 0 | 31% | 44% | 0 | 25% | 16 | Fischer et al., 2001 |
| Mouse ES cells | 85% | 0 | 0 | 8% | 8% | 13 | Luo et al., 1998 |
| Mouse Liver | 88% | 0 | 0 | 0 | 12% | 8 | This study |

TABLE 5

Footprint sequences from mouse liver

| | Left-flanking | Footprint | Right-flanking | Events |
|---|---|---|---|---|
| Major band of expected size ~456 bp | | | | |
| Canonical footprints | GACTCACTATAGGGCGAATTGGAGCTCGGTACCC | TA CAG TA | GGGGATCCTCTAGCTAGAGT | 6 |
| | GACTCACTATAGGGCGAATTGGAGCTCGGTACCC | TA CTG TA | GGGGATCCTCTAGCTAGAGT | 1 |
| Gaps | GACTCACTA............... | ....... | ............TAGAGT | 1 |

Use of the Excision Assay to Evaluate SB Activity in Adult Animals.

The SB transposon system has been used for gene transfer into mice as a model for use in human gene therapy (Yant et al., *Nature Genet.*, 2000; 25:35-41; Yant et al., *Nature Biotech.*, 2002; 20:999-1005). However, evaluating the efficacy of transposition is difficult because delivery of transposons to many different cells of an organ results in integration events in different sites of various chromosomes. One can evaluate the overall effects by gene expression, but measuring actual transposition has depended on cloning of individual insertions to confirm transposition. This method is not suitable for measuring overall transposition rates, which is necessary to evaluate various techniques of introducing genes. Hence, we examined whether the excision assay could be used for this purpose.

The hydrodynamic delivery method of Liu et al., *Gene Ther.*, 1999; 6:1258-1266 and Zhang et al., *Hum. Gene Ther.*, 1999; 10:1735-1737, was used to deliver an SB transposon to MPS VII mice that are completely deficient in lysosomal hydrolase β-glucuronidase (Birkenmeier et al., *J. Clin.*

Discussion

We developed a plasmid-based excision assay for Sleeping Beauty-mediated transposition and confirm preliminary findings that suggested that excision rates correlate to transposition rates. Here we have used this assay to separate excision from the multi-step transposition process and facilitated our understanding of the cis-elements required for SB excision. This PCR-based excision assay is independent of the transposon content and has shown that the excision assay can be used to monitor transposition in systems wherein drug selection is not feasible, such as in non-dividing cells of whole animal tissues. We have shown that the excision assay offers a high-throughput means to detect and measure transposition in somatic tissues in which multiple transposition events occur in a large number of cells. This assay should be of special use in non-viral, DNA-mediated gene therapy.

The excision assay was used to elucidate several parameters of transposition that have not been appreciated before. The first involves footprints left in the excision site. The ability to revert transposition event after remobilization of the transposon is one potential advantage of using transposable elements in functional genomics. Consequently, it is important to know whether the footprint left after excision would maintain the open reading frame for translation. Two previous studies have provided conflicting results regarding the SB footprint. Luo et al., *Proc. Natl. Acad. Sci. USA*, 1998; 95:10769-10773, observed canonical footprints in mouse embryonic stem cells, whereas Fischer et al., *Proc. Natl. Acad. Sci. USA*, 2001; 98:6759-6764, observed non-canonical footprints in mouse haploid spermatids. In this study, we determined the footprints in tissue cultured cells and whole animals. As summarized in Table 4, in HeLa cells there is a mixture of canonical footprints and non-canonical footprints. In zebrafish, mouse embryonic stem cells and mouse liver cells, most footprints are canonical. In haploid spermatids, none of the footprints were canonical. Together, these results show that SB leaves different footprints in different cell types and that the ability to revert to wild type after remobilization may be limited by the cell or tissue type. In zebrafish embryos, and mouse embryonic stem cells and cells of the adult liver, 90% of the footprints add 5 bp (TA+CAG or CTG), to the open reading frame, which should cause a frame shift. In mouse haploid spermatids, over 40% of the footprints add only 3 bp, which would allow reversion to the wild type phenotype. Thus, for experimental studies, reversion to wild type would be rare when using SB in zebrafish embryos, mouse embryonic stem cells, and tissues in mice.

Double-strand breaks generated by transposon excision are thought to be repaired by a process called non-homologous end-joining (Fischer et al., *Proc. Nail. Acad. Sci. USA*, 2001; 98:6759-6764). In vertebrates, this process is catalyzed by a group of enzymes including Ku70 and Ku80 end-binding factors, the catalytic subunit of DNA-dependent protein kinase (DNA-PK), and the XRCC4/DNA ligase IV heteromeric complex. Mutation studies in yeast have shown that loss of different subsets of these enzymes leads to different repair products, including accurate repair, inaccurate repair, and a mixture of accurate and inaccurate repair (Critchlow et al., *Trends Biochem. Sci.*, 1998; 23:394-398). These results resemble the different footprint patterns we observed in different cell types—mostly canonical footprints in zebrafish and mouse ES cells, non-canonical footprints in mouse haploid spermatids and a mixture of canonical and non-canonical footprints in HeLa cells. We suspect that the DNA repair machineries differ in some way that leaves characteristic footprints for each cell type. This hypothesis could be further investigated by examining SB footprints in cell lines with known repair defects.

Sequences equivalent to the outer DRs in T-transposons have been extensively studied in other transposable elements. The inverted repeats in these prokaryotic transposons all have two functional parts. The inner part is primarily the DNA-binding site for the transposase whereas the terminal nucleotides at the transposon-donor junction are involved in steps subsequent to DNA binding but before excision (Allingham et al., *EMBO J*, 2001; 20:2931-2942). In Mu, the terminal nucleotides at the transposon-junction sequences are involved in transpososome assembly (Coros et al., *J. Mol. Biol.*, 2001; 310:299-309; Lee et al., *J. Mol. Biol.*, 2001; 314:433-444). In Tn5, the end sequences are specifically required for synaptic complex formation (Bhasin et al., *J. Mol. Biol.*, 2000; 302:49-63). In Tn10, mutations in these nucleotides prevent hairpin formation and strand transfer (Allingham et al., *EMBO J*, 2001; 20:2931-2942). In SB-mediated transposition, mutations in terminal nucleotides do not affect transposase binding, but do affect excision activity, indicating that they are involved in steps subsequent to DNA binding but before excision. These results suggest that the terminal nucleotides in the transposon-donor junction of SB's outer DRs may have a similar function as in the other DNA transposons. Our results with the SB transposon system show that the nucleotides at the transposon-host junction clearly influence transposon-transposase interactions. Physical properties of the DNA/chromatin also affect target site selection (Vigdal et al., *J. Mol. Biol.*, 2002; 323:441-452). Perturbing these interactions results in a less favorable environment leading to a decrease in the rate of excision and an approximately equal decrease in the rate of transposition. When we mutated both positions together, excision activity was reduced to below the limit of detection of about 5%, which would be predicted by the separate reductions in efficiency at both sites (13% x14%<5%). These results suggest that these nucleotides may work synergistically to contribute to the interaction between the transposase and the transposon. Thus, with the excision assay, we should be able to improve further the flanking sites, which like improving the activity of SB transposase, should lead to more powerful transposons. The improvements then can be evaluated using our excision assay in animal models for applications to human gene therapy.

Example 3

Gene Transfer into Genomes of Human Cells by the Sleeping Beauty Transposon System Materials and Methods
Construction of Test Transposons.

The maps for plasmids pFV3CAT (Caldovic et al., *Mol. Mar. Biol. Biotech.*, 1995; 4:51-61), pCMV-SB and pT/Neo are disclosed at FIG. 9. For this example the official designation of pT/SVNeo has been shortened to pT/Neo. For all of the experiments pT/plasmids, where pT designates a T transposon in a plasmid, p, were used as vectors. The BglII-EcoRI fragment of pCMV-Bsd (Clontech, Palo Alto, Calif.) was cloned into pT/BH between BglII and EcoRI to give pT/Bsd. Cutting with SalI, Klenow fill-in, and re-ligation destroyed a SalI site outside the transposon ITR-R to give pT/Bsd(-SalI). A linker containing NotI and XbaI sites, made by annealing two oligos: 5'-AATTCGCGGCCGCTCTAGA (SEQ ID NO:58) and 5'-ACGTTCTAGAGCGGCCGCG (SEQ ID NO:59), leaving staggered ends compatible with EcoRI and HindIII was cloned into an EcoRI/HindIII restriction of pT/Bsd(-SalI) to give pT/Bsd(-SalI+XbaI). The 3.7kb XbaI fragment of pFV3CAT, containing 1.1 kb of β-actin promoter/upstream sequence and intron 1 driving the chloramphenicol acetyltransferase (CAT) gene and a polyadenylation signal from the Chinook salmon growth hormone (CSGH) gene, was cloned into the XbaI site of pT/Bsd(-SalI+XbaI) to give pT/Bsd/5.6. About 1.1 kb of the intron sequence from pT/Bsd/5.6 was deleted by AgeI restriction and then religation to give pT/Bsd/4.5. The upstream β-actin promoter sequence was partially deleted to about 250 bp, from EcoRI to StuI, by EcoRI restriction and Klenow treatment followed by StuI restriction and religation to give pT/Bsd/3.5. A 3.5-kb SalI fragment of upstream carp β-actin promoter sequence from the pSalI/SalICAT (Izsvák et al., *J. Mol. Biol.*, 2000; 302:93-102) was cloned into the SalI site of pT/Bsd/3.5 to give pT/Bsd/7.2 and two tandem fragments cloned in to give pT/Bsd/10.8.

Cell Culture and Transposition Assays.

HeLa cells were maintained in Dulbecco's Modified Eagle Medium (DMEM) supplemented with 10% Characterized Fetal Bovine Serum (Hyclone, Logan, Utah), 2 mM L-Glutamine and 1× Antibiotic-Antimycotic (Gibco-BRL, Carlsbad, Calif.). $3 \times 10^5$ cells were plated on 60 mm dishes 24 hours before transfection. Qiagen column-prepped plasmid DNA (Qiagen, Valencia, Calif.) was transfected with TransIT-LT1 (Mirus, Madison, Wis.). 24 hour post transfection, media was changed to remove remaining transfection reagents and 48 hour post transfection, cells were split into selective media. G418-resistant colonies were obtained after 12 days selection with 800 μg/mL G418 (Mediatech, Herndon, Va.). Blasticidin-resistant colonies were obtained after 20 days of selection at 100 μg/mL blasticidin (ICN Chemicals, Irvine, Calif.). After selection, colonies were fixed with 10% formaldehyde, stained with methylene blue, air-dried and counted.

Mutagenesis of SB10 to Create SB11.

We used the following sequences, listed as GenBank Accession Numbers, to obtain consensus amino acids for each position in Tc1/mariner-like transposases: AAD03792, AAD03793, AAD03794, CAA82359, S26856, CAB51371, CAB51372, CAC28060, AAB02109, S33560, B46189 and CAB63420. For SB(M243Q) construction, the Transformer Site-Directed Mutagenesis Kit from Clontech (Palo Alto, Calif.) was used with a 5' phosphorylated Trans oligo SspI/EcoRV: 5'-CTTCCTTTTTCGATATCATTGAAGCTTT (SEQ ID NO:52), and the M243Q Primer: 5'-GGTCTTC-CAACAAGACAATGACC (SEQ ID NO:53). Following denaturation of the template pCMV-SB, a single round of T4-polymerase extension from annealed primers created heteroduplex double stranded DNA containing both the mutation and a conversion of a unique SspI site to an EcoRV site on one strand. The reaction was sealed by addition of T4 DNA ligase before digestion with SspI restriction endonuclease to remove parental plasmid. Transformation into mutS (repair-deficient) $E. coli$ amplified the mutated strands. The parental strands were counter-selected after isolation of plasmids by cleavage with SspI. After sequencing, the SacII fragment, containing the mutant SB(M243Q) open reading frame, was then subcloned back into pCMV-SB to create pCMV-SB (M243Q). Additional mutations to pCMV-SB(M243Q) were made via a PCR-mutagenesis strategy using primers designed to amplify the plasmid and generate overlapping 12-16 bp homologous ends containing the mutations. The following primers were used for the T136R mutations: 5'-TTTGCAA-GAGCACATGGGGACAAAGATCGTACTTTTTG (SEQ ID NO:54) and 5'-ATGTGCTCTTGCAAACCGTAGTCTG-GCTTTCTTATG (SEQ ID NO:55), for the V253H and A255R mutations: 5'-AACTACAGAGACATCTTGAAG-CAACATCTCAAGACATC (SEQ ID NO:56) and 5'-TTTTCTCACGTGTTTGGAAGTATGCTTGGGGTCAT (SEQ ID NO:57). Once amplified, PCR reactions were digested with DpnI to remove template DNA. PCR products were transformed into TOP10F' competent cells (Invitrogen, Carlsbad, Calif.) and homologous recombination by the bacteria produced the desired products. After sequencing, the amplified coding sequence was subcloned back into pCMV-SB as described above to generate the final vector pCMV-SB11 without PCR-induced mutations.

Western Blotting of SB Transposases and Analysis.

HeLa cells were plated at ~80% confluency on 100 mm dishes and transfected in duplicate with 8 μg pCMV-SB (SB10) or pCMV-SB11 along with 2 μg pRL-TK, a renilla luciferase-expressing plasmid (Promega, Madison, Wis.), as a control for transfection efficiency. At 24 hours post transfection, media was changed, and at 48 hours, the cells were equally split among six 100 mm plates. At 72 hours, lysates from one representative plate (0 hour, FIG. 24) were collected in lysis buffer (50 mM Tris-Cl pH 7.4, 250 mM NaCl, 2 mM EDTA, 50 mM NaF, 1% NP-40, 1 mM NaVO$_4$, 1 mM Na2PO4) and 100 μg/mL cycloheximide was added to the remaining five plates from each experiment. Lysates were subsequently collected every ~24 hours for five days. Forty micrograms of total protein lysate was run on 8% polyacrylamide gels, transferred to Immuno-blot PVDF membrane (BioRad, Hercules, Calif.), and probed with rabbit polyclonal antibodies for both SB transposase and Erk-1 (cat # sc-93, Santa Cruz Biotechnology, Santa Cruz, Calif.). A second probing with Horseradish peroxidase-conjugated donkey anti-rabbit Ig (cat # NA9340, Amersham Pharmacia, UK) and detection with SuperSignal West Pico Chemiluminescent Substrate (Pierce, Rockford, Ill.) revealed the expression of the proteins in the cell lysates. Luciferase readings were quantified from a sample of the 0 hour lysate to determine transfection efficiency using the Dual-Luciferase Reporter Assay System (Promega, Madison, Wis.) substrate for renilla luciferase. Protein levels were quantified by digitally measuring the intensity of western blot signals electronically scanned into the NIH Image 1.63 densitometry program (NIH, U.S.A.) from an autoradiogram. Levels of transposase were compared to levels of Erk-1 for each sample at each time point. Protein levels were adjusted for transfection efficiency as determined by the luciferase activity per μg protein at the 0 hour time point. Statistical analyses for this and all other experiments were performed using Statview 5.0.1 (SAS Institute, Cary, N.C.).

Results Tc1/mariner-type transposons, initially found in nematodes and Drosophila, are widespread in nature and are extremely able to invade genomes, including those of vertebrates (Plasterk et al., *Trends Genet.*, 1999; 15:326-332) and humans (Lander et al., *Nature*, 2001; 409:860-921; Venter et al., *Science*, 2001; 291:1304-1351). Tc1/mariner transposons are simple structures consisting of inverted terminal repeats (ITRs) that flank a single transposase gene. Transposase binds at precise sites in each of the ITRs where it cuts out the transposon and inserts it into a new DNA locus (a "cut-and-paste" mechanism, FIG. 17). All of the Tc1/mariner-type transposons scattered throughout vertebrate genomes contained transposase genes that are highly mutated, leaving them as repetitive, inactive DNA sequences (Izsvak et al., *Mol. Gen. Genet.*, 1995; 247:312-322). Consequently, a transposon system was resurrected from sequences of inactive Tc1/mariner-like transposons found in salmonids, and designated Sleeping Beauty (SB) (Ivics et al., *Proc. Natl. Acad. Sci. USA*, 1996; 93:5008-5013; Ivics et al., *Cell*, 1997; 91:501-510). The SB system consists of two parts, a transposon and a source of transposase.

The SB transposon system has four features that make it attractive as a vector for gene therapy. 1) Both parts of the SB system can be supplied as naked DNA or as DNA (transposon) plus RNA or protein for the sources of transposase. Therefore, the system is likely to have low immunoreactivity. 2) SB transposase, which has a nuclear localization signal, binds to four sites on a transposon, which may facilitate uptake of transposons into nuclei of cells (Zanta et al., *Proc. Natl. Acad. Sci. USA*, 1999; 96:91-96). 3) The transposase catalytically inserts a single copy of precise sequence into recipient DNA sequences rather than relying on random integration of variable lengths of DNA. 4) The expression of transposed genes is reliable and long-term (Luo et al., *Proc. Natl. Acad. Sci. USA*, 1998; 95:10769-10773; Yant et al., *Nature Genet.*, 2000; 25:35-40), even following passage through the germ line (Fischer et al., *Proc. Natl. Acad. Sci. USA*, 2001; 98:6759-6764; Dupuy et al., *Genesis*, 2001; 30:82-88; Dupuy et al., *Proc. Natl. Acad. Sci. USA*, 2002; 99:4495-4499; Horie et al., *Proc. Natl. Acad. Sci. USA*, 2001; 98:9191-9196). The SB transposon system is nearly an order of magnitude higher for gene transfer into chromosomes of HeLa cells than all other transposons tested (Fischer et al.,

*Proc. Natl. Acad. Sci. USA*, 2001; 98:6759-6764). Using both a hydrodynamic injection technique (Zhang et al., *Hum. Gene Ther.*, 1999; 10:1735-1737; Liu et al., *Gene Ther.*, 1999; 6:1258-1266) and a "gutted" adenovirus Yant et al., *Nature Genet.*, 2000; 25:35-40; Yant et al., *Nature Biotech.*, 2002; 20:999-1005, delivered a Factor IX-harboring SB transposon to about 1-5% of hepatocytes in mice, a reasonable goal for effective gene therapy in many cases (Verma et al., *Nature*, 1997; 389:239-242). Hydrodynamic injection of the SB transposon system has also been used to deliver transgenes to lungs in mice. The stable expression of genes in SB transposons in mouse tissues demonstrates their high potential for gene therapy.

In the following sections below, several features of the SB transposon system have been examined to determine the potential of the system for gene therapy. These include the effects of transposon length on transposition efficiency, the ratio of transposase to transposons and the improvements on activity of transposase when selected amino acids are mutated for higher efficiency.

Transposon Carrying Capacity

Figure 18:
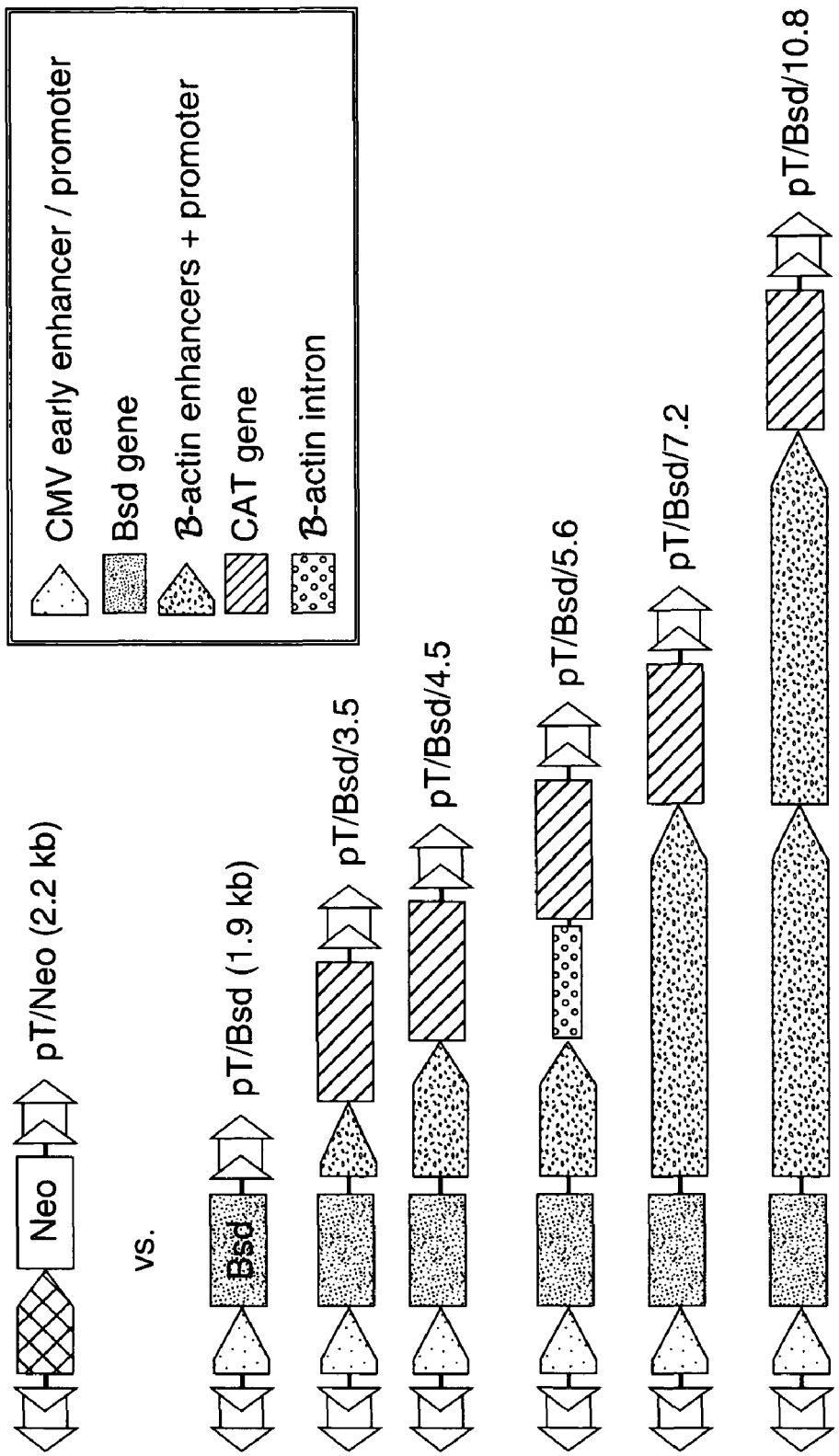
FIG. 18. Transposons with drug resistances used in Example 3. pT/Neo (2,236 bp) was used as a standard for comparison to blasticidin resistance transposons that are variations of the parent construct pT/Bsd (1901 bp). Fragments of a carp β-actin promoter-driven CAT gene, with the Chinook salmon poly(A) addition sequence, were cloned into pT/Bsd to obtain larger pT/Bsd transposons that have sizes of 3512 bp, 4495 bp, 5626 bp, 7157 bp, and 10,802 bp. The number at the end of each construct designates the total length of each transposon in kbp.

Previous studies (Izsvák et al., *J. Mol. Biol.*, 2000; 302:93-102; Karsi et al., *Mar. Biotechnol.*, 2002; 3:241-245), indicated that transposition efficiency decreases at approximately a logarithmic rate as a function of length. Transposons 10 kbp or larger were not integrated into genomes at rates higher with transposase than without. The first study indicated that transposons longer than about 5 kbp had low transposition frequencies that dampened enthusiasm for their use with genetic cargo in excess of about 5 kbp. However, these conclusions were based on protocols that required active expression of a selectable neo resistance marker for scoring transposition. Because the transposons used in these studies contained "stuffer" DNA fragments from lambda phage that is relatively rich in CpG sequences, methylation of the prokaryotic DNA could have attenuated gene expression from the transposon or the sequences could have induced RNA silencing (Plasterk, *Science*, 2000; 296:1263-1265). If so, the transposition rates might have been higher for the longer transposons than the experiments suggested. Consequently, we re-examined the carrying capacity of SB transposons by reducing the potential effects of prokaryotic sequences on transposition and/or expression of the transgene. We constructed pT/Bsd, a 1.9 kbp transposon that would confer blasticidin (Bsd) resistance to HeLa cells following integration (FIG. 18). We constructed larger transposons of 3.5 kbp, 4.5 kbp, 5.6 kbp, 7.2 kbp and 10.8 kbp by introducing various lengths of "stuffer" DNA composed of the carp β-actin enhancer/promoter-chloramphenicol acetyltransferase gene (CAT) cassette (Liu et al., *Mol. Cell. Biol.*, 1990; 10:3432-3440; Caldovic et al., *Mol. Mar. Biol. Biotech.*, 1995; 4:51-61). In all of the transposons the amount of prokaryotic DNA, the bsd and neo genes, was constant. Equal molar ratios of pT/Bsd (of varying length) and pT/Neo, a 2.2 kbp transposon used as an internal standard for transposition activity, were transfected into HeLa cells. Because the various transposon donor plasmids vary in size, a plasmid pGL-1, which has a CMV-GFP cassette, was used as "filler" DNA to maintain a constant amount of the total DNA in all experiments to control for transfection efficiency. We routinely transfected about 50-60% of the cells as measured by transient GFP expression. Cells were divided into several culture dishes and grown in medium containing either blasticidin or G418.

Figure 19A:
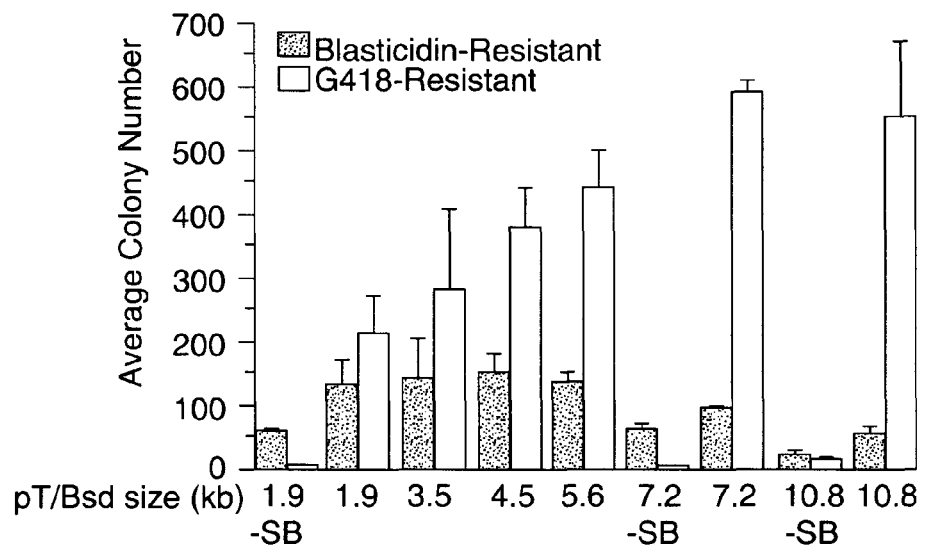
FIG. 19. Effects of transposon size on transposition. A) Equal molar numbers of the pT/Bsd transposons were cotransfected with 500 ng pT/Neo, 500 ng pCMV-SB, and pGL-1 as filler DNA into HeLa cells in equal molar numbers (~$3.7 \times 10^{11}$ total transposons per transfection) and $3 \times 10^4$ replica-split into either 800 μg/mL G418 or 100 μg/mL blasticidin. The numbers of G418r-resistant colonies were scored after 14-days whereas Bsdr-resistant colonies were counted after 19 days of selection. pT/Bsd, pT/Bsd/7.2 and pT/Bsd/10.8 cotransfections were tested with and without pCMV-SB. At least three independent experiments were run for each construct. Standard errors are indicated for each average. B) Relationship of transposition efficiency to transposon size. The black diamonds denote the average efficiencies compared to pT/Neo, adjusted to 100% for pT/Bsd. Individual efficiencies per experiment are shown by hash marks on the range bars. The "X" value for the 10.8-kbp plasmid is a corrected value based on the suggestion that pT/Bsd10.8 has a lower transfection efficiency than pT/Bsd (1.9 kbp). Asterisks indicate colony-forming values for each point that are t-test statistically different ($P>0.05$) from the value of the point to its left, e.g., pT/Bsd3.5 compared to pT/Bsd1.9, pT/Bsd5.6 compared to pT/Bsd4.5, etc.
Figure 19B:
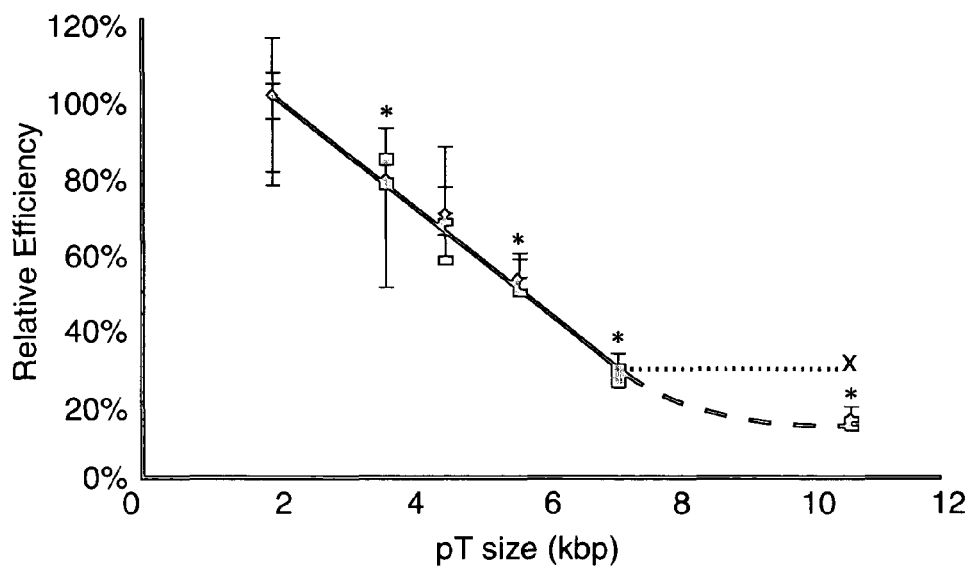

Transposition efficiency was measured as the ratio of colonies that were resistant to blasticidin compared to G418 (FIG. 19A). There was an approximately inverse linear relationship between transposon length and transposition frequency for transposons between 1.9 kbp and 7.2 kbp (FIG. 19B). SB transposase mediated the delivery of 5.5 kbp-transposons half as efficiently as 2 kbp transposons. At 10.8 kbp, a size at which transposition rates in the other studies were nil, we observed a residual enhancement of integration by SB transposase as demonstrated by transfections done with and without SB transposase (FIG. 19A). For the 10.8 kb transposons we verified that the amplification in integration rates was due to transposition rather than an enhanced rate of recombination by examining the junction sequences of several bsd transgenes. Three of the four insertions had the specific junction fragments expected for transposition and flanking TA sites indicative of transposition (Plasterk et al., *Trends Genet.*, 1999; 15:326-332) rather than random recombination. We noted that the background level for the 10.8 kbp transposon without added SB transposase is about half that of the smaller constructs. Random recombination of the bsd gene into HeLa chromosomes should be influenced not by the size of the plasmids but by transfection of the plasmids into cells, suggesting that the observed transposition value for the 10.8-kbp transposon may be lower than the actual transposition rate. Correcting for the apparent decrease in uptake of the pT/Bsd 10.8 plasmid is shown in FIG. 19B by the dotted line. Thus, our results indicate that 1) the size-efficiency curve for transposition is not linear for transposons longer than about 7 kbp and 2) that SB transposase confers a significant advantage for gene delivery even for long genes, an important consideration for gene therapy.

Figure 17:
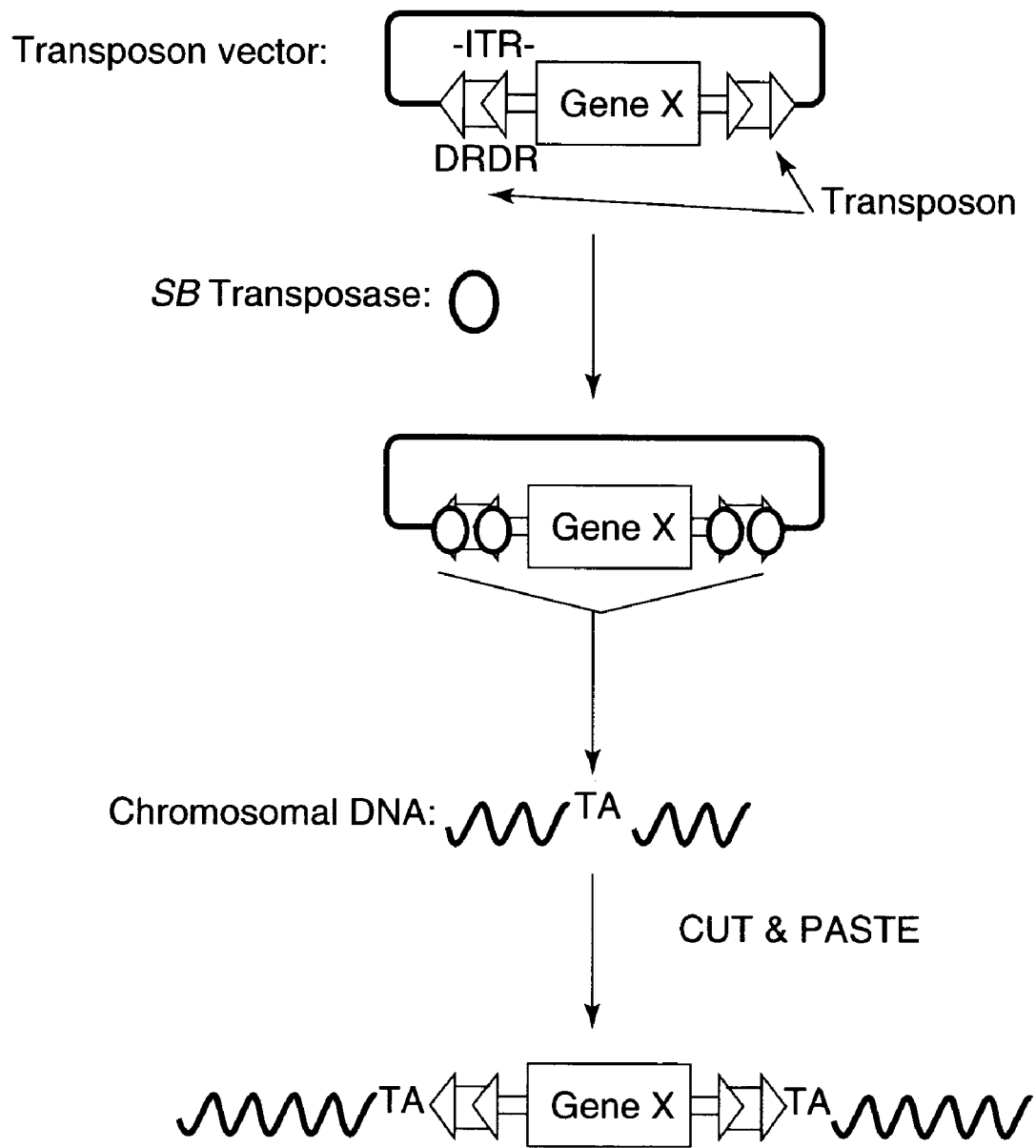
FIG. 17. Cut-and-paste mechanism by Sleeping Beauty transposons. Sleeping Beauty transposase binds to two direct repeats (called DRs) in each of the inverted terminal repeats (ITRs) of the transposon (shown as arrows in the figure), precisely cuts the transposon out of the plasmid and inserts the transposon in a target DNA, which is chromosomal DNA in the figure.
Figure 20:
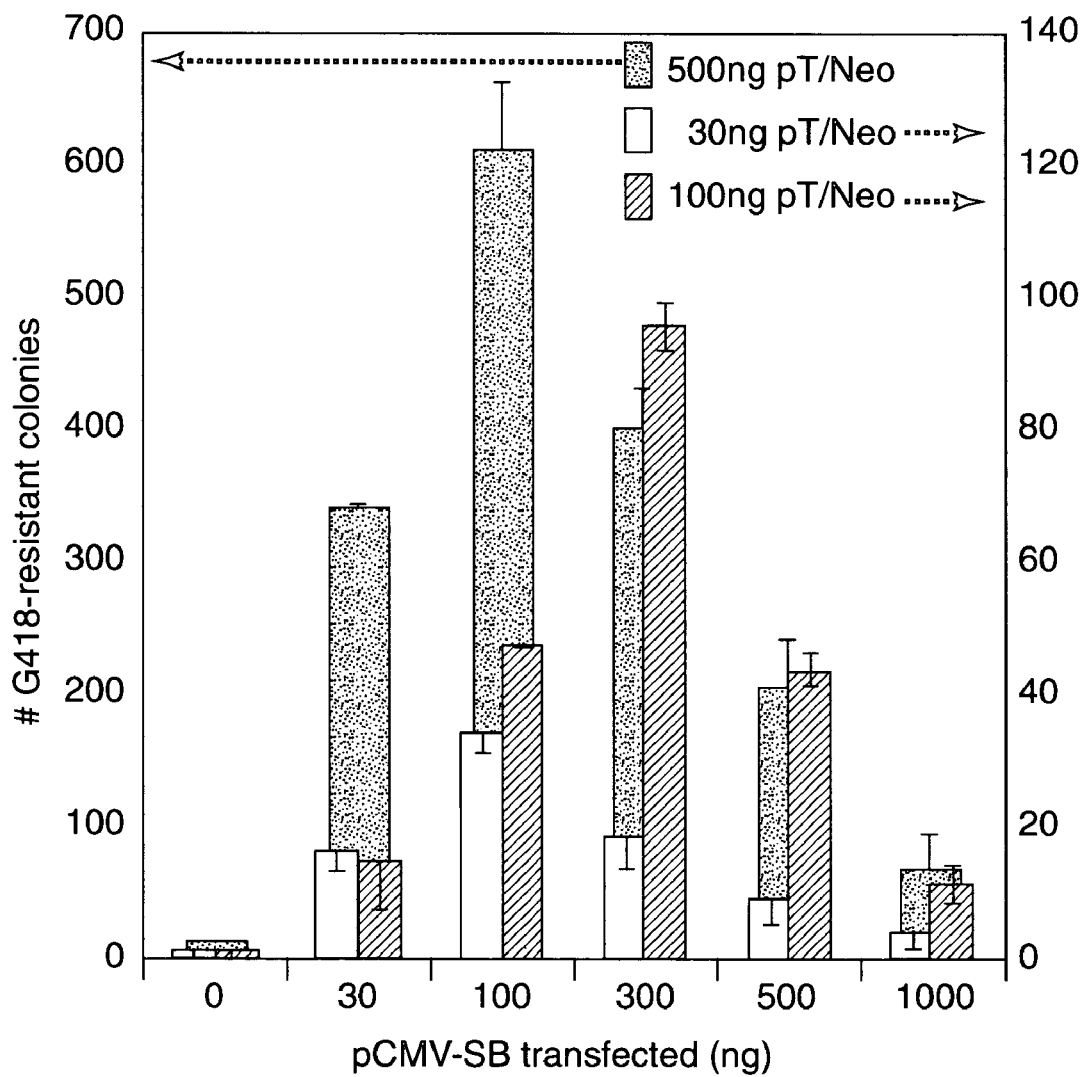
FIG. 20. Effects of pT:SB ratios on transposition efficiency. Either 30, 100 or 500 ng of pT/Neo were cotransfected with either 0, 30, 100, 300, 500, or 1000 ng of pCMV-SB. pGL-1 was added as filler DNA to maintain a constant amount of DNA per transfection. The results of the 30 ng and 100 ng pT doses are measured on the right ordinate, while the 500 ng pT dose results are measured using the left ordinate.

Overexpression Inhibition and Optimization of the Transposon to Transposase Ratio There are four transposase-binding sites in an SB transposon—the two "direct repeats" (DRs) in each ITR bind transposase molecules (FIG. 17). Our model for transposition indicates that the transposase molecules can bind to each other in a cris-cross manner to juxtapose the two ends of the transposon (Cui et al., *J. Mol. Biol.*, 2002; 318:1221-1235). This model predicts that the transposition rate should rise as the ratio of transposase (SB) to transposon (pT) increases—up to a point. When the ratio of SB to pT exceeds about 4 to 1, the efficiency of transposition should decrease due to quenching (Hartl et al., *Trends Genet.*, 1997; 13:197-201) of the transposases bound to the ITRs. Binding of free SB transposase molecules to those bound to the ITRs would prevent the juxtaposition of the transposon ends, which is required for mobilization. Izsvák, et al., *J. Mol. Biol*, 2000; 302:93-102, used different promoters to drive expression of SB transposase and did not find evidence that overexpression of SB inhibited transposition over the 17-fold range of expression they tested. Accordingly, we tested the effects of transposition over a much broader range, from almost 17:1 to 1:33 of pT to SB plasmids, a 560-fold range. We transfected either 30, 100, or 500 ng of pT/Neo with 30, 100, 300, 500, or 1000 ng of pCMV-SB, using pGL-1 to maintain a constant level of total transfectable DNA. The data shown in FIG. 20 demonstrate the dramatic inhibitory effect observed with the higher doses of SB. At 1000 ng of pCMV-SB, the resistant colony formation approached background for all three concentrations of pT/Neo. These results are consistent with overexpression inhibition. When 30 or 100 ng of pT/Neo was used, 100 or 300 ng pCMV-SB, respectively, yielded the highest colony formation, giving the same ratio of pT:SB of 1:3. At the highest pT/Neo level of 500 ng, the maximal level of transposition occurred at 100 ng of pCMV-SB, a 5:1 ratio. At this lowered dose of transposase, the number of G418-resistant colonies was about 6-fold higher than that seen with 100 ng of pT/Neo plus 300 ng of transposase.

The dramatic effect of lowered transposition efficiency at higher SB doses suggested that transposition at a very high rate might be cytotoxic. We examined this possibility by determining the average number of inserted transposons per genome. We hypothesized that the sizes of the colonies might be indicative of the numbers of transposons per genome if insertional mutagenesis were to lower the fitness of the cells and increase its generation time. Hence, we selected large, >2 mm diameter, medium, 1-2 mm diameter, and small, <1 mm diameter, colonies from which we isolated high molecular weight DNA. There was no significant difference in the number of inserts in smaller compared to larger colonies. However, there was a difference in the numbers of transposon inserts as a function of SB dose when the starting concentration was kept at 500 ng of pT/Neo. Thus, transfections with 500 ng pT/Neo and 100 ng pCMV-SB, which is at the peak of gene transfer, had an average of about 3 inserts/genome whereas doses of transposase of 500 ng and 1000 ng yielded an average of about 1.1 and 1.2 inserts per genome, respectively. Colonies smaller than 1 mm diameter were difficult to grow, and often did not have detectable bands on the Southern blots, suggesting that if the colonies were G418-resistant (rather than "feeder colonies") then the inserts might have been unstable.

Improvements to SB Transposase

Figure 21A:
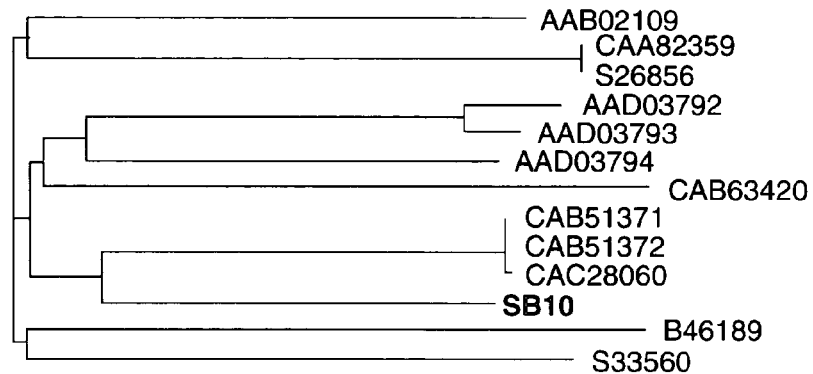
FIG. 21. A) Phylogenetic tree representation of active mariner transposases (identified by Genbank accession number) aligned to assign possible amino acid changes based on a consensus of conserved regions. B) Transposition activities of mutated SB10 transposases. Original SB10 and mutant transposases were co-transfected in various amounts, either 100, 500 or 1000 ng, along with 500 ng pT/Neo. Colony counts for three independent experiments each were obtained 14 days post-transfection in G418 selection. pGL-1 was added as filler DNA to maintain a constant amount of DNA per transfection. Transposition efficiency for SB10 transposase was adjusted to 100% for each transposase dose and mutant transposases are shown as relative activity compared to SB10 at their respective doses. Asterisks indicate values that are t-test statistically different from the SB10+pT values ($P>0.05$) at each given level of transposase.
Figure 21B:
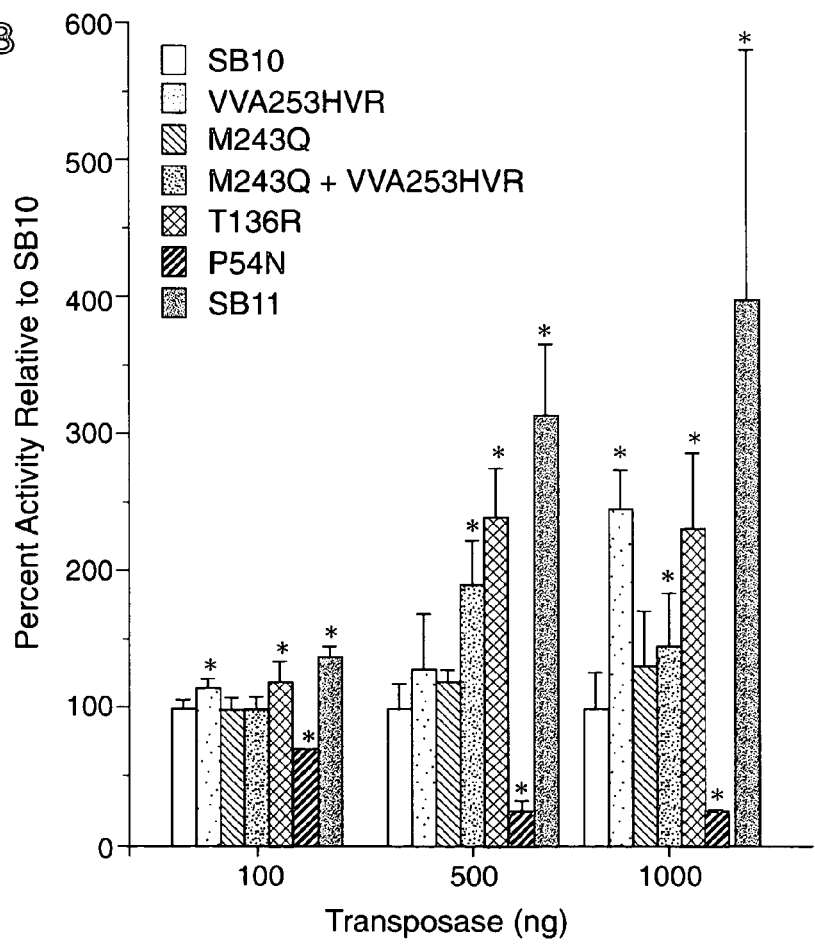
Figure 22:
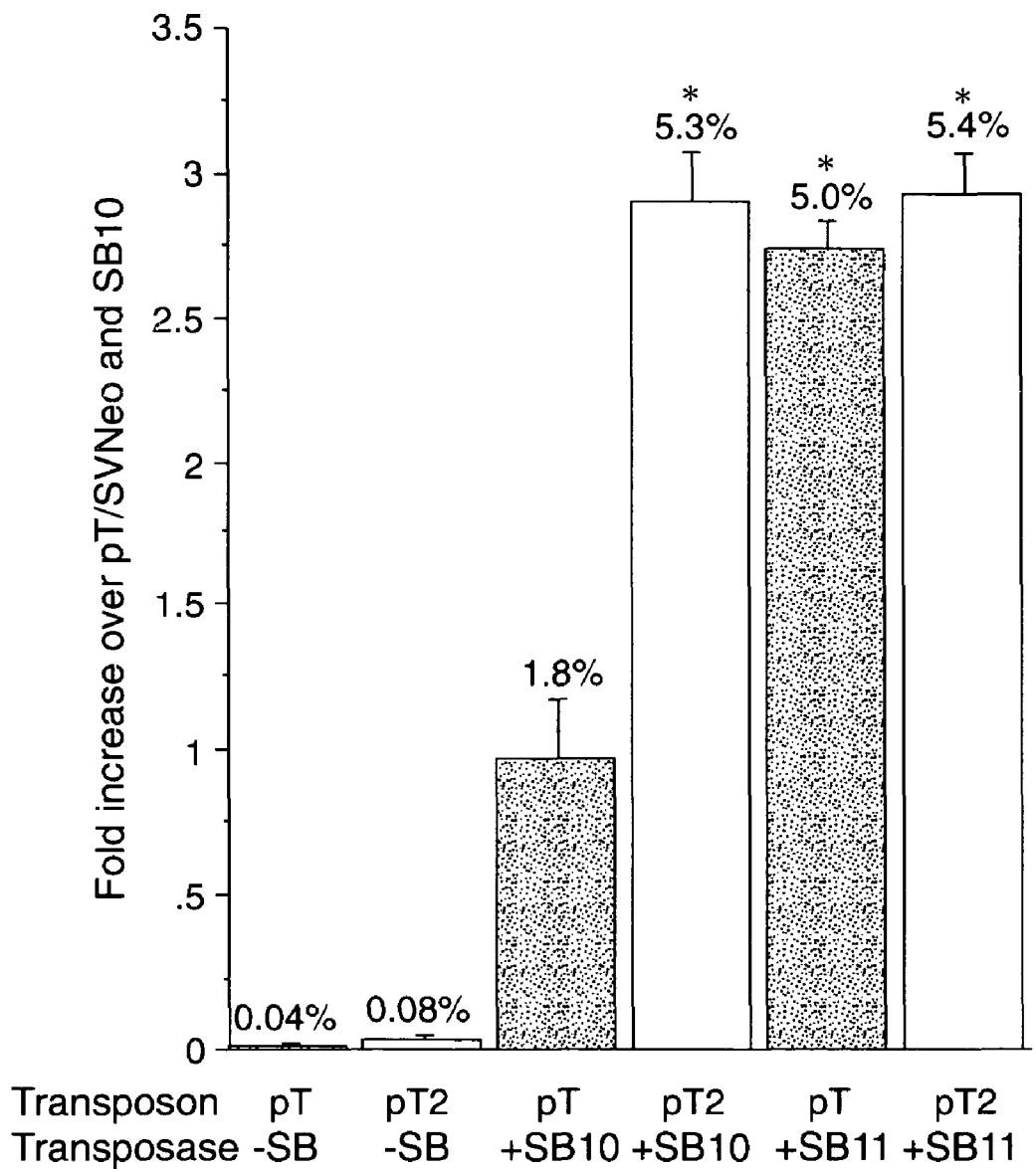
FIG. 22. Comparison of transposition activities of improved SB transposases and transposons. 500 ng pGL-1, original SB10 or improved SB11 transposase were co-transfected with 500 ng pT/Neo or the improved pT2/SVNeo. Colony counts were obtained 14 days post-transfection under G418 selection. Transposition efficiency for SB10 transposase plus pT/Neo was adjusted to 100% and other combinations are shown as relative activities. Standard errors are indicated for each set of conditions. Noted above each bar is an estimate of the percentage of cells transfected that received pT/Neo and were G418 resistant. Percentages were determined by the average number of resistant colonies out of the total number plated into selection, based on a 60% transfection efficiency and 0.66 plating efficiency for these experiments. Asterisks indicate values that are t-test statistically different from the SB10+pT values ($P>0.05$).

The original SB10 sequence was constructed from consensus active and inactive Tc1/mariner transposase sequences from a variety of metazoans (Ivies et al., *Cell,* 1997; 91:501-510). We sought to improve the transposase by further modifications of the amino acid sequence based on a phylogenetic comparison with active mariner transposases (FIG. 21A). In total, 14 amino acid changes were made by site-directed PCR mutagenesis and tested in the cell-culture transposition assay. FIG. 21B shows the results of all changes that resulted in an improved activity as well as one representative change that gave diminished activity (P54N). The combination of the T136R, M243Q, V253H, and A255R changes were incorporated into a new transposase, SB11, which enhanced transposition of T/neo about 3-fold. The P54N change in the DNA-binding domain of SB transposase resulted in a 3- to 4-fold decrease in transposition activity and consequently was not incorporated into SB11. The P54N substitution may have increased the binding strength of the SB transposase to its binding sites on the transposon, a change that would be expected to lower transposition frequency (Cui et al., *J. Mol. Biol,* 2002; 318:1221-1235). The combined increase in transposition with the positive amino acid substitutions is about the same improvement in transposition as seen with SB10 and an improved transposon, T2 (Cui et al., *J. Mol. Biol.,* 2002; 318:1221-1235). When the improved SB11 transposase was used with the improved transposon, T2, we did not see any further increase over that achieved with just one of the improved components of the transposon system (FIG. 22, right-hand entry). Two important considerations in comparing the activities of SB10 and SB11 are their relative expression levels and lifetimes. Differences in either the expression levels or stabilities of SB10 compared to SB11 due to the changes in their amino acid sequences would confuse our conclusions about the relative activities of these two enzymes. Consequently, we examined both the expression levels and stabilities of SB10 and SB in transfected HeLa cells by measuring the levels of transposase protein over time following inhibition of translation with cycloheximide. Expressed in similar amounts (FIGS. 23 A and B), the half-life of SB11 transposase was approximately the same as that of SB10, about 80 hours in tissue culture (FIG. 23C). An alternative examination of the half-lives of the two transposases by western blotting of cultures over time without use of cycloheximide also indicated that the lifetimes of SB10 and SB11 were indistinguishable. SB11 consistently migrated slower than SB10 in our polyacrylamide gels, with an apparent shift in mobility of ~1 kDa, presumably because three of four substitutions replaced hydrophobic residues with positively charged residues, T(136), V(253) and A(255) to R, H and R respectively. This changes the predicted overall charge at pH 7.0 from (+)50.94 for SB10 to (+)53.03 for SB11 and increased the molecular weight from 39.5 kDA for SB10 to 39.7 kDA for SB11. Nevertheless, the amino acid substitutions had no apparent effect on the lifetime of the transposase.

Discussion

Sleeping Beauty has opened the possibility for efficient, non-viral gene delivery for human therapy. To be effective, the transposon system needs to be capable of integrating cDNA coding regions and regulatory motifs for appropriate expression in targeted tissues. The average protein-coding sequence in humans is about 1,300 nucleotides and about 80% of human cDNAs are less than 7 kbp (Lander et al., *Nature,* 2001; 409:860-921), suggesting that most human cDNAs could be efficiently integrated using the SB transposon system. This is not the case for many viral vectors. For instance, whereas adeno-associated virus can accommodate the small coding regions such as that for Factor IX (1,497 bp) for human gene therapy, the 6,996-bp Factor VIII cDNA is too large. The SB transposon system does not appear to have hard size limitations. Our results that transposons larger than 10 kbp can transpose differ from those of others (Izsvák et al., *J. Mol. Biol.,* 2000; 302:93-102; Karsi et al., *Mar. Biotechnol.,* 2002; 3:241-245). This may be due to differences in experimental design, including the content of the tested transposons. The use of CpG-rich sequences for expanding the length of the transposon may have led to an additional reduction in apparent transposition frequency due to an increasing loss of transgene expression as the CpG-rich content increased in the larger transposons. Moreover, it is clear that transfection of larger plasmids is lower than that of smaller DNAs, which will further lower the level of G418-resistant colony formation regardless of transposition rates.

As the pT/Bsd vectors increase in size, the transposition rate of pT/Neo, which we used as an internal standard, increased (see FIG. 19A). This was unexpected. There may be two contributing factors. First, as the pT/Bsd plasmids increase in size, their efficiency of transfecting HeLa cells may decrease—this appears to be the case for pT/Bsd10.8. As a result, there would be fewer competing transposase-binding sites from pT/Bsd vectors allowing more transposase to interact with pT/Neo constructs, thereby enhancing the odds of its transposition. Second, we used pGL-1 as a control for total mass-amount of transfectable DNA in our experiments. pGL-1 has a CMV promoter that might have altered the overall expression of SB transposase from pCMV-SB by competing for transcription factors. As we have shown in FIG. 20, the ratio of SB transposase to transposon affects the efficiency of transposition. Regardless of the causes of this unexpected observation, the data clearly support the hypothesis that the SB transposon system can deliver large genetic constructs to human chromosomes. In support of our findings, efficient remobilization of large SB transposons resident in chromosomes of mouse tissues has been observed.

A criterion for effective gene therapy is sufficient chromosomal integration activity. Four changes in the amino acid sequence of SB10 transposase improved transposition about 3-fold, which corresponds to an integration rate about 100-fold above background recombination rates. Optimization of the ITR sequences and of the sequences flanking the transposon in the donor plasmid, pT2 (Cui et al., *J. Mol. Biol.*, 2002; 318:1221-1235), improves transposition another 3-fold. All together, we expected these changes would result in about a 10-fold improvement over the standard transposon system used in most of the experiments in this report. However, the data in FIG. 22 indicates that combining the improved transposase and improved transposon results in a 3-fold enhancement. Transposition appears to be very inefficient in tissue culture compared to cells of whole animals. For instance, whereas initial tests indicated a relatively low rate of remobilization of SB transposons of about $2 \times 10^{-5}$ transposon events per mouse ES cell (Luo et al., *Proc. Nail. Acad. Sci. USA*, 1998; 95:10769-10773), the rates of transposition in offspring of mice harboring transposons and expressing SB transposase are between 0.2 and 2.0 remobilizations per pup (Fischer et al., *Proc. Natl. Acad. Sci. USA*, 2001; 98:6759-6764; Dupuy et al., *Genesis*, 2001; 30:82-88; Dupuy et al., *Proc. Natl. Acad. Sci. USA*, 2002; 99:4495-4499; Horie et al., *Proc. Natl. Acad. Sci. USA*, 2001; 98:9191-9196), an increase of nearly 100,000-fold. The T2/SB11 system should be even more active. We have shown in FIG. 20 that the relative amounts of transposon and transposase are important for optimal transposition. By incorporating a transposase gene on the same plasmid as the transposon, it will be possible to adjust in each cell the relative ratios of the two components by appropriate choice of promoter for the transposase gene. The cis-constructs that have been tested are more efficient at gene transfer than using two constructs. Ratios of transposase to transposon can be regulated by enhancer/promoter strength.

In addition to their greater efficiency at directing integration of genes into genomes than naked DNA alone, transposons are delivered with precise borders in single units for each mobilization. In contrast, random recombination of naked DNA often results in integration of concatamers, which have a propensity of being repressed over time (Garrick et al., *Nature Genetics*, 1998; 18:56-59; Henikoff, BioEssays, 1998; 20:532-534). Concatemers are not transposed at a measurable frequency.

A third criterion for a gene-therapy vector is safety. Human diploid genomes have about 28,000 mariner-type transposons but none have an active transposase gene (Lander et al., *Nature*, 2001; 409:860-921). Mobility-shift experiments done with the SB transposase on its natural target sequence, salmonid transposons, and related transposons in zebrafish indicated that there was no detectable binding to the heterotropic species. Nevertheless, it is possible that even residual binding of SB transposase to endogenous human transposons could mobilize them at an exceedingly low rate to elicit a cytotoxic effect. However, no one has reported any unexpected toxicities in transgenic mice that constitutively express SB transposase. Nevertheless, the duration of transposase activity should be kept as short as possible. We presume that in the future the SB transposase activity will come from transfer of SB protein bound to transposons to form transpososomes. This will further curtail possible binding of SB transposase to human sequences. The other safety issue is insertional mutagenesis. SB transposons appear to integrate more or less randomly in mammalian genomes (Fischer et al., *Proc. Natl. Acad. Sci. USA*, 2001; 98:6759-6764; Dupuy et al., *Genesis*, 2001; 30:82-88; 1 Dupuy et al., *Proc. Nail. Acad. Sci. USA*, 2002; 99:4495-4499; Horie et al., *Proc. Natl Acad. Sci. USA*, 2001; 98:9191-9196; Vigdal et al., *J. Mol. Biol.*, 2002; 323:441-452). The insertional consequences of SB transposons should be similar to those for any other insertional vector and less consequential than retroviruses that have double sets of enhancers in each of their long terminal repeat sequences. As a further safety feature for SB transposons, we are including insulator elements (Bell et al., *Science*, 2001; 291:447-450) to protect endogenous chromosomal genes from inactivation by the transgene enhancers.

The best gene-therapy vectors will be those that can be targeted to specific tissues or cell types. While the plasmids harboring the transposon and/or transposase have no signals for targeting to specific organs or tissues, conjugating plasmids with modified DNA-condensing agents such as lactosylated-polyethylenimine can direct DNA to specific cell types such as hepatocytes (Kren et al., *Proc. Natl. Acad. Sci. USA*, 1991; 96:10349-10354). With its ability to integrate genes of variable size leading to long-term expression, the SB transposon system has great potential for gene therapy to ameliorate both acute and chronic disorders (Factor, *Mol. Therapy*, 2001; 4:515-524; Zhang et al., *Curr. Genomics*, 2000; 1:117-133; Isner, *Nature*, 2002; 415:234-239).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A polynucleotide, or complement thereof, comprising a nucleic acid sequence flanked by first and second inverted repeats,
   wherein the first inverted repeat comprises a first outer direct repeat comprising the nucleotide sequence of SEQ ID NO: 3, and the first inner direct repeat comprising the nucleotide sequence of SEQ ID NO: 4,
   wherein the second inverted repeat comprises a second inner direct repeat and a second outer direct repeat, the second inner direct repeat comprising the complement of the nucleotide sequence of SEQ ID NO: 4, and the second outer direct repeat comprising the complement of the nucleotide sequence of SEQ ID NO: 3.

2. The polynucleotide of claim 1 wherein the polynucleotide is part of a vector.

3. The polynucleotide of claim 2 wherein the vector is a plasmid.

4. The polynucleotide of claim 3 wherein the vector nucleotides flanking the polynucleotide are TATA and ATAT.

5. The polynucleotide of claim 3 wherein the vector nucleotides flanking the polynucleotide are CTGTA and TGATA.

6. The polynucleotide of claim 1 wherein the nucleic acid sequence flanked by first and second inverted repeats comprises a coding sequence.

7. A gene transfer system to introduce a polynucleotide into the DNA of a cell, the system comprising:
   an SB polypeptide or a polynucleotide encoding the SB polypeptide, wherein the SB polypeptide comprises an amino acid sequence comprising SEQ ID NO: 5, SEQ ID NO: 20, or SEQ ID NO: 21, and
   a polynucleotide, or complement thereof, comprising a nucleic acid sequence flanked by first and second inverted repeats,
   wherein the first inverted repeat comprises a first outer direct repeat and a first inner direct repeat, the first outer direct repeat comprising the nucleotide sequence of SEQ ID NO: 3, and the first inner direct repeat comprising the nucleotide sequence of SEQ ID NO: 4,
   wherein the second inverted repeat comprises a second inner direct repeat and a second outer direct repeat, the second inner direct repeat comprising the complement of the nucleotide sequence of SEQ ID NO: 4, and the second outer direct repeat comprising the complement of the nucleotide sequence of SEQ ID NO: 3.

8. The gene transfer system of claim 7 wherein the SB polypeptide comprises SEQ ID NO:20.

9. The gene transfer system of claim 7 wherein the polynucleotide encoding the SB polypeptide is RNA.

10. The gene transfer system of claim 7 wherein the polynucleotide encoding the SB polypeptide is integrated into the genome of a cell.

11. The gene transfer system of claim 7 wherein the polynucleotide comprising a nucleic acid sequence flanked by first and second inverted repeats is part of a vector.

12. The gene transfer system of claim 7 wherein the nucleic acid sequence flanked by first and second inverted repeats comprises a coding sequence.

13. A method for recombining an exogenous DNA into a DNA in a cell comprising:
   introducing into a cell a polynucleotide, or a complement thereof, comprising a nucleic acid sequence flanked by first and second inverted repeats, wherein the first inverted repeat comprises a first outer direct repeat and a first inner direct repeat, the first outer direct repeat comprising the nucleotide sequence of SEQ ID NO: 3, and the first inner direct repeat comprising the nucleotide sequence of SEQ ID NO: 4, wherein the second inverted repeat comprises a second inner direct repeat and a second outer direct repeat, the second inner direct repeat comprising the complement of the nucleotide sequence of SEQ ID NO: 4, and the second outer direct repeat comprising the complement of the nucleotide sequence of SEQ ID NO: 3, and wherein the cell comprises an SB polypeptide comprising the amino acid sequence of SEQ ID NO: 5, SEQ ID NO: 20, or SEQ ID NO: 21, wherein the polynucleotide, or complement thereof, recombines into DNA of the cell.

14. The method of claim 13, further comprising introducing the SB polypeptide or a polynucleotide encoding the SB polypeptide into a cell.

15. The method of claim 14 wherein the SB polypeptide comprises an amino acid sequence comprising SEQ ID NO:21.

16. The method of claim 13 wherein the cell comprises a polynucleotide encoding an SB polypeptide.

17. The method of claim 16 wherein the SB polypeptide comprises an amino acid sequence comprising SEQ ID NO:21.

18. The method of claim 16 wherein the polynucleotide encoding the SB polypeptide is integrated into the cell genome.

19. The method of claim 13 wherein introducing the polynucleotide to the cell comprises using a method selected from the group consisting of microinjection, electroporation, combining the nucleic acid fragment with cationic lipid vesicles or DNA condensing reagents, and incorporating the nucleic acid fragment into a viral vector and contacting the viral vector with the cell.

20. The method of claim 13, wherein the nucleic acid sequence flanked by the first and second inverted repeats comprises a coding sequence.

21. The method of claim 13 wherein the cell is a vertebrate cell.

22. The method of claim 21 wherein the vertebrate cell is an ex vivo cell.

23. A method for recombining a polynucleotide into DNA in a cell comprising:
  introducing into a cell a polynucleotide, or complement thereof, comprising a nucleic acid sequence flanked by first and second inverted repeats,
    wherein the first inverted repeat comprises a first outer direct repeat and a first inner direct repeat, the first outer direct repeat comprising the nucleotide sequence of SEQ ID NO: 3, and the first inner direct repeat comprising the nucleotide sequence of SEQ ID NO: 4,
    and wherein the second inverted repeat comprises a second inner direct repeat and a second outer direct repeat, the second inner direct repeat comprising the complement of the nucleotide sequence of SEQ ID NO: 4, and the second outer direct repeat comprising the complement of the nucleotide sequence of SEQ ID NO: 3, and
  introducing an SB polypeptide or a polynucleotide encoding the SB polypeptide into the cell, wherein the SB polypeptide comprises the amino acid sequence of SEQ ID NO: 20 or SEQ ID NO: 21,
wherein the polynucleotide or complement thereof recombines into DNA in the cell.

24. The method of claim 22 wherein the SB polypeptide comprises SEQ ID NO:20.

25. The method of claim 23 wherein introducing the polynucleotide to the cell comprises using a method selected from the group consisting of microinjection, electroporation, combining the nucleic acid fragment with cationic lipid vesicles or DNA condensing reagents, and incorporating the nucleic acid fragment into a viral vector and contacting the viral vector with the cell.

26. The method of claim 23 wherein the nucleic acid sequence comprises a coding sequence.

27. The method of claim 23 wherein the cell is a vertebrate cell.

28. The method of claim 23 wherein the vertebrate cell is an ex vivo cell.

29. A polypeptide comprising the amino acid sequence of SEQ ID NO:21.

30. A polynucleotide encoding a polypeptide comprising SEQ ID NO:21.

31. A gene transfer system to recombine a polynucleotide into the DNA of a cell, the system comprising:
  an SB polypeptide or a polynucleotide encoding the SB polypeptide, wherein the SB polypeptide comprises the amino acid sequence of SEQ ID NO: 21; and
  a polynucleotide, or complement thereof, comprising a nucleic acid sequence flanked by first and second inverted repeats,
    wherein the first inverted repeat comprises a first outer direct repeat and a first inner direct repeat, the first outer direct repeat comprising the nucleotide sequence of SEQ ID NO: 3, and the first inner direct repeat comprising the nucleotide sequence of SEQ ID NO: 4,
    wherein the second inverted repeat comprises a second inner direct repeat and a second outer direct repeat, the second inner direct repeat comprising the complement of the nucleotide sequence of SEQ ID NO: 4, and the second outer direct repeat comprising the complement of the nucleotide sequence of SEQ ID NO: 3.

32. The gene transfer system of claim 31 wherein the polynucleotide encoding the SB polypeptide is RNA.

33. The gene transfer system of claim 31 wherein the polynucleotide encoding the SB polypeptide is integrated into the genome of a cell.

34. The gene transfer system of claim 31 wherein the polynucleotide comprising a nucleic acid sequence flanked by first and second inverted repeats is part of a vector.

35. The gene transfer system of claim 31 wherein the nucleic acid flanked by first and second inverted repeats sequence comprises a coding sequence.

36. A polynucleotide encoding a polypeptide comprising an amino acid sequence comprising SEQ ID NO:20.

37. A polypeptide comprising the amino acid sequence of SEQ ID NO:20.

* * * * *

UNITED STATES PATENT AND TRADEMARK OFFICE
CERTIFICATE OF CORRECTION

PATENT NO. : 8,227,432 B2  
APPLICATION NO. : 10/420529  
DATED : July 24, 2012  
INVENTOR(S) : Hackett et al.

Page 1 of 1

It is certified that error appears in the above-identified patent and that said Letters Patent is hereby corrected as shown below:

Title Page – Page 5 – Line 1  
Delete "Hone et al" and insert --Horie et al.--

Column 1, Lines 14-17  
Delete "The present invention was made with government support under Grant No. R01-RR066525-07 and P01-HD32652, awarded by National Institutes of Health. The Government has certain rights in this invention."  
and  
Insert --This invention was made with government support under RR006625 and HD032652 awarded by the National Institutes of Health. The government has certain rights in this invention.--

Signed and Sealed this  
Fourth Day of September, 2012

David J. Kappos  
*Director of the United States Patent and Trademark Office*

SEQUENCE LISTING

```
<160> NUMBER OF SEQ ID NOS: 188

<210> SEQ ID NO 1
<211> LENGTH: 229
<212> TYPE: DNA
<213> ORGANISM: ARTIFICIAL
<220> FEATURE:
<223> OTHER INFORMATION: inverted repeat sequence

<400> SEQUENCE: 1
cagttgaagt cggaagttta catacactta agttggagtc attaaaactc gtttttcaac        60
tactccacaa atttcttgtt aacaaacaat agttttggca agtcagttag gacatctact       120
```

```
ttgtgcatga cacaagtcat ttttccaaca attgtttaca gacagattat ttcacttata    180
attcactgta tcacaattcc agtgggtcag aagtttacat acactaagt                229

<210> SEQ ID NO 2
<211> LENGTH: 229
<212> TYPE: DNA
<213> ORGANISM: ARTIFICIAL
<220> FEATURE:
<223> OTHER INFORMATION: inverted repeat sequence

<400> SEQUENCE: 2
attgagtgta tgtaaacttc tgacccactg ggaatgtgat gaaagaaata aaagctgaaa    60
tgaatcattc tctctactat tattctgaya tttcacattc ttaaaataaa gtggtgatcc    120
taactgacct aagacaggga atttttacta ggattaaatg tcaggaattg tgaaaasgtg    180
agtttaaatg tatttggcta aggtgtatgt aaacttccga cttcaactg              229

<210> SEQ ID NO 3
<211> LENGTH: 32
<212> TYPE: DNA
<213> ORGANISM: ARTIFICIAL
<220> FEATURE:
<223> OTHER INFORMATION: consensus direct repeat

<400> SEQUENCE: 3
cagttgaagt cggaagttta catacacyta ag                                  32

<210> SEQ ID NO 4
<211> LENGTH: 32
<212> TYPE: DNA
<213> ORGANISM: ARTIFICIAL
<220> FEATURE:
<223> OTHER INFORMATION: consensus direct repeat

<400> SEQUENCE: 4
yccagtgggt cagaagttta catacactma rt                                  32

<210> SEQ ID NO 5
<211> LENGTH: 340
<212> TYPE: PRT
<213> ORGANISM: ARTIFICIAL
<220> FEATURE:
<223> OTHER INFORMATION: SB polypeptide

<400> SEQUENCE: 5
```

Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
                20                  25                  30

Lys Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

```
Lys Ala Arg Leu Arg Phe Ala Thr Ala His Gly Asp Lys Asp Arg Thr
            130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Ser Ile
            180                 185                 190

Met Leu Trp Gly Cys Phe Ala Ala Gly Gly Thr Gly Ala Leu His Lys
            195                 200                 205

Ile Asp Gly Ile Met Arg Lys Glu Asn Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
            275                 280                 285

Val Arg Ala Arg Arg Pro Thr Asn Leu Thr Gln Leu His Gln Leu Cys
290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340

<210> SEQ ID NO 6
<211> LENGTH: 229
<212> TYPE: DNA
<213> ORGANISM: ARTIFICIAL
<220> FEATURE:
<223> OTHER INFORMATION: left inverted repeat sequence

<400> SEQUENCE: 6
cagttgaagt cggaagttta catacactta rgttggagtc attaaaactc gttttcaac    60 yacwccacaa atttcttgtt aacaaacwat agttttggca agcragttag gacatctact  120
ttgtgcatga cacaagtmat ttttccaaca attgtttaca gacagattat ttcacttata  180
attcactgta tcacaattcc agtgggtcag aagtttacat acactaagt                229

<210> SEQ ID NO 7
<211> LENGTH: 229
<212> TYPE: DNA
<213> ORGANISM: ARTIFICIAL
<220> FEATURE:
<223> OTHER INFORMATION: inverted repeat sequence

<400> SEQUENCE: 7
ttgagtgtat gttaacttct gacccactgg aatgtgatg aaagaaataa aagctgaaat     60
gaatcattct ctctactatt attctgayat ttcacattct taaataaag tggtgatcct   120 aactgacctt aagacaggga atctttactc ggattaaatg tcaggaattg tgaaaaastg  180
agtttaaatg tatttggcta aggtgtatgt aaacttccga cttcaactg                229
```

<210> SEQ ID NO 8
<211> LENGTH: 4732
<212> TYPE: DNA
<213> ORGANISM: artificial
<220> FEATURE:
<223> OTHER INFORMATION: nucleotide sequence of pCMV/SB

<400> SEQUENCE: 8

| | | | | | |
|---|---|---|---|---|---|
| gatccgacat | catgggaaaa | tcaaaagaaa | tcagccaaga | cctcagaaaa | aaaattgtag | 60 |
| acctccacaa | gtctggttca | tccttgggag | caatttccaa | acgcctgaaa | gtaccacgtt | 120 |
| catctgtaca | aacaatagta | cgcaagtata | aacaccatgg | gaccacgcag | ccgtcatacc | 180 |
| gctcaggaag | gagacgcgtt | ctgtctccta | gagatgaacg | tactttggtg | cgaaaagtgc | 240 |
| aaatcaatcc | cagaacaaca | gcaaaggacc | ttgtgaagat | gctggaggaa | acaggtacaa | 300 |
| aagtatctat | atccacagta | aaacgagtcc | tatatcgaca | taacctgaaa | ggccgctcag | 360 |
| caaggaagaa | gccactgctc | caaaaccgac | ataagaaagc | cagactacgg | tttgcaactg | 420 |
| cacatgggga | caaagatcgt | acttttttgga | gaaatgtcct | ctggtctgat | gaaacaaaaa | 480 |
| tagaactgtt | tggccataat | gaccatcgtt | atgtttggag | gaagaagggg | gaggcttgca | 540 |
| agccgaagaa | caccatccca | accgtgaagc | acggggggtgg | cagcatcatg | ttgtgggggt | 600 |
| gctttgctgc | aggagggact | ggtgcacttc | acaaaataga | tggcatcatg | aggaaggaaa | 660 |
| attatgtgga | tatattgaag | caacatctca | agacatcagt | caggaagtta | aagcttggtc | 720 |
| gcaaatgggt | cttccaaatg | gacaatgacc | ccaagcatac | ttccaaagtt | gtggcaaaat | 780 |
| ggcttaagga | caacaaagtc | aaggtattgg | agtggccatc | acaaagccct | gacctcaatc | 840 |
| ctatagaaaa | tttgtgggca | gaactgaaaa | agcgtgtgcg | agcaaggagg | cctacaaacc | 900 |
| tgactcagtt | acaccagctc | tgtcaggagg | aatgggccaa | aattcaccca | acttattgtg | 960 |
| ggaagcttgt | ggaaggctac | ccgaaacgtt | tgacccaagt | taaacaattt | aaaggcaatg | 1020 |
| ctaccaaata | ctagaattgg | ccgcggggat | ccagacatga | taagatacat | tgatgagttt | 1080 |
| ggacaaacca | caactagaat | gcagtgaaaa | aaatgcttta | tttgtgaaat | ttgtgatgct | 1140 |
| attgctttat | ttgtaaccat | tataagctgc | aataaacaag | ttaacaacaa | caattgcatt | 1200 |
| cattttatgt | ttcaggttca | gggggaggtg | tgggaggttt | tttcggatcc | tctagagtcg | 1260 |
| acctgcaggc | atgcaagctt | ggcgtaatca | tggtcatagc | tgtttcctgt | gtgaaattgt | 1320 |
| tatccgctca | caattccaca | caacatacga | gccggaagca | taaagtgtaa | agcctggggt | 1380 |
| gcctaatgag | tgagctaact | cacattaatt | gcgttgcgct | cactgcccgc | tttccagtcg | 1440 |
| ggaaacctgt | cgtgccagct | gcattaatga | atcggccaac | gcgcgggggag | aggcggtttg | 1500 |
| cgtattgggc | gctcttccgc | ttcctcgctc | actgactcgc | tgcgctcggt | cgttcggctg | 1560 |
| cggcgagcgg | tatcagctca | ctcaaaggcg | gtaatacggt | tatccacaga | atcagggggat | 1620 |
| aacgcaggaa | agaacatgtg | agcaaaaggc | cagcaaaagg | ccaggaaccg | taaaaaggcc | 1680 |
| gcgttgctgg | cgtttttcca | taggctccgc | cccccctgacg | agcatcacaa | aaatcgacgc | 1740 |
| tcaagtcaga | ggtggcgaaa | cccgacagga | ctataaagat | accaggcgtt | tccccctgga | 1800 |
| agctccctcg | tgcgctctcc | tgttccgacc | ctgccgctta | ccggatacct | gtccgccttt | 1860 |
| ctcccttcgg | gaagcgtggc | gctttctcat | agctcacgct | gtaggtatct | cagttcggtg | 1920 |
| taggtcgttc | gctccaagct | gggctgtgtg | cacgaacccc | ccgttcagcc | cgaccgctgc | 1980 |
| gccttatccg | gtaactatcg | tcttgagtcc | aacccggtaa | gacacgactt | atcgccactg | 2040 |
| gcagcagcca | ctggtaacag | gattagcaga | gcgaggtatg | taggcggtgc | tacagagttc | 2100 |
| ttgaagtggt | ggcctaacta | cggctacact | agaaggacag | tatttggtat | ctgcgctctg | 2160 |

```
ctgaagccag ttaccttcgg aaaaagagtt ggtagctctt gatccggcaa acaaaccacc    2220
gctggtagcg gtggttttt tgtttgcaag cagcagatta cgcgcagaaa aaaggatct    2280 caagaagatc ctttgatctt ttctacgggg tctgacgctc agtggaacga aaactcacgt    2340
taagggattt tggtcatgag attatcaaaa aggatcttca cctagatcct tttaaattaa    2400
aaatgaagtt ttaaatcaat ctaaagtata tatgagtaaa cttggtctga cagttaccaa    2460
tgcttaatca gtgaggcacc tatctcagcg atctgtctat ttcgttcatc catagttgcc    2520 tgactcccg tcgtgtagat aactacgata cgggagggct taccatctgg ccccagtgct    2580
gcaatgatac cgcgagaccc acgctcaccg gctccagatt tatcagcaat aaaccagcca    2640
gccggaaggg ccgagcgcag aagtggtcct gcaactttat ccgcctccat ccagtctatt    2700
aattgttgcc gggaagctag agtaagtagt tcgccagtta atagtttgcg caacgttgtt    2760
gccattgcta caggcatcgt ggtgtcacgc tcgtcgtttg gtatggcttc attcagctcc    2820
ggttcccaac gatcaaggcg agtacatga tcccccatgt tgtgcaaaaa agcggttagc    2880
tccttcggtc ctccgatcgt tgtcagaagt aagttggccg cagtgttatc actcatggtt    2940
atggcagcac tgcataattc tcttactgtc atgccatccg taagatgctt ttctgtgact    3000
ggtgagtact caaccaagtc attctgagaa tagtgtatgc ggcgaccgag ttgctcttgc    3060
ccggcgtcaa tacgggataa taccgcgcca catagcagaa ctttaaaagt gctcatcatt    3120
ggaaaacgtt cttcggggcg aaaactctca aggatcttac cgctgttgag atccagttcg    3180
atgtaaccca ctcgtgcacc caactgatct tcagcatctt ttactttcac cagcgtttct    3240
gggtgagcaa aaacaggaag gcaaaatgcc gcaaaaaagg aataagggc gacacggaaa    3300 tgttgaatac tcatactctt cctttttcaa tattattgaa gcatttatca gggttattgt    3360
ctcatgagcg gatacatatt tgaatgtatt tagaaaaata acaaataggg gttccgcgc    3420 acatttcccc gaaaagtgcc acctgacgtc taagaaacca ttattatcat gacattaacc    3480
tataaaaata ggcgtatcac gaggcccttt cgtctcgcgc gtttcggtga tgacggtgaa    3540
aacctctgac acatgcagct cccggagacg gtcacagctt gtctgtaagc ggatgccggg    3600
agcagacaag cccgtcaggg cgcgtcagcg ggtgttggcg ggtgtcgggg ctggcttaac    3660
tatgcggcat cagagcagat tgtactgaga gtgcaccata tgcggtgtga ataccgcac    3720 agatgcgtaa ggagaaaata ccgcatcagg cgccattcgc cattcaggct gcgcaactgt    3780
tgggaagggc gatcggtgcg ggcctcttcg ctattacgcc agctggcgaa agggggatgt    3840
gctgcaaggc gattaagttg ggtaacgcca gggttttccc agtcacgacg ttgtaaaacg    3900
acggccagtg aattcgagct tgcatgcctg caggtcgtta cataacttac ggtaaatggc    3960
ccgcctggct gaccgcccaa cgacccccgc ccattgacgt caataatgac gtatgttccc    4020
atagtaacgc caatagggac tttccattga cgtcaatggg tggagtattt acggtaaact    4080
gcccacttgg cagtacatca agtgtatcat atgccaagta cgccccctat tgacgtcaat    4140
gacggtaaat ggcccgcctg gcattatgcc cagtacatga ccttatggga ctttcctact    4200
tggcagtaca tctacgtatt agtcatcgct attaccatgg tgatgcggtt ttggcagtac    4260
atcaatgggc gtggatagcg gtttgactca cggggatttc caagtctcca ccccattgac    4320
gtcaatggga gtttgttttg gcaccaaaat caacgggact ttccaaaatg tcgtaacaac    4380
tccgccccat tgacgcaaat gggcggtagg cgtgtacggt gggaggtcta tataagcaga    4440
gctcgtttag tgaaccgtca gatcgcctgg agacgccatc cacgctgttt tgacctccat    4500
agaagacacc gggaccgatc cagcctccgg actctagagg atccggtact cgaggaactg    4560
```

-continued

| | | |
|---|---|---|
| aaaaaccaga aagttaactg gtaagtttag tcttttttgtc ttttatttca ggtcccggat | 4620 |
| ccggtggtgg tgcaaatcaa agaactgctc ctcagtggat gttgccttta cttctaggcc | 4680 |
| tgtacggaag tgttacttct gctctaaaag ctgcggaatt gtacccgcgg cc | 4732 |

<210> SEQ ID NO 9
<211> LENGTH: 4410
<212> TYPE: DNA
<213> ORGANISM: ARTIFICIAL
<220> FEATURE:
<223> OTHER INFORMATION: nucleotide sequence of pCMV/SB-DDE

<400> SEQUENCE: 9

| | | |
|---|---|---|
| ccatcacaaa gccctgacct caatcctata gaaaatttgt gggcagaact gaaaaagcgt | 60 |
| gtgcgagcaa ggaggcctac aaacctgact cagttacacc agctctgtca ggaggaatgg | 120 |
| gccaaaattc acccaactta ttgtgggaag cttgtggaag ctacccgaa acgtttgacc | 180 |
| caagttaaac aatttaaagg caatgctacc aaatactaga attggccgcg gggatccaga | 240 |
| catgataaga tacattgatg agtttggaca accacaact agaatgcagt gaaaaaaatg | 300 |
| ctttatttgt gaaatttgtg atgctattgc tttatttgta accattataa gctgcaataa | 360 |
| acaagttaac aacaacaatt gcattcattt tatgtttcag gttcaggggg aggtgtggga | 420 |
| ggttttttcg gatcctctag agtcgacctg caggcatgca agcttggcgt aatcatggtc | 480 |
| atagctgttt cctgtgtgaa attgttatcc gctcacaatt ccacacaaca tacgagccgg | 540 |
| aagcataaag tgtaaagcct ggggtgccta atgagtgagc taactcacat taattgcgtt | 600 |
| gcgctcactg cccgctttcc agtcgggaaa cctgtcgtgc cagctgcatt aatgaatcgg | 660 |
| ccaacgcgcg gggagaggcg gtttgcgtat tgggcgctct tccgcttcct cgctcactga | 720 |
| ctcgctgcgc tcggtcgttc ggctgcggcg agcggtatca gctcactcaa aggcggtaat | 780 |
| acggttatcc acagaatcag gggataacgc aggaaagaac atgtgagcaa aaggccagca | 840 |
| aaaggccagg aaccgtaaaa aggccgcgtt gctggcgttt ttccataggc tccgcccccc | 900 |
| tgacgagcat cacaaaaatc gacgctcaag tcagaggtgg cgaaacccga caggactata | 960 |
| aagataccag gcgtttcccc ctggaagctc cctcgtgcgc tctcctgttc cgaccctgcc | 1020 |
| gcttaccgga tacctgtccg cctttctccc ttcgggaagc gtggcgcttt ctcatagctc | 1080 |
| acgctgtagg tatctcagtt cggtgtaggt cgttcgctcc aagctgggct gtgtgcacga | 1140 |
| accccccgtt cagcccgacc gctgcgcctt atccggtaac tatcgtcttg agtccaaccc | 1200 |
| ggtaagacac gacttatcgc cactggcagc agccactggt aacaggatta gcagagcgag | 1260 |
| gtatgtaggc ggtgctacag agttcttgaa gtggtggcct aactacggct acactagaag | 1320 |
| gacagtattt ggtatctgcg ctctgctgaa gccagttacc ttcggaaaaa gagttggtag | 1380 |
| ctcttgatcc ggcaaacaaa ccaccgctgg tagcggtggt ttttttgttt gcaagcagca | 1440 |
| gattacgcgc agaaaaaaag gatctcaaga agatcctttg atcttttcta cggggtctga | 1500 |
| cgctcagtgg aacgaaaact cacgttaagg gattttggtc atgagattat caaaaaggat | 1560 |
| cttcacctag atccttttaa attaaaaatg aagttttaaa tcaatctaaa gtatatatga | 1620 |
| gtaaacttgg tctgacagtt accaatgctt aatcagtgag gcacctatct cagcgatctg | 1680 |
| tctatttcgt tcatccatag ttgcctgact ccccgtcgtg tagataacta cgatacggga | 1740 |
| gggcttacca tctggcccca gtgctgcaat gataccgcga cccacgct caccggctcc | 1800 |
| agatttatca gcaataaacc agccagccgg aagggccgag cgcagaagtg gtcctgcaac | 1860 |
| tttatccgcc tccatccagt ctattaattg ttgccgggaa gctagagtaa gtagttcgcc | 1920 |

```
agttaatagt tgcgcaacg ttgttgccat tgctacaggc atcgtggtgt cacgctcgtc    1980
gtttggtatg gcttcattca gctccggttc ccaacgatca aggcgagtta catgatcccc    2040
catgttgtgc aaaaaagcgg ttagctcctt cggtcctccg atcgttgtca gaagtaagtt    2100
ggccgcagtg ttatcactca tggttatggc agcactgcat aattctctta ctgtcatgcc    2160
atccgtaaga tgcttttctg tgactggtga gtactcaacc aagtcattct gagaatagtg    2220
tatgcggcga ccgagttgct cttgcccggc gtcaatacgg gataataccg cgccacatag    2280
cagaacttta aaagtgctca tcattggaaa acgttcttcg gggcgaaaac tctcaaggat    2340
cttaccgctg ttgagatcca gttcgatgta acccactcgt gcacccaact gatcttcagc    2400
atcttttact tcaccagcg tttctgggtg agcaaaaaca ggaaggcaaa atgccgcaaa    2460
aaagggaata agggcgacac ggaaatgttg aatactcata ctcttccttt ttcaatatta    2520
ttgaagcatt tatcagggtt attgtctcat gagcggatac atatttgaat gtatttagaa    2580
aaataaacaa atagggtttc cgcgcacatt tccccgaaaa gtgccacctg acgtctaaga    2640
aaccattatt atcatgacat aacctataa aaataggcgt atcacgaggc cctttcgtct    2700
cgcgcgtttc ggtgatgacg gtgaaaacct ctgacacatg cagctcccgg agacggtcac    2760
agcttgtctg taagcggatg ccgggagcag acaagcccgt cagggcgcgt cagcgggtgt    2820
tggcgggtgt cggggctggc ttaactatgc ggcatcagag cagattgtac tgagagtgca    2880
ccatatgcgg tgtgaaatac cgcacagatg cgtaaggaga aaataccgca tcaggcgcca    2940
ttcgccattc aggctgcgca actgttggga agggcgatcg gtgcgggcct cttcgctatt    3000
acgccagctg gcgaaagggg gatgtgctgc aaggcgatta agttgggtaa cgccagggtt    3060
ttcccagtca cgacgttgta aaacgacggc cagtgaattc gagcttgcat gcctgcaggt    3120
cgttacataa cttacggtaa atggcccgcc tggctgaccg cccaacgacc cccgcccatt    3180
gacgtcaata atgacgtatg ttcccatagt aacgccaata gggactttcc attgacgtca    3240
atgggtggag tatttacggt aaactgccca cttggcagta catcaagtgt atcatatgcc    3300
aagtacgccc cctattgacg tcaatgacgg taaatggccc gcctggcatt atgcccagta    3360
catgacctta tgggactttc ctacttggca gtacatctac gtattagtca tcgctattac    3420
catggtgatg cggttttggc agtacatcaa tgggcgtgga tagcggtttg actcacgggg    3480
atttccaagt ctccacccca ttgacgtcaa tgggagtttg ttttggcacc aaaatcaacg    3540
ggactttcca aaatgtcgta caactccgc cccattgacg caaatgggcg gtaggcgtgt    3600
acggtgggag gtctatataa gcagagctcg tttagtgaac cgtcagatcg cctggagacg    3660
ccatccacgc tgttttgacc tccatagaag acaccgggac cgatccagcc tccggactct    3720
agaggatccg gtactcgagg aactgaaaaa ccagaaagtt aactggtaag tttagtcttt    3780
ttgtctttta tttcaggtcc cggatccggt ggtggtgcaa atcaaagaac tgctcctcag    3840
tggatgttgc ctttacttct aggcctgtac ggaagtgtta cttctgctct aaaagctgcg    3900
gaattgtacc cgcggccgat ccgacatcat gggaaaatca aaagaaatca gccaagacct    3960
cagaaaaaaa attgtagacc tccacaagtc tggttcatcc ttgggagcaa tttccaaacg    4020
cctgaaagta ccacgttcat ctgtacaaac aatagtacgc aagtataaac accatgggac    4080
cacgcagccg tcataccgct caggaaggag acgcgttctg tctcctagag atgaacgtac    4140
tttggtgcga aaagtgcaaa tcaatcccag aacaacagca aaggaccttg tgaagatgct    4200
ggaggaaaca ggtacaaaag tatctatatc cacagtaaaa cgagtcctat atcgacataa    4260
cctgaaaggc cgctcagcaa ggaagaagcc actgctccaa aaccgacata agaaagccag    4320
```

| | |
|---|---:|
| actacggttt gcaactgcac atggggacaa agatcgtact ttttggagaa atgtcctctg | 4380 |
| gtctgatgaa acaaaaatag aactgtttgg | 4410 |

<210> SEQ ID NO 10
<211> LENGTH: 4928
<212> TYPE: DNA
<213> ORGANISM: ARTIFICIAL
<220> FEATURE:
<223> OTHER INFORMATION: nucleotide sequence of pT/SVneo

<400> SEQUENCE: 10

| | |
|---|---:|
| ggcatgcaag cttggcgtaa tcatggtcat agctgtttcc tgtgtgaaat tgttatccgc | 60 |
| tcacaattcc acacaacata cgagccggaa gcataaagtg taaagcctgg ggtgcctaat | 120 |
| gagtgagcta actcacatta attgcgttgc gctcactgcc cgctttccag tcgggaaacc | 180 |
| tgtcgtgcca gctgcattaa tgaatcggcc aacgcgcggg gagaggcggt ttgcgtattg | 240 |
| ggcgctcttc cgcttcctcg ctcactgact cgctgcgctc ggtcgttcgg ctgcggcgag | 300 |
| cggtatcagc tcactcaaag gcggtaatac ggttatccac agaatcaggg gataacgcag | 360 |
| gaaagaacat gtgagcaaaa ggccagcaaa aggccaggaa ccgtaaaaag gccgcgttgc | 420 |
| tggcgttttt ccataggctc cgcccccctg acgagcatca caaaaatcga cgctcaagtc | 480 |
| agaggtggcg aaacccgaca ggactataaa gataccaggc gtttccccct ggaagctccc | 540 |
| tcgtgcgctc tcctgttccg accctgccgc ttaccggata cctgtccgcc tttctccctt | 600 |
| cgggaagcgt ggcgctttct catagctcac gctgtaggta tctcagttcg gtgtaggtcg | 660 |
| ttcgctccaa gctgggctgt gtgcacgaac cccccgttca gcccgaccgc tgcgccttat | 720 |
| ccggtaacta tcgtcttgag tccaacccgg taagacacga cttatcgcca ctggcagcag | 780 |
| ccactggtaa caggattagc agagcgaggt atgtaggcgg tgctacagag ttcttgaagt | 840 |
| ggtggcctaa ctacggctac actagaagga cagtatttgg tatctgcgct ctgctgaagc | 900 |
| cagttacctt cggaaaaaga gttggtagct cttgatccgg caaacaaacc accgctggta | 960 |
| gcggtggttt ttttgtttgc aagcagcaga ttacgcgcag aaaaaaagga tctcaagaag | 1020 |
| atcctttgat cttttctacg gggtctgacg ctcagtggaa cgaaaactca cgttaaggga | 1080 |
| ttttggtcat gagattatca aaaaggatct caccctagat cctttttaaat taaaaatgaa | 1140 |
| gttttaaatc aatctaaagt atatatgagt aaacttggtc tgacagttac caatgcttaa | 1200 |
| tcagtgaggc acctatctca gcgatctgtc tatttcgttc atccatagtt gcctgactcc | 1260 |
| ccgtcgtgta gataactacg atacgggagg gcttaccatc tggccccagt gctgcaatga | 1320 |
| taccgcgaga cccacgctca ccggctccag atttatcagc aataaaccag ccagccggaa | 1380 |
| gggccgagcg cagaagtggt cctgcaactt tatccgcctc catccagtct attaattgtt | 1440 |
| gccgggaagc tagagtaagt agttcgccag ttaatagttt cgcaacgtt gttgccattg | 1500 |
| ctacaggcat cgtggtgtca cgctcgtcgt ttggtatggc ttcattcagc tccggttccc | 1560 |
| aacgatcaag gcgagttaca tgatccccca tgttgtgcaa aaaagcggtt agctccttcg | 1620 |
| gtcctccgat cgttgtcaga agtaagttgg ccgcagtgtt atcactcatg gttatggcag | 1680 |
| cactgcataa ttctcttact gtcatgccat ccgtaagatg cttttctgtg actggtgagt | 1740 |
| actcaaccaa gtcattctga gaatagtgta tgcggcgacc gagttgctct tgcccggcgt | 1800 |
| caatacggga taataccgcg ccacatagca gaactttaaa agtgctcatc attggaaaac | 1860 |
| gttcttcggg gcgaaaactc tcaaggatct taccgctgtt gagatccagt tcgatgtaac | 1920 |
| ccactcgtgc acccaactga tcttcagcat cttttacttt caccagcgtt tctgggtgag | 1980 |

```
caaaaacagg aaggcaaaat gccgcaaaaa agggaataag ggcgacacgg aaatgttgaa    2040
tactcatact cttccttttt caatattatt gaagcattta tcagggttat tgtctcatga    2100
gcggatacat atttgaatgt atttagaaaa ataaacaaat aggggttccg cgcacatttc    2160
cccgaaaagt gccacctgac gtctaagaaa ccattattat catgacatta acctataaaa    2220
ataggcgtat cacgaggccc tttcgtctcg cgcgtttcgg tgatgacggt gaaaacctct    2280
gacacatgca gctcccggag acggtcacag cttgtctgta agcggatgcc gggagcagac    2340
aagcccgtca gggcgcgtca gcgggtgttg gcgggtgtcg gggctggctt aactatgcgg    2400
catcagagca gattgtactg agagtgcacc atatgcggtg tgaaataccg cacagatgcg    2460
taaggagaaa ataccgcatc aggcgccatt cgccattcag gctgcgcaac tgttgggaag    2520
ggcgatcggt gcgggcctct cgctattac gccagctggc gaaaggggga tgtgctgcaa    2580
ggcgattaag ttgggtaacg ccagggtttt cccagtcacg acgttgtaaa acgacggcca    2640
gtgaattcga gctcggtacc ctacagttga agtcggaagt ttacatacac ttaagttgga    2700
gtcattaaaa ctcgttttc aactacacca caaatttctt gttaacaaac aatagttttg    2760
gcaagtcagt taggacatct actttgtgca tgacacaagt catttttcca acaattgttt    2820
acagacagat tatttcactt ataattcact gtatcacaat tccagtgggt cagaagttta    2880
catacactaa gttgactgtg cctttaaaca gcttggaaaa ttccagaaaa tgatgtcatg    2940
gctttagaag cttctgatag actaattgac atcatttgag tcaattggag gtgtacctgt    3000
ggatgtattt caagggatcc agacatgata agatacattg atgagtttgg acaaaccaca    3060
actagaatgc agtgaaaaaa atgctttatt tgtgaaattt gtgatgctat tgctttattt    3120
gtaaccatta taagctgcaa taaacaagtt ggggtgggcg aagaactcca gcatgagatc    3180
cccgcgctgg aggatcatcc agccggcgtc ccggaaaacg attccgaagc ccaacctttc    3240
atagaaggcg gcggtggaat cgaaatctcg tgatggcagg ttgggcgtcg cttggtcggt    3300
catttcgaac cccagagtcc cgctcagaag aactcgtcaa gaaggcgata aaggcgatg    3360 cgctgcgaat cgggagcggc gataccgtaa agcacgagga gcggtcagc ccattcgccg    3420 ccaagctctt cagcaatatc acgggtagcc aacgctatgt cctgatagcg gtccgccaca    3480
cccagccggc cacagtcgat gaatccagaa aagcggccat tttccaccat gatattcggc    3540
aagcaggcat cgccatgggt cacgacgaga tcctcgccgt cgggcatgcg cgccttgagc    3600
ctggcgaaca gttcggctgg cgcgagcccc tgatgctctt cgtccagatc atcctgatcg    3660
acaagaccgg cttccatccg agtacgtgct cgctcgatgc gatgtttcgc ttggtggtcg    3720
aatgggcagg tagccggatc aagcgtatgc agccgccgca ttgcatcagc catgatggat    3780
actttctcgg caggagcaag gtgagatgac aggagatcct gccccggcac ttcgcccaat    3840
agcagccagt cccttcccgc ttcagtgaca acgtcgagca cagctgcgca aggaacgccc    3900
gtcgtggcca gccacgatag ccgcgctgcc tcgtcctgca gttcattcag ggcaccggac    3960
aggtcggtct tgacaaaaag aaccgggcgc ccctgcgctg acagccggaa cacggcggca    4020
tcagagcagc cgattgtctg ttgtgcccag tcatagccga atagcctctc cacccaagcg    4080
gccggagaac ctgcgtgcaa tccatcttgt tcaatcatgc gaaacgatcc tcatcctgtc    4140
tcttgatcag atccgaaaat ggatatccaa gctcccggga gcttttgca aaagcctagg    4200 cctccaaaaa agcctcctca ctacttctgg aatagctcag aggccgaggc ggcctcggcc    4260
tctgcataaa taaaaaaaat tagtcagcca tgggcggag aatgggcgga actgggcgga    4320
gttaggggcg ggatgggcgg agttaggggc gggactatgg ttgctgacta attgagatgc    4380
```

```
atgctttgca tacttctgcc tgctggggag cctggggact ttccacacct ggttgctgac      4440
taattgagat gcatgctttg catacttctg cctgcctggg gagcctgggg actttccaca      4500
ccctaactga cacacattcc acagaattcc catcacaaag ctctgacctc aatcctatag      4560
aaaggaggaa tgagccaaaa ttcacccaac ttattgtggg aagcttgtgg aaggctactc      4620
gaaatgtttg acccaagtta aacaatttaa aggcaatgct accaaatact aattgagtgt      4680
atgttaactt ctgacccact gggaatgtga tgaaagaaat aaaagctgaa atgaatcatt      4740
ctctctacta ttattctgat atttcacatt cttaaaataa agtggtgatc ctaactgacc      4800
ttaagacagg gaatctttac tcggattaaa tgtcaggaat tgtgaaaaag tgagtttaaa      4860
tgtatttggc taaggtgtat gtaaacttcc gacttcaact gtagggatc ctctagagtc       4920 gacctgca                                                               4928
```

<210> SEQ ID NO 11
<211> LENGTH: 3497
<212> TYPE: DNA
<213> ORGANISM: ARTIFICIAL
<220> FEATURE:
<223> OTHER INFORMATION: nucleotide sequence of pT/HindIIIneo

<400> SEQUENCE: 11

```
cacctgacgc gccctgtagc ggcgcattaa gcgcggcggg tgtggtggtt acgcgcagcg        60
tgaccgctac acttgccagc gccctagcgc ccgctccttt cgctttcttc ccttcctttc       120
tcgccacgtt cgccggcttt ccccgtcaag ctctaaatcg gggctccct ttagggttcc        180 gatttagtgc tttacggcac ctcgacccca aaaaacttga ttagggtgat ggttcacgta       240
gtgggccatc gccctgatag acggtttttc gccctttgac gttggagtcc acgttcttta       300
atagtggact cttgttccaa actggaacaa cactcaaccc tatctcggtc tattcttttg       360
atttataagg gattttgccg atttcggcct attggttaaa aaatgagctg atttaacaaa       420
aatttaacgc gaattttaac aaaatattaa cgcttacaat ttccattcgc cattcaggct       480
gcgcaactgt tgggaagggc gatcggtgcg ggcctcttcg ctattacgcc agctggcgaa       540 aggggggatgt gctgcaaggc gattaagttg ggtaacgcca gggttttccc agtcacgacg       600
ttgtaaaacg acggccagtg aattgtaata cgactcacta tagggcgaat tggagctcgg       660
taccctacag ttgaagtcgg aagtttacat acacttaagt tggagtcatt aaaactcgtt       720
tttcaactac accacaaatt tcttgttaac aaacaatagt tttggcaagt cagttaggac       780
atctactttg tgcatgacac aagtcatttt tccaacaatt gtttacagac agattatttc       840
acttataatt cactgtatca caattccagt gggtcagaag tttacataca ctaagttgac       900
tgtgccttta aacagcttgg aaaattccag aaaatgatgt catggcttta gaagcttgtg       960
gaaggctact cgaaatgttt gacccaagtt aaacaattta aggcaatgc taccaaatac       1020 taattgagtg tatgttaact tctgacccac tgggaatgtg atgaaagaaa taaaagctga      1080
aatgaatcat tctctctact attattctga tatttcacat tcttaaaata agtggtgat      1140 cctaactgac cttaagacag ggaatcttta ctcggattaa atgtcaggaa ttgtgaaaaa      1200
gtgagtttaa atgtatttgg ctaaggtgta tgtaaacttc cgacttcaac tgtagggat       1260 cctctagcta gagtcgacct cgagggggg cccggtaccc agcttttgtt cccttagtg        1320 agggttaatt tcgagcttgg cgtaatcatg gtcatagctg tttcctgtgt gaaattgtta      1380
tccgctcaca attccacaca acatacgagc cggaagcata aagtgtaaag cctggggtgc      1440
ctaatgagtg agctaactca cattaattgc gttgcgctca ctgcccgctt tccagtcggg      1500
```

```
aaacctgtcg tgccagctgc attaatgaat cggccaacgc gcggggagag gcggtttgcg   1560
tattgggcgc tcttccgctt cctcgctcac tgactcgctg cgctcggtcg ttcggctgcg   1620
gcgagcggta tcagctcact caaaggcggt aatacggtta ccacagaat cagggatataa   1680 cgcaggaaag aacatgtgag caaaaggcca gcaaaaggcc aggaaccgta aaaaggccgc   1740
gttgctggcg tttttccata ggctccgccc ccctgacgag catcacaaaa atcgacgctc   1800
aagtcagagg tggcgaaacc cgacaggact ataaagatac caggcgtttc ccctggaag   1860 ctccctcgtg cgctctcctg ttccgaccct gccgcttacc ggatacctgt ccgcctttct   1920
cccttcggga agcgtggcgc tttctcatag ctcacgctgt aggtatctca gttcggtgta   1980
ggtcgttcgc tccaagctgg gctgtgtgca cgaaccccc gttcagcccg accgctgcgc   2040
cttatccggt aactatcgtc ttgagtccaa cccggtaaga cacgacttat cgccactggc   2100
agcagccact ggtaacagga ttagcagagc gaggtatgta ggcggtgcta cagagttctt   2160
gaagtggtgg cctaactacg gctacactag aaggacagta tttggtatct gcgctctgct   2220
gaagccagtt accttcggaa aaagagttgg tagctcttga tccggcaaac aaaccaccgc   2280
tggtagcggt ggtttttttg tttgcaagca gcagattacg cgcagaaaaa aaggatctca   2340
agaagatcct ttgatctttt ctacggggtc tgacgctcag tggaacgaaa actcacgtta   2400
agggattttg gtcatgagat tatcaaaaag gatcttcacc tagatccttt taaattaaaa   2460
atgaagtttt aaatcaatct aaagtatata tgagtaaact tggtctgaca gttaccaatg   2520
cttaatcagt gaggcaccta tctcagcgat ctgtctattt cgttcatcca tagttgcctg   2580
actccccgtc gtgtagataa ctacgatacg ggagggctta ccatctggcc ccagtgctgc   2640
aatgataccg cgagacccac gctcaccggc tccagattta tcagcaataa accagccagc   2700
cggaagggcc gagcgcagaa gtggtcctgc aactttatcc gcctccatcc agtctattaa   2760
ttgttgccgg gaagctagag taagtagttc gccagttaat agtttgcgca acgttgttgc   2820
cattgctaca ggcatcgtgg tgtcacgctc gtcgtttggt atggcttcat tcagctccgg   2880
ttcccaacga tcaaggcgag ttacatgatc ccccatgttg tgcaaaaaag cggttagctc   2940
cttcggtcct ccgatcgttg tcagaagtaa gttggccgca gtgttatcac tcatggttat   3000
ggcagcactg cataattctc ttactgtcat gccatccgta agatgctttt ctgtgactgg   3060
tgagtactca accaagtcat tctgagaata gtgtatgcgg cgaccgagtt gctcttgccc   3120
ggcgtcaata cgggataata ccgcgccaca tagcagaact ttaaaagtgc tcatcattgg   3180
aaaacgttct cggggcgaa aactctcaag gatcttaccg ctgttgagat ccagttcgat   3240
gtaacccact cgtgcaccca actgatcttc agcatctttt actttcacca gcgtttctgg   3300
gtgagcaaaa acaggaaggc aaaatgccgc aaaaaaggga ataagggcga cacggaaatg   3360
ttgaatactc atactcttcc ttttcaata ttattgaagc atttatcagg gttattgtct   3420
catgagcgga tacatatttg aatgtattta gaaaaataaa caataggggg ttccgcgcac   3480
atttccccga aaagtgc                                                  3497
```

<210> SEQ ID NO 12
<211> LENGTH: 6782
<212> TYPE: DNA
<213> ORGANISM: ARTIFICIAL
<220> FEATURE:
<223> OTHER INFORMATION: nucleotide sequence of pFV3CAT

<400> SEQUENCE: 12

```
agcgcccaat acgcaaaccg cctctccccg cgcgttggcc gattcattaa tgcagctggc     60
```

-continued

```
acgacaggtt tcccgactgg aaagcgggca gtgagcgcaa cgcaattaat gtgagttagc      120
tcactcatta ggcacccag gctttacact ttatgcttcc ggctcgtatg ttgtgtggaa       180
ttgtgagcgg ataacaattt cacacaggaa acatctagaa ccatgattac gccaagcttt     240
tagaccttct tacttttggg gattatataa gtattttctc aataaatatc tcatatctta     300
ctgtggttta actgctgaat ctaaaatttt aatacaaaag tagttatatt tgttgtacat     360
tgtaaactat aacttaactt cagtttcaga gaaactcatg tgctcaaaat gtaaaaaaag     420
tttcctgtta aatattttgt aaatgtattg aagacaaaat aagaaaaaaa aaatataag      480 ccactaaatc acactgtcct tggtatcagc aagagattct gacataatca gctgttttg      540 tttattactg ccattgaagg ccatgtgcat tagtcccaag ttacacatta aaaagtcaca     600
tgtagcttac caacatcagt gctgttcaag cacagcctca tctactattc aaactgtggc    660
accatctaaa atatgccaga attttttat ttaatgaatt tgaccctgaa atatgtatta      720
atatcactcc tgtgattttt ttgtaatcag cttacaatta caggaatgca agcctgattc     780
attacaagtt tcactacact ttctctgaca acatcaccta ctgaactcag accagctagt    840
tgctccttaa gtatacaatc atgtcactaa tcctcatttc aatgaaaaat acccctattg     900
tacttggtac ttggtagata accacagagc agtattatgc cattattgtg aatacaataa    960
gaggtaaatg acctacagag ctgctgctgc tgttgtgtta gattgtaaac acagcacagg    1020
atcaaggagg tgtccatcac tatgaccaat actagcactt tgcacaggct ctttgaaagg    1080
ctgaaaagag cctattggc gttatcacaa caaaatacgc aaatacggaa aacaacgtat     1140
tgaacttcgc aaacaaaaa cagcgatttt gatgaaaatc gcttaggcct tgctcttcaa     1200
acaatccagc ttctccttct ttcactctca agttgcaaga agcaagtgta gcaatgtgca    1260
cgcgacagcc gggtgtgtga cgctggacca atcagagcgc agagctccga aagtttacct    1320
tttatggcta gagccggcat ctgccgtcat ataaaagagc gcgcccagcg tctcagcctc    1380
actttgagct cctccacacg cagctagtgc ggaatatcat ctgcctgtaa cccattctct    1440
aaagtcgaca aaccccccca aacctaaggt gagttgatct ttaagctttt tacatttca    1500 gctcgcatat atcaattcga acgtttaatt agaatgttta aataaagcta gattaaatga   1560
ttaggctcag ttaccggtct tttttttctc atttacgtgc gaactctgct taaactctag    1620 ttattctta ttaatatgtg gttatttta tatatgtatg ttatcataac tgtactggct     1680
atgtcaggtg gtaatgactg taacgttacg ttactcgttg taggcacgac attgaatggg    1740
ccggtgttga aataagtctt caaccccttt taacctcaaa atgtgctctg gttaacaagg    1800
attttaacag ctatcagtat gactgtgcgg ttttaaagcc gttagtgagg cacgttgcac    1860
acttgatgga tggccggaat gggaagttct ttatgcaggc agtgctgcag cagggtgtga    1920
cctactttag ctaacgttag ccggctaacc agcattcatc tgccggtaac ttgagtctaa    1980
tattctctat gtgatatcga agtgatcaaa gacacgtctg ttagctcact ttaaccaact    2040
gtagtgaaaa atagcgcagt gtgcagccct tcaagtcttt catttaggct gattattcaa    2100
tcattttatt aactattaac gcgttactaa acgtaaggta acgtagtcag ttttaataa    2160 ctggtgaaaa gtactggttg ggtttaaatg gtgacttata attgtgttgg aggggaaac    2220 cttttgata aaggctatat aatctcaaat gaatgggctg aggatggtgt tcacaggtgc    2280
tttagtgaag tccgctcgtg aagagtcgct gaagtgactg cagatctgta gcgcatgcgt    2340
tttggcagac ggccgttgaa attcggttga gtaattgata ccaggtgagg ctagaggatg    2400
tagaaattca tttgtgtaga atttagggag tggcctggcg tgatgaatgt cgaaatccgt    2460
```

```
tccttttttac tgaaccctat gtctctgctg agtgccacac cgccggcaca aagcgtctca   2520
aaccattgcc ttttatggta ataatgagaa tgcagaggga cttcctttgt ctggcacatc   2580
tgaggcgcgc attgtcacac tagcacccac tagcggtcag actgcagaca aacaggaagc   2640
tgactccaca tggtcacatg ctcactgaag tgttgacttc cctgacagct gtgcactttc   2700
taaaccggtt ttctcattca tttacagttc agccgggtac cctcgaccga gcttggcgag   2760
attttcagga gctaaggaag ctaaaatgga gaaaaaatc actggatata ccaccgttga   2820
tatatcccaa tggcatcgta aagaactttt gaggcatttc agtcagttgc tcaatgtacc   2880
tataaccaga ccgttcagct ggatattacg gcctttttta aagaccgtaa agaaaaataa   2940
gcacaagttt tatccggcct ttattcacat tcttgcccgc ctgatgaatg ctcatccgga   3000
attccgtatg gcaatgaaag acggtgagct ggtgatatgg gatagtgttc acccttgtta   3060
caccgttttc catgagcaaa ctgaaacgtt tcatcgctc tggagtgaat accacgacga   3120
tttccggcag tttctacaca tatattcgca agatgtggcg tgttacggtg aaaacctggc   3180
ctatttccct aaagggttta ttgagaatat gttttcgtc tcagccaatc cctgggtgag   3240
tttcaccagt tttgatttaa acgtggccaa tatggacaac ttcttcgccc cgttttcac   3300 catgggcaaa tattatacgc aaggcgacaa ggtgctgatg ccgctggcga ttctggttca   3360
tcatgccgtc tgtgatggct tccatgtcgg cagaatgctt aatgaattac aacagtactg   3420
cgatgagtgg cagggcgggg cgtaatttt ttaaggcagt tattggtgcc cttaaacgcc   3480
tggtgctacg cctgaataag tgataataag cggatgaatg gcagaaattc gccggatcgg   3540
gtaccctaga gtaattttat tttggatctg gtagtagcct gactccaggg gttttcaggc   3600
atttgcattt ttttctctga aatcaataac aacactttct atattgactc tatcactctg   3660
agctaccatt gattagtaca tttatattaa aggttattaa atgtcttatt tagatatatg   3720
gttcatggcg gtgctactta tgcactacgt taatatttag gggtgaaatg gaacttgta   3780 gagctccaag cttttggata atatattta gagtaatttc ctttaagtat tttcattcct   3840
taatcttatt gtttgaaact aatagtgatt catgtttcaa taaagatgtt cattctctgc   3900
aaagaattcc actggccgtc gttttacaac gtctagactg gaaaaccct ggcgttaccc   3960 aacttaatcg ccttgcagca catccccctt tcgccagctg gcgtaatagc gaagaggccc   4020
gcaccgatcg cccttcccaa cagttgcgca gcctgaatgg cgaatggcgc ctgatgcggt   4080
attttctcct tacgcatctg tgcggtattt cacaccgcat acgtcaaagc aaccatagta   4140
cgcgccctgt agcggcgcat taagcgcggc gggtgtggtg gttacgcgca gcgtgaccgc   4200
tacacttgcc agcgccctag cgcccgctcc tttcgctttc ttcccttcct ttctcgccac   4260
gttcgccggc tttccccgtc aagctctaaa tcggggctc cctttagggt tccgatttag   4320
tgctttacgg cacctcgacc ccaaaaaact tgatttgggt gatggttcac gtagtgggcc   4380
atcgccctga tagacggttt ttcgcccttt gacgttggag tccacgttct ttaatagtgg   4440
actcttgttc caaactggaa caacactcaa ccctatctcg gctattctt ttgatttata   4500 agggattttg ccgatttcgg cctattggtt aaaaaatgag ctgatttaac aaaaatttaa   4560
cgcgaatttt aacaaaatat taacgtttac aatttatgg tgcactctca gtacaatctg   4620
ctctgatgcc gcatagttaa gccagccccg acacccgcca acacccgctg acgcgccctg   4680
acgggcttgt ctgctcccgg catccgctta cagacaagct gtgaccgtct ccgggagctg   4740
catgtgtcag aggttttcac cgtcatcacc gaaacgcgcg agacgaaagg gcctcgtgat   4800
acgcctattt ttataggtta atgtcatgat aataatggtt tcttagacgt caggtggcac   4860
```

-continued

```
ttttcgggga aatgtgcgcg gaaccccctat tgtttatttt ttctaaatac attcaaatat    4920
gtatccgctc atgagacaat aaccctgata aatgcttcaa taatattgaa aaggaagag     4980 tatgagtatt caacatttcc gtgtcgccct tattccctttt tttgcggcat tttgccttcc    5040 tgttttttgct cacccagaaa cgctggtgaa agtaaaagat gctgaagatc agttgggtgc   5100
acgagtgggt tacatcgaac tggatctcaa cagcggtaag atccttgaga gttttcgccc    5160
cgaagaacgt tttccaatga tgagcacttt taaagttctg ctatgtggcg cggtattatc    5220
ccgtattgac gccgggcaag agcaactcgg tcgccgcata cactattctc agaatgactt    5280
ggttgagtac tcaccagtca cagaaaagca tcttacggat ggcatgacag taagagaatt    5340
atgcagtgct gccataacca tgagtgataa cactgcggcc aacttacttc tgacaacgat    5400
cggaggaccg aaggagctaa ccgcttttttt gcacaacatg gggatcatg taactcgcct    5460 tgatcgttgg gaaccggagc tgaatgaagc cataccaaac gacgagcgtg acaccacgat    5520
gcctgtagca atggcaacaa cgttgcgcaa actattaact ggcgaactac ttactctagc    5580
ttcccggcaa caattaatag actggatgga ggcggataaa gttgcaggac cacttctgcg    5640
ctcggccctt ccggctggct ggtttattgc tgataaatct ggagccggtg agcgtgggtc    5700
tcgcggtatc attgcagcac tggggccaga tggtaagccc tcccgtatcg tagttatcta    5760
cacgacgggg agtcaggcaa ctatggatga acgaaataga cagatcgctg agataggtgc    5820
ctcactgatt aagcattggt aactgtcaga ccaagtttac tcatatatac tttagattga    5880
tttaaaactt catttttaat ttaaaaggat ctaggtgaag atccttttg ataatctcat     5940 gaccaaaatc ccttaacgtg agttttcgtt ccactgagcg tcagaccccg tagaaaagat    6000
caaaggatct tcttgagatc cttttttttct gcgcgtaatc tgctgcttgc aaacaaaaaa   6060
accaccgcta ccagcggtgg tttgtttgcc ggatcaagag ctaccaactc ttttttccgaa   6120 ggtaactggc ttcagcagag cgcagatacc aaatactgtc cttctagtgt agccgtagtt    6180
aggccaccac ttcaagaact ctgtagcacc gcctacatac ctcgctctgc taatcctgtt    6240
accagtggct gctgccagtg gcgataagtc gtgtcttacc gggttggact caagacgata    6300
gttaccggat aaggcgcagc ggtcgggctg aacggggggt tcgtgcacac agcccagctt    6360
ggagcgaacg acctacaccg aactgagata cctacagcgt gagctatgag aaagcgccac    6420
gcttcccgaa gggagaaagg cggacaggta tccggtaagc ggcagggtcg gaacaggaga    6480
gcgcacgagg gagcttccag ggggaaacgc ctggtatctt tatagtcctg tcgggtttcg    6540
ccacctctga cttgagcgtc gatttttgtg atgctcgtca ggggggcgga gcctatggaa    6600
aaacgccagc aacgcggcct ttttacggtt cctggccttt tgctggcctt ttgctcacat    6660
gttctttcct gcgttatccc ctgattctgt ggataaccgt attaccgcct ttgagtgagc    6720
tgataccgct cgccgcagcc gaacgaccga gcgcagcgag tcagtgagcg aggaagcgga    6780
ag                                                                   6782
```

<210> SEQ ID NO 13
<211> LENGTH: 32
<212> TYPE: DNA
<213> ORGANISM: ARTIFICIAL
<220> FEATURE:
<223> OTHER INFORMATION: left outer repeat

<400> SEQUENCE: 13

```
cagttgaagt cggaagttta catacactta ag                                    32
```

```
<210> SEQ ID NO 14
<211> LENGTH: 32
<212> TYPE: DNA
<213> ORGANISM: ARTIFICIAL
<220> FEATURE:
<223> OTHER INFORMATION: left inner repeat

<400> SEQUENCE: 14
tccagtgggt cagaagttta catacactaa gt                                     32

<210> SEQ ID NO 15
<211> LENGTH: 32
<212> TYPE: DNA
<213> ORGANISM: ARTIFICIAL
<220> FEATURE:
<223> OTHER INFORMATION: left inner repeat

<400> SEQUENCE: 15
tccagtgggt cagaagttta catacactta ag                                     32

<210> SEQ ID NO 16
<211> LENGTH: 32
<212> TYPE: DNA
<213> ORGANISM: ARTIFICIAL
<220> FEATURE:
<223> OTHER INFORMATION: right inner repeat

<400> SEQUENCE: 16
cccagtgggt cagaagttta catacactca at                                     32

<210> SEQ ID NO 17
<211> LENGTH: 32
<212> TYPE: DNA
<213> ORGANISM: ARTIFICIAL
<220> FEATURE:
<223> OTHER INFORMATION: right outer repeat

<400> SEQUENCE: 17
cagttgaagt cggaagttta catacacctt ag                                     32

<210> SEQ ID NO 18
<211> LENGTH: 26
<212> TYPE: DNA
<213> ORGANISM: ARTIFICIAL
<220> FEATURE:
<223> OTHER INFORMATION: consensus direct repeat

<400> SEQUENCE: 18
cagtggtcga agtttacata cactaa                                            26

<210> SEQ ID NO 19
<211> LENGTH: 34
<212> TYPE: DNA
<213> ORGANISM: ARTIFICIAL
<220> FEATURE:
<223> OTHER INFORMATION: nucleotide sequence encoding SEQ ID NO:5

<400> SEQUENCE: 19
tacagttgaa gtcggaagtt tacatacact taag                                   34

<210> SEQ ID NO 20
<211> LENGTH: 340
<212> TYPE: PRT
<213> ORGANISM: ARTIFICIAL
<220> FEATURE:
<223> OTHER INFORMATION: SB polypeptide
<220> FEATURE:
<221> NAME/KEY: misc_feature
```

<222> LOCATION: (136)..(136)
<223> OTHER INFORMATION: arginine, a lysine, or a histidine
<220> FEATURE:
<221> NAME/KEY: misc_feature
<222> LOCATION: (243)..(243)
<223> OTHER INFORMATION: glutamine or an asparagine
<220> FEATURE:
<221> NAME/KEY: misc_feature
<222> LOCATION: (253)..(253)
<223> OTHER INFORMATION: arginine, a lysine, or a histidine
<220> FEATURE:
<221> NAME/KEY: misc_feature
<222> LOCATION: (255)..(255)
<223> OTHER INFORMATION: arginine, a lysine, or a histidine

<400> SEQUENCE: 20

```
Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
            20                  25                  30

Lys Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

Lys Ala Arg Leu Arg Phe Ala Xaa Ala His Gly Asp Lys Asp Arg Thr
130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Arg Lys Glu Asn Tyr Val Asp Ile Leu Lys Gln
210                 215                 220

His Leu Lys Thr Ser Val Arg Lys Leu Lys Leu Gly Arg Lys Trp Val
225                 230                 235                 240

Phe Gln Xaa Asp Asn Asp Pro Lys His Thr Ser Lys Xaa Val Xaa Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335
```

Ala Thr Lys Tyr
            340

<210> SEQ ID NO 21
<211> LENGTH: 340
<212> TYPE: PRT
<213> ORGANISM: ARTIFICIAL
<220> FEATURE:
<223> OTHER INFORMATION: SB polypeptide

<400> SEQUENCE: 21

Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
            20                  25                  30

Lys Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

Lys Ala Arg Leu Arg Phe Ala Arg Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Arg Lys Glu Asn Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln Gln Asp Asn Asp Pro Lys His Thr Ser Lys His Val Arg Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Gln Phe Lys Gly Asn
                325                 330                 335

Ala Thr Lys Tyr
            340

```
<210> SEQ ID NO 22
<211> LENGTH: 32
<212> TYPE: DNA
<213> ORGANISM: ARTIFICIAL
<220> FEATURE:
<223> OTHER INFORMATION: left outer repeat

<400> SEQUENCE: 22
cagttgaagt cggaagtttta catacacttr ag                                    32

<210> SEQ ID NO 23
<211> LENGTH: 32
<212> TYPE: DNA
<213> ORGANISM: ARTIFICIAL
<220> FEATURE:
<223> OTHER INFORMATION: left inner direct repeat

<400> SEQUENCE: 23
tccagtgggt cagaagttta catacactaa gt                                     32

<210> SEQ ID NO 24
<211> LENGTH: 32
<212> TYPE: DNA
<213> ORGANISM: ARTIFICIAL
<220> FEATURE:
<223> OTHER INFORMATION: right inner direct repeat

<400> SEQUENCE: 24
cccagtgggt cagaagttaa catacactca at                                     32

<210> SEQ ID NO 25
<211> LENGTH: 32
<212> TYPE: DNA
<213> ORGANISM: ARTIFICIAL
<220> FEATURE:
<223> OTHER INFORMATION: right outer repeat

<400> SEQUENCE: 25
cagttgaagt cggaagtttta catacacctt ag                                    32

<210> SEQ ID NO 26
<211> LENGTH: 1023
<212> TYPE: DNA
<213> ORGANISM: ARTIFICIAL
<220> FEATURE:
<223> OTHER INFORMATION: nucleotide sequence encoding SEQ ID NO:5

<400> SEQUENCE: 26
atgggaaaat caaagaaaat cagccaagac ctcagaaaaa aaattgtaga cctccacaag        60
tctggttcat ccttgggagc aatttccaaa cgcctgaaag taccacgttc atctgtacaa       120
acaatagtac gcaagtataa acaccatggg accacgcagc cgtcataccg ctcaggaagg       180
agacgcgttc tgtctcctag agatgaacgt actttggtgc gaaaagtgca atcaatccc        240 agaacaacag caaaggacct tgtgaagatg ctggaggaaa caggtacaaa agtatctata       300
tccacagtaa aacgagtcct atatcgacat aacctgaaag gccgctcagc aaggaagaag       360
ccactgctcc aaaaccgaca taagaaagcc agactacggt ttgcaactgc catggggac        420 aaagatcgta ctttttggag aaatgtcctc tggtctgatg aaacaaaaat agaactgttt       480
ggccataatg accatcgtta tgtttggagg aagaaggggg aggcttgcaa gccgaagaac       540
accatcccaa ccgtgaagca cgggggtggc agcatcatgt tgtggggggtg ctttgctgca      600 ggagggactg gtgcacttca caaaatagat ggcatcatga ggaaggaaaa ttatgtggat       660
atattgaagc aacatctcaa gacatcagtc aggaagttaa agcttggtcg caaatgggtc       720
```

```
ttccaaatgg acaatgaccc caagcatact tccaaagttg tggcaaaatg gcttaaggac    780
aacaaagtca aggtattgga gtggccatca caaagccctg acctcaatcc tatagaaaat    840
ttgtgggcag aactgaaaaa gcgtgtgcga gcaaggaggc ctacaaacct gactcagtta    900
caccagctct gtcaggagga atgggccaaa attcacccaa cttattgtgg gaagcttgtg    960
gaaggctacc cgaaacgttt gacccaagtt aaacaattta aaggcaatgc taccaaatac   1020
tag                                                                 1023
```

<210> SEQ ID NO 27
<211> LENGTH: 1023
<212> TYPE: DNA
<213> ORGANISM: ARTIFICIAL
<220> FEATURE:
<223> OTHER INFORMATION: nucleotide sequence encoding SEQ ID NO:20
<220> FEATURE:
<221> NAME/KEY: misc_feature
<222> LOCATION: (406)..(406)
<223> OTHER INFORMATION: A or C
<220> FEATURE:
<221> NAME/KEY: misc_feature
<222> LOCATION: (407)..(407)
<223> OTHER INFORMATION: A of G
<220> FEATURE:
<221> NAME/KEY: misc_feature
<222> LOCATION: (408)..(408)
<223> OTHER INFORMATION: any nucleotide
<220> FEATURE:
<221> NAME/KEY: misc_feature
<222> LOCATION: (727)..(727)
<223> OTHER INFORMATION: C or G
<220> FEATURE:
<221> NAME/KEY: misc_feature
<222> LOCATION: (728)..(728)
<223> OTHER INFORMATION: A
<220> FEATURE:
<221> NAME/KEY: misc_feature
<222> LOCATION: (729)..(729)
<223> OTHER INFORMATION: any nucleotide
<220> FEATURE:
<221> NAME/KEY: misc_feature
<222> LOCATION: (757)..(757)
<223> OTHER INFORMATION: A or C
<220> FEATURE:
<221> NAME/KEY: misc_feature
<222> LOCATION: (758)..(758)
<223> OTHER INFORMATION: A of G
<220> FEATURE:
<221> NAME/KEY: misc_feature
<222> LOCATION: (759)..(759)
<223> OTHER INFORMATION: any nucleotide
<220> FEATURE:
<221> NAME/KEY: misc_feature
<222> LOCATION: (763)..(765)
<223> OTHER INFORMATION: n is a, c, g, or t
<220> FEATURE:
<221> NAME/KEY: misc_feature
<222> LOCATION: (773)..(773)
<223> OTHER INFORMATION: A or C
<220> FEATURE:
<221> NAME/KEY: misc_feature
<222> LOCATION: (774)..(774)
<223> OTHER INFORMATION: A of G
<220> FEATURE:
<221> NAME/KEY: misc_feature
<222> LOCATION: (775)..(775)
<223> OTHER INFORMATION: any nucleotide

<400> SEQUENCE: 27

```
atgggaaaat caaaagaaat cagccaagac ctcagaaaaa aaattgtaga cctccacaag     60
tctggttcat ccttgggagc aatttccaaa cgcctgaaag taccacgttc atctgtacaa    120
acaatagtac gcaagtataa acaccatggg accacgcagc cgtcataccg ctcaggaagg    180
```

```
agacgcgttc tgtctcctag agatgaacgt actttggtgc gaaaagtgca aatcaatccc    240
agaacaacag caaaggacct tgtgaagatg ctggaggaaa caggtacaaa agtatctata    300
tccacagtaa aacgagtcct atatcgacat aacctgaaag gccgctcagc aaggaagaag    360
ccactgctcc aaaaccgaca taagaaagcc agactacggt ttgcannngc acatggggac    420
aaagatcgta cttttggag aaatgtcctc tggtctgatg aaacaaaaat agaactgttt    480
ggccataatg accatcgtta tgtttggagg aagaaggggg aggcttgcaa gccgaagaac    540
accatcccaa ccgtgaagca cggggtggc agcatcatgt tgtggggtg ctttgctgca     600 ggagggactg gtgcacttca caaaatagat ggcatcatga ggaaggaaaa ttatgtggat    660
atattgaagc aacatctcaa gacatcagtc aggaagttaa agcttggtcg caaatgggtc    720
ttccaannng acaatgaccc caagcatact tccaaannng tgnnnaaatg gcttaaggac    780
aacaaagtca aggtattgga gtggccatca caaagccctg acctcaatcc tatagaaaat    840
ttgtgggcag aactgaaaaa gcgtgtgcga gcaaggaggc ctacaaacct gactcagtta    900
caccagctct gtcaggagga atgggccaaa attcacccaa cttattgtgg gaagcttgtg    960
gaaggctacc cgaaacgttt gacccaagtt aaacaattta aaggcaatgc taccaaatac    1020
tag                                                                 1023
```

<210> SEQ ID NO 28
<211> LENGTH: 1023
<212> TYPE: DNA
<213> ORGANISM: ARTIFICIAL
<220> FEATURE:
<223> OTHER INFORMATION: nucleotide sequence encoding SEQ ID NO:21

<400> SEQUENCE: 28

```
atgggaaaat caaagaaat cagccaagac ctcagaaaaa aaattgtaga cctccacaag     60
tctggttcat ccttgggagc aatttccaaa cgcctgaaag taccacgttc atctgtacaa    120
acaatagtac gcaagtataa acaccatggg accacgcagc cgtcataccg ctcaggaagg    180
agacgcgttc tgtctcctag agatgaacgt actttggtgc gaaaagtgca aatcaatccc    240
agaacaacag caaaggacct tgtgaagatg ctggaggaaa caggtacaaa agtatctata    300
tccacagtaa aacgagtcct atatcgacat aacctgaaag gccgctcagc aaggaagaag    360
ccactgctcc aaaaccgaca taagaaagcc agactacggt ttgcaagagc acatggggac    420
aaagatcgta cttttggag aaatgtcctc tggtctgatg aaacaaaaat agaactgttt    480
ggccataatg accatcgtta tgtttggagg aagaaggggg aggcttgcaa gccgaagaac    540
accatcccaa ccgtgaagca cggggtggc agcatcatgt tgtggggtg ctttgctgca     600 ggagggactg gtgcacttca caaaatagat ggcatcatga ggaaggaaaa ttatgtggat    660
atattgaagc aacatctcaa gacatcagtc aggaagttaa agcttggtcg caaatgggtc    720
ttccaaatgg acaatgaccc caagcatact tccaaacacg tgagaaaatg gcttaaggac    780
aacaaagtca aggtattgga gtggccatca caaagccctg acctcaatcc tatagaaaat    840
ttgtgggcag aactgaaaaa gcgtgtgcga gcaaggaggc ctacaaacct gactcagtta    900
caccagctct gtcaggagga atgggccaaa attcacccaa cttattgtgg gaagcttgtg    960
gaaggctacc cgaaacgttt gacccaagtt aaacaattta aaggcaatgc taccaaatac    1020
tag                                                                 1023
```

<210> SEQ ID NO 29
<211> LENGTH: 19

```
<212> TYPE: DNA
<213> ORGANISM: ARTIFICIAL
<220> FEATURE:
<223> OTHER INFORMATION: direct repeat sequence

<400> SEQUENCE: 29
gtcrgaagtt tacatacac                                                19

<210> SEQ ID NO 30
<211> LENGTH: 165
<212> TYPE: DNA
<213> ORGANISM: ARTIFICIAL
<220> FEATURE:
<223> OTHER INFORMATION: intervening region

<400> SEQUENCE: 30
ttggagtcat taaaactcgt ttttcaacya cwccacaaat ttcttgttaa caaacwatag    60
ttttggcaag tcrgttagga catctacttt gtgcatgaca caagtmatttt ttccaacaat  120 tgtttacaga cagattattt cacttataat tcactgtatc acaat                   165

<210> SEQ ID NO 31
<211> LENGTH: 166
<212> TYPE: DNA
<213> ORGANISM: ARTIFICIAL
<220> FEATURE:
<223> OTHER INFORMATION: intervening region

<400> SEQUENCE: 31
aatgtgatga agaaataaa agctgaaatg aatcattctc tctactatta ttctgayatt    60
tcacattctt aaaataaagt ggtgatccta actgaccttta agacagggaa tctttactcg  120
gattaaatgt caggaattgt gaaaaastga gtttaaatgt atttgg                  166

<210> SEQ ID NO 32
<211> LENGTH: 165
<212> TYPE: DNA
<213> ORGANISM: ARTIFICIAL
<220> FEATURE:
<223> OTHER INFORMATION: intervening region

<400> SEQUENCE: 32
aatgtgatga agaaataaa agctgaaatg aatcattctc tctactatta ttctgayatt    60
tcacattctt aaaataaagt ggtgatccta actgacctaa gacagggaat ttttactagg   120
attaaatgtc aggaattgtg aaaasgtgag tttaaatgta tttgg                   165

<210> SEQ ID NO 33
<211> LENGTH: 229
<212> TYPE: DNA
<213> ORGANISM: ARTIFICIAL
<220> FEATURE:
<223> OTHER INFORMATION: left inverted repeat sequence

<400> SEQUENCE: 33
cagttgaagt cggaagttta catacacggg gtttggagtc attaaaactc gttttttcaac  60 tactccacaa atttcttgtt aacaaacaat agttttggca agtcagttag gacatctact  120
ttgtgcatga cacaagtcat ttttccaaca attgtttaca gacagattat ttcacttata  180
attcactgta tcacaattcc agtgggtcag aagtttacat acactaagt              229

<210> SEQ ID NO 34
<211> LENGTH: 18
<212> TYPE: DNA
<213> ORGANISM: ARTIFICIAL
```

```
<220> FEATURE:
<223> OTHER INFORMATION: direct repeat sequence

<400> SEQUENCE: 34
tcrgaagttt acatacac                                                   18

<210> SEQ ID NO 35
<211> LENGTH: 29
<212> TYPE: DNA
<213> ORGANISM: ARTIFICIAL
<220> FEATURE:
<223> OTHER INFORMATION: primer

<400> SEQUENCE: 35
ttggagctcg gtaccctaaa attgaagtc                                       29

<210> SEQ ID NO 36
<211> LENGTH: 29
<212> TYPE: DNA
<213> ORGANISM: ARTIFICIAL
<220> FEATURE:
<223> OTHER INFORMATION: primer

<400> SEQUENCE: 36
ttggagctcg gtaccctaca attgaagtc                                       29

<210> SEQ ID NO 37
<211> LENGTH: 29
<212> TYPE: DNA
<213> ORGANISM: ARTIFICIAL
<220> FEATURE:
<223> OTHER INFORMATION: primer

<400> SEQUENCE: 37
ttggagctcg gtaccctaaa gttgaagtc                                       29

<210> SEQ ID NO 38
<211> LENGTH: 29
<212> TYPE: DNA
<213> ORGANISM: ARTIFICIAL
<220> FEATURE:
<223> OTHER INFORMATION: primer

<400> SEQUENCE: 38
agctagagga tccctaaaa ttgaagtcg                                        29

<210> SEQ ID NO 39
<211> LENGTH: 29
<212> TYPE: DNA
<213> ORGANISM: ARTIFICIAL
<220> FEATURE:
<223> OTHER INFORMATION: primer

<400> SEQUENCE: 39
agctagagga tccctacaa ttgaagtcg                                        29

<210> SEQ ID NO 40
<211> LENGTH: 29
<212> TYPE: DNA
<213> ORGANISM: ARTIFICIAL
<220> FEATURE:
<223> OTHER INFORMATION: primer

<400> SEQUENCE: 40
agctagagga tccctaaag ttgaagtcg                                        29
```

-continued

```
<210> SEQ ID NO 41
<211> LENGTH: 29
<212> TYPE: DNA
<213> ORGANISM: ARTIFICIAL
<220> FEATURE:
<223> OTHER INFORMATION: primer

<400> SEQUENCE: 41
agctagagga tcccccccag ttgaagtcg                                    29

<210> SEQ ID NO 42
<211> LENGTH: 29
<212> TYPE: DNA
<213> ORGANISM: ARTIFICIAL
<220> FEATURE:
<223> OTHER INFORMATION: primer

<400> SEQUENCE: 42
ttggagctcg gtacccggca gttgaagtc                                    29

<210> SEQ ID NO 43
<211> LENGTH: 25
<212> TYPE: DNA
<213> ORGANISM: ARTIFICIAL
<220> FEATURE:
<223> OTHER INFORMATION: primer

<400> SEQUENCE: 43
ggctggctta actatgcggc atcag                                        25

<210> SEQ ID NO 44
<211> LENGTH: 25
<212> TYPE: DNA
<213> ORGANISM: ARTIFICIAL
<220> FEATURE:
<223> OTHER INFORMATION: primer

<400> SEQUENCE: 44
gtcagtgagc gaggaagcgg aagag                                        25

<210> SEQ ID NO 45
<211> LENGTH: 30
<212> TYPE: DNA
<213> ORGANISM: ARTIFICIAL
<220> FEATURE:
<223> OTHER INFORMATION: primer

<400> SEQUENCE: 45
ccaaactgga acaacactca accctatctc                                   30

<210> SEQ ID NO 46
<211> LENGTH: 25
<212> TYPE: DNA
<213> ORGANISM: ARTIFICIAL
<220> FEATURE:
<223> OTHER INFORMATION: primer

<400> SEQUENCE: 46
gtcagtgagc gaggaagcgg aagag                                        25

<210> SEQ ID NO 47
<211> LENGTH: 27
<212> TYPE: DNA
<213> ORGANISM: ARTIFICIAL
<220> FEATURE:
<223> OTHER INFORMATION: primer

<400> SEQUENCE: 47
```

```
cgattaagtt gggtaacgcc agggttt                                              27

<210> SEQ ID NO 48
<211> LENGTH: 25
<212> TYPE: DNA
<213> ORGANISM: ARTIFICIAL
<220> FEATURE:
<223> OTHER INFORMATION: primer

<400> SEQUENCE: 48
agctcactca ttaggcaccc caggc                                                25

<210> SEQ ID NO 49
<211> LENGTH: 18
<212> TYPE: DNA
<213> ORGANISM: ARTIFICIAL
<220> FEATURE:
<223> OTHER INFORMATION: primer

<400> SEQUENCE: 49
ggctcgtatg ttgtgtgg                                                        18

<210> SEQ ID NO 50
<211> LENGTH: 20
<212> TYPE: DNA
<213> ORGANISM: ARTIFICIAL
<220> FEATURE:
<223> OTHER INFORMATION: primer

<400> SEQUENCE: 50
ctggaacaac actcaaccct                                                      20

<210> SEQ ID NO 51
<211> LENGTH: 20
<212> TYPE: DNA
<213> ORGANISM: ARTIFICIAL
<220> FEATURE:
<223> OTHER INFORMATION: primer

<400> SEQUENCE: 51
cacacaggaa acagctatga                                                      20

<210> SEQ ID NO 52
<211> LENGTH: 28
<212> TYPE: DNA
<213> ORGANISM: ARTIFICIAL
<220> FEATURE:
<223> OTHER INFORMATION: primer

<400> SEQUENCE: 52
cttccttttt cgatatcatt gaagcttt                                             28

<210> SEQ ID NO 53
<211> LENGTH: 23
<212> TYPE: DNA
<213> ORGANISM: ARTIFICIAL
<220> FEATURE:
<223> OTHER INFORMATION: primer

<400> SEQUENCE: 53
ggtcttccaa caagacaatg acc                                                  23

<210> SEQ ID NO 54
<211> LENGTH: 38
<212> TYPE: DNA
<213> ORGANISM: ARTIFICIAL
```

```
<220> FEATURE:
<223> OTHER INFORMATION: primer

<400> SEQUENCE: 54
tttgcaagag cacatgggga caaagatcgt acttttttg                              38

<210> SEQ ID NO 55
<211> LENGTH: 36
<212> TYPE: DNA
<213> ORGANISM: ARTIFICIAL
<220> FEATURE:
<223> OTHER INFORMATION: primer

<400> SEQUENCE: 55
atgtgctctt gcaaaccgta gtctggcttt cttatg                                 36

<210> SEQ ID NO 56
<211> LENGTH: 38
<212> TYPE: DNA
<213> ORGANISM: ARTIFICIAL
<220> FEATURE:
<223> OTHER INFORMATION: primer

<400> SEQUENCE: 56
aactacagag acatcttgaa gcaacatctc aagacatc                               38

<210> SEQ ID NO 57
<211> LENGTH: 35
<212> TYPE: DNA
<213> ORGANISM: ARTIFICIAL
<220> FEATURE:
<223> OTHER INFORMATION: primer

<400> SEQUENCE: 57
ttttctcacg tgtttggaag tatgcttggg gtcat                                  35

<210> SEQ ID NO 58
<211> LENGTH: 19
<212> TYPE: DNA
<213> ORGANISM: ARTIFICIAL
<220> FEATURE:
<223> OTHER INFORMATION: primer

<400> SEQUENCE: 58
aattcgcggc cgctctaga                                                    19

<210> SEQ ID NO 59
<211> LENGTH: 19
<212> TYPE: DNA
<213> ORGANISM: ARTIFICIAL
<220> FEATURE:
<223> OTHER INFORMATION: primer

<400> SEQUENCE: 59
acgttctaga gcggccgcg                                                    19

<210> SEQ ID NO 60
<211> LENGTH: 34
<212> TYPE: DNA
<213> ORGANISM: ARTIFICIAL
<220> FEATURE:
<223> OTHER INFORMATION: direct repeat sequence

<400> SEQUENCE: 60
tacaattgaa gtcggaagtt tacatacact taag                                   34
```

```
<210> SEQ ID NO 61
<211> LENGTH: 34
<212> TYPE: DNA
<213> ORGANISM: ARTIFICIAL
<220> FEATURE:
<223> OTHER INFORMATION: direct repeat sequence

<400> SEQUENCE: 61
taaaattgaa gtcggaagtt tacatacact taag                              34

<210> SEQ ID NO 62
<211> LENGTH: 34
<212> TYPE: DNA
<213> ORGANISM: ARTIFICIAL
<220> FEATURE:
<223> OTHER INFORMATION: direct repeat sequence

<400> SEQUENCE: 62
tacagcccaa gtcggaagtt tacatacact taag                              34

<210> SEQ ID NO 63
<211> LENGTH: 34
<212> TYPE: DNA
<213> ORGANISM: ARTIFICIAL
<220> FEATURE:
<223> OTHER INFORMATION: direct repeat sequence

<400> SEQUENCE: 63
tacagttgcc ctcggaagtt tacatacact taag                              34

<210> SEQ ID NO 64
<211> LENGTH: 34
<212> TYPE: DNA
<213> ORGANISM: ARTIFICIAL
<220> FEATURE:
<223> OTHER INFORMATION: direct repeat sequence

<400> SEQUENCE: 64
tacagttgaa gaacgaagtt tacatacact taag                              34

<210> SEQ ID NO 65
<211> LENGTH: 30
<212> TYPE: DNA
<213> ORGANISM: ARTIFICIAL
<220> FEATURE:
<223> OTHER INFORMATION: direct repeat sequence

<400> SEQUENCE: 65
tacagttgag gaagtttaca tacacttaag                                   30

<210> SEQ ID NO 66
<211> LENGTH: 34
<212> TYPE: DNA
<213> ORGANISM: ARTIFICIAL
<220> FEATURE:
<223> OTHER INFORMATION: direct repeat sequence

<400> SEQUENCE: 66
tacagttgaa gtcggaagtt tacatacacg ggag                              34

<210> SEQ ID NO 67
<211> LENGTH: 34
<212> TYPE: DNA
<213> ORGANISM: ARTIFICIAL
<220> FEATURE:
<223> OTHER INFORMATION: direct repeat sequence

<400> SEQUENCE: 67
```

```
tacagttgaa gtcggaagtt tacatacatg gaag                              34

<210> SEQ ID NO 68
<211> LENGTH: 30
<212> TYPE: DNA
<213> ORGANISM: ARTIFICIAL
<220> FEATURE:
<223> OTHER INFORMATION: direct repeat sequence

<400> SEQUENCE: 68
tacagttgaa gtcaggactg aagttgacat                                   30

<210> SEQ ID NO 69
<211> LENGTH: 32
<212> TYPE: DNA
<213> ORGANISM: ARTIFICIAL
<220> FEATURE:
<223> OTHER INFORMATION: direct repeat sequence

<400> SEQUENCE: 69
tacagtgggt cagaagttta catacactaa gt                                32

<210> SEQ ID NO 70
<211> LENGTH: 36
<212> TYPE: DNA
<213> ORGANISM: ARTIFICIAL
<220> FEATURE:
<223> OTHER INFORMATION: direct repeat sequence

<400> SEQUENCE: 70
tatacagttg aagtcggaag tttacataca cttaag                            36

<210> SEQ ID NO 71
<211> LENGTH: 36
<212> TYPE: DNA
<213> ORGANISM: ARTIFICIAL
<220> FEATURE:
<223> OTHER INFORMATION: direct repeat sequence

<400> SEQUENCE: 71
tatacagttg aagtcggaag tttacataca ccttag                            36

<210> SEQ ID NO 72
<211> LENGTH: 38
<212> TYPE: DNA
<213> ORGANISM: ARTIFICIAL
<220> FEATURE:
<223> OTHER INFORMATION: direct repeat sequence
<220> FEATURE:
<221> NAME/KEY: misc_feature
<222> LOCATION: (3)..(6)
<223> OTHER INFORMATION: any nucleotide

<400> SEQUENCE: 72
tannnncagt tgaagtcgga agtttacata cacttaag                          38

<210> SEQ ID NO 73
<211> LENGTH: 38
<212> TYPE: DNA
<213> ORGANISM: ARTIFICIAL
<220> FEATURE:
<223> OTHER INFORMATION: direct repeat sequence
<220> FEATURE:
<221> NAME/KEY: misc_feature
<222> LOCATION: (3)..(6)
<223> OTHER INFORMATION: any nucleotide

<400> SEQUENCE: 73
```

```
tannnncagt tgaagtcgga agtttacata cacttaag                              38

<210> SEQ ID NO 74
<211> LENGTH: 27
<212> TYPE: DNA
<213> ORGANISM: ARTIFICIAL
<220> FEATURE:
<223> OTHER INFORMATION: left junction sequence

<400> SEQUENCE: 74
gtcatcacct taggtacagt tgaagtc                                          27

<210> SEQ ID NO 75
<211> LENGTH: 27
<212> TYPE: DNA
<213> ORGANISM: ARTIFICIAL
<220> FEATURE:
<223> OTHER INFORMATION: left junction sequence

<400> SEQUENCE: 75
cactggaggt tacatacagt tgaagtc                                          27

<210> SEQ ID NO 76
<211> LENGTH: 27
<212> TYPE: DNA
<213> ORGANISM: ARTIFICIAL
<220> FEATURE:
<223> OTHER INFORMATION: left junction sequence

<400> SEQUENCE: 76
tgtgtgtgtg tgtgtacagt tgaagtc                                          27

<210> SEQ ID NO 77
<211> LENGTH: 27
<212> TYPE: DNA
<213> ORGANISM: ARTIFICIAL
<220> FEATURE:
<223> OTHER INFORMATION: left junction sequence

<400> SEQUENCE: 77
aggtatttca tatctacagt tgaagtc                                          27

<210> SEQ ID NO 78
<211> LENGTH: 27
<212> TYPE: DNA
<213> ORGANISM: ARTIFICIAL
<220> FEATURE:
<223> OTHER INFORMATION: left junction sequence

<400> SEQUENCE: 78
cagtaaaaag gacctacagt tgaagtc                                          27

<210> SEQ ID NO 79
<211> LENGTH: 27
<212> TYPE: DNA
<213> ORGANISM: ARTIFICIAL
<220> FEATURE:
<223> OTHER INFORMATION: left junction sequence

<400> SEQUENCE: 79
tgaaatgaac actatacagt tgaagtc                                          27

<210> SEQ ID NO 80
<211> LENGTH: 27
<212> TYPE: DNA
<213> ORGANISM: ARTIFICIAL
```

```
<220> FEATURE:
<223> OTHER INFORMATION: left junction sequence

<400> SEQUENCE: 80
tgtttctaag tatatacagt tgaagtc                                              27

<210> SEQ ID NO 81
<211> LENGTH: 27
<212> TYPE: DNA
<213> ORGANISM: ARTIFICIAL
<220> FEATURE:
<223> OTHER INFORMATION: left junction sequence

<400> SEQUENCE: 81
acccagcttc caggtacagt tgaagtc                                              27

<210> SEQ ID NO 82
<211> LENGTH: 27
<212> TYPE: DNA
<213> ORGANISM: ARTIFICIAL
<220> FEATURE:
<223> OTHER INFORMATION: left junction sequence

<400> SEQUENCE: 82
aagacagagg aagttacagt tgaagtc                                              27

<210> SEQ ID NO 83
<211> LENGTH: 27
<212> TYPE: DNA
<213> ORGANISM: ARTIFICIAL
<220> FEATURE:
<223> OTHER INFORMATION: left junction sequence

<400> SEQUENCE: 83
agggcgcgga cagatacagt tgaagtc                                              27

<210> SEQ ID NO 84
<211> LENGTH: 27
<212> TYPE: DNA
<213> ORGANISM: ARTIFICIAL
<220> FEATURE:
<223> OTHER INFORMATION: left junction sequence

<400> SEQUENCE: 84
aatgctgacg tatttacagt tgaagtc                                              27

<210> SEQ ID NO 85
<211> LENGTH: 27
<212> TYPE: DNA
<213> ORGANISM: ARTIFICIAL
<220> FEATURE:
<223> OTHER INFORMATION: left junction sequence

<400> SEQUENCE: 85
aaaggattac cttttacagt tgaagtc                                              27

<210> SEQ ID NO 86
<211> LENGTH: 27
<212> TYPE: DNA
<213> ORGANISM: ARTIFICIAL
<220> FEATURE:
<223> OTHER INFORMATION: left junction sequence

<400> SEQUENCE: 86
tgagacaacc cacatacagt tgaagtc                                              27
```

-continued

```
<210> SEQ ID NO 87
<211> LENGTH: 27
<212> TYPE: DNA
<213> ORGANISM: ARTIFICIAL
<220> FEATURE:
<223> OTHER INFORMATION: left junction sequence

<400> SEQUENCE: 87
ttaatctaaa atactacagc ccaagtc                                             27

<210> SEQ ID NO 88
<211> LENGTH: 27
<212> TYPE: DNA
<213> ORGANISM: ARTIFICIAL
<220> FEATURE:
<223> OTHER INFORMATION: left junction sequence

<400> SEQUENCE: 88
caaaagagtt aacatacagc ccaagtc                                             27

<210> SEQ ID NO 89
<211> LENGTH: 27
<212> TYPE: DNA
<213> ORGANISM: ARTIFICIAL
<220> FEATURE:
<223> OTHER INFORMATION: left junction sequence

<400> SEQUENCE: 89
atattctatt aacatacagc ccaagtc                                             27

<210> SEQ ID NO 90
<211> LENGTH: 27
<212> TYPE: DNA
<213> ORGANISM: ARTIFICIAL
<220> FEATURE:
<223> OTHER INFORMATION: left junction sequence

<400> SEQUENCE: 90
gtcaggtaca gatatacagc ccaagtc                                             27

<210> SEQ ID NO 91
<211> LENGTH: 27
<212> TYPE: DNA
<213> ORGANISM: ARTIFICIAL
<220> FEATURE:
<223> OTHER INFORMATION: left junction sequence

<400> SEQUENCE: 91
cttttgcccc tagatacagc ccaagtc                                             27

<210> SEQ ID NO 92
<211> LENGTH: 27
<212> TYPE: DNA
<213> ORGANISM: ARTIFICIAL
<220> FEATURE:
<223> OTHER INFORMATION: left junction sequence

<400> SEQUENCE: 92
gaaggacggt acaatacagt tgccctc                                             27

<210> SEQ ID NO 93
<211> LENGTH: 27
<212> TYPE: DNA
<213> ORGANISM: ARTIFICIAL
<220> FEATURE:
<223> OTHER INFORMATION: left junction sequence

<400> SEQUENCE: 93
```

-continued

```
tgctggacgg tacttacagt tgccctc                                              27

<210> SEQ ID NO 94
<211> LENGTH: 27
<212> TYPE: DNA
<213> ORGANISM: ARTIFICIAL
<220> FEATURE:
<223> OTHER INFORMATION: left junction sequence

<400> SEQUENCE: 94
taataatgtt tttatacagt tgccctc                                              27

<210> SEQ ID NO 95
<211> LENGTH: 27
<212> TYPE: DNA
<213> ORGANISM: ARTIFICIAL
<220> FEATURE:
<223> OTHER INFORMATION: left junction sequence

<400> SEQUENCE: 95
tctaggtcat aaactacagt tgccctc                                              27

<210> SEQ ID NO 96
<211> LENGTH: 27
<212> TYPE: DNA
<213> ORGANISM: ARTIFICIAL
<220> FEATURE:
<223> OTHER INFORMATION: left junction sequence

<400> SEQUENCE: 96
cagtaaaaag gacctacagt tgaagtc                                              27

<210> SEQ ID NO 97
<211> LENGTH: 27
<212> TYPE: DNA
<213> ORGANISM: ARTIFICIAL
<220> FEATURE:
<223> OTHER INFORMATION: left junction sequence

<400> SEQUENCE: 97
gtctttattg tctatacagt tgaagtc                                              27

<210> SEQ ID NO 98
<211> LENGTH: 27
<212> TYPE: DNA
<213> ORGANISM: ARTIFICIAL
<220> FEATURE:
<223> OTHER INFORMATION: left junction sequence

<400> SEQUENCE: 98
ggagctgggt accatacagt tgaagtc                                              27

<210> SEQ ID NO 99
<211> LENGTH: 27
<212> TYPE: DNA
<213> ORGANISM: ARTIFICIAL
<220> FEATURE:
<223> OTHER INFORMATION: left junction sequence

<400> SEQUENCE: 99
ctccaatgct tacatacagt tgaagtc                                              27

<210> SEQ ID NO 100
<211> LENGTH: 27
<212> TYPE: DNA
<213> ORGANISM: ARTIFICIAL
```

```
<220> FEATURE:
<223> OTHER INFORMATION: left junction sequence

<400> SEQUENCE: 100
ccttccattt cttatacagt tgaagtc                                    27

<210> SEQ ID NO 101
<211> LENGTH: 27
<212> TYPE: DNA
<213> ORGANISM: ARTIFICIAL
<220> FEATURE:
<223> OTHER INFORMATION: left junction sequence

<400> SEQUENCE: 101
gaagcactta atgatacagt tgaagtc                                    27

<210> SEQ ID NO 102
<211> LENGTH: 27
<212> TYPE: DNA
<213> ORGANISM: ARTIFICIAL
<220> FEATURE:
<223> OTHER INFORMATION: left junction sequence

<400> SEQUENCE: 102
ccaccagcct ggtctacagt tgaagtc                                    27

<210> SEQ ID NO 103
<211> LENGTH: 27
<212> TYPE: DNA
<213> ORGANISM: ARTIFICIAL
<220> FEATURE:
<223> OTHER INFORMATION: left junction sequence

<400> SEQUENCE: 103
taataggata tatgtacagt tgaagtc                                    27

<210> SEQ ID NO 104
<211> LENGTH: 27
<212> TYPE: DNA
<213> ORGANISM: ARTIFICIAL
<220> FEATURE:
<223> OTHER INFORMATION: left junction sequence

<400> SEQUENCE: 104
agcttggaac taactacagt tgaagtc                                    27

<210> SEQ ID NO 105
<211> LENGTH: 27
<212> TYPE: DNA
<213> ORGANISM: ARTIFICIAL
<220> FEATURE:
<223> OTHER INFORMATION: left junction sequence

<400> SEQUENCE: 105
gctacctgtt tatatacagt tgaagtc                                    27

<210> SEQ ID NO 106
<211> LENGTH: 27
<212> TYPE: DNA
<213> ORGANISM: ARTIFICIAL
<220> FEATURE:
<223> OTHER INFORMATION: left junction sequence

<400> SEQUENCE: 106
caaagccttg accctacagt tgaagtc                                    27
```

```
<210> SEQ ID NO 107
<211> LENGTH: 27
<212> TYPE: DNA
<213> ORGANISM: ARTIFICIAL
<220> FEATURE:
<223> OTHER INFORMATION: left junction sequence

<400> SEQUENCE: 107
aaatataata tatatacagt tgaagtc                                           27

<210> SEQ ID NO 108
<211> LENGTH: 27
<212> TYPE: DNA
<213> ORGANISM: ARTIFICIAL
<220> FEATURE:
<223> OTHER INFORMATION: left junction sequence

<400> SEQUENCE: 108
attcatacag cacatacagt tgaagtc                                           27

<210> SEQ ID NO 109
<211> LENGTH: 26
<212> TYPE: DNA
<213> ORGANISM: ARTIFICIAL
<220> FEATURE:
<223> OTHER INFORMATION: portion of a right inverted repeat

<400> SEQUENCE: 109
ccgagtaaag attccctgtc ttaagg                                            26

<210> SEQ ID NO 110
<211> LENGTH: 25
<212> TYPE: DNA
<213> ORGANISM: ARTIFICIAL
<220> FEATURE:
<223> OTHER INFORMATION: portion of a right inverted repeat

<400> SEQUENCE: 110
cctagtaaaa attccctgtc ttagg                                             25

<210> SEQ ID NO 111
<211> LENGTH: 20
<212> TYPE: DNA
<213> ORGANISM: ARTIFICIAL
<220> FEATURE:
<223> OTHER INFORMATION: portion of a right inverted repeat

<400> SEQUENCE: 111
gaagttaaca tacactcaat                                                   20

<210> SEQ ID NO 112
<211> LENGTH: 24
<212> TYPE: DNA
<213> ORGANISM: ARTIFICIAL
<220> FEATURE:
<223> OTHER INFORMATION: sequence of excision site of mutation
      transposons

<400> SEQUENCE: 112
cggtacccgg cagtaggggga tcct                                             24

<210> SEQ ID NO 113
<211> LENGTH: 24
<212> TYPE: DNA
<213> ORGANISM: ARTIFICIAL
<220> FEATURE:
<223> OTHER INFORMATION: sequence of excision site of mutation
      transposons
```

```
<400> SEQUENCE: 113
cggtacccta ctgggggggga tcct                                              24

<210> SEQ ID NO 114
<211> LENGTH: 19
<212> TYPE: DNA
<213> ORGANISM: ARTIFICIAL
<220> FEATURE:
<223> OTHER INFORMATION: primer

<400> SEQUENCE: 114
cctctagcta gagtcgacc                                                     19

<210> SEQ ID NO 115
<211> LENGTH: 18
<212> TYPE: DNA
<213> ORGANISM: ARTIFICIAL
<220> FEATURE:
<223> OTHER INFORMATION: primer

<400> SEQUENCE: 115
catggctcga ggttaagc                                                      18

<210> SEQ ID NO 116
<211> LENGTH: 23
<212> TYPE: DNA
<213> ORGANISM: ARTIFICIAL
<220> FEATURE:
<223> OTHER INFORMATION: primer

<400> SEQUENCE: 116
taacactatg tcacttaata ttc                                                23

<210> SEQ ID NO 117
<211> LENGTH: 18
<212> TYPE: DNA
<213> ORGANISM: ARTIFICIAL
<220> FEATURE:
<223> OTHER INFORMATION: primer

<400> SEQUENCE: 117
atcccatggc tcgaggtt                                                      18

<210> SEQ ID NO 118
<211> LENGTH: 51
<212> TYPE: DNA
<213> ORGANISM: ARTIFICIAL
<220> FEATURE:
<223> OTHER INFORMATION: primer

<400> SEQUENCE: 118
tcagaagttt acatacacta agtttggagt cattaaaact cgttttcaa c                  51

<210> SEQ ID NO 119
<211> LENGTH: 53
<212> TYPE: DNA
<213> ORGANISM: ARTIFICIAL
<220> FEATURE:
<223> OTHER INFORMATION: primer

<400> SEQUENCE: 119
aagttaacat acactcaatc caaatacatt taaactcact ttttcacaat tcc               53

<210> SEQ ID NO 120
<211> LENGTH: 47
```

```
<212> TYPE: DNA
<213> ORGANISM: ARTIFICIAL
<220> FEATURE:
<223> OTHER INFORMATION: primer

<400> SEQUENCE: 120
tcggaagttt acatacactt aagtgactgt gcctttaaac agcttgg                47

<210> SEQ ID NO 121
<211> LENGTH: 46
<212> TYPE: DNA
<213> ORGANISM: ARTIFICIAL
<220> FEATURE:
<223> OTHER INFORMATION: primer

<400> SEQUENCE: 121
cgacttcaac tgaatgtgat gaaagaaata aaagctgaaa tgaatc                 46

<210> SEQ ID NO 122
<211> LENGTH: 28
<212> TYPE: DNA
<213> ORGANISM: ARTIFICIAL
<220> FEATURE:
<223> OTHER INFORMATION: primer

<400> SEQUENCE: 122
gaagtttaca tacacttaag ttggagtc                                     28

<210> SEQ ID NO 123
<211> LENGTH: 24
<212> TYPE: DNA
<213> ORGANISM: ARTIFICIAL
<220> FEATURE:
<223> OTHER INFORMATION: primer

<400> SEQUENCE: 123
cttaagtgta tgtaaacttc cgac                                         24

<210> SEQ ID NO 124
<211> LENGTH: 18
<212> TYPE: DNA
<213> ORGANISM: ARTIFICIAL
<220> FEATURE:
<223> OTHER INFORMATION: primer

<400> SEQUENCE: 124
aaactattgt ttgttaac                                                18

<210> SEQ ID NO 125
<211> LENGTH: 21
<212> TYPE: DNA
<213> ORGANISM: ARTIFICIAL
<220> FEATURE:
<223> OTHER INFORMATION: primer

<400> SEQUENCE: 125
gaaaaatgac ttgtgtcatg c                                            21

<210> SEQ ID NO 126
<211> LENGTH: 22
<212> TYPE: DNA
<213> ORGANISM: ARTIFICIAL
<220> FEATURE:
<223> OTHER INFORMATION: primer

<400> SEQUENCE: 126
ataatagtag agagaatgat tc                                           22
```

<210> SEQ ID NO 127
<211> LENGTH: 42
<212> TYPE: DNA
<213> ORGANISM: ARTIFICIAL
<220> FEATURE:
<223> OTHER INFORMATION: primer

<400> SEQUENCE: 127
caatagcatc acaaatttca caaacaacaa ttgtttacag ac                42

<210> SEQ ID NO 128
<211> LENGTH: 39
<212> TYPE: DNA
<213> ORGANISM: ARTIFICIAL
<220> FEATURE:
<223> OTHER INFORMATION: primer

<400> SEQUENCE: 128
gaagactggg tgaccttaac actatgtcac ttaatattc                    39

<210> SEQ ID NO 129
<211> LENGTH: 31
<212> TYPE: DNA
<213> ORGANISM: ARTIFICIAL
<220> FEATURE:
<223> OTHER INFORMATION: primer

<400> SEQUENCE: 129
ccaacttcca tgtatgtaaa cttccgactt c                            31

<210> SEQ ID NO 130
<211> LENGTH: 31
<212> TYPE: DNA
<213> ORGANISM: ARTIFICIAL
<220> FEATURE:
<223> OTHER INFORMATION: primer

<400> SEQUENCE: 130
ccaactcccg tgtatgtaaa cttccgactt c                            31

<210> SEQ ID NO 131
<211> LENGTH: 35
<212> TYPE: DNA
<213> ORGANISM: ARTIFICIAL
<220> FEATURE:
<223> OTHER INFORMATION: primer

<400> SEQUENCE: 131
tggagctcgg taccctaaaa ttgaagtcgg aagtt                        35

<210> SEQ ID NO 132
<211> LENGTH: 35
<212> TYPE: DNA
<213> ORGANISM: ARTIFICIAL
<220> FEATURE:
<223> OTHER INFORMATION: primer

<400> SEQUENCE: 132
tggagctcgg taccctacag cccaagtcgg aagtt                        35

<210> SEQ ID NO 133
<211> LENGTH: 35
<212> TYPE: DNA
<213> ORGANISM: ARTIFICIAL
<220> FEATURE:
<223> OTHER INFORMATION: primer

```
<400> SEQUENCE: 133
tggagctcgg taccctacag ttgccctcgg aagtt                          35

<210> SEQ ID NO 134
<211> LENGTH: 35
<212> TYPE: DNA
<213> ORGANISM: ARTIFICIAL
<220> FEATURE:
<223> OTHER INFORMATION: primer

<400> SEQUENCE: 134
tggagctcgg taccctacag ttgaagaacg aagtt                          35

<210> SEQ ID NO 135
<211> LENGTH: 35
<212> TYPE: DNA
<213> ORGANISM: ARTIFICIAL
<220> FEATURE:
<223> OTHER INFORMATION: primer

<400> SEQUENCE: 135
ggagctcgga tccctataca gttgaagtcg gaagt                          35

<210> SEQ ID NO 136
<211> LENGTH: 35
<212> TYPE: DNA
<213> ORGANISM: ARTIFICIAL
<220> FEATURE:
<223> OTHER INFORMATION: primer

<400> SEQUENCE: 136
ggagctcgga tccctataca gttgaagtcg gaagt                          35

<210> SEQ ID NO 137
<211> LENGTH: 34
<212> TYPE: DNA
<213> ORGANISM: ARTIFICIAL
<220> FEATURE:
<223> OTHER INFORMATION: primer

<400> SEQUENCE: 137
ggagctccct ataggggcag ttgaagtcgg aagt                           34

<210> SEQ ID NO 138
<211> LENGTH: 34
<212> TYPE: DNA
<213> ORGANISM: ARTIFICIAL
<220> FEATURE:
<223> OTHER INFORMATION: primer

<400> SEQUENCE: 138
gaggatccct ataggggcag ttgaagtcgg aagt                           34

<210> SEQ ID NO 139
<211> LENGTH: 34
<212> TYPE: DNA
<213> ORGANISM: ARTIFICIAL
<220> FEATURE:
<223> OTHER INFORMATION: primer

<400> SEQUENCE: 139
tggagctcgg taccctacag ttgaagtcgg aagt                           34

<210> SEQ ID NO 140
<211> LENGTH: 29
```

```
<212> TYPE: DNA
<213> ORGANISM: ARTIFICIAL
<220> FEATURE:
<223> OTHER INFORMATION: primer

<400> SEQUENCE: 140
gaggatcccc tacagttgaa gtcggaagt                                      29

<210> SEQ ID NO 141
<211> LENGTH: 37
<212> TYPE: DNA
<213> ORGANISM: ARTIFICIAL
<220> FEATURE:
<223> OTHER INFORMATION: primer

<400> SEQUENCE: 141
tggagctcgg taccctacaa ttgaagtcgg aagttta                             37

<210> SEQ ID NO 142
<211> LENGTH: 48
<212> TYPE: DNA
<213> ORGANISM: ARTIFICIAL
<220> FEATURE:
<223> OTHER INFORMATION: primer

<400> SEQUENCE: 142
tggagctcgg taccctacag ttgaggaagt ttacatacac ttaagttg                 48

<210> SEQ ID NO 143
<211> LENGTH: 35
<212> TYPE: DNA
<213> ORGANISM: ARTIFICIAL
<220> FEATURE:
<223> OTHER INFORMATION: primer

<400> SEQUENCE: 143
tggagctcgg taccctacag tgggtcggaa gttta                               35

<210> SEQ ID NO 144
<211> LENGTH: 35
<212> TYPE: DNA
<213> ORGANISM: ARTIFICIAL
<220> FEATURE:
<223> OTHER INFORMATION: primer

<400> SEQUENCE: 144
ggagctcgga tccctacagt tgaagtcaga agttt                               35

<210> SEQ ID NO 145
<211> LENGTH: 29
<212> TYPE: DNA
<213> ORGANISM: ARTIFICIAL
<220> FEATURE:
<223> OTHER INFORMATION: primer

<400> SEQUENCE: 145
gtgaaaaact gagtttaaat gtatttggc                                      29

<210> SEQ ID NO 146
<211> LENGTH: 29
<212> TYPE: DNA
<213> ORGANISM: ARTIFICIAL
<220> FEATURE:
<223> OTHER INFORMATION: primer

<400> SEQUENCE: 146
gggaattttt actaggatta aatgtcagg                                      29
```

<210> SEQ ID NO 147
<211> LENGTH: 30
<212> TYPE: DNA
<213> ORGANISM: ARTIFICIAL
<220> FEATURE:
<223> OTHER INFORMATION: primer

<400> SEQUENCE: 147
ctgacatttc acattcttaa aataaagtgg                                30

<210> SEQ ID NO 148
<211> LENGTH: 33
<212> TYPE: DNA
<213> ORGANISM: ARTIFICIAL
<220> FEATURE:
<223> OTHER INFORMATION: primer

<400> SEQUENCE: 148
gtatgtaaac ttctgaccca ctgggaatgt gat                            33

<210> SEQ ID NO 149
<211> LENGTH: 18
<212> TYPE: DNA
<213> ORGANISM: ARTIFICIAL
<220> FEATURE:
<223> OTHER INFORMATION: primer

<400> SEQUENCE: 149
ccacaagctt ctaaagcc                                             18

<210> SEQ ID NO 150
<211> LENGTH: 20
<212> TYPE: DNA
<213> ORGANISM: ARTIFICIAL
<220> FEATURE:
<223> OTHER INFORMATION: primer

<400> SEQUENCE: 150
cagtaccgaa atcttcgaac                                           20

<210> SEQ ID NO 151
<211> LENGTH: 20
<212> TYPE: DNA
<213> ORGANISM: ARTIFICIAL
<220> FEATURE:
<223> OTHER INFORMATION: primer

<400> SEQUENCE: 151
actgacacgg aaatttgtcg                                           20

<210> SEQ ID NO 152
<211> LENGTH: 21
<212> TYPE: DNA
<213> ORGANISM: ARTIFICIAL
<220> FEATURE:
<223> OTHER INFORMATION: primer

<400> SEQUENCE: 152
aacctcagta attttgagca a                                         21

<210> SEQ ID NO 153
<211> LENGTH: 34
<212> TYPE: DNA
<213> ORGANISM: ARTIFICIAL
<220> FEATURE:
<223> OTHER INFORMATION: primer

<400> SEQUENCE: 153
cccactggat agggtaccga gctccaattc gccc                                34

<210> SEQ ID NO 154
<211> LENGTH: 45
<212> TYPE: DNA
<213> ORGANISM: ARTIFICIAL
<220> FEATURE:
<223> OTHER INFORMATION: primer

<400> SEQUENCE: 154
ctgacccact gggtaggga tcctctagct agagtcgacc tcgag                     45

<210> SEQ ID NO 155
<211> LENGTH: 44
<212> TYPE: DNA
<213> ORGANISM: ARTIFICIAL
<220> FEATURE:
<223> OTHER INFORMATION: primer

<400> SEQUENCE: 155
cttcaactga ttgtgataca gtgaattata agtgaaataa tctg                     44

<210> SEQ ID NO 156
<211> LENGTH: 55
<212> TYPE: DNA
<213> ORGANISM: ARTIFICIAL
<220> FEATURE:
<223> OTHER INFORMATION: primer

<400> SEQUENCE: 156
gaagtttaca taccttag tagtatttgg tagcattgcc tttaaattgt ttaac           55

<210> SEQ ID NO 157
<211> LENGTH: 37
<212> TYPE: DNA
<213> ORGANISM: ARTIFICIAL
<220> FEATURE:
<223> OTHER INFORMATION: primer

<400> SEQUENCE: 157
cgacttcaac tgattgtgat acagtgaatt ataagtg                             37

<210> SEQ ID NO 158
<211> LENGTH: 24
<212> TYPE: DNA
<213> ORGANISM: ARTIFICIAL
<220> FEATURE:
<223> OTHER INFORMATION: primer

<400> SEQUENCE: 158
ttttggcaag tcagttagga catc                                           24

<210> SEQ ID NO 159
<211> LENGTH: 18
<212> TYPE: DNA
<213> ORGANISM: ARTIFICIAL
<220> FEATURE:
<223> OTHER INFORMATION: primer

<400> SEQUENCE: 159
caacaattgt ttacagac                                                  18

<210> SEQ ID NO 160
<211> LENGTH: 23

```
<212> TYPE: DNA
<213> ORGANISM: ARTIFICIAL
<220> FEATURE:
<223> OTHER INFORMATION: primer

<400> SEQUENCE: 160
attccagtgg gtcagaagtt tac                                              23

<210> SEQ ID NO 161
<211> LENGTH: 20
<212> TYPE: DNA
<213> ORGANISM: ARTIFICIAL
<220> FEATURE:
<223> OTHER INFORMATION: primer

<400> SEQUENCE: 161
gacagggaat ctttactcgg                                                  20

<210> SEQ ID NO 162
<211> LENGTH: 44
<212> TYPE: DNA
<213> ORGANISM: ARTIFICIAL
<220> FEATURE:
<223> OTHER INFORMATION: primer

<400> SEQUENCE: 162
ctttatttgt aaccattata agctcaaaac tattgtttgt taac                       44

<210> SEQ ID NO 163
<211> LENGTH: 36
<212> TYPE: DNA
<213> ORGANISM: ARTIFICIAL
<220> FEATURE:
<223> OTHER INFORMATION: primer

<400> SEQUENCE: 163
aaatgtatgt gaattcaaat cttcgaacac cttccg                                36

<210> SEQ ID NO 164
<211> LENGTH: 17
<212> TYPE: DNA
<213> ORGANISM: ARTIFICIAL
<220> FEATURE:
<223> OTHER INFORMATION: primer

<400> SEQUENCE: 164
gagtagcctt ccacaag                                                     17

<210> SEQ ID NO 165
<211> LENGTH: 20
<212> TYPE: DNA
<213> ORGANISM: ARTIFICIAL
<220> FEATURE:
<223> OTHER INFORMATION: primer

<400> SEQUENCE: 165
tgatgtcatg gctttagaag                                                  20

<210> SEQ ID NO 166
<211> LENGTH: 28
<212> TYPE: DNA
<213> ORGANISM: ARTIFICIAL
<220> FEATURE:
<223> OTHER INFORMATION: primer

<400> SEQUENCE: 166
ctcagttttt cacaattcct gacattta                                         28
```

<210> SEQ ID NO 167
<211> LENGTH: 30
<212> TYPE: DNA
<213> ORGANISM: ARTIFICIAL
<220> FEATURE:
<223> OTHER INFORMATION: primer

<400> SEQUENCE: 167
gtaaaaattc cctgtcttag gtcagttagg                                30

<210> SEQ ID NO 168
<211> LENGTH: 31
<212> TYPE: DNA
<213> ORGANISM: ARTIFICIAL
<220> FEATURE:
<223> OTHER INFORMATION: primer

<400> SEQUENCE: 168
gaatgtgaaa tgtcagaata atagtagaga g                              31

<210> SEQ ID NO 169
<211> LENGTH: 35
<212> TYPE: DNA
<213> ORGANISM: ARTIFICIAL
<220> FEATURE:
<223> OTHER INFORMATION: primer

<400> SEQUENCE: 169
gaagtttaca tacactcaat tagtatttgg tagca                          35

<210> SEQ ID NO 170
<211> LENGTH: 39
<212> TYPE: DNA
<213> ORGANISM: ARTIFICIAL
<220> FEATURE:
<223> OTHER INFORMATION: footprint sequence

<400> SEQUENCE: 170
ttcgagctcg gtaccctaca gtaggggatc ctctagagt                      39

<210> SEQ ID NO 171
<211> LENGTH: 39
<212> TYPE: DNA
<213> ORGANISM: ARTIFICIAL
<220> FEATURE:
<223> OTHER INFORMATION: footprint sequence

<400> SEQUENCE: 171
ttcgagctcg gtaccctact gtaggggatc ctctagagt                      39

<210> SEQ ID NO 172
<211> LENGTH: 36
<212> TYPE: DNA
<213> ORGANISM: ARTIFICIAL
<220> FEATURE:
<223> OTHER INFORMATION: footprint sequence

<400> SEQUENCE: 172
ttcgagctcg gtaccctgta ggggatcctc tagagt                         36

<210> SEQ ID NO 173
<211> LENGTH: 36
<212> TYPE: DNA
<213> ORGANISM: ARTIFICIAL
<220> FEATURE:
<223> OTHER INFORMATION: footprint sequence

<400> SEQUENCE: 173
ttcgagctcg gtaccctata ggggatcctc tagagt                                    36

<210> SEQ ID NO 174
<211> LENGTH: 37
<212> TYPE: DNA
<213> ORGANISM: ARTIFICIAL
<220> FEATURE:
<223> OTHER INFORMATION: footprint sequence

<400> SEQUENCE: 174
ttcgagctcg gtaccctact agggatcct ctagagt                                    37

<210> SEQ ID NO 175
<211> LENGTH: 37
<212> TYPE: DNA
<213> ORGANISM: ARTIFICIAL
<220> FEATURE:
<223> OTHER INFORMATION: footprint sequence

<400> SEQUENCE: 175
ttcgagctcg gtaccttgt agggatcct ctagagt                                     37

<210> SEQ ID NO 176
<211> LENGTH: 36
<212> TYPE: DNA
<213> ORGANISM: ARTIFICIAL
<220> FEATURE:
<223> OTHER INFORMATION: footprint sequence

<400> SEQUENCE: 176
ttcgagctcg gtaccctaca ggggatcctc tagagt                                    36

<210> SEQ ID NO 177
<211> LENGTH: 19
<212> TYPE: DNA
<213> ORGANISM: ARTIFICIAL
<220> FEATURE:
<223> OTHER INFORMATION: footprint sequence

<400> SEQUENCE: 177 gtagggatc ctctagagt                                                        19

<210> SEQ ID NO 178
<211> LENGTH: 42
<212> TYPE: DNA
<213> ORGANISM: ARTIFICIAL
<220> FEATURE:
<223> OTHER INFORMATION: footprint sequence
<220> FEATURE:
<221> NAME/KEY: misc_feature
<222> LOCATION: (31)..(31)
<223> OTHER INFORMATION: any nucleotide
<220> FEATURE:
<221> NAME/KEY: misc_feature
<222> LOCATION: (39)..(39)
<223> OTHER INFORMATION: n is a, c, g, or t

<400> SEQUENCE: 178
ttcgagcttg catgtgggag gtttttttcgg atcctctana gt                            42

<210> SEQ ID NO 179
<211> LENGTH: 39
<212> TYPE: DNA
<213> ORGANISM: ARTIFICIAL
<220> FEATURE:
<223> OTHER INFORMATION: footprint sequence

<400> SEQUENCE: 179
ttcgagctcg gtaccctact gtagggatc ctctagagt             39

<210> SEQ ID NO 180
<211> LENGTH: 39
<212> TYPE: DNA
<213> ORGANISM: ARTIFICIAL
<220> FEATURE:
<223> OTHER INFORMATION: footprint sequence
<220> FEATURE:
<221> NAME/KEY: misc_feature
<222> LOCATION: (8)..(8)
<223> OTHER INFORMATION: any nucleotide

<400> SEQUENCE: 180
ttccaacncg gtaccctaca gtagggaatc ctctagagt            39

<210> SEQ ID NO 181
<211> LENGTH: 61
<212> TYPE: DNA
<213> ORGANISM: ARTIFICIAL
<220> FEATURE:
<223> OTHER INFORMATION: footprint sequence

<400> SEQUENCE: 181
gactcactat agggcgaatt ggagctcggt accctacagt agggatcct ctagctagag    60 t                                                                  61

<210> SEQ ID NO 182
<211> LENGTH: 61
<212> TYPE: DNA
<213> ORGANISM: ARTIFICIAL
<220> FEATURE:
<223> OTHER INFORMATION: footprint sequence

<400> SEQUENCE: 182
gactcactat agggcgaatt ggagctcggt accctactgt agggatcct ctagctagag    60 t                                                                  61

<210> SEQ ID NO 183
<211> LENGTH: 15
<212> TYPE: DNA
<213> ORGANISM: ARTIFICIAL
<220> FEATURE:
<223> OTHER INFORMATION: footprint sequence

<400> SEQUENCE: 183
gactcactat agagt                                      15

<210> SEQ ID NO 184
<211> LENGTH: 38
<212> TYPE: DNA
<213> ORGANISM: ARTIFICIAL
<220> FEATURE:
<223> OTHER INFORMATION: primer

<400> SEQUENCE: 184
agtcattaaa actcgtttta gtcattaaaa ctcgtttt             38

<210> SEQ ID NO 185
<211> LENGTH: 34
<212> TYPE: DNA
<213> ORGANISM: artificial
<220> FEATURE:
<223> OTHER INFORMATION: right outer repeat

```
<400> SEQUENCE: 185
tacagttgaa gtcggaagtt tacatacacc ttag                                    34

<210> SEQ ID NO 186
<211> LENGTH: 20
<212> TYPE: DNA
<213> ORGANISM: artificial
<220> FEATURE:
<223> OTHER INFORMATION: portion of right inverted repeat

<400> SEQUENCE: 186
gaagtttaca tacactcaat                                                    20

<210> SEQ ID NO 187
<211> LENGTH: 19
<212> TYPE: DNA
<213> ORGANISM: artificial
<220> FEATURE:
<223> OTHER INFORMATION: primer

<400> SEQUENCE: 187
agtcattaaa actcgtttt                                                     19

<210> SEQ ID NO 188
<211> LENGTH: 20
<212> TYPE: DNA
<213> ORGANISM: artificial
<220> FEATURE:
<223> OTHER INFORMATION: primer

<400> SEQUENCE: 188
tgacgttgga gtccacgttc                                                    20
```